US006942981B1

(12) United States Patent
Lu et al.

(10) Patent No.: US 6,942,981 B1
(45) Date of Patent: Sep. 13, 2005

(54) METHOD OF DETERMINING INTERACTIONS WITH PDZ-DOMAIN POLYPEPTIDES

(75) Inventors: Peter S. Lu, Mountain View, CA (US); Joshua D. Rabinowitz, Mountain View, CA (US); Johannes Schweizer, Mountain View, CA (US)

(73) Assignee: Arbor Vita Corporation, Sunnyvale, CA (US)

(*) Notice: Subject to any disclaimer, the term of this patent is extended or adjusted under 35 U.S.C. 154(b) by 0 days.

(21) Appl. No.: 09/688,017

(22) Filed: Oct. 13, 2000

Related U.S. Application Data

(63) Continuation-in-part of application No. 09/570,118, filed on May 12, 2000, now abandoned, and a continuation-in-part of application No. 09/570,364, filed on May 12, 2000, now abandoned, and a continuation-in-part of application No. 09/569,525, filed on May 12, 2000, now abandoned, and a continuation-in-part of application No. 09/547,276, filed on Apr. 11, 2000, now abandoned.

(60) Provisional application No. 60/196,460, filed on Apr. 11, 2000, provisional application No. 60/196,528, filed on Apr. 11, 2000, provisional application No. 60/196,527, filed on Apr. 11, 2000, provisional application No. 60/196,267, filed on Apr. 11, 2000, provisional application No. 60/182,296, filed on Feb. 14, 2000, provisional application No. 60/176,195, filed on Jan. 14, 2000, provisional application No. 60/170,453, filed on Dec. 13, 1999, provisional application No. 60/162,498, filed on Oct. 29, 1999, provisional application No. 60/160,860, filed on Oct. 21, 1999, provisional application No. 60/134,118, filed on May 14, 1999, provisional application No. 60/134,117, filed on May 14, 1999, and provisional application No. 60/134,114, filed on May 14, 1999.

(51) Int. Cl.[7] .............................................. G01N 33/53
(52) U.S. Cl. ........................................................ 435/7.1
(58) Field of Search .................................. 435/7.1, 7.21

(56) References Cited

U.S. PATENT DOCUMENTS

| 5,632,994 A | 5/1997 | Reed et al. |
| 5,747,245 A | 5/1998 | Reed et al. |
| 5,863,898 A | 1/1999 | Goli et al. |
| 5,876,939 A | 3/1999 | Reed et al. |
| 5,958,731 A | 9/1999 | Yue et al. |
| 5,976,819 A | 11/1999 | Finkel et al. |
| 6,174,702 B1 | 1/2001 | Lal et al. |
| 2002/0058607 A1 | 5/2002 | Sato et al. |
| 2002/0147306 A1 | 10/2002 | Lin et al. |
| 2003/0049695 A1 | 3/2003 | Lu et al. |
| 2003/0203414 A1 | 10/2003 | Sato et al. |

FOREIGN PATENT DOCUMENTS

| CA | 2273622 A1 | 12/2000 |
| WO | WO 98/05347 A1 | 2/1998 |
| WO | WO 98/23781 A1 | 6/1998 |
| WO | WO 98/40407 A1 | 9/1998 |
| WO | WO 99/03974 A1 | 1/1999 |
| WO | WO 99/07846 A1 | 2/1999 |
| WO | WO 00/15794 A1 | 3/2000 |
| WO | WO 00/31124 A2 | 6/2000 |
| WO | WO 00/48002 A1 | 8/2000 |
| WO | WO 00/69896 A2 | 11/2000 |
| WO | WO 00/69897 A2 | 11/2000 |
| WO | WO 00/69898 A2 | 11/2000 |
| WO | WO 02/31512 A2 | 4/2002 |
| WO | WO 02/42422 A2 | 5/2002 |
| WO | WO 03/014303 A2 | 2/2003 |

OTHER PUBLICATIONS

Gee et al. The Journal of Neuroscience, Jan. 1, 1998, 18(1):128–137.*

Coligam et al. Current Protocols in Immunology, 1991, pp. 2.03–2.1.9.*

U.S. Appl. No. 07/724,553, Lu et al.

U.S. Appl. No. 09/722,069, Lu et al.

Altin, J. and Sloan, E. "The role of CD45 and CD45–associated molecules in T cell activation" *Immunology and Cell Biology*, 1997, pp. 430–445, vol. 75.

Bals, R. et al. "Augmentation of Innate Host Defense by Expression of a Cathelicidin Antimicrobial Peptide", *Infection and Immunity*, Nov. 1999, pp. 6084–6089, vol. 67, No. 11.

Barclay, A., et al., "The Leukocyte Antigen Factsbook", *Harcourt Braces & Company*, p. 363, (1997).

Bruyns, E. et al. "Identification of the Sites of Interaction between Lyphocyte Phosphatase–associated Phophoprotein (LPAP) and CD45", *Journal of Biological Chemistry*, Dec. 29, 1996, pp. 31372–31376, vol. 270, No. 52, U.S.A.

Cherukuri, A. et al. "Floating the raft hypothesis: lipid rafts play a role in immune cell activation", *Immunity*, Jun. 2001, pp. 657–660, vol. 14, Cell Press.

Ding, I. Et al., "Biochemical and Functional Analysis of Mice Deficient in Expression of the CD45–Associated Phosphoprotein LPAP", *European Journal of Immunology*, 29(12):3956–61 (1999).

Doyle, D. A., et al., "Crystal structures of a complexed and peptide–free membrane protein–binding domain: molecular basis of peptide recognition by PDZ", *Cell*, 85(7):1067–76, (1996).

Faulkner, G. et al. "A New Z–band Alternatively Spliced PDZ–motif Protein." *The Journal of Cell Biology*, Jul. 26, 1999; pp. 465–475, vol. 146, No. 2.

(Continued)

*Primary Examiner*—Christina Chan
*Assistant Examiner*—Michail A Belyavskyi
(74) *Attorney, Agent, or Firm*—Townsend and Townsend and Crew LLP; Mark G. Sandbaken

(57) ABSTRACT

Methods are provided for determining interactions between multiple PDZ-domain polypeptides and PDZ Ligand Proteins.

8 Claims, 14 Drawing Sheets

OTHER PUBLICATIONS

Figure 1B:
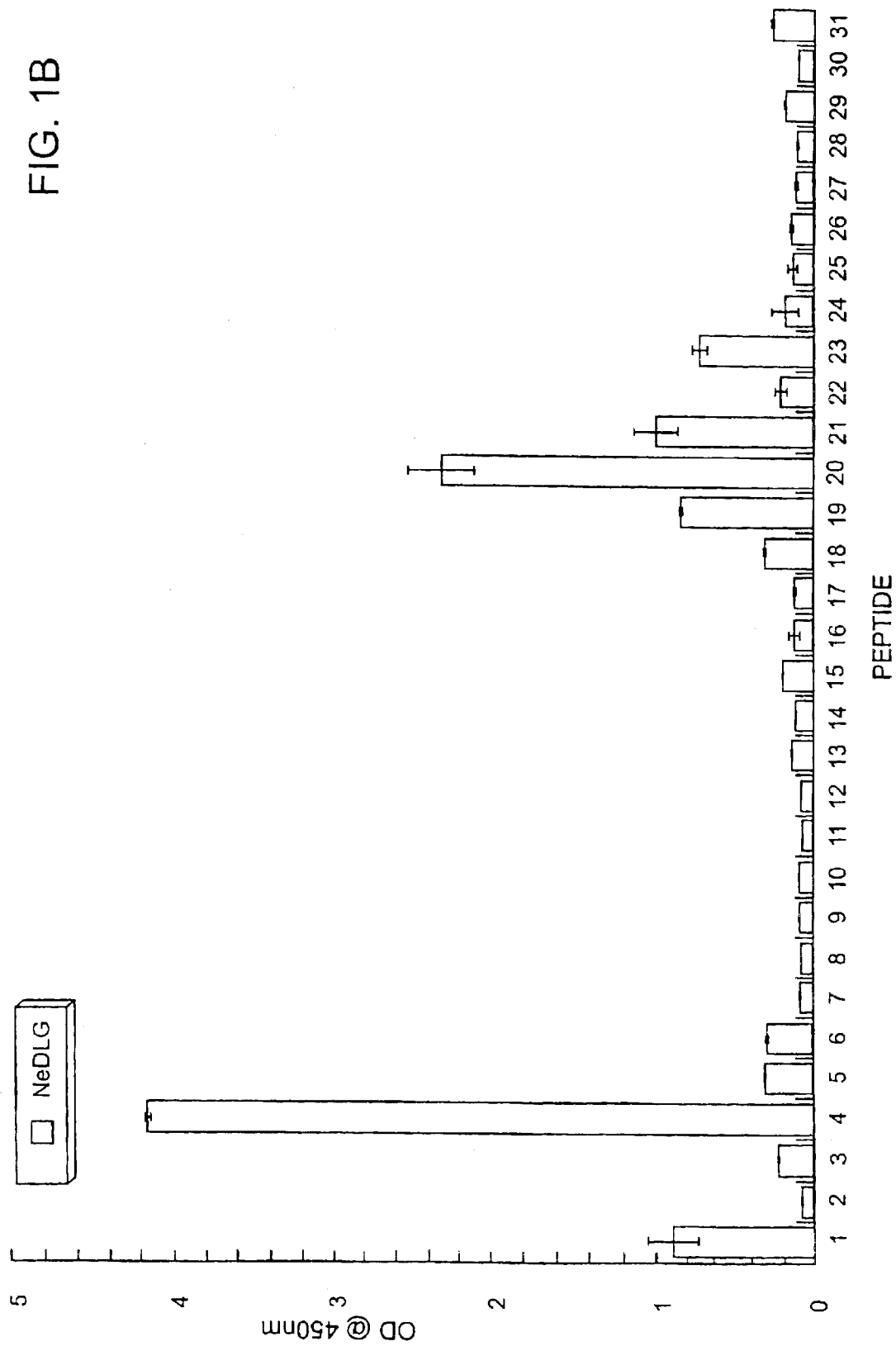
Figure 1C:
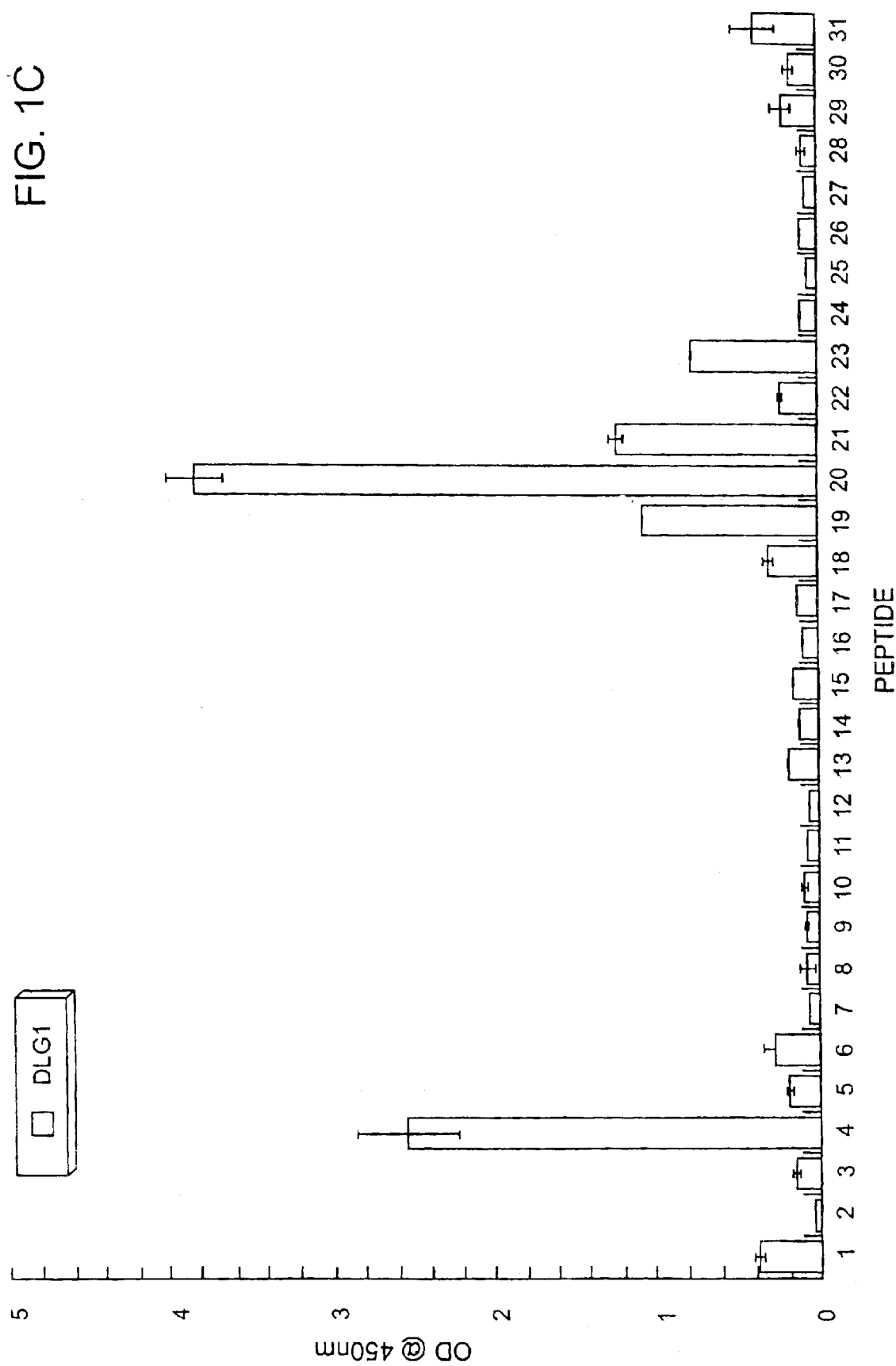

Gardiol, D. et al. "Oncogenic human papillomavirus E6 proteins target the discs large tumour suppressor for proteasome–mediated degradation", *Oncogene*, 18(40):5487–5496, (1999).

Gee., S.H., et al., "Cyclic Peptides as Non–carboxyl–terminal Ligands of Syntrophin PDZ Domains", *The Journal of Biological Chemistry*, 273(34):21980–21987, (1998).

Hanada, T., et al., "Human Homologue of the *Drosophila* Discs Larger Tumor Suppressor Binds to p56$^{lck}$ Tyrosine Kinase and Shaker Type Kv1.3 Potassium Channel in T. Lymphocytes", *The Journal of Biological Chemistry*, 272(43):26899–26904, (1997).

Kiyono, T. et al. "Binding of high–risk human papillomavirus E6 oncoproteins to the human homologue of the *Drosophila* discs large tumor suppressor protein", *Proc. Natl. Acad. Sci.*, Oct. 1997, pp. 11612–11616, vol. 94, U.S.A.

Kobayashi, I., et al., "Identification of an Autoimmune Enteropathy–related 75–kilodalton Antigen", *Gastroenterology*, Oct. 1999, pp. 823–830, vol. 17, No. 4.

Maekawa, K., et al., "Association of Protein–Tyrosine Phosphatasee PTP–BAS with the Transcription–factor–inhibitory Protein IκBα Through Interaction Between the PDZ1 Domain and Ankyrin Repeats", *Biochemical Journal*, 337(2):179–187, (1999).

McKusick, Victor A.; OMIM Database entry entitled, '147138 Fc Fragment of IgE, High Affinity I, Receptor for, Beta Subunit; FCER1B', www.ncbi.nlm.nih.gov/htbin–post/Omim/dispmim?147138, Aug. 27, 1992.

Nagase, T. et al. "Prediction of the Coding Sequence of Unidentified Human Genes. V1. The Coding Sequences of 80 New Genes (KIAA0201–KIAA0280) Deduced by Analysis of cDNA Clones from Cell Line KG–1 and Brain", *DNA Research*, 1996, pp. 321–329, vol. 3.

Nagase, T. et al. "Prediction of the Coding Sequence of Unidentified Human Genes. V1. The Coding Sequences of 80 New Genes (KIAA0201–KIAA0280) Deduced by Analysis of cDNA Clones from Cell Line KG–1 and Brain (Supplement)", *DNA Research*, 1996, pp. 341–354, vol. 3, Supplement.

Nishihara, H. et al, "Non–adherent cell–specific expression of DOCK2, a member of the human CDM–family proteins", *Biochimica et Biophysica Acta*, 1999, pp. 179–187, Elsevier Publishing.

Nishihara, H. "Analysis of Hematopoietic Cell Specific Protein, M–DOCK", Hokkaido Igaku Zasshi, Mar. 1999, pp. 157–166, vol. 74, No. 2.

Patel, V. et al., "A Molecular Framework for 2–Step T Cell Signaling: Lck Src Homology 3 Mutations Discriminate Distinctly Regulated Lipid Raft Reorganization Events", *Journal of Immunology*, 166(2):754–64 (2001).

Rasooly, Rebekah S.; OMIM Database entry entitled, "603122 Dedicator of Cytokinesis 2; Dock 2" www.ncbi.nlm.nih.gov/htbin–post/Omim/dispmim?603122, Oct. 12, 1998.

Reynaud, C. et al., "The PDZ Protein TIP–1 Interacts with the Rho Effector Rhotekin and Is Involved in Rho Signaling to the Serum Response Element", *The Journal of Biological Chemistry*, 275(43):33962–33968, (2000).

Rousset, R., et al., "The C–terminus of the HTLV–1 Tax oncoprotein mediates interaction with the PDZ domain of cellular proteins" *Oncogene*, 16(5):643–54, (1998).

Saras, J., et al., "PDZ Domains Bind Carboxy–Terminal Sequences of Target Proteins", *Tibs Trends in Biochemical Sciences, en, Elsevier Publication, Cambridge*, 21(12):455–458, (1996).

Schepens, J., et al., "The Neuronal Nitric Oxide Synthase PDZ Motif Binds to –G(D.E)XV Carboxy Terminal Sequences", *Febs Letters*, 409(1–2):53–56, (1997).

Schraven, Burkhart et al. "LPAP, a Novel 32–kDa Phosphoprotein That Interacts with CD45 in Human Lymphocytes", *J. Biological Chemistry*, Nov. 18, 1994; pp. 29102–29111, vol. 269, No. 46.

Shibuya, A., et al., "DNAM–1 A Novel Adhesion Molecule Invovled in the Cytolytic Function of T Lymphocytes", *Immunity*, 4:573–581, (1996).

Shibuya, A., et al., "Protein Kinase C is Involved in the Regulation of Both Signaling and Adhesion Mediated by DNAX Accessory Molecule–1 Receptor", *The Journal of Immunology*, 161:1671–1676, (1998).

Shibuya, K., et al., "Physical and Functional Association of LFA–1 with DNAM–1 Adhesion Molecule", *Immunity*, 11:615–623, (1999).

Suzuki, T., et al., "Tax oncoprotein of HTLV–1 binds to the human homologue of *Drosophila* discs large tumor suppressor protein, hDLG, and perturbs its function in cell growth control", *Oncogene*, 18(44):5967–72, (1999).

Vallenius, T. et al. "CLP–36 PDZ–LIM Protein Associates with Nonmuscle alpha–Actinin–1 and alpha–Actinin–4." *The Journal of Biological Chemistry*, Apr. 14, 2000; pp. 11100–11105, vol. 275, No. 15.

Wechsler, A. et al. "Brain Spectrin binding to the NMDA receptor is regulated by phosophorylation, calcium and calmodulin." *The EMBO Journal*, 1998, pp. 3931–3939, vol. 17, No. 14.

Xia, H. et al. "Actinin–associated LIM Protein: Identification of a Domain Interaction between PDZ and Spectrin–like Repeat Motifs", *The Journal of Cell Biology*, Oct. 1997, pp. 507–515, vol. 139, No. 2.

Yanagisawa, J., et al., "The Molecular interaction of Fas and FAP–1. A tripeptide blocker of human Fas interaction with FAP–1 promotes Fas–induced apoptosis", *J. Biol. Chem.*, 272(13):8539–8545.

GenBank, Accession No. AF028823, Dec. 1, 1999.

GenBank, Accession No. BM845132, Mar. 6, 2002.

GenBank, Accession No. CB131761, Jan. 29, 2003.

GenBank, Accession No. CB961389, Apr. 28, 2003.

GenBank, Accession No. CB995033, Apr. 30, 2003.

Genbank, Accession No. D86964, Feb. 7, 1999.

Burgess, Wilson H. et al. "Possible Dissociation of the Heparin–binding and Mitogenic Activities of Heparin–binding (Acidic Fibroblast) Growth Factor–1 from Its Receptor–binding Activities by Site–directed Mutagenesis of a Single Lysine Residue" Journal of Cell Biology, Nov. 1990, pp. 2129–2138, vol. 111, The Rockefeller University Press.

Lazar, Eliane et al. "Transforming Growth Factor γ:Mutation of Aspartic Acid 47 and Leucine 48 Results in Different Biological Activities" Molecular and Cellular Biology, Mar. 1988, pp. 1247–1252, vol. 8, No. 3.

Mikayama, Toshifumi et al. "Molecular cloning and functional expression of a cDNA encoding glycosylation–inhibiting factor" Proc. Natl. Acad. Sci., Nov. 1993, pp. 10056–10060, vol. 90.

Brenman et al. "Interaction of nitric oxide synthase with the postsynaptic density protein PSD–95 and alpha1–syntrophin mediated by PDZ domains." Cell, 1996, pp. 757–767, vol. 84, No. 5.

Fabre, Stéphane et al. "Identification of functional PDZ domain binding sites in several human proteins" Molecular Biology Reports, 2000, pp. 217–224, vol. 27, No. 4.

Kornau et al. "Domain interaction between NMDA receptor subunits and the postsynaptic density protein PSD–95." Science, 1995, pp. 1737–1740, vol. 269, No. 5231.

Lee, Siu Sylvia et al. "Binding of human virus oncoproteins to hDig/SAP97, a mammalian homolog of the *Drosophila* discs large tumor suppressor protein" Proceedings of the Nat. Acad. Of Sci. USA, Jun. 1997, pp. 6670–6675, vol. 94.

Marfatia, Shirin et al. "The PDZ domain of human erythrocyte p55 mediates its binding to the cytoplasmic carboxy terminus of Glycophorin C" The Journal of Biological Chemistry, Sep. 1997, pp. 24191–24197, vol. 272, No. 39.

Niethammer, Martin et al. "CRIPT, a Novel Postsynaptic Protein that Binds to the Third PDZ Domain of PSD–95/SAP90" Neuron, Apr. 1998, pp. 693–707, vol. 20, Cell Press.

Songyang, Z. et al. "Recognition of Unique Carboxyl–Terminal Motifs by Distinct PDZ Domains" Science, Jan. 3, 1997, pp. 73–77, vol. 275.

Wang, Yu Tian et al. "Ca2+–independent reduction of N–methyl–D–aspartate channel activity by protein tyrosine phoshphatase" PNAS USA, Feb. 1996, pp. 1721–1725, vol. 93.

* cited by examiner

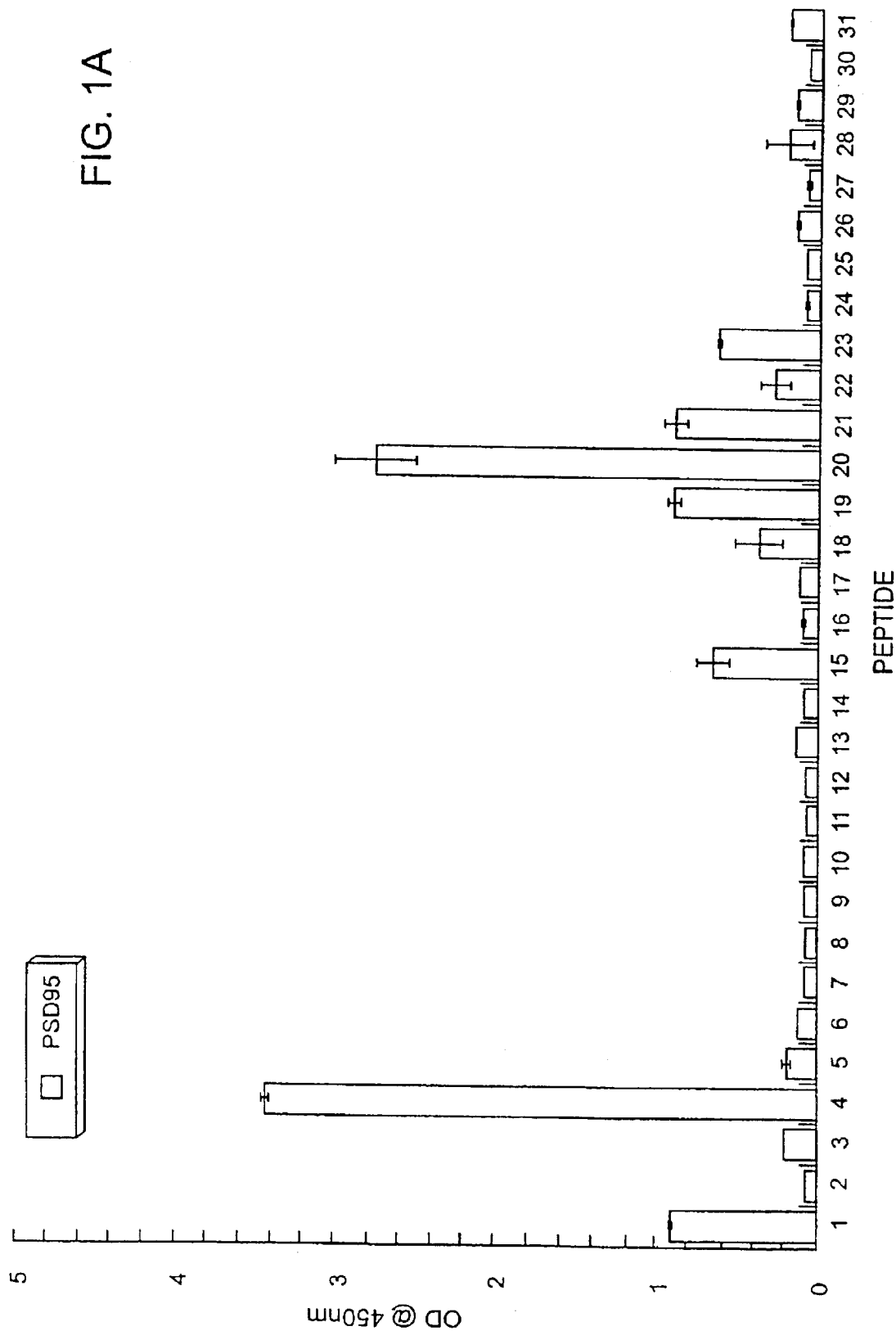

METHOD OF DETERMINING INTERACTIONS WITH PDZ-DOMAIN POLYPEPTIDES

REFERENCE TO RELATED APPLICATIONS

This application is (1) a continuation-in-part of U.S. application Ser. Nos. 09/570,118, 09/570,364, and 09/569,525 (all filed May 12, 2000 and all abandoned), each of which claims the benefit of U.S. Provisional Application Nos. 60/196,460, 60/196,528, 60/196,527, and 60/196,267 (all filed Apr. 11, 2000), and (2) a continuation-in-part of U.S. application Ser. No. 09/547,276 now abandoned, filed Apr. 11, 2000, which claims the benefit of U.S. Provisional Application Nos. 60/182,296 (filed Feb. 14, 2000); 60/176,195 (filed Jan. 14, 2000); 60/170,453 (filed Dec. 13, 1999); 60/162,498 (filed Oct. 29, 1999); 60/160,860 (filed Oct. 21, 1999); and 60/134,118; 60/134,117; and 60/134,114 (all filed May 14, 1999); the disclosures of each of which are incorporated herein in their entirety.

1. FIELD OF THE INVENTION

The present invention relates to peptides and peptide analogues, and methods for using such compositions to regulate activities of cells of the hematopoietic system. In one aspect, the invention provides methods of modulating metabolism (e.g., activation) of hematopoietic cells (e.g., T cells and B cells) by antagonizing an interaction between a PDZ domain containing protein and a protein that binds a PDZ domain. In one aspect, it relates to fusion peptides containing an amino acid sequence corresponding to the carboxyl terminus of a surface receptor expressed by a hematopoietic cell and a transmembrane transporter sequence; such fusion peptides are useful in regulating hematopoietic cells by inhibiting cell activation.

2. BACKGROUND OF THE INVENTION

PDZ domains of proteins are named after three prototypical proteins: PSD95, Drosophila large disc protein and Zonula Occludin 1 protein (Gomperts et al., 1996, *Cell* 84:659–662). PDZ domain-containing proteins are involved in synapse formation by organizing transmembrane neurotransmitter receptors through intracellular interactions. PDZ domains contain the signature sequence GLGF (SEQ ID NO:29). In the nervous system, typical PDZ domain-containing proteins contain three PDZ domains, one SH3 domain and one guanylate kinase domain. Examples of intracellular PDZ domain-containing proteins include LIN-2, LIN-7 and LIN-10 at the pre-synapse, and PSD95 at the post-synapse.

PDZ domains have been shown to bind the carboxyl termini of transmembrane proteins in neuronal cells. Songyang et al. reported that proteins capable of binding PDZ domains contain a carboxyl terminal motif sequence of E-S/T-X-V/I (Songyang et al., 1997, *Science* 275:73). X-ray crystallography studies have revealed the contact points between the motif sequence and PDZ domains (Doyle et al., 1996, *Cell* 88:1067–1076). While the interaction between PDZ domains and ion channels in neurons have been studied extensively, such interactions have had limited studies in other biological systems, especially the hematopoietic system.

The hematopoietic system is composed of different cell types that perform distinct functions. Many of its diverse function requires coordinated movement of cell surface receptors including ion channels, adhesion surface molecules to coordinate cell—cell interaction, and cytokine receptors. Despite their diverse functional activities, all hematopoietic cells are believed to develop from a multipotent bone marrow hematopoietic stem cell. Such stem cell has been shown to express a surface marker termed CD34. During differentiation, the stem cell gives rise to progenitor cells in each of several specific hematopoietic cell lineages. The progenitor cells then undergo a series of morphological and functional changes to produce mature functionally committed hematopoietic cells.

Among the functions performed by hematopoietic cells, certain cell types are involved exclusively in immunity. For example, lymphocytes, which include T cells, B cells and natural killer (NK) cells, are effectors in immune responses. Monocytes and granulocytes (i.e., neutrophils, basophils and eosinophils) play a role in non-specific forms of defense. Lymphocytes, monocytes and granulocytes are collectively referred to as white blood cells or leukocytes. On the other hand, other hematopoietic cells perform functions that are unrelated to the immune system. For example, erythrocytes are involved in gas transport, and cells of the thrombocytic series are involved in blood clotting.

T cells and B cells recognize antigens and generate an immune response. T cells recognize antigens by heterodimeric surface receptors termed the T cell receptor (TCR). The TCR is associated with a series of polypeptides collectively referred to as CD3 complex. B cells recognize antigens by surface immunoglobulins (Ig), which are also secretory molecules. In addition, a large number of co-stimulatory surface receptors have been identified in T cells and B cells, which augment cellular activation during antigen-induced activation.

In addition to the T cell antigen receptor/CD3 complex (TCR/CD3), other molecules expressed by T cells which mediate an activation signal, include but are not limited to, CD2, CD4, CD5, CD6, CD8, CD18, CD27, CD28, CD43, CD45, CD152 (CTLA-4), CD154, MHC class I, MHC class II, CDw137 (4-1BB), CDw150, and the like (Barclay et al., The Leucocyte Antigen Facts Book, 1997, Second edition, Academic Press; Leucocyte Typing, 1984, Bernard et al. (eds.), Springer-Verlag; Leukocyte Typing II, 1986, Reinherz et al. (eds.), Springer-Verlag; Leukocyte Typing III, 1987, McMichael (ed.), Oxford University Press; Leukocyte Typing IV, 1989, Knapp et al. (eds.), Oxford University Press; CD Antigens, 1996, VI Internet Workshop and Conference on Human Leukocyte Differentiation Antigens. Cell surface antigens that work together with TCR/CD3 are often referred to as co-receptors in the art.

Specific antibodies have been generated against all of the aforementioned T cell surface antigens. Other molecules that bind to the aforementioned T cell surface receptors include antigen-binding antibody derivatives such as variable domains, peptides, superantigens, and their natural ligands such as CD58 (LFA-3) for CD2, HIV gp120 for CD4, CD27L for CD27, CD80 or CD86 for CD28 or CD152, ICAM1, ICAM2 and ICAM3 for CD11a/CD18, 4-1BBL for CDw137.

Activation molecules expressed by B cells, include but are not limited to, surface Ig, CD18, CD19, CD20, CD21, CD22, CD23, CD40, CD45, CD80, CD86 and ICAM1. Similarly, natural ligands of these molecules and antibodies directed to them as well as antibody derivatives may be used to deliver an activation signal to B cells.

However, prior to the present invention, it was not known that signal transduction following stimulation of any leukocyte receptor was mediated by receptor interactions with PDZ domain-containing proteins. Therefore, it was not even contemplated in the art that an interference of leukocyte surface receptor/PDZ domain interactions could regulate leukocyte activation.

3. SUMMARY OF THE INVENTION

In one aspect, the invention provides a method of modulating a biological function of a cell, e.g., an endothelial cell or hematopoietic cell (such as a a leukocyte, e.g., T cell or B cell), by introducing into the cell an antagonist that inhibits binding of a PDZ protein and a PL protein in the cell, or a agonist that enhances binding of a PDZ protein and a PL protein in the cell. In various embodiments the PL protein is an adhesion protein, an adaptor protein, or an intracellular protein. In embodiments it is CD6, CD49E, CD49F, CD138, Clasp-1, Clasp-4, VCAM1, Clasp-2, CD95, DNAM-1, CD83, CD44, CD4, CD97, CD3n, DOCK2, CD34, FceRIb, or FasLigand. In an embodiment the PL protein is characterized by a carboxy-terminal amino acid motif that is X-S-X-A, X-A-D/E-V, X-V/I/L-X*-V, or X-S/T-X-F (where X is any amino acid and X* is any non-aromatic amino acid). In embodiments, the PL protein is expressed by T lymphocytes or B lymphocytes. In some embodiments of this method, the PDZ protein is CASK, MPP1, DLG1, PSD95, NeDLG, SYN1a, TAX43, LDP, LIM, LIMK, AF6, PTN-4, prIL16, 41.8, RGS12, DVL1, TAX 40, TIAM1, MINT1, K303, TAX2, or KIAA561.

In some embodiments, the cell is a leukocyte and the biological function is cell activation, cell proliferation, maintenance of cell structure, cell metabolic activity, or cytokine production. In some embodiments, the method further includes detecting a change in leukocyte activation.

In preferred embodiments, the antagonist is an agent that inhibits the binding of a PL peptide to a PDZ domain polypeptide in an "A" assay, in a "G" assay, or in both an A assay and a G assay. The antagonist can be a polypeptide, such as a polypeptide having at the carboxyterminus at least two residues that are the same as the carboxy-terminal two residues of a PL protein, such as a PL protein is expressed in a hematopoietic or endothelial cell that is an adhesion protein, an adaptor protein, or an intracellular protein. In an embodiment, at least the carboxy-terminal four residues of the polypeptide are the same as the carboxy-terminal four residues of the PL protein. In an embodiment, the PL protein has a carboxy-terminal amino acid motif selected from X-S-X-A, X-A-D/E-V, X-V/I/L-X*-V, or X-S/T-X-F, where X is any amino acid and X* is any non-aromatic amino acid. In embodiment, the PL protein is CD6, CD49E, CD49F, CD138, Clasp-1, Clasp-4, VCAM1, Clasp-2, CD95, DNAM-1, CD83, CD44, CD97, CD3n, DOCK2, CD34, FceRIb, or FasLigand.

In a related aspect, the antagonist is a peptide mimetic of a PL inhibitor sequence peptide. In another related aspect the antagonist is a fusion polypeptide having a PL sequence and transmembrane transporter amino acid sequence (such as HIV tat, Drosophila antenapedia, herpes simplex virus VP22 or anti-DNA CDR 2 and 3).

In another aspect, the invention provides a method of determining whether a test compound is an inhibitor of binding between a PDZ protein and a PL protein by contacting a PDZ domain polypeptide having a sequence from the PDZ protein, and a PL peptide under conditions in which they form a complex, in the presence and in the absence of a test compound, and detecting the formation of the complex in the presence and absence of the test compound, where less complex formation in the presence of the test compound than in the absence of the compound indicates that the test compound is an inhibitor of a PDZ protein-PL protein binding. The PL peptide has a sequence that includes the a C-terminal sequence of a PL protein, such as CD6, CD49E, CD49F, CD138, Clasp-1, Clasp-4, VCAM1, Clasp-2, CD95, DNAM-1, CD83, CD44, CD97, CD3n, DOCK2, CD34, FceRIb, or FasLigand. In some embodiments, the PDZ domain polypeptide is a fusion polypeptide.

In a related aspect, the invention provides a method of determining whether a test compound is an agonist of binding between a PDZ protein and a PL protein by contacting a PDZ domain polypeptide, and a PL peptide under conditions in which they form a complex, in the presence and in the absence of a test compound, and detecting the formation of the complex in the presence and absence of the test compound, where more complex formation in the presence of the test compound than in the absence of the compound indicates that the test compound is an agonist of a PDZ protein-PL protein binding.

The invention further provides an inhibitor of binding of a PDZ protein and a PL protein. In an embodiment, the inhibitor is characterized in that it reduces binding of a peptide selected from the group consisting of a PL peptide selected from the group consisting of CD6, CD49E, CD49F, CD138, Clasp-1, Clasp-4, VCAM1, Clasp-2, CD95, DNAM-1, CD83, CD44, CD97, CD3n, DOCK2, CD34, FceRIb, and FasLigand and a PDZ domain polypeptide. In various embodiments, the inhibitor is a peptide comprising a sequence that is from 3 to about 20 residues of a C-terminal sequence of a PL protein selected from CD6, CD49E, CD49F, CD138, Clasp-1, Clasp-4, VCAM1, Clasp-2, CD95, DNAM-1, CD83, CD44, CD97, CD3n, DOCK2, CD34, FceRIb, and FasLigand; a peptide having a motif X-S-X-A, X-A-D/E-V, X-V/I/L-X*-V, or X-S/T-X-F, (where X is any amino acid and X* is any non-aromatic amino acid); a peptide mimetic, or a small organic molecule. The invention also provides a pharmaceutical composition containing the inhibitor.

The invention also provides a method for treating a disease characterized by leukocyte activation by administering a therapeutically effective amount of an inhibitor of a PL-PDZ interaction. In embodiments, the disease is characterized by an inflammatory or humoral immune response or is an autoimmune disease. The invention further provides a method of reducing inflammation in a subject, by administering an agent that inhibits binding of a PDZ protein and a PL protein, where the PL protein is an adhesion protein, an adaptor protein, or an intracellular protein.

The invention also provides use of an inhibitor of the binding of a PDZ protein and a PL protein to inhibit leukocyte activation or to treat a disease mediated by hematopoietic cells, such as a disease is characterized by an inflammatory or humoral immune response. The invention also provides use of an inhibitor of the binding of a PDZ protein and a PL protein in the preparation of a medicament for treatment of a disease mediated by hematopoietic cells.

The invention also provides a method of modulating a biological function of a hematopoietic cell, comprising introducing into the cell an antagonist that inhibits binding of a PDZ protein and a PL protein in the cell as deduced from Table 2, for example, where the PL protein is DNAM-1 and the PDZ protein is MPP1, MPP2, DLG1, NeDLG, PSD95, LIM, AF6, 41.8 or RGS12, the PL protein is LPAP and the PDZ protein is DLG1 or MINT1, or the PL protein is DNAM-1 and the PDZ protein is PSD95 or MPP2.

The present invention also relates to peptides and peptide analogues that bind PDZ domains in hematopoietic cells. In particular, it relates to fusion peptides and peptide analogues containing a hematopoietic cell surface receptor carboxyl terminal sequence and a transmembrane transporter sequence which facilitates entry of the peptides into a target cell. The invention also relates to methods of using such compositions in inhibiting leukocyte activation as measured by cytokine production, cell proliferation, apoptosis and cytotoxicity.

It is an object of the invention to administer a therapeutically effective amount of the aforementioned fusion peptides or peptide analogues as pharmaceutical compositions to a subject to inhibit undesirable leukocyte-mediated events.

It is also an object of the invention to administer a therapeutically effective amount of the aforementioned fusion peptides or peptide analogues as pharmaceutical compositions to a subject to treat an autoimmune disorder or to prevent transplantation rejection of a solid organ transplant.

In one aspect, the invention provides a method of determining the apparent affinity (Kd) of binding between a PDZ domain and a ligand, by (a) immobilizing a polypeptide comprising the PDZ domain and at least one non-PDZ domain on a surface; (b) contacting the immobilized polypeptide with a plurality of different concentrations of the ligand; (c) determining the amount of binding of the ligand to the immobilized polypeptide at each of the concentrations of ligand; (d) calculating the apparent affinity of the binding from the binding determined in (c). In an embodiment, the polypeptide is immobilized by binding the polypeptide to an immobilized immunoglobulin that binds the non-PDZ domain. In an embodiment, the polypeptide comprising the PDZ domain is a fusion protein, for example a GST-PDZ domain fusion protein.

In one aspect, the invention provides a method of determining the Ki of an inhibitor or suspected inhibitor of binding between a PDZ domain and a ligand, by (a) immobilizing a polypeptide comprising the PDZ domain and a non-PDZ domain on a surface; (b) contacting the immobilized polypeptide with a plurality of different mixtures of the ligand and inhibitor, wherein the different mixtures comprise a fixed amount of ligand, at least a portion of which is detectably labeled, and different concentrations of the inhibitor; (c) determining the amount of ligand bound at the different concentrations of inhibitor; (d) calculating the Ki of the inhibitor from the binding determined in (c). In an embodiment, the polypeptide is immobilized by binding the polypeptide to an immobilized immunoglobulin that binds the non-PDZ domain. In an embodiment, the fixed amount of ligand is between about 0.01 Kd and about 2 Kd.

In another aspect, the invention provides a method of identifying an agent that enhances the binding of a PDZ domain to a ligand, by immobilizing a polypeptide comprising the PDZ domain and a non-PDZ domain on a surface; (b) contacting the immobilized polypeptide with the ligand in the presence of a test agent and determining the amount of ligand bound; and, (c) comparing the amount of ligand bound in the presence of the test agent with the amount of ligand bound by the polypeptide in the absence of the test agent, wherein at least two-fold greater binding in the presence of the test agent compared to the absence of the test agent indicates that the test agent is an agent that enhances the binding of the PDZ domain to the ligand. In an embodiment, the polypeptide is immobilized by binding the polypeptide to an immobilized immunoglobulin that binds the non-PDZ domain.

In another aspect, the invention provides a method of determining the potency ($K_{enhancer}$) of an enhancer of binding between a PDZ domain and a ligand, by (a) immobilizing a polypeptide comprising the PDZ domain and a non-PDZ domain on a surface; (b) contacting the immobilized polypeptide with a plurality of different mixtures of the ligand and enhancer, wherein the different mixtures comprise a fixed amount of ligand, at least a portion of which is detectably labeled, and different concentrations of the enhancer; (c) determining the amount of ligand bound at the different concentrations of enhancer; (d) calculating the potency ($K_{enhancer}$) of the enhancer from the binding determined in (c). In an embodiment, the polypeptide is immobilized by binding the polypeptide to an immobilized immunoglobulin that binds the non-PDZ domain in an embodiment, the fixed amount of ligand is between about 0.01 Kd and about 0.5 Kd.

In another aspect, the invention provides a method of identifying a high specificity interaction between a particular PDZ domain and a ligand known or suspected of binding at least one PDZ domain, by (a) providing a plurality of different immobilized polypeptides, each of said polypeptides comprising a PDZ domain and a non-PDZ domain; (b) determining the affinity of the ligand for each of said polypeptides; (c) comparing the affinity of binding of the ligand to each of said polypeptides. An interaction between the ligand and a particular PDZ domain is deemed to have high specificity when the ligand binds an immobilized polypeptide comprising the particular PDZ domain with at least 2-fold higher affinity than to immobilized polypeptides not comprising the particular PDZ domain (a). In an embodiment, the polypeptide is immobilized by binding the polypeptide to an immobilized immunoglobulin that binds the non-PDZ domain.

In another aspect, the invention provides a method for determining the PDZ-PL inhibition profile of a compound by (a) providing (i) a plurality of different immobilized polypeptides, each of said polypeptides comprising a PDZ domain and a non-PDZ domain; (ii) a plurality of corresponding ligands, wherein each ligand binds at least one PDZ domain in (i); (b) contacting each of said immobilized polypeptides in (i) with a corresponding ligand in (ii) in the presence and absence of a test compound; (c) determining for each polypeptide-ligand pair in (b) whether the test compound inhibits binding between the immobilized polypeptide and the corresponding ligand thereby determining the PDZ-PL inhibition profile of the test compound.

In another aspect, the invention provides an array comprising a plurality of different immobilized polypeptides, each of said polypeptides comprising a PDZ domain and a non-PDZ domain. In an embodiment, the array is situated in a plastic multiwell plate. In an embodiment, the array has at least 12 different polypeptides comprising at least 12 different PDZ domains, for example, at least 12 different PDZ domains are from PDZs expressed in lymphocytes. In an embodiment, the PDZs are selected from those listed in Table 2 or 6.

In an aspect, the invention provides an assay device comprising a plurality of different immobilized PDZ-containing proteins organized in an array. In one embodiment, the device has at least 25 different PDZ-containing proteins.

In a further aspect, the invention provides a method for identifying an interaction between a PDZ domain and a PL by contacting a PL to a plurality of PDZ containing polypeptides and detecting binding of at least one PL to a PDZ. In an embodiment, the contacting occurs on assay device comprising a plurality of different immobilized PDZ-containing proteins organized in an array. In one embodiment, the device has at least 25 different PDZ-containing proteins. In embodiments, an interaction between a PDZ and more than one PL, or between a PL and more than one PDZ, is detected.

In a related aspect, the invention provides method for identifying a modulator of an interaction between a PDZ and a PL by conducting any of the aforementioned assays in the presence and absence of a test compound and detecting a difference in at least one PDZ-PL interaction in the presence and absence of the test compound. In embodiments, the the modulator is an enhancer of the interaction. In other embodiments, the modulator is an inhibitor of the interaction.

4. BRIEF DESCRIPTION OF THE DRAWINGS

Figure 1D:
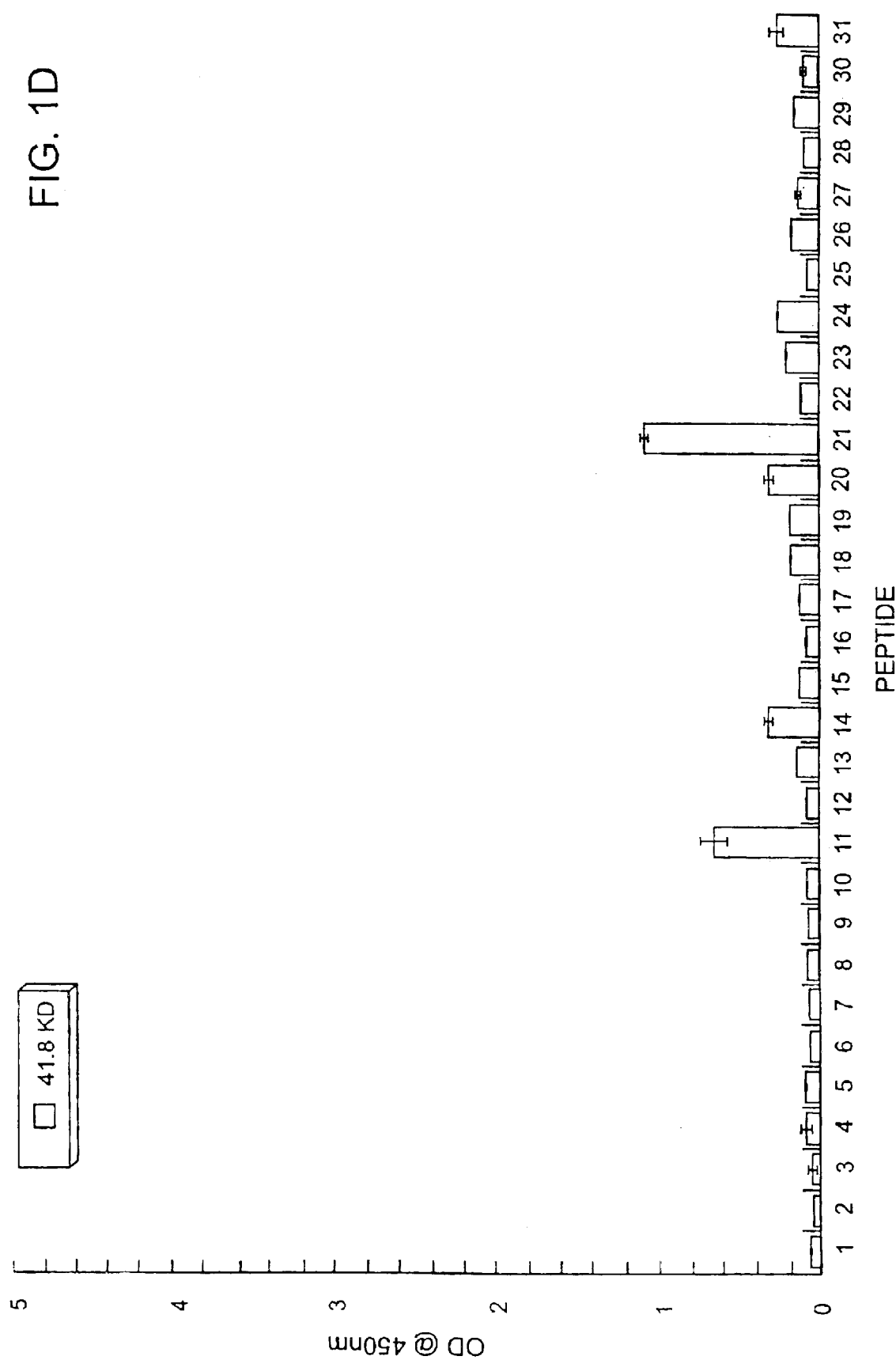

FIGS. 1A–1D show the results of exemplary assays in which the binding of biotinylated peptides having a sequence of the carboxyl-terminus ("c-terminus") of various leukocyte proteins to PDZ domains (i.e., GST-PDZ domain fusion proteins) was determined using the "G" assay described infra. The PDZ domains are: PSD95 (FIG. 1A); NeDLG (FIG. 1B); DLG1 (FIG. 1C); and 41.8 (FIG. 1D). These and other PDZ domain fusion proteins are described infra (e.g., TABLE 2). In the figure, peptides 1–31 refer to the biotinylated PL peptide used in the assay, and are identified in the Key, infra. "Peptide IDs" are defined in TABLE 3.

Key:

| # | Test Protein | Peptide IDs |
|---|---|---|
| 1 | Clasp-2 | AA2L |
| 2 | FceRIb | AA25L |
| 3 | CDW128B | AA29.2 |
| 4 | KV1.3 | AA33L |
| 5 | Neurexin | AA38L |
| 6 | DOCK2 | AA40L |
| 7 | CC CKR-1R | AA41L |
| 8 | CC CKR-2 | AA42L |
| 9 | CC CKR-4 | AA44L |
| 10 | BLR-1 | AA45L |
| 11 | CD49E | AA11L |
| 12 | CD97 | AA14L |
| 13 | VCAM1 | AA17L |
| 14 | CD138 | AA18L |
| 15 | DNAM-1 | AA22L |
| 16 | CDW128A | AA29.1L |
| 17 | CC CKR-3 | AA43L |
| 18 | Clasp-1 | AA1L-R |
| 19 | CD46 (Form 1) | AA10L |
| 20 | CD95 | AA13L |
| 21 | CDW125 | AA28L |
| 22 | CD83 | AA47L |
| 23 | CD62E | AA48L |
| 24 | CD3n | AA4L |
| 25 | Clasp-4 | AA3L-V |
| 26 | CD44 | AA9L |
| 27 | CD166 | AA20L |
| 28 | CD62E | AA48L |
| 29 | CD5 | AA49L |
| 30 | CD148 | AA55L |
| 31 | DOCK2 | AA40L |

Figure 2A:
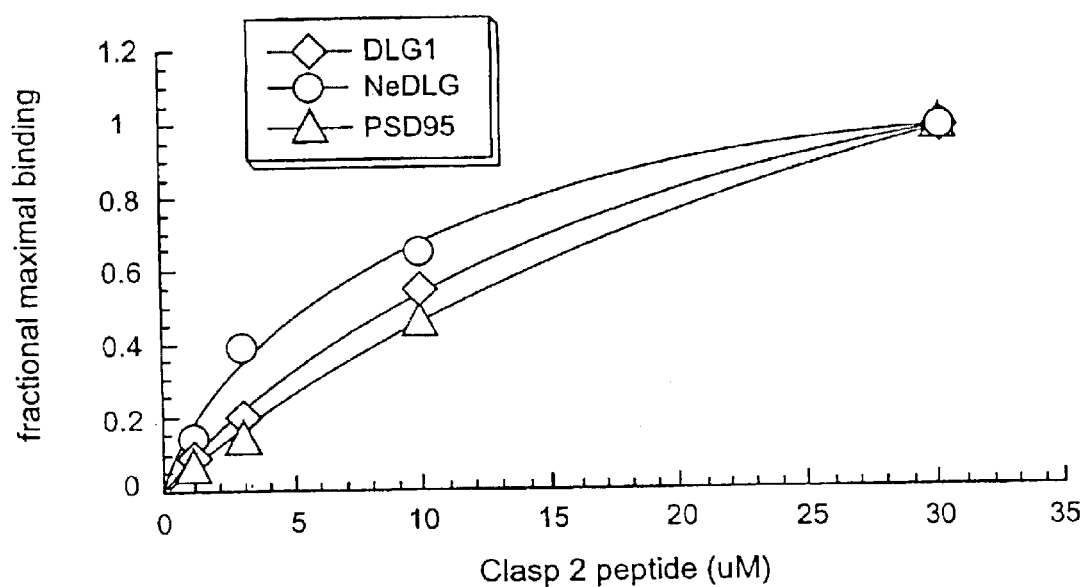
Figure 2B:
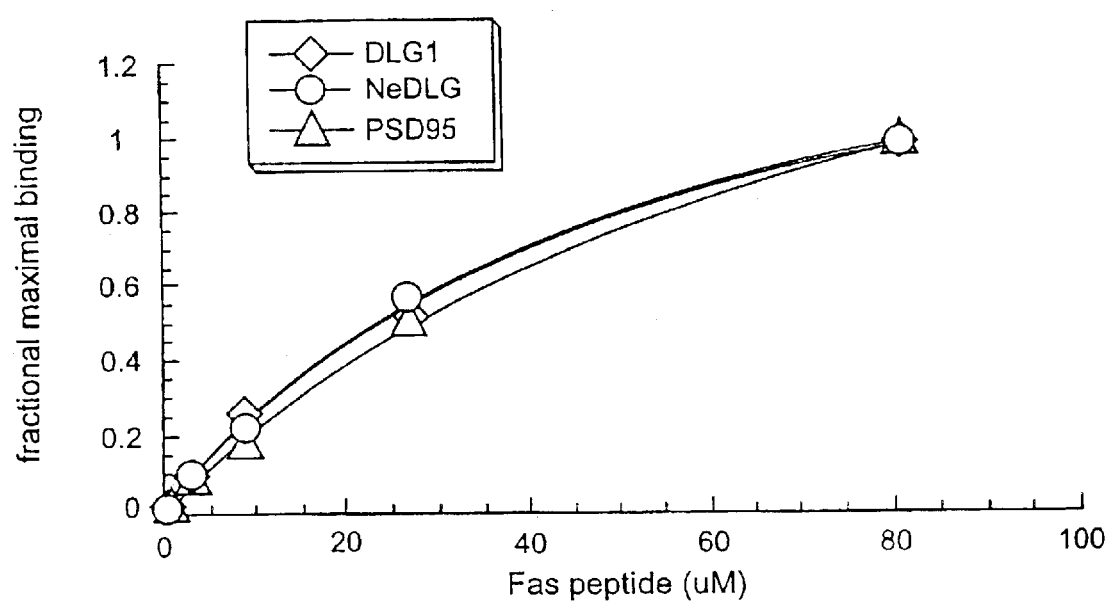

FIGS. 2A and 2B show the Apparent Affinity Determination for PDZ-Ligand Interactions. Varying concentrations of biotinylated CLASP-2 (FIG. 2A; TABLE 4) or Fas (FIG. 2B; TABLE 4) C-terminal peptides were reacted with immobilized (plate bound) GST polypeptide or GST-PDZ fusion proteins (GST-DLG1, GST-NeDLG, and GST-PSD95). The binding to GST alone (<0.2 OD units) was subtracted from the binding to the fusion proteins to obtain the signal at each peptide concentration. This signal was then normalized by dividing the signal at each peptide concentration by the maximum signal observed for each peptide-PDZ pair (i.e. the signal obtained at 30 uM Clasp 2 peptide or 100 uM Fas peptide; 0.4–1.0 OD units for Clasp 2 and 1.2–2.0 OD units for Fas). The normalized signals were then plotted and fit to a saturation binding curve, yielding an apparent affinity of 21 uM for DLG1-Clasp 2 interaction, 7.5 uM for NeDLG-Clasp 2 interaction, 45 uM for PSD95-Clasp 2 interaction, 54 uM for DLG1-Fas interaction, 54 uM for NeDLG-Fas interaction, and 85 uM for PSD95-Fas interaction. Data are means of duplicate data points, with standard errors between duplicate data points<20%.

Figure 3A:
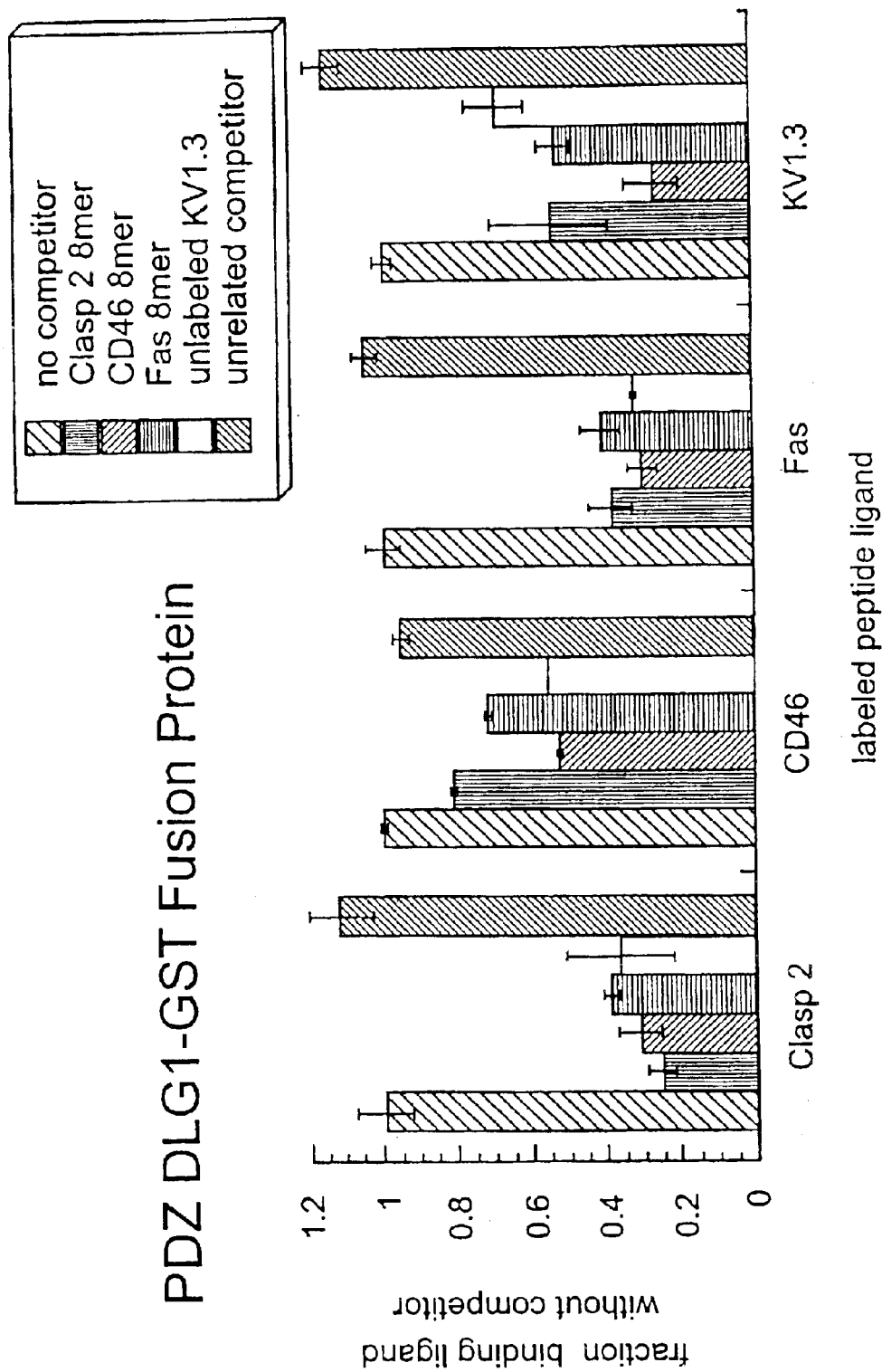
Figure 3B:
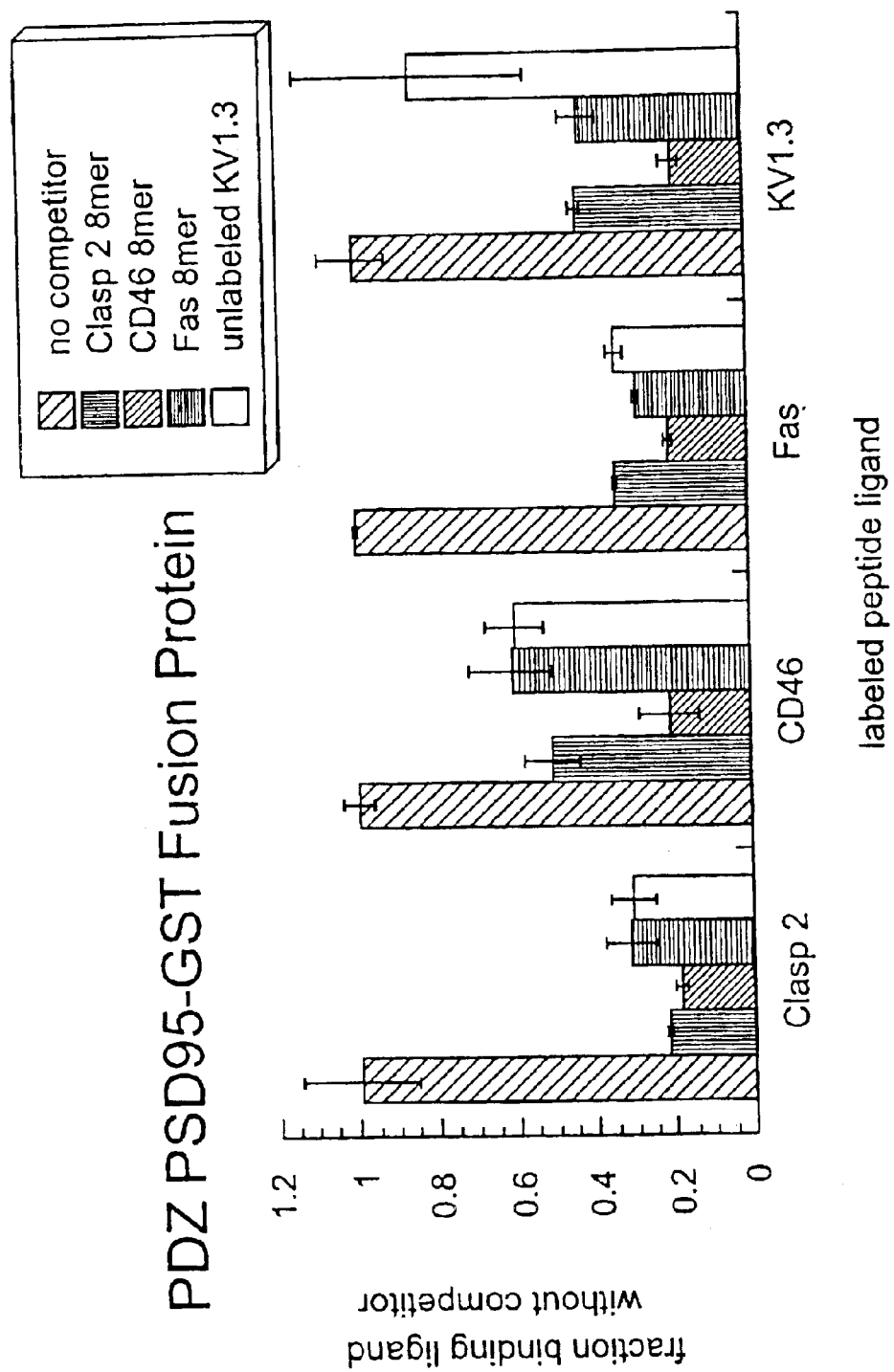
Figure 3C:
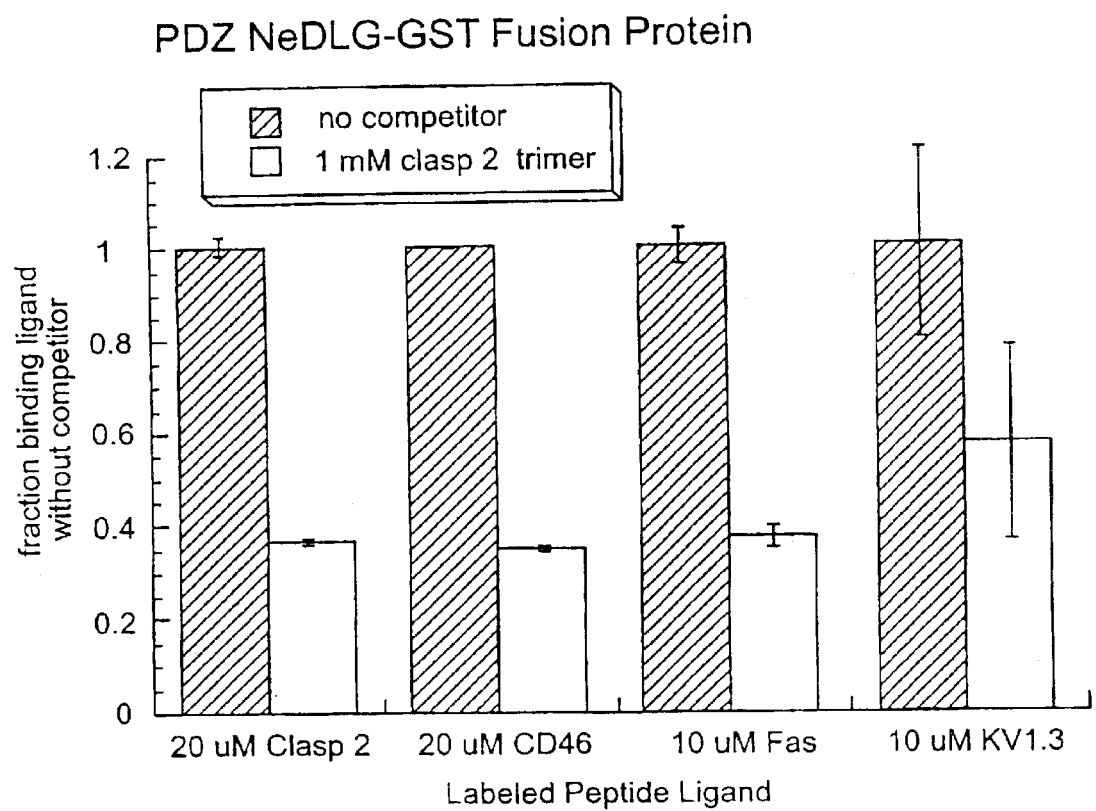
Figure 3D:
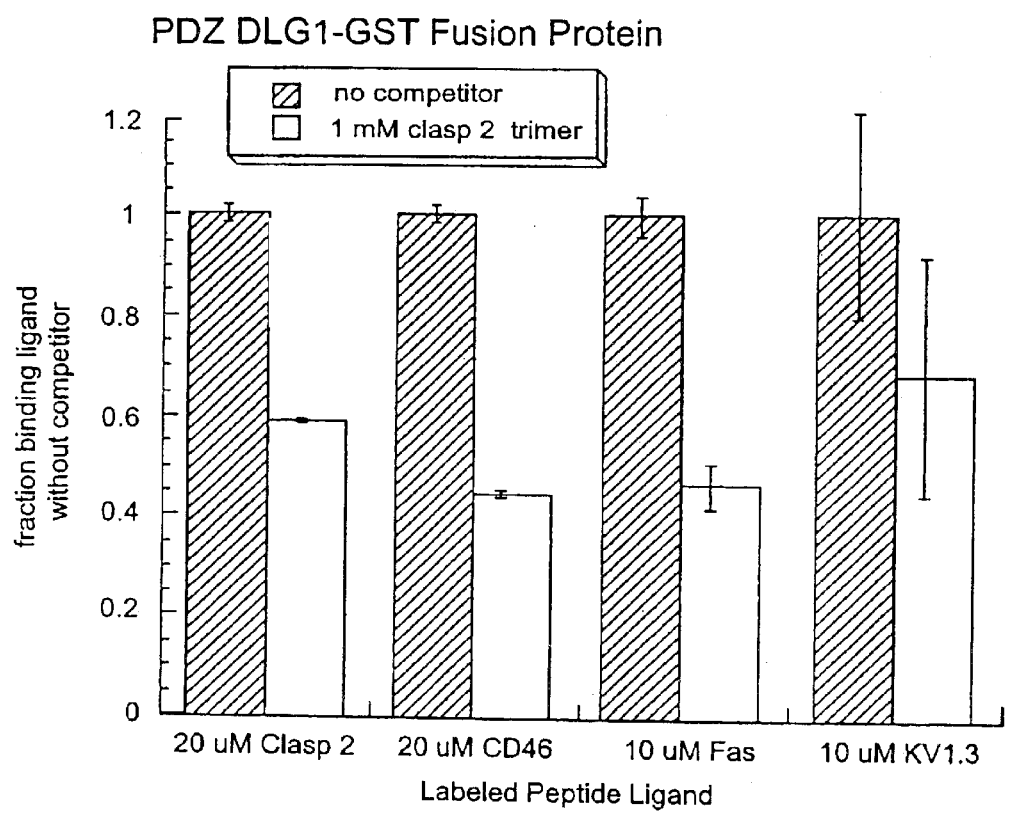

FIGS. 3A–3F show inhibition of PDZ-PL peptide interactions. A fixed concentration of biotinylated C-terminal peptide having a sequence based on the C-terminal sequence of a cell surface receptor protein (Clasp 2, CD46, Fas, and KV1.3; see TABLE 4) was bound to immobilized GST polypeptide or the GST-fusion protein indicated at the top left of each frame, in the presence or absence of the competitor peptides indicated in the legend of each frame and the level of inhibition determined. FIG. 3A-DLG1; FIG. 3B-PSD95; FIG. 3C NeDLG; FIG. 3D-DLG1, FIG. 3E, PSD95; FIG. F–41.8. In FIGS. 3A–B the competitor peptides are present at 100 uM; in FIGS. 3C–F the competitor is present at the indicated concentration.

Figure 4A:
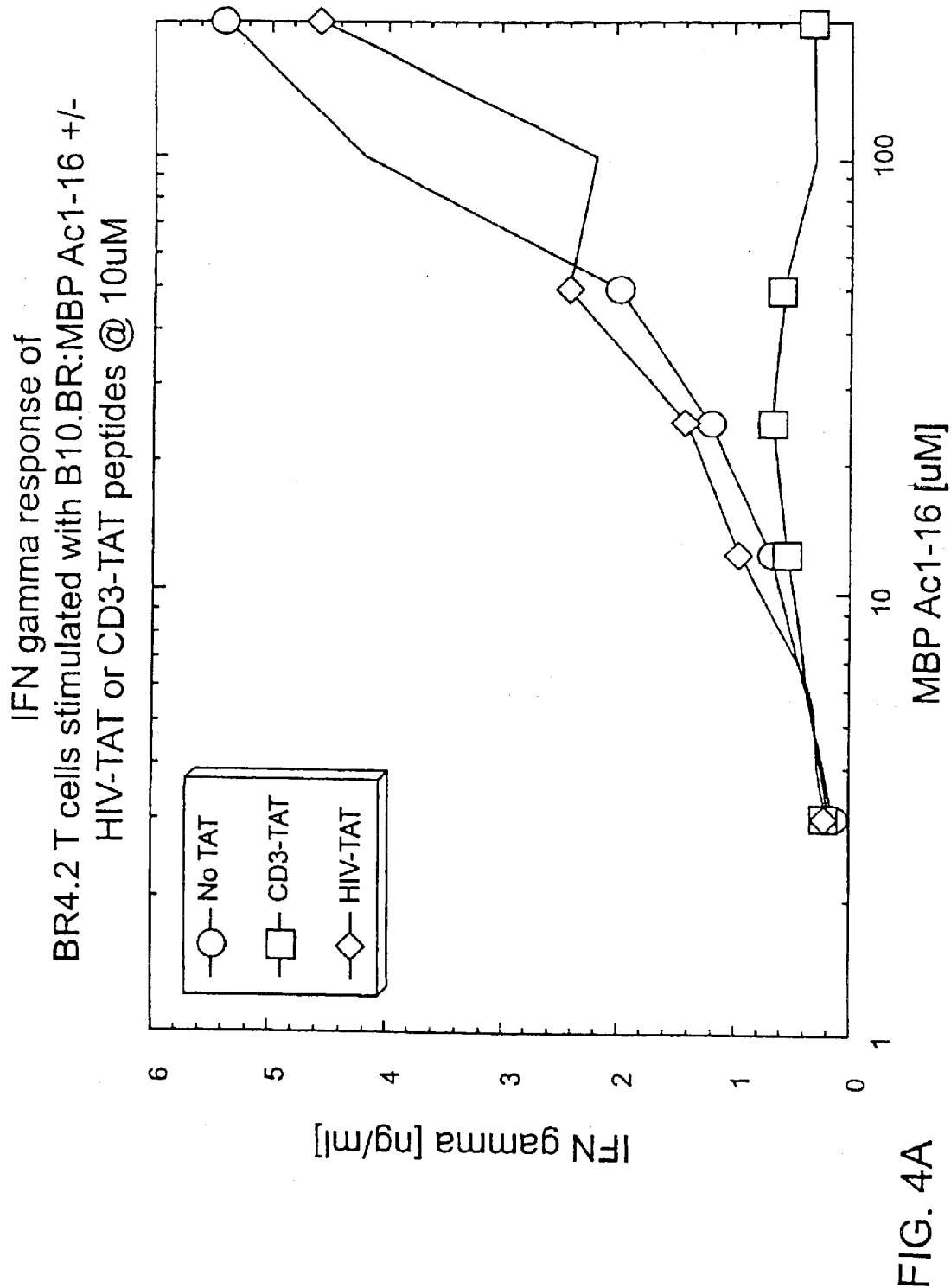
Figure 4B:
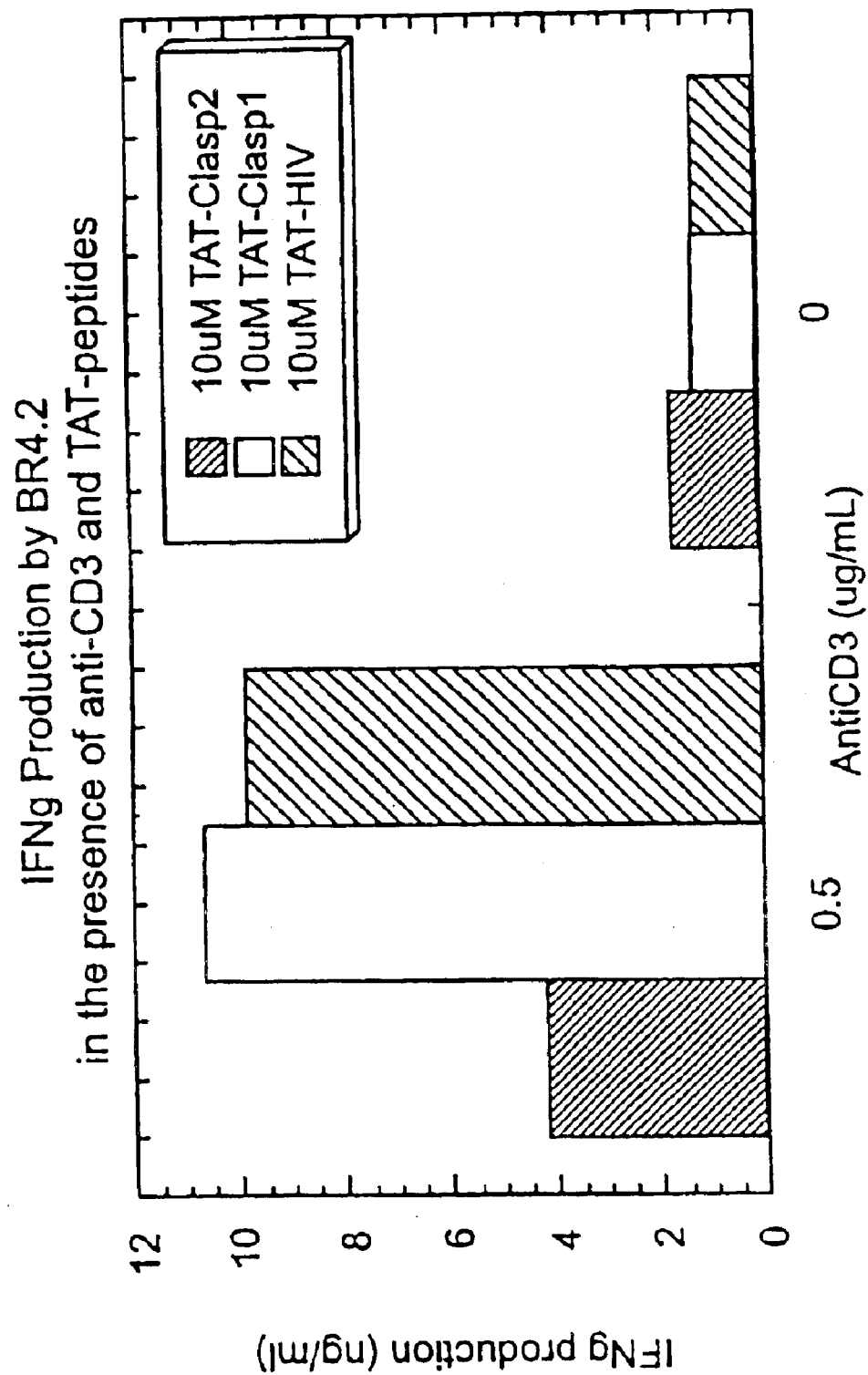

FIGS. 4A and 4B shows the results of introduction of a Tat-CD3 fusion peptide on T cell activation. Antigen-specific T cell activation was measured by cytokine production. Fusion peptides containing tat and a T cell surface molecule carboxyl terminus inhibited γ-interferon (IFN) production by a T cell line in response to myelin basic protein (MBP) stimulation. The level of inhibition was determined by first subtracting the binding of the labeled peptide to GST alone from the binding to the fusion protein and dividing by the signal in the absence of competitor peptide.

| Tables | |
|---|---|
| Table 1 | Amino Acid Classification |
| Table 2 | Protein-Ligand Pairs |
| Table 3 | PDZ Domains |
| Table 3A | Note on Table 3 |
| Table 4 | PL Peptides |
| Table 5A&B | Exemplary PL Motifs |
| Table 6 | PDZ Domain-Containing Genes Expressed in T Cells and B Cells |

5. DEFINITIONS 5.1 A "fusion protein" or "fusion polypeptide" as used herein refers to a composite protein, i.e., a single contiguous amino acid sequence, made up of two (or more) distinct, heterologous polypeptides which are not normally fused together in a single amino acid sequence. Thus, a fusion protein can include a single amino acid sequence that contains two entirely distinct amino acid sequences or two similar or identical polypeptide sequences, provided that these sequences are not normally found together in the same configuration in a single amino acid sequence found in nature. Fusion proteins can generally be prepared using either recombinant nucleic acid methods, i.e., as a result of transcription and translation of a recombinant gene fusion product, which fusion comprises a segment encoding a polypeptide of the invention and a segment encoding a heterologous protein, or by chemical synthesis methods well known in the art.

5.2 A "fusion protein construct" as used herein is a polynucleotide encoding a fusion protein.

5.3 As used herein, the term "PDZ domain" refers to protein sequence (i.e., modular protein domain) of approximately 90 amino acids, characterized by homology to the brain synaptic protein PSD-95, the Drosophila septate junction protein Discs-Large (DLG), and the epithelial tight junction protein ZO1 (ZO1). PDZ domains are also known as Discs-Large homology repeats ("DHRs") and GLGF (SEQ ID NO:29) repeats). PDZ domains generally appear to maintain a core consensus sequence (Doyle, D. A., 1996, Cell 85: 1067–1076).

PDZ domains are found in diverse membrane-associated proteins including members of the MAGUK family of guanylate kinase homologs, several protein phosphatases and kinases, neuronal nitric oxide synthase, and several dystrophin-associated proteins, collectively known as syntrophins.

Exemplary PDZ domain-containing proteins and PDZ domain sequences are shown in TABLE 3. The term "PDZ domain" also encompasses variants (e.g., naturally occuring variants) of the sequences of TABLE 3 (e.g., polymorphic variants, variants with conservative substitutions, and the like). Typically, PDZ domains are substantially identical to those shown in TABLE 3, e.g., at least about 70%, at least about 80%, or at least about 90% amino acid residue identity when compared and aligned for maximum correspondence.

5.4 As used herein, the term "PDZ protein" refers to a naturally occurring protein containing a PDZ domain, e.g., a human protein. Exemplary PDZ proteins include CASK, MPP1, DLG1, PSD95, NeDLG, TAX33, SYN1a, TAX43, LDP, LIM, LIMK1, LIMK2, MPP2, NOS1, AF6, PTN-4, prIL16, 41.8 kD, KIAA0559, RGS12, KIAA0316, DVL1, TAX40, TIAM1, MINT1, KIAA0303, CBP, MINT3, TAX2, KIAA0561. Exemplary PDZ proteins are listed in TABLE 2 and TABLE 3.

5.5 As used herein, the term "PDZ-domain polypeptide" refers to a polypeptide containing a PDZ domain, such as a fusion protein including a PDZ domain sequence, a naturally occurring PDZ protein, or an isolated PDZ domain peptide.

5.6 As used herein, the term "PL protein" or "PDZ Ligand protein" refers to a naturally occurring protein that forms a molecular complex with a PDZ-domain, or to a protein whose carboxy-terminus, when expressed separately from the full length protein (e.g., as a peptide fragment of 4–25 residues, e.g., 16 residues), forms such a molecular complex. The molecular complex can be observed in vitro using the "A assay" or "G assay" described infra, or in vivo. Exemplary PL proteins listed in TABLE 2 are demonstrated to bind specific PDZ proteins. This definition is not intended to include anti-PDZ antibodies and the like.

5.7 As used herein, a "PL sequence" refers to the amino acid sequence of the C-terminus of a PL protein (e.g., the C-terminal 2, 3, 4, 5, 6, 7, 8, 9, 10, 12, 14, 16, 20 or 25 residues) ("C-terminal PL sequence") or to an internal sequence known to bind a PDZ domain ("internal PL sequence).

5.8 As used herein, a "PL peptide" is a peptide of having a sequence from, or based on, the sequence of the C-terminus of a PL protein. Exemplary PL peptides (biotinylated) are listed in TABLE 4.

5.9 As used herein, a "PL fusion protein" is a fusion protein that has a PL sequence as one domain, typically as the C-terminal domain of the fusion protein. An exemplary PL fusion protein is a tat-PL sequence fusion.

5.10 As used herein, the term "PL inhibitor peptide sequence" refers to PL peptide an amino acid sequence that (in the form of a peptide or PL fusion protein) inhibits the interaction between a PDZ domain polypeptide and a PL peptide (e.g., in an A assay or a G assay).

5.11 As used herein, a "PDZ-domain encoding sequence" means a segment of a polynucleotide encoding a PDZ domain. In various embodiments, the polynucleotide is DNA, RNA, single stranded or double stranded.

5.12 As used herein, the terms "antagonist" and "inhibitor," when used in the context of modulating a binding interaction (such as the binding of a PDZ domain sequence to a PL sequence), are used interchangeably and refer to an agent that reduces the binding of the, e.g., PL sequence (e.g., PL peptide) and the, e.g., PDZ domain sequence (e.g., PDZ protein, PDZ domain peptide).

5.13 As used herein, the terms "agonist" and "enhancer," when used in the context of modulating a binding interaction (such as the binding of a PDZ domain sequence to a PL sequence), are used interchangeably and refer to an agent that increases the binding of the, e.g., PL sequence (e.g., PL peptide) and the, e.g., PDZ domain sequence (e.g., PDZ protein, PDZ domain peptide).

5.14 As used herein, the terms "peptide mimetic," "peptidomimetic," and "peptide analog" are used interchangeably and refer to a synthetic chemical compound which has substantially the same structural and/or functional characteristics of an PL inhibitory or PL binding peptide of the invention. The mimetic can be either entirely composed of synthetic, non-natural analogues of amino acids, or, is a chimeric molecule of partly natural peptide amino acids and partly non-natural analogs of amino acids. The mimetic can also incorporate any amount of natural amino acid conservative substitutions as long as such substitutions also do not substantially alter the mimetic's structure and/or inhibitory or binding activity. As with polypeptides of the invention which are conservative variants, routine experimentation will determine whether a mimetic is within the scope of the invention, i.e., that its structure and/or function is not substantially altered. Thus, a mimetic composition is within the scope of the invention if it is capable of binding to a PDZ domain and/or inhibiting a PL-PDZ interaction.

Polypeptide mimetic compositions can contain any combination of nonnatural structural components, which are typically from three structural groups: a) residue linkage groups other than the natural amide bond ("peptide bond") linkages; b) non-natural residues in place of naturally occurring amino acid residues; or c) residues which induce secondary structural mimicry, i.e., to induce or stabilize a secondary structure, e.g., a beta turn, gamma turn, beta sheet, alpha helix conformation, and the like.

A polypeptide can be characterized as a mimetic when all or some of its residues are joined by chemical means other than natural peptide bonds. Individual peptidomimetic residues can be joined by peptide bonds, other chemical bonds or coupling means, such as, e.g., glutaraldehyde, N-hydroxysuccinimide esters, bifunctional maleimides, N,N-dicyclohexylcarbodiimide (DCC) or N,N-diisopropylcarbodiimide (DIC). Linking groups that can be an alternative to the traditional amide bond ("peptide bond") linkages include, e.g., ketomethylene (e.g., —C(=O)—$CH_2$— for —C(=O)—NH—), aminomethylene ($CH_2$—NH), ethylene, olefin (CH=CH), ether ($CH_2$—O), thioether ($CH_2$—S), tetrazole ($CN_4$—), thiazole, retroamide, thioamide, or ester (see, e.g., Spatola (1983) in Chemistry and Biochemistry of Amino Acids, Peptides and Proteins, Vol. 7, pp 267–357, A Peptide Backbone Modifications, Marcell Dekker, NY).

A polypeptide can also be characterized as a mimetic by containing all or some non-natural residues in place of naturally occurring amino acid residues. Nonnatural residues are well described in the scientific and patent literature; a few exemplary nonnatural compositions useful as mimetics of natural amino acid residues and guidelines are described below.

Mimetics of aromatic amino acids can be generated by replacing by, e.g., D- or L-naphylalanine; D- or L-phenylglycine; D- or L-2 thieneylalanine; D- or L-1, -2,3-, or 4-pyreneylalanine; D- or L-3 thieneylalanine; D- or L-(2-pyridinyl)-alanine; D- or L-(3-pyridinyl)-alanine; D- or L-(2-pyrazinyl)-alanine; D- or L-(4-isopropyl)-phenylglycine; D-(trifluoromethyl)-phenylglycine; D-(trifluoromethyl)-phenylalanine; D-p-fluorophenylalanine; D- or L-p-biphenylphenylalanine; K- or L-p-methoxybiphenylphenylalanine; D- or L-2-indole (alkyl)alanines; and, D- or L-alkylainines, where alkyl can be substituted or unsubstituted methyl, ethyl, propyl, hexyl, butyl, pentyl, isopropyl, iso-butyl, sec-isotyl, iso-pentyl, or a non-acidic amino acids. Aromatic rings of a nonnatural amino acid include, e.g., thiazolyl, thiophenyl, pyrazolyl, benzimidazolyl, naphthyl, furanyl, pyrrolyl, and pyridyl aromatic rings.

Mimetics of acidic amino acids can be generated by substitution by, e.g., non-carboxylate amino acids while maintaining a negative charge; (phosphono)alanine; sulfated threonine. Carboxyl side groups (e.g., aspartyl or glutamyl) can also be selectively modified by reaction with carbodiimides (R=N—C—N—R=) such as, e.g., 1-cyclohexyl-3 (2-morpholinyl-(4-ethyl) carbodiimide or 1-ethyl-3(4-azonia-4,4-dimetholpentyl) carbodiimide. Aspartyl or glutamyl can also be converted to asparaginyl and glutaminyl residues by reaction with ammonium ions.

Mimetics of basic amino acids can be generated by substitution with, e.g., (in addition to lysine and arginine) the amino acids ornithine, citrulline, or (guanidino)-acetic acid, or (guanidino)alkyl-acetic acid, where alkyl is defined above. Nitrile derivative (e.g., containing the CN-moiety in place of COOH) can be substituted for asparagine or glutamine. Asparaginyl and glutaminyl residues can be deaminated to the corresponding aspartyl or glutamyl residues.

Arginine residue mimetics can be generated by reacting arginyl with, e.g., one or more conventional reagents, including, e.g., phenylglyoxal, 2,3-butanedione, 1,2-cyclohexanedione, or ninhydrin, preferably under alkaline conditions.

Tyrosine residue mimetics can be generated by reacting tyrosyl with, e.g., aromatic diazonium compounds or tetranitromethane. N-acetylimidizol and tetranitromethane can be used to form O-acetyl tyrosyl species and 3-nitro derivatives, respectively.

Cysteine residue mimetics can be generated by reacting cysteinyl residues with, e.g., alpha-haloacetates such as 2-chloroacetic acid or chloroacetamide and corresponding amines; to give carboxymethyl or carboxyamidomethyl derivatives. Cysteine residue mimetics can also be generated by reacting cysteinyl residues with, e.g., bromo-trifluoroacetone, alpha-bromo-beta-(5-imidozoyl) propionic acid; chloroacetyl phosphate, N-alkylmaleimides, 3-nitro-2-pyridyl disulfide; methyl 2-pyridyl disulfide; p-chloromercuribenzoate; 2-chloromercuri-4 nitrophenol; or, chloro-7-nitrobenzo-oxa-1,3-diazole.

Lysine mimetics can be generated (and amino terminal residues can be altered) by reacting lysinyl with, e.g., succinic or other carboxylic acid anhydrides. Lysine and other alpha-amino-containing residue mimetics can also be generated by reaction with imidoesters, such as methyl picolinimidate, pyridoxal phosphate, pyridoxal, chloroborohydride, trinitrobenzenesulfonic acid, O-methylisourea, 2,4, pentanedione, and transamidase-catalyzed reactions with glyoxylate.

Mimetics of methionine can be generated by reaction with, e.g., methionine sulfoxide. Mimetics of proline include, e.g., pipecolic acid, thiazolidine carboxylic acid, 3- or 4-hydroxy proline, dehydroproline, 3- or 4-methylproline, or 3,3,-dimethylproline. Histidine residue mimetics can be generated by reacting histidyl with, e.g., diethylprocarbonate or para-bromophenacyl bromide.

Other mimetics include, e.g., those generated by hydroxylation of proline and lysine; phosphorylation of the hydroxyl groups of seryl or threonyl residues; methylation of the alpha-amino groups of lysine, arginine and histidine; acetylation of the N-terminal amine; methylation of main chain amide residues or substitution with N-methyl amino acids; or amidation of C-terminal carboxyl groups.

A component of a natural polypeptide (e.g., a PL polypeptide or PDZ polypetide) can also be replaced by an amino acid (or peptidomimetic residue) of the opposite chirality. Thus, any amino acid naturally occurring in the L-configuration (which can also be referred to as the R or S, depending upon the structure of the chemical entity) can be replaced with the amino acid of the same chemical structural type or a peptidomimetic, but of the opposite chirality, generally referred to as the D-amino acid, but which can additionally be referred to as the R- or S-form.

The mimetics of the invention can also include compositions that contain a structural mimetic residue, particularly a residue that induces or mimics secondary structures, such as a beta turn, beta sheet, alpha helix structures, gamma turns, and the like. For example, substitution of natural amino acid residues with D-amino acids; N-alpha-methyl amino acids; C-alpha-methyl amino acids; or dehydroamino acids within a peptide can induce or stabilize beta turns, gamma turns, beta sheets or alpha helix conformations. Beta turn mimetic structures have been described, e.g., by Nagai (1985) Tet. Lett. 26:647–650; Feigl (1986) J. Amer. Chem. Soc. 108:181–182; Kahn (1988) J. Amer. Chem. Soc. 110:1638–1639; Kemp (1988) Tet. Lett. 29:5057–5060; Kahn (1988) J. Molec. Recognition 1:75–79. Beta sheet mimetic structures have been described, e.g., by Smith (1992) J. Amer. Chem. Soc. 114:10672–10674. For example, a type VI beta turn induced by a cis amide surrogate, 1,5-disubstituted tetrazol, is described by Beusen (1995) Biopolymers 36:181–200. Incorporation of achiral omega-amino acid residues to generate polymethylene units as a substitution for amide bonds is described by Banerjee (1996) Biopolymers 39:769–777. Secondary structures of polypeptides can be analyzed by, e.g., high-field 1H NMR or 2D NMR spectroscopy, see, e.g., Higgins (1997) J. Pept. Res. 50:421–435. See also, Hruby (1997) Biopolymers 43:219–266, Balaji, et al., U.S. Pat. No. 5,612,895.

5.15 As used herein, "peptide variants" and "conservative amino acid substitutions" refer to peptides that differ from a reference peptide (e.g., a peptide having the sequence of the carboxy-terminus of a specified PL protein) by substitution of an amino acid residue having similar properties (based on size, polarity, hydrophobicity, and the like). Thus, insofar as the compounds that are encompassed within the scope of the invention are partially defined in terms of amino acid residues of designated classes, the amino acids may be generally categorized into three main classes: hydrophilic amino acids, hydrophobic amino acids and cysteine-like amino acids, depending primarily on the characteristics of the amino acid side chain. These main classes may be further divided into subclasses. Hydrophilic amino acids include amino acids having acidic, basic or polar side chains and hydrophobic amino acids include amino acids having aromatic or apolar side chains. Apolar amino acids may be further subdivided to include, among others, aliphatic amino acids. The definitions of the classes of amino acids as used herein are as follows:

"Hydrophobic Amino Acid" refers to an amino acid having a side chain that is uncharged at physiological pH and that is repelled by aqueous solution. Examples of genetically encoded hydrophobic amino acids include Ile, Leu and Val. Examples of non-genetically encoded hydrophobic amino acids include t-BuA.

"Aromatic Amino Acid" refers to a hydrophobic amino acid having a side chain containing at least one ring having a conjugated π-electron system (aromatic group). The aromatic group may be further substituted with groups such as alkyl, alkenyl, alkynyl, hydroxyl, sulfanyl, nitro and amino groups, as well as others. Examples of genetically encoded aromatic amino acids include Phe, Tyr and Trp. Commonly encountered non-genetically encoded aromatic amino acids include phenylglycine, 2-naphthylalanine, β-2-thienylalanine, 1,2,3,4-tetrahydroisoquinoline-3-carboxylic acid, 4-chloro-phenylalanine, 2-fluorophenylalanine, 3-fluorophenylalanine and 4-fluorophenylalanine.

"Apolar Amino Acid" refers to a hydrophobic amino acid having a side chain that is generally uncharged at physiological pH and that is not polar. Examples of genetically encoded apolar amino acids include Gly, Pro and Met. Examples of non-encoded apolar amino acids include Cha.

"Aliphatic Amino Acid" refers to an apolar amino acid having a saturated or unsaturated straight chain, branched or cyclic hydrocarbon side chain. Examples of genetically encoded aliphatic amino acids include Ala, Leu, Val and Ile. Examples of non-encoded aliphatic amino acids include Nle.

"Hydrophilic Amino Acid" refers to an amino acid having a side chain that is attracted by aqueous solution. Examples of genetically encoded hydrophilic amino acids include Ser and Lys. Examples of non-encoded hydrophilic amino acids include Cit and hCys.

"Acidic Amino Acid" refers to a hydrophilic amino acid having a side chain pK value of less than 7. Acidic amino acids typically have negatively charged side chains at physiological pH due to loss of a hydrogen ion. Examples of genetically encoded acidic amino acids include Asp and Glu.

"Basic Amino Acid" refers to a hydrophilic amino acid having a side chain pK value of greater than 7. Basic amino acids typically have positively charged side chains at physiological pH due to association with hydronium ion. Examples of genetically encoded basic amino acids include Arg, Lys and His. Examples of non-genetically encoded basic amino acids include the non-cyclic amino acids ornithine, 2,3-diaminopropionic acid, 2,4-diaminobutyric acid and homoarginine.

"Polar Amino Acid" refers to a hydrophilic amino acid having a side chain that is uncharged at physiological pH, but which has a bond in which the pair of electrons shared in common by two atoms is held more closely by one of the atoms. Examples of genetically encoded polar amino acids include Asx and Glx. Examples of non-genetically encoded polar amino acids include citrulline, N-acetyl lysine and methionine sulfoxide.

"Cysteine-Like Amino Acid" refers to an amino acid having a side chain capable of forming a covalent linkage with a side chain of another amino acid residue, such as a disulfide linkage. Typically, cysteine-like amino acids generally have a side chain containing at least one thiol (SH) group. Examples of genetically encoded cysteine-like amino acids include Cys. Examples of non-genetically encoded cysteine-like amino acids include homocysteine and penicillamine.

As will be appreciated by those having skill in the art, the above classification are not absolute—several amino acids exhibit more than one characteristic property, and can therefore be included in more than one category. For example, tyrosine has both an aromatic ring and a polar hydroxyl group. Thus, tyrosine has dual properties and can be included in both the aromatic and polar categories. Similarly, in addition to being able to form disulfide linkages, cysteine also has apolar character. Thus, while not strictly classified as a hydrophobic or apolar amino acid, in many instances cysteine can be used to confer hydrophobicity to a peptide.

Certain commonly encountered amino acids which are not genetically encoded of which the peptides and peptide analogues of the invention may be composed include, but are not limited to, β-alanine (b-Ala) and other omega-amino acids such as 3-aminopropionic acid (Dap), 2,3-diaminopropionic acid (Dpr), 4-aminobutyric acid and so forth; α-aminoisobutyric acid (Aib); ε-aminohexanoic acid (Aha); δ-aminovaleric acid (Ava); N-methylglycine or sarcosine (MeGly); ornithine (Orn); citrulline (Cit); t-butylalanine (t-BuA); t-butylglycine (t-BuG); N-methylisoleucine (MeIle); phenylglycine (Phg); cyclohexylalanine (Cha); norleucine (Nle); 2-naphthylalanine (2-Nal); 4-chlorophenylalanine (Phe(4-Cl)); 2-fluorophenylalanine (Phe(2-F)); 3-fluorophenylalanine (Phe(3-F)); 4-fluorophenylalanine (Phe(4-F)); penicillamine (Pen); 1,2,3,4-tetrahydroisoquinoline-3-carboxylic acid (Tic); β-2-thienylalanine (Thi); methionine sulfoxide (MSO); homoarginine (hArg); N-acetyl lysine (AcLys); 2,3-diaminobutyric acid (Dab); 2,3-diaminobutyric acid (Dbu); p-aminophenylalanine (Phe(pNH$_2$)); N-methyl valine (MeVal); homocysteine (hCys) and homoserine (hSer). These amino acids also fall conveniently into the categories defined above.

The classifications of the above-described genetically encoded and non-encoded amino acids are summarized in TABLE 1, below. It is to be understood that TABLE 1 is for illustrative purposes only and does not purport to be an exhaustive list of amino acid residues which may comprise the peptides and peptide analogues described herein. Other amino acid residues which are useful for making the peptides and peptide analogues described herein can be found, e.g., in Fasman, 1989, CRC Practical Handbook of Biochemistry and Molecular Biology, CRC Press, Inc., and the references cited therein. Amino acids not specifically mentioned herein can be conveniently classified into the above-described categories on the basis of known behavior and/or their characteristic chemical and/or physical properties as compared with amino acids specifically identified.

TABLE 1

| Classification | Genetically Encoded | Genetically Non-Encoded |
| --- | --- | --- |
| Hydrophobic | | |
| Aromatic | F, Y, W | Phg, Nal, Thi, Tic, Phe(4-Cl), Phe(2-F), Phe(3-F), Phe(4-F), Pyridyl Ala, Benzothienyl Ala |
| Apolar | M, G, P | |
| Aliphatic | A, V, L, I | t-BuA, t-BuG, MeIle, Nle, MeVal, Cha, bAla, MeGly, Aib |
| Hydrophilic | | |
| Acidic | D, E | |
| Basic | H, K, R | Dpr, Orn, hArg, Phe(p-$NH_2$), DBU, $A_2$BU |
| Polar | Q, N, S, T, Y | Cit, AcLys, MSO, hSer |
| Cysteine-Like | C | Pen, hCys, p-methyl Cys |

5.16 As used herein, a "detectable label" has the ordinary meaning in the art and refers to an atom (e.g., radionuclide), molecule (e.g., fluorescein), or complex, that is or can be used to detect (e.g., due to a physical or chemical property), indicate the presence of a molecule or to enable binding of another molecule to which it is covalently bound or otherwise associated. The term "label" also refers to covalently bound or otherwise associated molecules (e.g., a biomolecule such as an enzyme) that act on a substrate to produce a detectable atom, molecule or complex. Detectable labels suitable for use in the present invention include any composition detectable by spectroscopic, photochemical, biochemical, immunochemical, electrical, optical or chemical means. Labels useful in the present invention include biotin for staining with labeled streptavidin conjugate, magnetic beads (e.g., Dynabeads™), fluorescent dyes (e.g., fluorescein, Texas red, rhodamine, green fluorescent protein, enhanced green fluorescent protein, and the like), radiolabels (e.g., 3H, 125I, 35S, 14C, or 32P), enzymes (e.g., hydrolases, particularly phosphatases such as alkaline phosphatase, esterases and glycosidases, or oxidoreductases, particularly peroxidases such as horse radish peroxidase, and others commonly used in ELISAs), substrates, cofactors, inhibitors, chemiluminescent groups, chromogenic agents, and calorimetric labels such as colloidal gold or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241. Means of detecting such labels are well known to those of skill in the art. Thus, for example, radiolabels and chemiluminescent labels may be detected using photographic film or scintillation counters, fluorescent markers may be detected using a photodetector to detect emitted light (e.g., as in fluorescence-activated cell sorting). Enzymatic labels are typically detected by providing the enzyme with a substrate and detecting the reaction product produced by the action of the enzyme on the substrate, and calorimetric labels are detected by simply visualizing the colored label. Thus, a label is any composition detectable by spectroscopic, photochemical, biochemical, immunochemical, electrical, optical or chemical means. The label may be coupled directly or indirectly to the desired component of the assay according to methods well known in the art. Non-radioactive labels are often attached by indirect means. Generally, a ligand molecule (e.g., biotin) is covalently bound to the molecule. The ligand then binds to an anti-ligand (e.g., streptavidin) molecule which is either inherently detectable or covalently bound to a signal generating system, such as a detectable enzyme, a fluorescent compound, or a chemiluminescent compound. A number of ligands and anti-ligands can be used. Where a ligand has a natural anti-ligand, for example, biotin, thyroxine, and cortisol, it can be used in conjunction with the labeled, naturally occurring anti-ligands. Alternatively, any haptenic or antigenic compound can be used in combination with an antibody. The molecules can also be conjugated directly to signal generating compounds, e.g., by conjugation with an enzyme or fluorophore. Means of detecting labels are well known to those of skill in the art. Thus, for example, where the label is a radioactive label, means for detection include a scintillation counter, photographic film as in autoradiography, or storage phosphor imaging. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Also, simple colorimetric labels may be detected by observing the color associated with the label. It will be appreciated that when pairs of fluorophores are used in an assay, it is often preferred that they have distinct emission patterns (wavelengths) so that they can be easily distinguished.

5.17 As used herein, the term "substantially identical" in the context of comparing amino acid sequences, means that the sequences have at least about 70%, at least about 80%, or at least about 90% amino acid residue identity when compared and aligned for maximum correspondence. An algorithm that is suitable for determining percent sequence identity and sequence similarity is the FASTA algorithm, which is described in *Pearson, W. R. & Lipman, D. J., 1988, Proc. Natl. Acad. Sci. U.S.A.* 85: 2444. See also *W. R. Pearson, 1996, Methods Enzymol.* 266: 227–258. Preferred parameters used in a FASTA alignment of DNA sequences to calculate percent identity are optimized, BL50 Matrix 15:–5, k-tuple=2; joining penalty=40, optimization=28; gap penalty –12, gap length penalty=–2; and width=16.

5.18 As used herein, "hematopoietic cells" include leukocytes including lymphocytes (T cells, B cells and NK cells), monocytes, and granulocytes (i.e., neutrophils, basophils and eosinophils), macrophages, dendritic cells, megakaryocytes, reticulocytes, erythrocytes, and $CD34^+$ stem cells.

5.19 As used herein, the terms "test compound" or "test agent" are used interchangably and refer to a candidate agent that may have enhancer/agonist, or inhibitor/antagonist activity, e.g., inhibiting or enhancing an interaction such as PDZ-PL binding. The candidate agents or test compounds may be any of a large variety of compounds, both naturally occurring and synthetic, organic and inorganic, and including polymers (e.g., oligopeptides, polypeptides, oligonucleotides, and polynucleotides), small molecules, antibodies (as broadly defined herein), sugars, fatty acids, nucleotides and nucleotide analogs, analogs of naturally occurring structures (e.g., peptide mimetics, nucleic acid analogs, and the like), and numerous other compounds. In certain embodiment, test agents are prepared from diversity libraries, such as random or combinatorial peptide or non-peptide libraries. Many libraries are known in the art that can be used, e.g., chemically synthesized libraries, recombinant (e.g., phage display libraries), and in vitro translation-based libraries. Examples of chemically synthesized libraries are described in Fodor et al., 1991, *Science* 251:767–773;

Houghten et al., 1991, *Nature* 354:84–86; Lam et al., 1991, *Nature* 354:82–84; Medynski, 1994, *Bio/Technology* 12:709–710; Gallop et al., 1994, *J. Medicinal Chemistry* 37(9):1233–1251; Ohlmeyer et al., 1993, *Proc. Natl. Acad. Sci. USA* 90:10922–10926; Erb et al., 1994, *Proc. Natl. Acad. Sci. USA* 91:11422–11426; Houghten et al., 1992, *Biotechniques* 13:412; Jayawickreme et al., 1994, *Proc. Natl. Acad. Sci. USA* 91:1614–1618; Salmon et al., 1993, *Proc. Natl. Acad. Sci. USA* 90:11708–11712; PCT Publication No. WO 93/20242; and Brenner and Lerner, 1992, *Proc. Natl. Acad. Sci. USA* 89:5381–5383. Examples of phage display libraries are described in Scott and Smith, 1990, *Science* 249:386–390; Devlin et al., 1990, *Science,* 249:404–406; Christian, R. B., et al., 1992, *J. Mol. Biol.* 227:711–718); Lenstra, 1992, *J. Immunol. Meth.* 152:149–157; Kay et al., 1993, *Gene* 128:59–65; and PCT Publication No. WO 94/18318 dated Aug. 18, 1994. In vitro translation-based libraries include but are not limited to those described in PCT Publication No. WO 91/05058 dated Apr. 18, 1991; and Mattheakis et al., 1994, *Proc. Natl. Acad. Sci. USA* 91:9022–9026. By way of examples of nonpeptide libraries, a benzodiazepine library (see e.g., Bunin et al., 1994, *Proc. Natl. Acad. Sci. USA* 91:4708–4712) can be adapted for use. Peptoid libraries (Simon et al., 1992, *Proc. Natl. Acad. Sci. USA* 89:9367–9371) can also be used. Another example of a library that can be used, in which the amide functionalities in peptides have been permethylated to generate a chemically transformed combinatorial library, is described by Ostresh et al. (1994, *Proc. Natl. Acad. Sci. USA* 91:11138–11142).

5.20 The term "specific binding" refers to binding between two molecules, for example, a ligand and a receptor, characterized by the ability of a molecule (ligand) to associate with another specific molecule (receptor) even in the presence of many other diverse molecules, i.e., to show preferential binding of one molecule for another in a heterogeneous mixture of molecules. Specific binding of a ligand to a receptor is also evidenced by reduced binding of a detectably labeled ligand to the receptor in the presence of excess unlabeled ligand (i.e., a binding competition assay).

5.21 As used herein, a "plurality" of PDZ proteins (or corresponding PDZ domains or PDZ fusion polypeptides) has its usual meaning. In some embodiments, the plurality is at least 5, and often at least 25, at least 40 or at least 60 different PDZ proteins. In some embodiments, the plurality is selected from the list of PDZ polypeptides listed in Table 2 or Table 6. In some embodiments, the plurality of different PDZ proteins are from (i.e., expressed in) a particular specified tissue or a particular class or type of cell. In some embodiments, the plurality of different PDZ proteins represents a substantial fraction (e.g., typically at least 50%, more often at least 80%) of all of the PDZ proteins known to be, or suspected of being, expressed in the tissue or cell(s), e.g., all of the PDZ proteins known to be present in lymphocytes or hematopoetic cells. In some embodiments, the plurality is at least 50%, usually at least 80%, at least 90% or all of the PDZ proteins disclosed herein as being expressed in hematopoietic cells (see Tables 2 and 6). In an embodiment, the plurality includes at least 1, often at least 2, sometimes at least 5 or at least 10 and sometimes all of the following PDZ proteins: BAI I associated prot., Connector enhancer, DLG5 (pdlg), DVL3, GTPase, Guanin-exchange factor 1, PDZ domain containing prot., KIAA147, KIAA0300, KIAA0380, KIAA0440, KIAA0545, KIAA0807, KIAA0858, KIAA0902, novel serine protease, PDZK1, PICK8, PTN-3, RPIP8, serine protease, 26s subunit p27, hSYNTENIN, TAX1-IP, TAX2-like protein, wwp3, X11 prot. beta, ZO1. When referring to PL ligands or corresponding PL proteins (e.g., corresponding to those listed in Table 2, Table 4, Table 5, or elsewhere herein) a "plurality" may refer to at least 5, at least 10, and often at least 25 PLs such as those specifcally listed herein, or to the classes and percentages set forth supra for PDZ domains.

6. DETAILED DESCRIPTION OF THE INVENTION

The present inventors have discovered that interactions between PDZ proteins and PL proteins play an important and extensive role in the biological function of hematopoietic cells and other cells involved in the immune response. Although PDZ-PL interactions were known in the nervous system (i.e., in neurons), their universal importance in hematopoietic cell function, especially in function of T cells and B cells, and their fundamental role in modulation of the immune response has not been recognized. In particular, the present inventors have surprisingly discovered that cell adhesion molecules that mediate cell—cell interaction in the hematopoietic system are PDZ-binding proteins (PL proteins) and bind to PDZ proteins. The inventors have identified numerous interactions between PDZ proteins and PL proteins present in immune system cells, and the invention provides reagents and methods for affecting biological function in the immune system by inhibiting these interactions. As used herein, the term "biological function" in the context of a cell, refers to a detectable biological activity normally carried out by the cell, e.g., a phenotypic change such as proliferation, cell activation (e.g., T cell activation, B cell activation, T-B cell conjugate formation), cytokine release, degranulation, tyrosine phosphorylation, ion (e.g., calcium) flux, metabolic activity, apoptosis, changes in gene expression, maintenance of cell structure, cell migration, adherance to a substrate, signal transduction, cell—cell interactions, and others described herein or known in the art.

In one aspect, the present invention relates to peptides, peptide analogues or mimetics, pharmaceutical compositions, and methods of using such compositions to regulate the biological activities of hematopoietic cells, e.g. T cells and B cells, or other cells (e.g., endothelial cells) that necessary for immune function. The invention further relates to methods of using the compositions to modulate hematopoietic cell activation and immune function, as well as assays for such inhibitors.

TABLE 2 summarizes interaction profiles for an extensive analysis of protein interactions in T cells and B cells. PDZ proteins, the vast majority of which were not previously known to be expressed in immune system cells, are listed in the top row of TABLE 2. The first column of the table lists PL proteins. Positions in the matrix denoted by the letter "A" or "G" indicate that an interaction between the PDZ protein and the PL has been detected in novel binding assays (described in detail in, e.g., Section 6.2, infra). A blank cell indicates that no interaction was detected using the assays of the invention. An asterisk (*) denotes a PL-PDZ interaction previously reported in the scientific literature.

TABLE 2

PDZ-LIGAND/PDZ INTERACTION SUMMARY

| PDZ LIGAND | CODE | SEQ | SEQ ID NO: | CASK | MPP1 | DLG1 | PSD95 | NeDLG | TAX33 | SYN1a | TAX 43 | LDP | LIM | LIMK1 | LIMK2 | MPP2 | NOS1 | AF6 | PTN-4 | prIL16 | 41.8 | K559 | RGS12 | K316 |
|---|---|---|---|---|---|---|---|---|---|---|---|---|---|---|---|---|---|---|---|---|---|---|---|---|
| CD6 | AA6L | ISAA | 14 | | | | | | | | | | | | | | | | | | A | | | |
| CD49E (alpha-4) | AA11L | TSDA | 24 | | | | | | | | | | | | | | | | | | A/G | | | |
| CD49F (Aform, alpha6) | AA12L | TSDA | 24 | | | | | | | | | | | | | | | | | | A/G | | | |
| CD166 (CD6L) | AA20L | KTEA | 64 | | | | | | | | | | | | | | | | | | | | | |
| CD148 | AA55L | KTIA | 278 | | | | | | | | | | | | | | | | | | | | | |
| CC CKR-2 | AA42L | KEGA | 283 | | | | | | | | | | | | | | | | | | | | | |
| CD138 (syndecan) | AA18L | EFYA | 89 | * | | | | | | | | | | | | | | | | | A/G | | | |
| CD148 (DEP-1) | AA19L | GYIA | 119 | | | | | | | | | | | | | | | | | | | | | |
| CD98 (2F4) | AA15L | PYAA | 54 | | | | | | | | | | | | | G | | | | | | | | |
| CLASP-1 | AA1L | SAEV | 284 | | | G | A | G | | | | | | | | | | | | | | | | |
| CLASP-4 | AA3L-V | YAEV | 228 | | | A | A | A | | | | A | | | | | | A | | | A | | | |
| NMDA | AA34.2L | ESDV | 263 | | A | A/G | A/G | A/G | | G | A | | | A | | G | | | A/G | | A/G | A/G | | |
| VCAM1 | AA17L | KSKV | 163 | | A | A | | A | | | | A | | | | | | | | | A | | | |
| CLASP-2 | AA2L | SSVV | 223 | | | A/G | A/G | A/G | | | | | | | | | | | | | A | | | |
| CD95 (Apo-1/Fas) | AA13L | QSLV | 44 | | | A/G | A/G | A/G | | | | | | | | | | | | | A/G | | | |
| KV1.3 | AA33L | FTDV | 238 | | | A/G* | A/G* | A/G | | | | | | A | | | | | | | A | A | | |
| DNAM-1 | AA22L | KTRV | 74 | | A | A | A/G | A | | | | | A | | | G | | A | | | A | A | | |
| CD83 | AA47L | TELV | 248 | | | A | A | A | | | | | | | | | | | | | | | | |
| CD44 (long form) | AA9L | KIGV | 104 | | G | | | | | | | | | | | | | | | G | | | | |
| Neurexin | AA38L | EYYV | 268 | G* | A* | A/G | A/G | G | | A | A | | | A | | | | A | A | | A | A | | |
| CD97 (CD55L) | AA14L | ESGI | 49 | | | A | | | | | | | | | | | | | | | A | | | |
| Glycophorin C | AA37L | EYFI | 273 | | * | G | G | G | | | | | | | | A | | A | | | A | | | |
| CDW128A (IL8RA) | AA29.1L | SSNL | 69 | | | A | | A | | | | | | | | | | | | | | | | |
| CD3n | AA4L | SSQL | 4 | | | A | A | | | | | | | | | | | | | | A/G | | | |
| LPAP | AA30L | VTAL | 84 | | | A | | | | | | | | | | | | | | | | | | |
| CD46 (form 1) | AA10L | FTSL | 109 | | | A/G | A/G | G | | | | | | | | | | | | | | | | |
| CDW128B (IL8RB) | AA29.2L | STTL | 233 | | | A/G | A | A/G | | | | | | | | | | | | | | A | | * |
| DOCK2 | AA40L | STDL | 243 | | | A | A/G | G | | G | | | | | | | | | | | | | | |
| CD34 | AA7L | DTEL | 149 | | | A | A | G | | | | | | | | | | | | | | | | |
| CD5 | AA49L | AQRL | 285 | | | | | | | | | | | | | | | | | | | | | |
| CC CKR-4 | AA44L | HDAL | 286 | | | | | | | | | | | | | | | | | | | | | |
| FceRlb | AA25L | PIDL | 129 | | | | | | | | | | | | | | | | | | | | | |
| FasLigand | AA23L-M | LYKL | 79 | | | | | | | | | | | | | | | | | | | | | |
| CD62E | AA48L | SYIL | 168 | | | | | | | | | | | | | | | | | | | | | |
| CC CKR-1R | AA41L | SAGF | 287 | | | | | | | | | | | | | | | | | | | | | |
| CDW125 (IL5R) | AA28L | DSVF | 94 | | | | | | | | | | | | | | | | | | | | | |
| BLR-1 | AA45L | LTTF | 253 | | | | | | | | | | | | | | | | | | | | | |
| CC CKR-3 | AA43L | SIVF | 288 | | | | | | | | | | | | | | | | | | | | | |

TABLE 2-continued

PDZ-LIGAND/PDZ INTERACTION SUMMARY

| PDZ LIGAND | CODE | SEQ | SEQ ID NO: | | | | | | | | | |
|---|---|---|---|---|---|---|---|---|---|---|---|---|
| CC CKR-4 | AA44L | HDAL | 286 | | | | | | | | | |
| FceRIb | AA25L | PIDL | 129 | | | | | | | | | |
| FasLigand | AA23L-M | LYKL | 79 | | | | | | | | | |
| CD62E | AA48L | SYIL | 168 | | | | | | | | | |
| CC CKR-1R | AA41L | SAGF | 287 | | | | | | | | | |
| CDW125 (IL5R) | AA28L | DSVF | 94 | | | | | | G | | G | |
| BLR-1 | AA45L | LTTF | 253 | | | | | | | | | |
| CC CKR-3 | AA43L | SIVF | 288 | | | | | | | | | |

| PDZ LIGAND | CODE | SEQ | SEQ ID NO: | DVL1 | TAX 40 | TIAM1 | MINT1 | K303 | CBP | MINT3 | TAX 2 | K561 |
|---|---|---|---|---|---|---|---|---|---|---|---|---|
| CD6 | AA6L | ISAA | 14 | | | | | | | | | |
| CD49E (alpha-4) | AA11L | TSDA | 24 | | | | | | | | | |
| CD49F (Aform, alpha6) | AA12L | TSDA | 24 | | | | | | | | | |
| CD166 (CD6L) | AA20L | KTEA | 64 | | | | | | | | | |
| CD148 | AA55L | KTIA | 278 | | | | | | | | | |
| CC CKR-2 | AA42L | KEGA | 283 | | | | | | | | | |
| CD138 (syndecan) | AA18L | EFYA | 89 | | | A | | | | | | |
| CD148 (DEP-1) | AA19L | GYIA | 119 | | | | | | | | | |
| CD98 (2F4) | AA15L | PYAA | 54 | | | | | | | | | |
| CLASP-1 | AA1L | SAEV | 284 | | | | | | | | | |
| CLASP-4 | AA3L-V | YAEV | 228 | | | | A | | | | | |
| NMDA | AA34.2L | ESDV | 263 | A | | | A/G | A | | | A | G |
| VCAM1 | AA17L | KSKV | 163 | | A | | | A | | | | |
| CLASP-2 | AA2L | SSVV | 223 | | | | | | | | | |
| CD95 (Apo-1/Fas) | AA13L | QSLV | 44 | | | | | | | | | |
| KV1.3 | AA33L | FTDV | 238 | A | | | G | | | | | |
| DNAM-1 | AA22L | KTRV | 74 | | | | | | | | | |
| CD83 | AA47L | TELV | 248 | | | | | | | | | |
| CD44 (long form) | AA9L | KIGV | 104 | | | | G | | | | | |
| Neurexin | AA38L | EYYV | 268 | A | A | A | A/G | | | | | |
| CD97 (CD55L) | AA14L | ESGI | 49 | | | | | | | | | |
| Glycophorin C | AA37L | EYFI | 273 | | | | A | | | | | |
| CDW128A (IL8RA) | AA29.1L | SSNL | 69 | | | | | | | | | |
| CD3n | AA4L | SSQL | 4 | | | | A/G | | | | | |
| LPAP | AA30L | VTAL | 84 | | | | G | | | | | |
| CD46 (form 1) | AA10L | FTSL | 109 | | | | | | | | | |
| CDW128B (IL8RB) | AA29.2L | STTL | 233 | | | | | | | | | |
| DOCK2 | AA40L | STDL | 243 | | | | | | | | | G |
| CD34 | AA7L | DTEL | 149 | | | | | | | | | |
| CD5 | AA49L | AQRL | 285 | | | | | | | | | |
| CC CKR-4 | AA44L | HDAL | 286 | | | | | | | | | |
| FceRIb | AA25L | PIDL | 129 | | | | A | | | | | |
| FasLigand | AA23L-M | LYKL | 79 | | | | | | | | | G |
| CD62E | AA48L | SYIL | 168 | | | | | | | | | |
| CC CKR-1R | AA41L | SAGF | 287 | | | | | | | | | |
| CDW125 (IL5R) | AA28L | DSVF | 94 | | | | | | | | | |
| BLR-1 | AA45L | LTTF | 253 | | | | G | | | | | |
| CC CKR-3 | AA43L | SIVF | 288 | | | | | | | | | |

*Interactions described in the scientific literature

As discussed in detail herein, the PDZ proteins listed in TABLE 2 are naturally occurring proteins containing a PDZ domain. The present invention is particularly directed to the detection and modulation of interactions between PDZ proteins and PL proteins in hematopoietic cells. Exemplary PL proteins are listed in TABLE 2. Notably, as discussed infra, many of these PL proteins have not previously been recognized as such in any cell system. A variety of PL protein classes are known, and the PL proteins described herein can be characterized as (1) "PL adhesion proteins" (2) "PL ion channel proteins" (3) "PL adaptor proteins" (4) "PL intracellular proteins" and (5) "PL cytokine receptor proteins."

As used herein, an adhesion protein is a cell surface protein involved in cell—cell interaction by direct contact with cell surface molecules (e.g., transmembrane proteins or surface proteins) on a different cell. Thus, when a cell expressing a PL adhesion protein contacts an appropriate other cell, the PL adhesion protein localizes at the interface of the two cells and directly contacts a cell surface molecule on the second cell. A cell—cell interface is a region where the plasma membranes of two different cells are in close (generally<10 nm, often about 1 nrn) apposition. Typically, direct molecular contact means interaction of molecules at distances where Van der Walls forces are significant, generally less than about 1 nm. Exemplary PL adhesion proteins include CD6; CD49E (alpha-4); CD49F (a form, alpha6); CD138 (syndecan); CLASP-1; CLASP-4; VCAM1; CLASP-2; DNAM-1; CD83; CD44 (long form); CD97; (CD55L); CD3n; DOCK2; CD34; and FceRIb. Thus, in one embodiment, the PL proteins of the invention are PL adhesion proteins. In an embodiment, the invention provides methods and reagents, as detailed herein, for inhibiting interactions between PL adhesion proteins and PDZ proteins to modulate an immune response. In an embodiment, the inhibition or modulation occurs in a hematopoietic cell. In a related embodiment, the inhibition or modulation occurs in an endothelial cell. In a related embodiment, the inhibition or modulation occurs in an endothelial cell. In a related embodiment, the inhibition or modulation occurs in an epithelial cells, keratinocytes, hepatocytes, cardiac myocytes.

As used herein, an ion channel protein means a transmembrane protein that itself catalyzes the passage of an ion from aqueous solution on one side of a lipid bilayer membrane to aqueous solution on the other side (e.g., by forming a small pore in the membrane). One exemplary PL ion channel proteins is Kv1.3. Thus, in one embodiment, the PL proteins of the invention are PL ion channel proteins. In an embodiment, the invention provides methods and reagents, as detailed herein, for inhibiting interactions between PL ion channel proteins and PDZ proteins to modulate an immune response. In an embodiment, the inhibition or modulation occurs in a hematopoeitic cell. In a related embodiment, the inhibition or modulation occurs in an endothelial cell.

As used herein, an intercellular (i.e., cytosolic) protein has the normal meaning in the art and refers to a protein that is not membrane bound, e.g., has no transmembrane domain. Thus, in one embodiment, the PL proteins of the invention are PL intercellular proteins. Exemplary PL intercellular proteins include Glycophorin C and LPAP. In an embodiment, the invention provides methods and reagents, as detailed herein, for inhibiting interactions between PL cytoplasmic proteins and PDZ proteins to modulate an immune response. In an embodiment, the inhibition or modulation occurs in a hematopoeitic cell. In a related embodiment, the inhibition or modulation occurs in an endothelial cell.

As used herein a cytokine receptor has the normal meaning in the art and refers to a membrane protein with an extracellular domain that specifically binds a cytokine. Exemplary PL cytokine receptor proteins include CDW125 (IL5R), CDW128A (IL8RA), and BRL-1. Thus, in one embodiment, the PL proteins of the invention are PL cytokine proteins. In an embodiment, the invention provides methods and reagents, as detailed herein, for inhibiting interactions between PL cytokine proteins and PDZ proteins to modulate an immune response. In an embodiment, the inhibition or modulation occurs in a hematopoeitic cell. In a related embodiment, the inhibition or modulation occurs in an endothelial cell.

As used herein, an adaptor protein means a molecule (e.g., protein) that contributes to the formation of a multimolecular complex by binding two or more other biomolecuics. The binding of the two or more other molecules by the adaptor molecule/protein generally involves direct molecular contact between the adaptor protein and each of the two or more other moiccules. One exemplary PL adaptor protein is LPAP. Thus, in one embodiment, the PL proteins of the invention are PL adaptor proteins. In an embodiment, the invention provides methods and reagents, as detailed herein, for inhibiting interactions between PL adaptor proteins and PDZ proteins to modulate an immune response. In an embodiment, the inhibition or modulation occurs in a hematopoeitic cell. In a related embodiment, the inhibition or modulation occurs in an endothelial cell.

In various embodiments, the PL proteins of the invention are characterized by specific C-terminal (i.e., PL domain) amino acid sequences or amino acid motifs, as described elsewhere in this disclosure.

In various embodiments of the invention, the PL proteins of the invention bind a PDZ protein expressed in T lymphocytes, B lymphocytes, or both T and B lymphocytes. In an embodiment, the PL protein binds a PDZ protein expressed in endothelial cells. In various embodiments, the PL proteins and/or the PDZ protein to which it binds are not expressed in the nervous system (e.g., neurons).

In various embodiments of the invention, the PL protein of the invention binds only one PDZ protein listed in TABLE 2. In other embodiment, the PL protein binds 1 to 3, 3 to 5, or more than 5 different PDZ proteins listed in TABLE 2.

In various embodiments of the invention, the PL protein is expressed or up-regulated upon cell activation (e.g., in activated B lymphocytes, T lymphocytes) or upon entry into mitosis (e.g., up-regulation in rapidly proliferating cell populations).

In various embodiments of the invention, the PL protein is (i) a protein that mediates immune cell (e.g., hematopoietic cell) activation or migration, (ii) a protein that does not mediate apoptosis in a cell type (iii) a protein that is other than a G-protein coupled seven transmembrane helix receptor, (iv) a protein that is G-protein coupled seven transmembrane helix receptor but not a cytokine receptor or (v) a protein that is not a G-protein coupled seven transmembrane helix receptor and is a cytokine receptor.

6.1 Detection of PDZ Domain-Containing Proteins Expressed in Hematopoietic Cells As noted supra, the present inventors surprisingly discovered that numerous PDZ proteins are expressed in immune system cells, and play a fundamental biological role in modulation of the immune response. PDZ proteins DLG1 and TIAM-1 have been previously described to be in T cells. The present inventors discovered, using a BLAST search of the Human EST database and the experiments described infra, that several additional PDZ proteins are present in hematopoietic cells including MPP1, P-DLG, VELI-1, PSD95, syntenin in T cells and CASK, DLG1, DLG2, ZIP KINASE, syntrophin 2, P-dig, PSD95, and syntenin in B cells.

To determine the full extent of PDZ proteins' involvement in hematopoietic function, the inventors embarked on a systematic investigation of PDZ proteins in T and B cells. A comprehensive list of PDZ domain-containing proteins was retrieved from the Sanger Centre database (Pfam) searching for the keyword, PDZ. The corresponding cDNA sequences were retrieved from GenBank using the NCBI "entrez" database (hereinafter, "GenBank PDZ protein cDNA sequences"). The DNA portion encoding PDZ domains was identified by alignment of cDNA and protein sequence using CLUSTALW. Based on the DNA/protein alignment information, primers encompassing the PDZ domains were designed. The expression of certain PDZ-containing proteins in immune cells was detected by polymerase chain reaction ("PCR") amplification of cDNAs obtained by reverse transcription ("RT") of immune cell derived RNA (i.e., "RT-PCR"). PCR, RT-PCR and other methods for analysis and manipulation of nucleic acids are well known and are described generally in Sambrook et al., (1989) MOLECULAR CLONING: A LABORATORY MANUAL, 2ND ED., VOLS. 1–3, Cold Spring Harbor Laboratory hereinafter, "Sambrook"); and Ausubel et al., CURRENT PROTOCOLS IN MOLECULAR BIOLOGY, Greene Publishing and Wiley-Interscience, New York (1997), as supplemented through January 1999 (hereinafter "Ausubel").

In the experiments summarized in TABLE 2, T-cells (Jurkat E6 cell line) and B-cells (MV 4–11 cell line) were tested for expression of specific PDZ domain containing genes by RT-PCR. RNA was prepared using the "trizol" RNA preparation kit (GIBCO-BRL; Cat. # 15596-018) according to the manufacturer's recommendations. Briefly, 1–5×10$^7$ lymphoblasts were harvested by centrifugation at 200× g for 10 minutes at 20° C. Cells were resuspended in 100 μl PBS buffer and 1 ml of TRIZOL reagent was added per 5×10$^6$ cells. The cells resuspension was mixed and after 5 minutes incubation at room temperature (RT), chloroform was added at 0.2 ml per ml TRIZOL. The resuspension was vigorously shaken and incubated for 3 more minutes at RT. Samples were then centrifuged at 12000× g for 15 minutes at 4° C., the aqueous phase was recovered and RNA was precipitated with 2-propanol. The precipitate was collected by centrifugation at 12000× g for 15 minutes at 4° C., washed with 75% ethanol, finally recollected by another spin at 12000× g for 15 minutes at 4° C., air dried and resuspended in an appropriate volume of DEPC treated water.

RNA concentration and purity were determined by the measurement of 260/280 nm light absorption by the nucleic acid. For cDNA synthesis, the SUPERSCRIPT II reverse transcriptase cDNA kit (GIBCO-BRL; Cat. # 18064-014) was used. RNA input per 200 μl cDNA reaction sample was 10 μg. Prior to cDNA synthesis RNA was treated with 1 unit/μl DNAse I in 110 μl water at 37° C. for 20 minutes. DNase I was then inactivated by a 10 minutes incubation at 70° C. Random primer was used for cDNA priming; 10 μl of random hexamer primer (100 ng/μl) was added, samples were heated to 70° C. for 5 minutes and chilled on ice. Subsequently 40 μl SUPERSCRIPT II "first strand" buffer, 20 μl of 0.1 M DDT, 10 μl of a 10 mM of mix of deoxynucleotide triphosphates (dATP, dCTP, dGTP, dUTP) and 10 μl of SUPERSCRIPT II reverse transcriptase were added and cDNA synthesis was done for 45 minutes at 42° C. Reavtions were stopped by a 5 minutes incubation at 95° C. and typically, 2–4 μl of such cDNA samples were used for PCR.

A portion of the cDNA (typically, 1/5 of a 20 μl reaction) was used for PCR. PCR was conducted using primers designed to amplify specifically PDZ domain-containing regions of PDZ proteins of interest. Oligonucleotide primers were designed to amplify one or more PDZ-encoding domains. The DNA sequences encoding the various PDZ domains of interest were identified by inspection (i.e., conceptual translation of the PDZ protein cDNA sequences obtained from GenBank, followed by alignment with the PDZ domain amino acid sequence). TABLE 3 shows the PCR primers, the PDZ-encoded domains amplified, and the GenBank accession number of the PDZ-domain containing proteins. To facilitate subsequent cloning of PDZ domains, the PCR primers included endonuclease restriction sequences at their ends to allow ligation with pGEX-3X cloning vector (Pharmacia, GenBank XX113852) in frame with glutathione-S transferase (GST).

TABLE 3 lists proteins detected in the aforementioned assays. The results showed that PDZ proteins are widely utilized in T and B cells in both lineage specific as well as lineage independent manner. INADL2/3 (PDZ dom.), KIAA0316, and 26s subunit p27 were detected in T cells, but not B cells. mCASK, KIAA0559, PTN-4, and X11 beta were detected in B cells, but not T cells. AF6, BAII associated prot., Cytohesin bind. Prot., DLG1, DLG5 (pdlg), DVL1, DVL3, GTPase, hypoth. 41.8 kd, KIAA147, KIAA0300, KIAA0303, KIAA0380, KIAA0440, KIAA0545, KIAA0561, LIMK1, LIMK2, LIM domain prot, LIM protein, MINT1, MINT3, MPP1, MPP2, NE-DLG, NOS1, novel serine protease, PTN-3, prIL 16, PSD95, RGS12, serine protease, SYNTENIN, SYNTR 1 alpha, TAX1, TAX2, TAX33, TAX40, Tax43 (SYN, Beta1), TIAM wwp3, and X11 prot. were detected in both T cells and B cells.

TABLE 3

PDZ DOMAINS

| GENE SYMBOL | PROTEIN | ACC. # | AMINO ACID SEQUENCE* | CLON. SITES | FORWARD PRIMER | REVERSE PRIMER |
|---|---|---|---|---|---|---|
| CASK | CASK | Y17138 | AA495–584; PDZ domain 1 (of 1) *HV*TRVRLVQFQKNTDEPMGITLK MNELNHCIVARIMHGGMIHRQGT LHVGDEIREINGISVANQTVEQL QKMLREMRGSITFKIVPSYRTQS *LNSS* (SEQ ID NO:292) | Bam HI/ Eco RI | 6CAF 5'- TCGGATCCAT GTGACCAGAG TTCGG-3' (SEQ ID NO:322) N1471–1494 | 7CAR 5'- TCGGAATTCAG ACTGAGTGCGG TA-3' (SEQ ID NO:323) N1761–1738 |
| MPP1 | 55 Kd erythrocyte membrane protein | M64925 | AA101–186; PDZ domain 1 (of 1) RKVRLIQFEKVTEEPMGITLKLN EKQSCTVARILHGGMIHRQGSLH VGDEILEINGTNVTNHSVDQLQK AMKETKGMISLKVIPNQ*REFIVT D* (SEQ ID NO:293) | Bam HI/ Bam HI | 62MPF 5'- GGGATCCGGA AAGTGCGACT CATAC-3' (SEQ ID NO:324) N296–320 | 63MPR 5'- ACGGATCCGCT GGTTGGGAATT ACTT-3' (SEQ ID NO:325) N568–543 |
| DLG1 | human homolog of Drosophila discs large protein | U13897 | AA275–477; PDZ domains 1–2 (of 3) *Q*VNGTDADYEYEEITLERGNSGL GFSIAGGTDNPHIGDDSSIFITK IITGGAAAQDGRLRVNDCILQVN EVDVRDVTHSKAVEALKEAGSIV RLYVKRRKPVSEKIMEIKLIKGP KGLGFSIAGGVGNQHIPGDNSIY VTKIIEGGAAHKDGKLQIGDKLL AVNNVCLEEVTHEEAVTALKNTS DFVYLKVAKPTSMYMNDGYA*PNS S* (SEQ ID NO:294) | Bam HI/ Eco RI | 1DF 5'- TCGGATCCAG GTTAATGGCT CAGATG-3' (SEQ ID NO:326) N815–841 | 2DR 5'- CGGAATTCGGT GCATAGCCATC-3' (SEQ ID NO:327) N1442–1421 |

TABLE 3-continued

PDZ DOMAINS

| GENE SYMBOL | PROTEIN | ACC. # | AMINO ACID SEQUENCE* | CLON. SITES | FORWARD PRIMER | REVERSE PRIMER |
|---|---|---|---|---|---|---|
| PSD95 | human post-synaptic density protein 95 | U83192 | AA387–724; PDZ domains 1–3 (of 3) *LEG*EGEMEYEEITLERGNSGLGF SIAGGTDNPHIGDDPSIFITKII PGGAAAQDGRLRVNDSILFVNEV DVREVTHSAAVEALKEAGSIVRL YVMRRKPPAEKVMEIKLIKGPKG LGFSIAGGVGNQHIPGDNSIYVT KIIEGGAAHKDGRLQIGDKILAV NSVGLEDVMHEDAVAALKNTYDV VYLKVAKPSNAYLSDSYAPPDIT TSYSQHLDNEISHSSYLGTDYPT AMTPTSPRRYSPVAKDLLGEEDI PREPRRIVIHRGSTGLGFNIVGG EDGEGIFISFILAGGPADLSGEL RKGDQILSVNGVDLRNASHEQAA IALKNAGQTVTIIAQYKPE*FIV* (SEQ ID NO:295) | Bam HI/ Eco RI | 8PSF 5'- TCGGATCCTT GAGGGGGAGA TGGA-3' (SEQ ID NO:328) N1150–1173 | 11PSR 5'- TCGGAATTCGC TATACTCTTCT GG-3' (SEQ ID NO:329) N2191–2168 |
| NeDLG | presynaptic protein sao102 (neuroendo-crine-dlg) | U49089 | AA205–1171; PDZ domains 1–2 (of 3) *Q*YEEIVLERGNSGLGFSIAGGID NPHVPDDPGIFITKIIPGGAAAM DGRLGVNDCVLRVNEVEVSEVVH SRAVEALKEAGPVVRLVVRRRQP PPETIMEVNLLKGPKGLGFSIAG GIGNQHIPGDNSIYITKIIEGGA AQKDGRLQIGDRLLAVNNTNLQD VRHEEAVASLKNTSDMVYLKVAK PGS*PR* (SEQ ID NO:296) | Bam HI/ Eco RI | 71NEDF 5'- CAGGATCCAA TATGAGGAAA TCGTACTTG-3' (SEQ ID NO:330) N608–635 | 72NEDR 5'- TTGAATTCGAG GCTGCCTGGCT TGGC-3' (SEQ ID NO:331) N1186–1161 |
| TAX33 | tax interaction protein 33 | AF028826 | AA73–162; PDZ domain 1 (of 1) HSHPRVVELPKTDEGLGFNVMGG KEQNSPIYISRIIPGGVAERHGG LKRGDQLLSVNGVSVEGEHHEKA VELLKAAKDSVKLVVRYTPKVL*E FIVTN* (SEQ ID NO:297) | Bam HI/ Eco RI | 92TAF 5'- GTGGGATCCA CTCCCACCCT CGAGTAG-3' (SEQ ID NO:332) N208–234 | 93TAR 5'- CATGAATTCCA GAACTTTTGGG TGTATCGC-3' (SEQ ID NO:333) N497–468 |
| SYN 1 α | alpha1-syntrophin | U40571 | AA96–189 PDZ domain 1 (of 1) QRRRVTVRKADAGGLGISIKGGR ENKMPILISKIFKGLAADQTEAL FVGDAILSVNGEDLSSATHDEAV QVLKKTGKEVVLEVKYMKDVSPY FK*NSS* (SEQ ID NO:298) | Bam HI/ Eco RI | 124SYF 5'- TACGGATCCA GCGGCCGCCG CGTGAC-3' (SEQ ID NO:334) N279–301 | 125SYR 5'- GTAGAATTCTT GAAATACGGTG AGAC-3' (SEQ ID NO:335) N576–551 |
| TAX43 | human tax interaction protein 43 | AF028828 | AA15–85 PDZ domain 1 (of 1) QKRGVKVLKQELGGLGISIKGGK ENKMPILISKIFKGLAADQTQAL YVGDAILSVNGADLRDATHDEAV QAL*QFIVTN* (SEQ ID NO:299) | Bam HI/ Eco RI | 97TAF 5'- TCTGGATCCA GAAGCGTGGC GTGAAGG-3' (SEQ ID NO:336) N37–63 | 98TAR 5'- CGGAATTCAAC GCCTGCACCGC CTC-3' (SEQ ID NO:337) N267–231 |
| LDP | lim domain protein clp-36 | U90878 | AA46–88 PDZ domain 1 (of 1) RGMTTQQIDLQGPGPWGFRLVGR KDFEQPLAISRVTPGSKAAL*ASS* (SEQ ID NO:300) | Bam HI/ Eco RI | 146LIF 5'- CCAGGATCCG CGGAATGACC ACCCAGC-3' (SEQ ID NO:338) N129–155 | 147LIR 5'- CATGAATTCGC TAGAGCCGCCT TGCTT-3' (SEQ ID NO:339) N276–239 |
| LIM | Human LIM protein | AF061258 | AA29–112; PDZ domain 1 (of 1) *L*SNYSVSLVGPAPWGFRLQGGKD FNMPLTISSLKDGGKAAQANVRI GDVVLSIDGINAQGMTHLEAQNK IKGCTGSLNMTLQRAS*C* (SEQ ID NO:301) | Bam HI/ Eco RI | 182LF 5'- TTAGGATCCT GAGCAAGTAC AGTGTGTCAC-3' (SEQ ID NO:340) N86–115 | 183LR 5'- CTTGAATTCAG CAGATGCTCTT TGCAGAGTC-3' (SEQ ID NO:341) N350–320 |

TABLE 3-continued

PDZ DOMAINS

| GENE SYMBOL | PROTEIN | ACC. # | AMINO ACID SEQUENCE* | CLON. SITES | FORWARD PRIMER | REVERSE PRIMER |
|---|---|---|---|---|---|---|
| LIMK1 | human LIM domain kinase 1 | NM_002314 | AA194–291; PDZ domain 1 (of 1) TVTLVSIPASSHGKRGLSVSIDP PHGPPGCGTEHSHTVRVQGVDPG CMSPDVKNSIHVGDRILEINGTP IRNVPLDEIDLLIQETSRLLQLT LEHD*PGIHRD* (SEQ ID NO:302) | SMA I | 52LIFP 5'-CTGCCCGGGA CCGTCACCCT GGTGTCC-3' (SEQ ID NO:342) N570–597 | 53LIRP 5'-TCGCCCGGGTC ATGCTCGAGGG TC-3' (SEQ ID NO:343) N874–851 |
| LIMK2 | human LIM domain kinase 2 | D45906 | AA185–275; PDZ domain 1 (of 1) PYSVTLISMPATTEGRRGFSVSV ESACSNYATTVQVKEVNRMHISP NNRNAIHPGDRILEINGTPVRTL RVEEVEDAISQTSQTLQLLIEH*E FIVTN* (SEQ ID NO:303) | Bam HI/ Eco RI | 185LF 5'-AGCGGATCCC CTACTCTGTC ACGCTCATC-3' (SEQ ID NO:344) N545–573 | 186LR 5'-GACGAATTCAT GTTCAATCAAC AGCTGAAG-3' (SEQ ID NO:345) N834–805 |
| MPP2 | maguk p55 subfamily member 2 (DLG2) | X82895 | AA185–273; PDZ domain 1 (of 1) QPVPPDAVRMVGIRKTAGEHLGV TFRVEGGELVIARILHGGMVAQQ GLLHVGDIIKEVNGQPVGSDPRA LQELLRNASGSVILKILPNYQ*VF IVTD* (SEQ ID NO:304) | Bam HI/ Eco RI | 142MF 5'-TCAGGATCCA GCCTGTACCT CCCGATGC-3' (SEQ ID NO:346) N542–569 | 143MR 5'-ATGGAATTCCT GGTAGTTGGGC AGGATC-3' (SEQ ID NO:347) N828–801 |
| NOS1 | human neuronal nitric oxide synthase | U17327 | AA239–988; PDZ domain 1 (of 1) IQPNVISVRLFKRKVGGLGFLVK ERVSKPPVIISDLIRGGAAEQSG LIQAGDIILAVNGRPLVDLSYDS ALEVLRGIASETHVVLILRGP*EF IVTD* (SEQ ID NO:305) | Bam HI/ Eco RI | 155NOF 5'-AGCGGATCCA GCCCAATGTC ATTTC-3' (SEQ ID NO:348) N711–733 | 156NOR 5'-GAAGAATTCAG GGCCCCTCAGA ATG-3' (SEQ ID NO:349) N994–970 |
| AF6 | af-6 protein | U02478 | AA985–1077; PDZ domain 1 (of 1) LRKEPEIITVTLKKQNGMGLSIV AAKGAGQDKLGIYVKSVVKGGAA DVDGRLAAGDQLLSVDGRSLVGL SQERAAELMTRTSSVVTLEVAKQ G*EFIVTD* (SEQ ID NO:306) | Bam HI/ Eco RI | 66AFF 5'-TCGGATCCTG AGGAAAGAAC CTGAA-3' (SEQ ID NO:350) N2946–2970 | 67AFR 5'-TAGAATTCACC CTGCTTTGCTA CTTC-3' (SEQ ID NO:351) N3239–3214 |
| PTN-4 | protein-tyrosine phosphatase meg1 | M68941 | AA774-862; PDZ domain 1 (of 1) LIRMKPDENGRFGFNVKGGYDQK MPVIVSRVAPGTPADLCVPRLNE GDQVVLINGRDIAEHTHDQVVLF IKASCERHSGELMLLVRPNA*EFI VTD* (SEQ ID NO:307) | Bam HI/ Eco RI | 247PTF 5'-ATCGGATCCT AATCAGAATG AAACCTG-3' (SEQ ID NO:352) N2312–2338 | 248PTR 5'-ATCGAATTCAG CATTAGGTCGA ACTAG-3' (SEQ ID NO:353) N2595–2569 |
| prIL16 | putative interleukin 16 precursor | S81601 | AA170–383; PDZ domain 1–2 (of 2) HVTILHKEEGAGLGFSLAGGADL ENKVITVHRVFPNGLASQEGTIQ KGNEVLSINGKSLKGTTHHDALA ILRQAREPRQAVIVTRKLTPEAM PDLNSSTDSAASASAASDVSVES TAEATVCTVTLEKMSAGLGFSLE GGKGSLHGDKPLTINRIFKGAAS EQSETVQPGDEILQLGGTAMQGL TRFEAWNIIKALPDGPVTIVIRR KSLQSK*EFIVTD* (SEQ ID NO:308) | Bam HI/ Eco RI | 75PRF 5'-ACGGGATCCA TGTCACCATC TTACAC-3' (SEQ ID NO:354) N503–528 | 76PRR 5'-GTGAATTCCTT GGACTGGAGGC TTTTTC-3' (SEQ ID NO:355) N1157–1129 |
| 41.8 kD | hypothetical 41.8 kD protein | AF007156 | AA4–85; PDZ domain 1 (of 1) RDSGAMLGLKVVGGKMTESGRLC AFITKVKKGSLADTVGHLRPGDE VLEWNGRLLQGATFEEVYNIILE SKPEPQVELVVSRA*NSS* (SEQ ID NO:309) | Bam HI/ Eco RI | 145HF 5'-GTGGGATCCG AGATTCAGGA GCAATGC-3' (SEQ ID NO:356) N4–30 | 146HR 5'-CTGGAATTCGC CTTGAAACTAC AAGTTC-3' (SEQ ID NO:357) N267–240 |

TABLE 3-continued

PDZ DOMAINS

| GENE SYMBOL | PROTEIN | ACC. # | AMINO ACID SEQUENCE* | CLON. SITES | FORWARD PRIMER | REVERSE PRIMER |
|---|---|---|---|---|---|---|
| K559 | KIAA0559 | AB011131 | AA766–870; PDZ1 (of 1) HYIFPHARIKITRDSKDHTVSGN GLGIRIVGGKEIPGHSGEIGAYI AKILPGGSAEQTGKLMEGMQVLE WNGIPLTSKTYEEVQSIISQQSG EAEICVRLDLNML*SNSS* (SEQ ID NO:310) | Bam HI/ Eco RI | 130KIF 5'- AAAGGATCCA CTACATCTTT CCTCACG-3' (SEQ ID NO:358) N2290–2312 | 131KIR 5'- TCACAATTGGA TAGCATATTGA GGTCCAG-3' (SEQ ID NO:359) N2623–2595 |
| RGS12 | human regulator of G-protein signalling 12 | AF035152 | AA35–103; PDZ domain 1 (of 1) *PPP*RVRSVEVARGRAGYGFTLSG QAPCVLSCVMRGSPADFVGLRAG DQILAVNEINVKKASHEDVVKLI G*NSS* (SEQ ID NO:311) | Bam HI/ Eco RI | 64RGF 5'- TGGGATCCCG CCCCCAAGGG TGCGGAG-3' (SEQ ID NO:360) N93–119 | 65RGR 5'- AGGAATTCCCA ATTAATTTCAC TAC-3' (SEQ ID NO:361) N316–291 |
| K316 | KIAA0316 | AB002314 | AA197–284; PDZ domain 1 (of 1) PPAPRKVEMRRDPVLGFGPVAGS EKPVVVRSVTPGGPSEGKLIPGD QIVMINDEPVSAAPRERVIDLVR SCKESILLTVIQPYPSPK*RNSS* (SEQ ID NO:312) | Bam HI/ Eco RI | 158KIF 5'- AAAGGATCCC TCCGGCTCCT CGGAAG-3' (SEQ ID NO:362) N586–611 | 159KIR 5'- TTAGAATTCTG ATTTGGGAGAA GGGTAAG-3' (SEQ ID NO:363) N866–839 |
| DVL1 | human dishevelled segment polarity protein homolog | AF006011 | AA248–340; PDZ domain 1 (of 1) *QSTVL*NIVTVTLNMERHHFLGIS IVGQSNDRGDGGIYIGSIMKGGA VAADGRIEPGDMLLQVNDVNFEN MSNDDAVRVLREIVSQTGPISLT VAKCW*EFIVTD* (SEQ ID NO:313) | Bam HI/ Eco RI | 1st PCR: 55DVISF 5'- TCATCCAGAC TCATCCGGAA G-3' (SEQ ID NO:364) N652–673 2nd PCR, nested: 37DVF 5'- TCGGATCCAA ACGGTCACTC TCAAC-3' (SEQ ID NO:366) N723–747 | 1st PCR: 56DVISR 5'- GCTCATGTCAC TCTTCACCG-3' (SEQ ID NO:365) N1195–1174 2nd PCR, nested: 38DVR 5'- TCGGAATTCCC AGCACTTGGCT ACAG-3' (SEQ ID NO:367) N1029–N1004 |
| TAX40 | human tax interaction protein 40 | AF028827 | AA35–137; PDZ domain 1 (of 1) LLPETHRRVRLHKHGSDRPLGFY IRDGMSVRVAPQGLERVPGIFIS RLVRGGLAESTGLLAVSDEILEV NGIEVAGKTLDQVTDMMVANSHN LIVTVKPANQA*NSS* (SEQ ID NO:314) | Bam HI/ Eco RI | 136TF 5'- ACGGGATCCT ACTGCCTGAG ACCCACC-3' (SEQ ID NO:368) N97–123 | 137TR 5'- ACGGAATTCCG CTGGTTGGCGG GCTTGAC-3' (SEQ ID NO:369) N421–393 |
| TIAM1 | T-lymphoma invasion and metastasis inducing protein 1 | NM_ 003253 | AA1001–1088; PDZ 1 (of 1) HSIHIEKSDTAADTYGFSLSSVE EDGIRRLYVNSVKETGLASKKGL KAGDEILEINNRAADALNSSMLK DFLSQPSLGLLVRTYPELE*EFIV TD* (SEQ ID NO:315) | Bam HI/ Eco RI | 39TF 5'- TCGGATCCAC AGCATCCACA TTGAG-3' (SEQ ID NO:370) N2995–3019 | 40TR 5'- TCGGAATTCCT CCAGCTCGGGG T-3' (SEQ ID NO:371) N3275–3253 |
| MINT1 | human X11 protein | L04953 | AA717–894; PDZ domains 1–2 (of 2) SENCKDVFIEKQKGEILGVVIVE SGWGSILPTVIIANMMHGGPAEK SGKLNIGDQIMSINGTSLVGLPL STCQSIIKGLENQSRVKLNIVRC PPVTTVLIRRPDLRYQLGFSVQN GIICSLMRGGIAERGGVRVGHRI IEINGQSVVATPHEKIVHILSNA VGEIHMKTMPAAMYRLL*NSS* (SEQ ID NO:316) | Eco RI/ Eco RI | 34MIF 5'- CGGAATTCGG AAAACTGTAA AGATG-3' (SEQ ID NO:372) N2149–2167 | 2OMR 5'- TCGGAATTCAG CAGCCTGTACA TCG-3' (SEQ ID NO:373) N2690–2666 |

TABLE 3-continued

PDZ DOMAINS

| GENE SYMBOL | PROTEIN | ACC. # | AMINO ACID SEQUENCE* | CLON. SITES | FORWARD PRIMER | REVERSE PRIMER |
|---|---|---|---|---|---|---|
| K303 | KIAA0303 | Ab002301 | AA652-742; PDZ domain 1 (of 1) PHQPIVIHSSGKNYGFTIRAIRV YVGDSDIYTVHHIVWNVEEGSPA CQAGLKAGDLITHINGEPVHGLV HTEVIELLLKSGNKVSITTTPF*E FIVTD* (SEQ ID NO:317) | Bam HI/ Eco RI | 152KIF 5'-CTGGGATCCC ACATCAGCCG ATTGTGA-3' (SEQ ID NO:374) N1948–1976 | 153KIR 5'-TGTGAATTCAA ATGGGGTAGTA GTGATTG-3' (SEQ ID NO:375) N2237–2209 |
| CBP | Cytohesin binding protein HE | AF68836 | AA85-176; PDZ domain 1 (of 1) QRKLVTVEKQDNETFGFEIQSYR PQNQNACSSEMFTLICKIQEDSP AHCAGLQAGDVLANINGVSTEGF TYKQVVDLIRSSGNLLTIETLNG *NSS* (SEQ ID NO:318) | Bam HI/ Eco RI | 235CYF 5'-CCTGGATCCA AAGAAAGCTT GTTACTGTG-3' (SEQ ID NO:376) N246–274 | 236CYR 5'-TCAGAATTCCA TTAAGAGTCTC TATC-3' (SEQ ID NO:377) N535–510 |
| MINT3 | human MINT3 | AF029110 | AA11-52; PDZ domain 1 (of 1) PVTTAIIHRPHAREQLGFCVEDG IVRPRPLAPGWGGRAALST*EFIV TD* (SEQ ID NO:319) | Bam HI/ Eco RI | 188MF 5'-ACTGGATCCC CGTCACCACC GCCATCATC-3' (SEQ ID NO:378) N23–51 | 189MR 5'-CTCGAATTCCG TGCTCAGGGCC GCCCTA-3' (SEQ ID NO:379) N165–138 |
| TAX2 | human tax interaction protein 2 | AF028824 | AA54–140; PDZ domain 1 (of 1) RKEVEVFKSEDALGLTITDNGAG YAFIKRIKEGSVIDHIHLISVGD MIEAINGQSLLGCRHYEVARLLK ELPRGRTFTLKLTEPRK*EFIVTD* (SEQ ID NO:320) | Bam HI/ Eco RI | 197TF 5'-AGGGGATCCG CAAGGAGGTG GAGGTGTTC-3' (SEQ ID NO:380) N154–182 | 198TR 5'-TGTGGAATTCC TTGCGAGGCTC CGTGAGC-3' (SEQ ID NO:381) N429–401 |
| K561 | KIAA0561 | AB011133 | AA948–1038; PDZ domain 1 (of 1) PPSLSTALARSTASACGRSASTW VIATSTLCTTSSGVWRTEAPPRR RACGLGTSSPTSTGSQCWGWCTW TSWSCCZRAATRYPCGPQPWR*IH RD* (SEQ ID NO:321) | Bam HI/ Eco RI | 161KIF 5'-CCTGGATCCC CCCATCGTTA TCCACAGC-3' (SEQ ID NO:382) N2836–2863 | 162KIR 5'-GAGGAATTCTC CAGGGCTGTGG TCCG-3' (SEQ ID NO:383) N3120–3095 |

Key:
Gene names and corresponding gene products are provided. In some cases, cDNA sequences representing the same gene have several database entries under different accession numbers and names. Accession numbers shown correspond to the gene name used in this description, and numbering of nucleotides and amino acids correlates to those Genbank entries. Amino acid sequences shown correspond to the cloned DNA portions of PDZ domain containing genes. Linker amino acid sequences (e.g., amino acids encoded by DNA flanking the cloning site of the pGEX-3X cloning vector) are in italics

*Note concerning TABLE 3

In several cases, sequence analysis of the PDZ clones revealed differences to the DNA and/or protein sequence as published in the databases, summarized in TABLE 3A.

TABLE 3A

| GENE | GENBANK ENTRY*** | ACTUAL CONSTRUCT |
|---|---|---|
| AF6 | N 3060: C | N 3060: T* |
| DLG1 | N 1021: A, = AA 340: Gln | N 1021: G, = AA 340: Arg |
| Lim dom. | N 202: G | N 202: C* |
|  | N 203: C, = AA 68: Arg | N 203: G, = AA 68: Gly |
| LIMK1 | N 855: C, = AA 285: Leu | N 855: A, = AA 285: Ile |
| MINT1 | N 2386: G, = AA 796: Glu** | N 2386: A, = AA 796: Lys** |
| NE-DLG | N 713: T | N 713: C* |
|  | N 766: G, = AA 255: Gly | N 766: A, = AA 255: Glu |

TABLE 3A-continued

| GENE | GENBANK ENTRY*** | ACTUAL CONSTRUCT |
|---|---|---|
|  | N 803: G, = AA 267: Glu | N 803: C, = AA 267: Asp |
|  | N 861: G, = AA 287: Val | N 861: A, = AA 287: Met |
| TIAM1 | N 3224: A | N 3224: G* |

*Note concerning TABLE 3

In several cases, sequence analysis of the PDZ clones revealed differences to the DNA and/or protein sequence as published in the databases, summarized in TABLE 3A.

(*) = silent mutation, does not effect the AA sequence;

(**) = MINT1 is the same as X11a. The database entry for X11a shows the same sequence as our actual construct with regard to N 2386 of the MINT1 GenBank entry.

(***) = Nucleotide ("N") and amino acid ("AA") annotations correspond to the numbering as found in the GenBank files.

6.2 Assays for Detection of Interactions Between PDZ-Domain Polypeptides and Candidate PDZ Ligand Proteins (PL Proteins)

Two complementary assays, termed "A" and "G," " were developed to detect binding between a PDZ-domain polypeptide and candidate PDZ ligand. In each of the two different assays, binding, is detected between a peptide having a sequence corresponding to the C-terminus of a protein anticipated to bind to one or more PDZ domain (i.e. a candidate PL peptide) and a PDZ-domain polypeptide (typically a fusion protein containing a PDZ domain). In the "A" assay, the candidate, PL peptide is immobilized and binding of a soluble PDZ-domain polypeptide to the immobilized peptide is detected (the "A" assay is named for the fact that in one embodiment an avidin surface is used to immobilize the peptide). In the "G" assay, the PDZ-domain polypeptide is immobilized and binding of a soluble PL peptide is detected (The "G" assay is named for the fact that in one embodiment a GST-binding surface is used to immobilize the PDZ-domain polypeptide). Preferred embodiments of these assays are described in detail infra. However, it will be appreciated by ordinarily skilled practitioners that these assays can be modified in numerous ways while remaining useful for the purposes of the present invention.

6.2.1 Production of Fusion Proteins Containing PDZ-Domains

GST-PDZ domain fusion proteins were prepared for use in the assays of the invention. PCR products containing PDZ encoding domains (as described in §6.1 supra) were subcloned into an expression vector to permit expression of fusion proteins containing a PDZ domain and a heterologous domain (i.e., a glutathione-S transferase sequence, "GST"). PCR products (i.e., DNA fragments) representing PDZ domain encoding DNA was extracted from agarose gels using the "sephaglas" gel extraction system (Pharmacia) according to the manufacturer's recommendations.

As noted supra, PCR primers were designed to include endonuclease restriction sites to facilitate ligation of PCR fragments into a GST gene fusion vector (pGEX-3X; Pharmacia, GenBank accession no. XXU13852) in-frame with the glutathione-S transferase coding sequence. This vector contains a IPTG inducible lacZ promoter. The pGEX-3X vector was linearized using Bam HI and Eco RI or, in some cases, Eco RI or Sma I, as shown in TABLE 3, and dephosphorylated. For most cloning approaches, double digest with Bam HI and Eco RI was performed, so that the ends of the PCR fragments to clone were Bam HI and Eco RI. In some cases, restriction endonuclease combinations used were Bgl II and Eco RI, Bam HI and Mfe I, or Eco RI only, Sma I only, or BamHI only (see TABLE 3). When more than one PDZ domain was cloned, the DNA portion cloned represents the PDZ domains and the cDNA portion located between individual domains. Precise locations of cloned fragments used in the assays are indicated in TABLE 3. DNA linker sequences between the GST portion and the PDZ domain containing DNA portion vary slightly, dependent on which of the above described cloning sites and approaches were used. As a consequence, the amino acid sequence of the GST-PDZ fusion protein varies in the linker region between GST and PDZ domain. Protein linkers sequences corresponding to different cloning sites/approaches are shown below. Linker sequences (vector DNA encoded) are bold, PDZ domain containing gene derived sequences are in italics.

1) GST-BamHI/BamHI—PDZ domain insert
   Gly-Ile—PDZ domain insert
2) GST-BamHI/BglII—PDZ domain insert
   Gly-Ile—PDZ domain insert
3) GST-EcoRI/EcoI—PDZ domain insert
   Gly-Ile-Pro-Gly-Asn—PDZ domain insert (SEQ ID NO:258)
4) GST-SmaI/SmaI—PDZ domain insert
   Gly-Ile-Pro—PDZ domain insert—

The PDZ-encoding PCR fragment and linearized pGEX-3X vector were ethanol precipitated and resuspended in 10 ul standard ligation buffer. Ligation was performed for 4–10 hours at 7° C. using T4 DNA ligase. It will be understood that some of the resulting constructs include very short linker sequences and that, when multiple PDZ domains were cloned, the constructs included some DNA located between individual PDZ domains.

The ligation products were transformed in DH5α or BL-21 E. coli bacteria strains. Colonies were screened for presence and identity of the cloned PDZ domain containing DNA as well as for correct fusion with the glutathione S-transferase encoding DNA portion by PCR and by sequence analysis. Positive clones were tested in a small scale assay for expression of the GST/PDZ domain fusion protein and, if expressing, these clones were subsequently grown up for large scale preparations of GST/PDZ fusion protein.

GST-PDZ domain fusion protein was overexpressed following addition of IPTG to the culture medium and purified. Detailed procedure of small scale and large scale fusion protein expression and purification are described in "GST Gene Fusion System" (second edition, revision 2; published by Pharmacia). In brief, a small culture (3–5mls) containing a bacterial strain (DH5α, BL21 or JM109) with the fusion protein construct was grown overnight in LB-media at 37° C. with the appropriate antibiotic selection (100 ug/ml ampicillin; a.k.a LB-amp). The overnight culture was poured into a fresh preparation of LB-amp (typically 250–500 mls) and grown until the optical density (OD) of the culture was between 0.5 and 0.9 (approximately 2.5 hours). IPTG (isopropyl β-D-thiogalactopyranoside) was added to a final concentration of 11.0 mM to induce production of GST fusion protein, and culture was grown an additional 1.5–2.5 hours. Bacteria were collect by centrifugation (4500 g) and resuspended in Buffer A– (50 mM Tris, pH 8.0, 50 mM dextrose, 1 mM EDTA, 200 uM phenylmethylsulfonylfluoride). An equal volume of Buffer A+ (Buffer A–, 4 mg/ml lysozyme) was added and incubated on ice for 3 min to lyse bacteria. An equal volume of Buffer B (10 mM Tris, pH 8.0, 50 mM KCl, 1 mM EDTA. 0.5% Tween-20, 0.5% NP40 (a.k.a. IGEPAL CA-630), 200 uM phenylmethylsulfonylfluoride) was added and incubated for an additional 20 min. The bacterial cell lysate was centrifuged (×20,000 g), and supernatant was added to glutathione sepharose 4B (Pharmacia, cat no. 17-0765-01) previous swelled (rehydrated) in 1× phosphate-buffered saline (PBS). The supernatant-sepharose slurry was poured into a column and washed with at least 20 bed volumes of 1×PBS. GST fusion protein was eluted off the glutathione sepharose by applying 0.5–1.0 ml aliquots of 5 mM glutathione and collected as separate fractions. Concentrations of fractions were determined using BioRad Protein Assay (cat no. 500-0006) according to manufacturer's specifications. Those fractions containing the highest concentration of fusion protein were pooled and dialyzed against 1× PBS/35% glycerol. Fusion proteins were assayed for size and quality by SDS gel electrophoresis (PAGE) as described in "Sambrook." Fusion protein aliquots were stored at minus 80° C. and at minus 20° C.

6.2.2 Identification of Candidate PL Proteins and Synthesis of Peptides

In some non-hematopoietic cells (e.g., neurons, epithelial cells), certain PDZ domains are known to be bound by the C-terminal residues of PDZ-binding proteins. To identify PL proteins that function in hematopoietic and endothelial cells, cell surface receptor proteins were identified and peptides having the sequence corresponding to the c-terminus of each protein were synthesized. TABLE 4 lists these proteins, and provides corresponding C-terminal sequences and GenBank accession numbers. "Clasp 1" is described in WO 00/20434 (published 13 Apr. 2000). "Clasp 2" and "Clasp 4" are described in copending applications U.S. Ser. No. 09/547,276 and 60/196,527, both filed Apr. 11, 2000.

Synthetic peptides of defined sequence (e.g., corresponding to the carboxyl-termini of the indicated proteins) can be synthesized by any standard resin-based method (see, e.g., U.S. Pat. No. 4,108,846; see also, Caruthers et al., 1980, *Nucleic Acids Res. Symp. Ser.,* 215–223; Horn et al., 1980, *Nucleic Acids Res. Symp. Ser.,* 225–232; Roberge, et al., 1995, *Science* 269:202). The peptides used in the assays described herein were prepared by the FMOC (see, e.g., Guy and Fields, 1997, *Meth. Enz.* 289:67–83; Wellings and Atherton, 1997, *Meth. Enz.* 289:44–67). In some cases (e.g., for use in the A and G assays of the invention), peptides were labeled with biotin at the amino-terminus by reaction with a four-fold excess of biotin methyl ester in dimethylsulfoxide with a catalytic amount of base. The peptides were cleaved from the resin using a halide containing acid (e.g. trifluoroacetic acid) in the presence of appropriate antioxidants (e.g. ethanedithiol) and excess solvent lyophilized.

Following lyophilization, peptides can be redissolved and purified by reverse phase high performance liquid chromatography (HPLC). One appropriate HPLC solvent system involves a Vydac C-18 semi-preparative column running at 5 mL per minute with increasing quantities of acetonitrile plus 0.1% trifluoroacetic acid in a base solvent of water plus 0.1% trifluoroacetic acid. After HPLC purification, the identities of the peptides are confirmed by MALDI cation-mode mass spectrometry. As noted, exemplary biotinylated peptides are provided in TABLE 4.

6.2.3 Detecting PDZ-PL Interactions

Based on the determination that immune system cells contain both many PDZ proteins and similarly many candidate PL proteins, it was apparent to the inventors that characterization of the specific PDZ-PL interactions among these proteins would require reliable and rapid assays for such interactions. A variety of assay formats known in the art can be used to select ligands that are specifically reactive with a particular protein. For example, solid-phase ELISA immunoassays, immunoprecipitation, Biacore, and Western blot assays can be used to identify peptides that specifically bind PDZ-domain polypeptides. As discussed supra, two different, complementary assays were developed to detect PDZ-PL-interactions. In each, one binding partner of a PDZ-PL pair is immobilized, and the ability of the second binding partner to bind is determined. These assays, which are described infra, can be readily used to screen for hundreds to thousand of potential PDZ-ligand interactions in a few hours. Thus these assays can be used to identify yet more novel PDZ-PL interactions in hematopoietic cells. In addition, they can be used to identify antagonists of PDZ-PL interactions (see infra). In various embodiments, fusion protein are used in the assays and devices of the invention. Methods for constructing and expressing fusion proteins are well known. Fusion proteins generally are described in Ausubel et al., supra, Kroll et al., 1993, DNA Cell. Biol. 12:441, and Imai et al., 1997, *Cell* 91:521–30. Usually, the fusion protein includes a domain to facilitate immobilization of the protein to a solid substrate ("an immobilization domain"). Often, the immobilization domain includes an epitope tag (i.e., a sequence recognized by a antibody, typically a monoclonal antibody) such as polyhistidine (Bush et al, 1991, *J. Biol Chem* 266:13811–14), SEAP (Berger et al, 1988, *Gene* 66:1–10), or M1 and M2 flag (see, e.g., U.S. Pat. Nos. 5,011,912; 4,851,341; 4,703,004; 4,782,137). In an embodiment, the immobilization domain is a GST coding region. It will be recognized that, in addition to the PDZ-domain and the particular residues bound by an immobilized antibody, protein A, or otherwise contacted with the surface, the protein (e.g., fusion protein), will contain additional residues. In some embodiments these are residues naturally associated with the PDZ-domain (i.e., in a particular PDZ-protein) but they may include residues of synthetic (e.g., poly(alanine)) or heterologous origin (e.g., spacers of, e.g., between 10 and 300 residues).

PDZ domain-containing polypeptide used in the methods of the invention (e.g., PDZ fusion proteins) of the invention are typically made by (1) constructing a vector (e.g., plasmid, phage or phagemid) comprising a polynucleotide sequence encoding the desired polypeptide, (2) introducing the vector into an suitable expression system (e.g., a prokaryotic, insect, mammalian, or cell free expression system), (3) expressing the fusion protein and (4) optionally purifying the fusion protein.

(1) In one embodiment, expression of the protein comprises inserting the coding sequence into an appropriate expression vector (i.e., a vector that contains the necessary elements for the transcription and translation of the inserted coding sequence required for the expression system employed, e.g., control elements including enhancers, promoters, transcription terminators, origins of replication, a suitable initiation codon (e.g., methionine), open reading frame, and translational regulatory signals (e.g., a ribosome binding site, a termination codon and a polyadenylation sequence. Depending on the vector system and host utilized, any number of suitable transcription and translation elements, including constitutive and inducible promoters, can be used.

The coding sequence of the fusion protein includes a PDZ domain and an immobilization domain as described elsewhere herein. Polynucleotides encoding the amino acid sequence for each domain can be obtained in a variety of ways known in the art; typically the polynucleotides are obtained by PCR amplification of cloned plasmids, cDNA libraries, and cDNA generated by reverse transcription of RNA, using primers designed based on sequences determined by the practitioner or, more often, publicly available (e.g., through GenBank). The primers include linker regions (e.g., sequences including restriction sites) to facilitate cloning and manipulation in production of the fusion construct. The polynucleotides corresponding to the PDZ and immobilization regions are joined in-frame to produce the fusion protein-encoding sequence.

The fusion proteins of the invention may be expressed as secreted proteins (e.g., by including the signal sequence encoding DNA in the fusion gene; see, e.g., Lui et al, 1993, *PNAS USA,* 90:8957–61) or as nonsecreted proteins.

In some embodiments, the PDZ-containing proteins are immobilized on a solid surface. The substrate to which the polypeptide is bound may in any of a variety of forms, e.g., a microtiter dish, a test tube, a dipstick, a microcentrifuge tube, a bead, a spinnable disk, and the like. Suitable materials include glass, plastic (e.g., polyethylene, PVC, polypropylene, polystyrene, and the like), protein, paper, carbohydrate, lipip monolayer or supported lipid bilayer, and other solid supports. Other materials that may be employed include ceramics, metals, metalloids, semiconductive materials, cements and the like.

In some embodiments, the fusion proteins are organized as an array. The term "array," as used herein, refers to an ordered arrangement of immobilized fusion proteins, in which particular different fusion proteins (i.e., having different PDZ domains) are located at different predetermined sites on the substrate. Because the location of particular fusion proteins on the array is known, binding at that location can be correlated with binding to the PDZ domain situated at that location. Immobilization of fusion proteins on beads (individually or in groups) is another particularly useful approach. In one embodiment, individual fusion proteins are immobilized on beads. In one embodiment, mixtures of distinguishable beads are used. Distinguishable beads are beads that can be separated from each other on the basis of a property such as size, magnetic property, color (e.g., using FACS) or affinity tag (e.g., a bead coated with protein A can be separated from a bead not coated with protein A by using IgG affinity methods). Binding to particular PDZ domain may be determined; similarly, the effect of test compounds (i.e., agonists and antagonists of binding) may be determined.

Methods for immobilizing proteins are well known in the art, and include covalent and non-covalent methods.

One suitable immobilization method is antibody-mediated immobilization. According to this method, an antibody specific for the sequence of an "immobilization domain" of the PDZ-domain containing protein is itself immobilized on the substrate (e.g., by adsorption). One advantage of this approach is that a single antibody may be adhered to the substrate and used for immobilization of a number of polypeptides (sharing the same immobilization domain). For example, an immobilization domain consisting of poly-histidine (Bush et al, 1991, *J. Biol Chem* 266:13811–14) can be bound by an anti-histidine monoclonal antibody (R&D Systems, Minneapolis, Minn.); an immobilization domain consisting of secreted alkaline phosphatase ("SEAP") (Berger et al, 1988, *Gene* 66:1–10) can be bound by anti-SEAP (Sigma Chemical Company, St. Louis, Mo.); an immobilization domain consisting of a FLAG epitope can be bound by anti-FLAG. Other ligand-antiligand immobilization methods are also suitable (e.g., an immobilization domain consisting of protein A sequences (Harlow and Lane, 1988, Antibodies A laboratory Manual, Cold Spring Harbor Laboratory; Sigma Chemical Co., St. Louis, Mo.) can be bound by IgG; and an immobilization domain consisting of strepavidin can be bound by biotin (Harlow & Lane, supra; Sigma Chemical Co., St. Louis, Mo.). In a preferred embodiment, the immobilization domain is a GST moiety, as described herein.

When antibody-mediated immobilization methods are used, glass and plastic are especially useful substrates. The substrates may be printed with a hydrophobic (e.g., Teflon) mask to form wells. Preprinted glass slides with 3, 10 and 21 wells per 14.5 $cm^2$ slide "working area" are available from, e.g., SPI Supplies, West Chester, Pa.; also see U.S. Pat. No. 4,011,350). In certain applications, a large format (12.4 cm×8.3 cm) glass slide is printed in a 96 well format is used; this format facilitates the use of automated liquid handling equipment and utilization of 96 well format plate readers of various types (fluorescent, calorimetric, scintillation). However, higher densities may be used (e.g., more than 10 or 100 polypeptides per $cm^2$). See, e.g., MacBeath et al, 2000, Science 289:1760–63.

Typically, antibodies are bound to substrates (e.g., glass substrates) by adsorption. Suitable adsorption conditions are well known in the art and include incubation of 0.5–50 ug/ml (e.g., 10 ug/ml) mAb in buffer (e.g., PBS, or 50 to 300 mM Tris, MOPS, HEPES, PIPES, acetate buffers, pHs 6.5 to 8, at 4° C.) to 37° C. and from 1 hr to more than 24 hours.

Proteins may be covalently bound or noncovalently attached through nonspecific bonding. If covalent bonding between a the fusion protein and the surface is desired, the surface will usually be polyfunctional or be capable of being polyfunctionalized. Functional groups which may be present on the surface and used for linking can include carboxylic acids, aldehydes, amino groups, cyano groups, ethylenic groups, hydroxyl groups, mercapto groups and the like. The manner of linking a wide variety of compounds to various surfaces is well known and is amply illustrated in the literature.

6.2.3.1 "A Assay" Detection of PDZ-Ligand Binding Using Immobilized PL Peptide.

In one aspect, the invention provides an assay in which biotinylated candidate PL peptides are immobilized on an avidin coated surface. The binding of PDZ-domain fusion protein to this surface is then measured. In a preferred embodiment, the PDZ-domain fusion protein is a GST/PDZ fusion protein and the assay is carried out as follows:

(1) Avidin is bound to a surface, e.g. a protein binding surface. In one embodiment, avidin is bound to a polystyrene 96 well plate (e.g., Nunc Polysorb (cat #475094) by addition of 100 uL per well of 20 ug/mL of avidin (Pierce) in phosphate buffered saline without calcium and magnesium, pH 7.4 ("PBS", GibcoBRL) at 4° C. for 12 hours. The plate is then treated to block nonspecific interactions by addition of 200 uL per well of PBS containing 2 g per 100 mL protease-free bovine serum albumin ("PBS/BSA") for 2 hours at 4° C. The plate is then washed 3 times with PBS by repeatedly adding 200 uL per well of PBS to each well of the, plate and then dumping the contents of the plate into a waste container and tapping the plate gently on a dry surface.

(2) Biotinylated PL peptides (or candidate PL peptides, e.g. see TABLE 4) are immobilized on the surface of wells of the plate by addition of 50 uL per well of 0.4 uM peptide in PBS/BSA for 30 minutes at 4° C. Usually, each different peptide is added to at least eight different wells so that multiple measurements (e.g. duplicates and also measurements using different (3ST/PDZ-domain fusion proteins and a GST alone negative control) can be made, and also additional negative control wells are prepared in which no peptide is immobilized. Following immobilization of the PL peptide on the surface, the plate is washed 3 times with PBS.

(3) GST/PDZ-domain fusion protein (prepared as described supra) is allowed to react with the surface by addition of 50 uL per well of a solution containing 5 ug/mL GST/PDZ-domain fusion protein in PBS/BSA for 2 hours at 4° C. As a negative control, GST alone (i.e. not a fusion protein) is added to specified wells, generally at least 2 wells (i.e. duplicate measurements) for each immobilized peptide. After the 2 hour reaction, the plate is washed 3 times with PBS to remove unbound fusion protein.

(4) The binding of the GST/PDZ-domain fusion protein to the avidin-biotinylated peptide surface can be detected using a variety of methods, and detectors known in the art. In one embodiment, 50 uL per well of an anti-GST antibody in PBS/BSA (e.g. 2.5 ug/mL of polyclonal goat-anti-GST antibody, Pierce) is added to the plate and allowed to react for 20 minutes at 4° C. The plate is washed 3 times with PBS and a second, detectably labeled antibody is added. In one embodiment, 50 uL per well of 2.5 ug/mL of horseradish peroxidase (HRP)-conjugated polyclonal rabbit anti-goat immunoglobulin antibody is added to the plate and allowed to react for 20 minutes at 4° C. The plate is washed 5 times with 50 mM Tris pH 8.0 containing 0.2% Tween 20, and developed by addition of 100 uL per well of HRP-substrate solution (TMB, Dako) for 20 minutes at room temperature (RT). The reaction of the HRP and its substrate is terminated by the addition of 100 uL per well of 1M sulfuric acid and the optical density (O.D.) of each well of the plate is read at 450 nm.

(5) Specific binding of a PL peptide and a PDZ-domain polypeptide is detected by comparing the signal from the well(s) in which the PL peptide and PDZ domain polypeptide are combined with the background signal(s). The background signal is the signal found in the negative controls. Typically a specific or selective reaction will be at least twice background signal, more typically more than 5 times background, and most typically 10 or more times the background signal. In addition, a statistically significant reaction will involve multiple measurements of the reaction with the signal and the background differing by at least two standard errors, more typically four standard errors, and most typically six or more standard errors. Correspondingly, a statistical test (e.g. a T-test) comparing repeated measurements of the signal with repeated measurements of the background will result in a p-value <0.05, more typically a p-value <0.01, and most typically a p-value <0.001 or less.

As noted, in an embodiment of the "A" assay, the signal from binding of a GST/PDZ-domain fusion protein to an avidin surface not exposed to (i.e. not covered with) the PL peptide is one suitable negative control (sometimes referred to as "B"). The signal from binding of GST polypeptide alone (i.e. not a fusion protein) to an avidin-coated surface that has been exposed to (i.e. covered with) the PL peptide is a second suitable negative control (sometimes referred to as "B2"). Because all measurements are done in multiples (i.e. at least duplicate) the arithmetic mean (or, equivalently, average) of several measurements is used in determining the binding, and the standard error of the mean is used in determining the probable error in the measurement of the binding. The standard error of the mean of N measurements equals the square root of the following: the sum of the squares of the difference between each measurement and the mean, divided by the product of (N) and (N−1). Thus, in one embodiment, specific binding of the PDZ protein to the plate-bound PL peptide is determined by comparing the mean signal ("mean S") and standard error of the signal ("SE") for a particular PL-PDZ combination with the mean B1 and/or mean B2. In TABLE 2, binding was detected to be specific (denoted by an "A" in the matrix) when (1) the, mean S was at least twice the mean B1 and at least twice the mean B2 and (2) the mean S was at least six standard errors (six SE) greater than both the mean B1 and the mean B2. In addition, in the experiments summarized in TABLE 2, an additional criterion was used to ensure that none of the interactions defined as specific arose from a combined tendency of both the particular PDZ fusion protein and PL peptide tested to each give a higher than usual background. This criteria was that (3) the mean S was at least twenty times the product of the mean B1 and the mean B2. The factor twenty times reflects that at least one of B1 and B2 is generally less than 0.1 O.D. units, and therefore twenty times the product of the mean B1 and the mean B2 is generally less than twice the mean B1 and twice the mean B2, making criteria (3) less stringent than criteria (1). Only in a few cases where the mean B1 and the mean B2 are both greater than 0.1 O.D. units (i.e. both the particular PDZ fusion protein and PL peptide tested tend to give a higher than usual background) is criteria (3) more stringent than criteria (1).

TABLE 4

PL Peptides

| CODE | PROTEIN NAME | GENBANK ACCESS | SEQUENCE | SEQ ID NO: |
|---|---|---|---|---|
| AA1L | Clasp-1 | | ISKATPALPTVSISSSAEV | 177 |
| AA2L | Clasp-2 | | ISGTPTSTMVHGMTSSSSVV | 178 |
| AA3L | Clasp-4 | | CAISGTSSDRGYGSPRYAEV | 179 |
| AA4L | CD3n | M33158 | SVFSIPTLWSPWPPSSSSQL | 180 |
| AA5L-M* | CD4 | M12807 | SEKKTSQSPHRFQKTCSPI | 181 |
| AA6L | CD6 | X60992 | SPQPDSTDNDDYDDISAA | 182 |
| AA7L | CD34 | M81104 | QATSRNGHSARQHVVADTEL | 183 |
| AA9L | CD44 | M69215 | QFMTADETRNLQNVDMKIGV | 184 |
| AA10L | CD46 (Form 1) | M58050 | KKGTYLTDETHREVKFTSL | 185 |
| AA11L | CD49E (4) | X06256 | PYGTAMEKAQLKPPATSDA | 186 |
| AA12L | CD49F | X53586 | HKAEIHAQPSDKERLTSDA | 187 |
| AA13L | CD95 | M67454 | KDITSDSENSNFRNEIQSLV | 188 |
| AA14L | CD97 | X84700 | TSGTGHNQTRALRASESGI | 189 |
| AA15L | CD98 | J02939 | ERLKLEPHEGLLLRFPYAA | 190 |
| AA16L | CD105 | X72012 | STNHSIGSTQSTPCSTSSMA | 191 |
| AA17L | VCAM1 | M73255 | ARKANMKGSYSLVEAQKSKV | 192 |
| AA18L | CD138 | J05392 | PKQANGGAYQKPTKQEEFYA | 193 |
| AA19L | CD148 | D37781 | ENLAPVTIFGKTNGYIA | 194 |
| AA20L | CD166 | L38608 | DLGNMEENKKLEENNHKTEA | 195 |
| AA22L | DNAM-1 | U56102 | TREDIYVNYPTFSRRPKTRV | 196 |
| AA23L-M* | FasL | U11821 | SSKSKSSEESQTFFGLYKL | 197 |
| AA25L | FceRIb | D10583 | YSATYSELEDPGEMSPPIDL | 198 |
| AA28L | CDW125 (IL5R) | X62156 | EVICYIEKPGVETLEDSVF | 199 |
| AA29.1L | CDW128A (IL8RA) | M68932 | ARHRVTSYTSSSVNVSSNL | 200 |
| AA29.2L | CDW128B (IL8RB) | M73969 | KDSRPSFVGSSSGHTSTTL | 201 |
| AA30L | LPAP | X81422 | AWDDSARAAGGQGLHVTAL | 202 |
| AA33L | KV1.3 | AAC31761 | TTNNNPNSAVNIKKIFTDV | 203 |
| AA34.2L | NMDA | NP000824 | LNSCSNRRVYKKMPSIESDV | 204 |
| AA37L | Glycophorin C | AAA52574 | QGDPALQDAGDSSRKEYFI | 205 |

TABLE 4-continued

PL Peptides

| CODE | PROTEIN NAME | GENBANK ACCESS | SEQUENCE | SEQ ID NO: |
|---|---|---|---|---|
| AA38L | Neurexin | AB011150 | SSAKSSNKNKKNKDKEYYV | 206 |
| AA39L | Syndecan-2 | A33880 | GERKPSSAAYQKAPTKEFYA | 207 |
| AA40L | DOCK2 | BAA13200 | LASKSAEEGKQIPDSLSTDL | 208 |
| AA41L | CC CKR-1R | L09230 | LERVSSTSPSTGEHELSAGF | 209 |
| AA42L | CC CKR-2 | U03882 | GKGKSIGRAPEASLQDKEGA | 210 |
| AA43L | CC CKR-3 | HSU28694 | LERTSSVSPSTAEPELSIVF | 211 |
| AA44L | CC CKR-4 | X85740 | DTPSSSYTQSTMDHDLHDAL | 212 |
| AA45L | BLR-1 | S56162 | PSWRRSSLSESENATSLTTF | 213 |
| AA47L | CD83 | Z11697 | VTSPNKHLGLVTPHKTELV | 214 |
| AA48L | CD62E | M30640 | SSSQSLESDGSYQKPSYIL | 215 |
| AA49L | CD5 | X04391 | SMQPDNSSDSDYDLHGAQRL | 216 |
| AA55L | CD148 | D37781 | TIYENLAPVTTFGKTIA | 217 |

*The Sequence studied is mutated at positions >10 amino acids from C-terminus to increase water solubility and/or eliminate intramolecular disulfides.

6.2.3.2 "G Assay"—Detection of PDZ-Ligand Binding using Immobilized PDZ-Domain Fusion Polypeptide In one aspect, the invention provides an assay in which a GST/PDZ fusion protein is immobilized on a surface ("G" assay). The binding of labeled PL peptide (as listed in TABLE 4) to this surface is then measured. In a preferred embodiment, the assay is carried out as follows:

(1) A PDZ-domain polypeptide is bound to a surface, e.g. a protein binding surface. In a preferred embodiment, a GST/PDZ fusion protein containing one or more PDZ domains is bound to a polystyrene 96-well plate. The GST/PDZ fusion protein can be bound to the plate by any of a variety of standard methods known to one of skill in the art, although some care must be taken that the process of binding the fusion protein to the plate does not alter the ligand-binding properties of the PDZ domain. In one embodiment, the GST/PDZ fusion protein is bound via an anti-GST antibody that is coated onto the 96-well plate. Adequate binding to the plate can be achieved when:

a. 100 uL per well of 5 ug/mL goat anti-GST polyclonal antibody (Pierce) in PBS is added to a polystyrene 96-well plate (e.g., Nunc Polysorb) at 4° C. for 12 hours.

b. The plate is blocked by addition of 200 uL per well of PBS/BSA for 2 hours at 4° C.

c. The plate is washed 3 times with PBS.

d. 50 uL per well of 5 ug/mL GST/PDZ fusion protein) or, as a negative control, GST polypeptide alone (i.e. not a fusion protein) in PBS/BSA is added to the plate for 2 hours at 4° C.

e. the plate is again washed 3 times with PBS.

(2) Biotinylated PL peptides (or candidate PL peptides, e.g. as shown in TABLE 4) are allowed to react with the surface by addition of 50 uL per well of 20 uM solution of the biotinylated peptide in PBS/BSA for 10 minutes at 4° C., followed by an additional 20 minute incubation at 25° C. The plate is washed 3 times with ice cold PBS.

(3) The binding of the biotinylated peptide to the GST/PDZ fusion protein surface can be detected using a variety of methods and detectors known to one of skill in the art. In one embodiment, 100 uL per well of 0.5 ug/mL streptavidin-horse radish peroxidase (HRP) conjugate dissolved in BSA/PBS is added and allowed to react for 20 minutes at 4° C. The plate is then washed 5 times with 50 mM Tris pH 8.0 containing 0.2% Tween 20, and developed by addition of 100 uL per well of HRP-substrate solution (TMB, Dako) for 20 minutes at room temperature (RT). The reaction of the HRP and its substrate is terminated by addition of 100 uL per well of 1 M sulfuric acid, and the optical density (O.D.) of each well of the plate is read at 450 um.

(4) Specific binding of a PL peptide and a PDZ domain polypeptide is determined by comparing the signal from the well(s) in which the PL peptide and PDZ domain polypeptide are combined, with the background signal(s). The background signal is the signal found in the negative control (s). Typically a specific or selective reaction will be at least twice background signal, more typically more than 5 times background, and most typically 10 or more times the background signal. In addition, a statistically significant reaction will involve multiple measurements of the reaction with the signal and the background differing by at least two standard errors, more typically four standard errors, and most typically six or more standard errors. Correspondingly, a statistical test (e.g. a T-test) comparing repeated measurements of the signal with repeated measurements of the background will result in a p-value <0.05, more typically a p-value <0.01, and most typically a p-value <0.001 or less. As noted, in an embodiment of the "G" assay, the signal from binding of a given PL peptide to immobilized (surface bound) GST polypeptide alone is one suitable negative control (sometimes referred to as "B 1"). Because all measurement are done in multiples (i.e. at least duplicate) the arithmetic mean (or, equivalently, average.) of several measurements is used in determining the binding, and the standard error of the mean is used in determining the probable error in the measurement of the binding. The standard error of the mean of N measurements equals the square root of the following: the sum of the squares of the difference between each measurement and the mean, divided by the product of (N) and (N−1). Thus, in one embodiment, specific binding of the PDZ protein to the platebound peptide is determined by comparing the mean signal ("mean S") and standard error of the signal ("SE") for a particular PL-PDZ combination with the mean B1. In experiments summarized in TABLE 2, binding was determined to be specific (denoted by a "G" in the matrix) when (1) the mean S was at least twice the mean B1 and (2) the mean S was at least six standard errors (six SE) greater than the mean B1. Results of exemplary "G" assays are shown in FIGS. 1A–1D.

6.2.4 Assay Variations

As discussed supra, it will be appreciated that many of the steps in the above-described assays can be varied, for example, various substrates can be used for binding the PL and PDZ-containing proteins; different types of PDZ containing fusion proteins can be used; different labels for detecting PDZ/PL interactions can be employed; and different ways of detection can be used.

The PDZ-PL detection assays can employ a variety of surfaces to bind the PL and PDZ-containing proteins. For example, a surface can be an "assay plate" which is formed from a material (e.g. polystyrene) which optimizes adherence of either the PL protein or PDZ-containing protein thereto. Generally, the individual wells of the assay plate will have a high surface area to volume ratio and therefore a suitable shape is a flat bottom well (where the proteins of the assays are adherent). Other surfaces include, but are not limited to, polystyrene or glass beads, polystyrene or glass slides, and alike.

For example, the assay plate can be a "microtiter" plate. The term "microtiter" plate when used herein refers to a multiwell assay plate, e.g., having between about 30 to 200 individual wells, usually 96 wells. Alternatively, high density arrays can be used. Often, the individual wells of the microtiter plate will hold a maximum volume of about 250 ul. Conveniently, the assay plate is a 96 well polystyrene plate (such as that sold by Becton Dickinson Labware, Lincoln Park, N.J.), which allows for automation and high throughput screening. Other surfaces include polystyrene microtiter ELISA plates such as that sold by Nunc Maxisorp, Inter Med, Denmark. Often, about 50 ul to 300 ul, more preferably 100 ul to 200 ul, of an aqueous sample comprising buffers suspended therein will be added to each well of the assay plate.

The detectable labels of the invention can be any detectable compound or composition which is conjugated directly or indirectly with a molecule (such as described above). The label can be detectable by itself (e.g., radioisotope labels or fluorescent labels) or, in the case of an enzymatic label, can catalyze a chemical alteration of a substrate compound or composition which is detectable. The preferred label is an enzymatic one which catalyzes a color change of a non-radioactive color reagent.

Sometimes, the label is indirectly conjugated with the antibody. One of skill is aware of various techniques for indirect conjugation. For example, the antibody can be conjugated with biotin and any of the categories of labels mentioned above can be conjugated with avidin, or vice versa (see also "A" and "G" assay above). Biotin binds selectively to avidin and thus, the label can be conjugated with the antibody in this indirect manner. See, Ausubel, supra, for a review of techniques involving biotin-avidin conjugation and similar assays. Alternatively, to achieve indirect conjugation of the label with the antibody, the antibody is conjugated with a small hapten (e.g. digoxin) and one of the different types of labels mentioned above is conjugated with an anti-hapten antibody (e.g. anti-digoxin antibody). Thus, indirect conjugation of the label with the antibody can be achieved.

Assay variations can include different washing steps. By "washing" is meant exposing the solid phase to an aqueous solution (usually a buffer or cell culture media) in such a way that unbound material (e.g., non-adhering cells, non-adhering capture agent, unbound ligand, receptor, receptor construct, cell lysate, or HRP antibody) is removed therefrom. To reduce background noise, it is convenient to include a detergent (e.g., Triton X) in the washing solution. Usually, the aqueous washing solution is decanted from the wells of the assay plate following washing. Conveniently, washing can be achieved using an automated washing device. Sometimes, several washing steps (e.g., between about 1 to 10 washing steps) can be required.

Various buffers can also be used in PDZ-PL detection assays. For example, various blocking buffers can be used to reduce assay background. The term "blocking buffer" refers to an aqueous, pH buffered solution containing at least one blocking compound which is able to bind to exposed surfaces of the substrate which are not coated with a PL or PDZ-containing protein. The blocking compound is normally a protein such as bovine serum albumin (BSA), gelatin, casein or milk powder and does not cross-react with any of the reagents in the assay. The block buffer is generally provided at a pH between about 7 to 7.5 and suitable buffering agents include phosphate and TRIS.

Various enzyme-substrate combinations can also be utilized in detecting PDZ-PL interactions. Examples of enzyme-substrate combinations include, for example:

(i) Horseradish peroxidase (HRPO) with hydrogen peroxidase as a substrate, wherein the hydrogen peroxidase oxidizes a dye precursor (e.g. orthophenylene diamine [OPD] or 3,3',5,5'-tetramethyl benzidine hydrochloride [TMB]) (as described above).

(ii) alkaline phosphatase (AP) with para-Nitrophenyl phosphate as chromogenic substrate.

(iii) β-D-galactosidase (β D-Gal) with a chromogenic substrate (e.g. p-nitrophenyl-β-D-galactosidase) or fluorogenic substrate 4-methylumbelliferyl-β-D-galactosidase.

Numerous other enzyme-substrate combinations are available to those skilled in the art. For a general review of these, see U.S. Pat. Nos. 4,275,149 and 4,318,980, both of which are herein incorporated by reference.

Further, it will be appreciated that, although, for convenience, the present discussion primarily refers antagonists of PDZ-PL interactions, agonists of PDZ-PL interactions can be identified using the methods disclosed herein or readily apparent variations thereof.

6.2.5 Results of PDL-PL Interaction Assays

TABLE 2, supra, shows the results of assays in which specific binding was detected using the "A" and "G" assays described herein. The top row of the table specifies the source of the PDZ domain used in the GST-PDZ fusion proteins (see TABLE 3). The first column lists the cell surface proteins from which C-terminal peptide sequences were derived and the second column ("code") identifies the peptide used in the assay (see TABLE 4). The third column, "Seq" provides the sequence of the four (4) C-terminal residues of the cell surface protein and peptide. In the matrix, "A" indicates specific binding as detected in the "A" assay. "G" indicates specific binding as shown in the "G" assay. A blank indicates that no specific binding was detected using the "A" or "G" assays. An asterisk (*) indicates that a pairwise interaction between the PDZ protein and the cell surface protein (or subdomains of either) has been described by others.

6.2.5.1 New PL Motifs

As noted supra, TABLE 2 shows the results of assays (referred to as "PRISM MATRIX") to detect binding between PDZ proteins and candidate PL peptides. A number of specific PDZ-PL interactions are identified by the MATRIX and key amino acids and positions important in PDZ binding ("PL motifs") are deduced from these results. Not only is the MATRIX useful to catalog comprehensively PDZ-PL binding combinations, the assay can further aid in the rapid discovery and characterization of novel PL proteins and PL motifs to help in rational drug design and synthesis of PL-PDZ interaction inhibitors.

Other investigators have reported certain PL motifs important in PDZ binding, e.g., the C-terminal motifs S/T-

X-V/I/L (for DLG1) and Y/F-Y/F-I/L/F for MPP1 (see, Doyle et al., 1996, Cell 85, 1067; Songyang et al., 1997, Science 275, 73). However, the reported motifs are not sufficiently specific (i.e. a large number of proteins meet these criteria yet are not necessarily actual PDZ ligands) and cover only a small number of PDZ proteins (approximately 10). The PRISM MATRIX can be used to determine ligand specificity and to deduce ligand binding motifs for any PDZ protein because it can precisely determine sequences of amino acids that do or do not result in specific PDZ binding. In addition, the assay has revealed a significant of new PDZ domain binding motifs (i.e. PL motifs): C-terminal sequence of CD6, ISAA (SEQ ID NO:14); C-terminal sequence of CD49E, TSDA (SEQ ID NO:24); C-terminal sequence of CD49F, TSDA (SEQ ID NO:24); C-terminal sequence of CLASP-1, SAEV (SEQ ID NO:289); C-terminal sequence of CLASP-4, YAEV (SEQ ID NO:228); C-terminal sequence of CD44, KIGV (SEQ ID NO:104); C-terminal sequence of IL5R, DSVF (SEQ ID NO:94); and C-terminal sequence of BLR-1, LTTF (SEQ ID NO:253). Identification of these novel PL sequences allows the definition of novel PL motifs (See TABLE 5A, infra). The specificity with which these novel motifs are defined is enhanced by the fact that the MATRIX reports both positive results (i.e. PDZ-PL) combinations that result in specific binding interactions) and negative results (i.e. PDZ-PL combinations that do not result in specific binding). For example, the C-terminal sequence of CD6, SAA and the C-terminal sequence of CD49E, SDA bind to the PDZ-domain polypeptide 41.8 while the related C-terminal sequence of CD166, TEA and C-terminal sequence of CD148, YIA do not. This identifies the novel PL motif (Motif 1, infra) of polypeptides terminating in alanine with serine at the −2 position and excludes polypeptides with threonine and tyrosine at the −2 position. This motif is therefore more specific than most previously identified motifs. Other novel motifs are described in TABLE 5A.

TABLE 5A

| Position: | −3 | −2 | −1 | C-terminal |
|---|---|---|---|---|
| Motif 1 | X | S | X | A |
| Motif 2 | X | A | D/E | V |
| Motif 3 | X | V/I/L | X* | V |
| Motif 4 | X | S/T | X | F |

X* is any non-aromatic amino acid (any residue other than T, F or W).

6.2.5.2 Binding Clusters

TABLE 2 is arranged so that both the PDZ/GST fusion proteins and the PL peptide ligands are ordered with structurally similar molecules close to each other. In preparing TABLE 2 and carrying out the experiments used to create this table, the PDZ domains of each of the GST-PDZ fusion proteins were ranked for amino acid sequence similarity using the CLUSTAL multiple sequence alignment software package. Proteins with greatest sequence similarity are closest to each other in the matrix. The PL peptide ligands were also ordered on the basis of amino acid similarity, but with weight given to residues reported to be important in PDZ binding (Doyle et al., 1996, Cell 85, 1067). In particular, peptides were first ordered based on the most C-terminal residue (zero position) in the following amino acid order: G, A, C, S, T, N, Q, D, E, H, K, R, V, I, L, M, P, F, Y, W. Among peptides with identical C-termini, the same ranking scheme was then applied to the next most important residue for peptide binding, the −2 position, followed by the −1 position and the −3 position. (In an alternative approach, the GST-PDZ fusions can also be arranged to give additional weight to residues known to be important for ligand binding when aligning the proteins.)

Regions of the TABLE 1 matrix that are densely filled with significant binding interactions indicate that a particular ligand structure tends to bind to a particular family of PDZ domains. The results indicate that PDZ domains with similar structures bind ligands with similar structures, as indicated by the presence in the matrix of some clusters of many significant binding interactions and other areas of few significant binding interactions. These results reveal a number of structural relationships between different PDZ proteins and their ligands. The understanding of these structural relationships can be used to scan databases for probable ligands of specific PDZ proteins, facilitating the design of inhibitors of such novel interactions and the prediction of the side-effect profile of such inhibitors.

The most striking example of a cluster occurs in columns 1–5 of the matrix (PDZ domains from CASK, MPP1, DLG1, PSD95, and NeDLG). In our assays, CASK bound significantly to only one of the tested ligands, neurexin (this interaction was previously identified in neuronal cells). MPP1, the closest relative to CASK in the ordering system used, bound a set of five different ligands, including neurexin. All of the MPP1 ligands identified are structurally similar in that they terminate in valine (V) and have a charged amino acid (E or K) at the −3 position from the C-terminus ((C-terminal motif: E/K-X-X-V).

Out of the five MPP1 ligands identified, four of these also bind to DLG1, the next most similar protein to CASK and MPP1. DLG1 is closely related to two other proteins, PSD95 and NeDLG. Each of these three proteins binds ligands that terminate in the motif S/T/Y-X-V/I/L, as previously described (Songyang et al., 1997, Science 275, 73). Interestingly, if the terminal ligand residue is valine, other previously unidentified residues at the −2 position are compatibile with binding, with the C-terminal sequences AEV and ELV resulting in significant binding events. While this reflects a previously unrecognized flexibility in PDZ-ligand binding, the specificity of the interactions detected in our assays is reflected in the large areas at the top and bottom of columns 1–5 that contain no significant binding event. These areas reflect that none of the potential ligands terminating in residues other than V/I/L bound significantly to CASK, MPP1, DLG1, PSD95, or NeDLG.

(With respect to MPP1, it is worth noting that Glycophorin C, a known ligand of MPP1, Marfatia et al., 1997, J. Biol. Chem. 272, 24191, did not bind significantly to MPP1 in our tests, but does terminate in isoleucine, an amino acids very similar to valine, and does have a charged residue at the −3 position of the C-terminus.)

Other smaller clusters on the matrix also provide valuable information about the ligand specificity of certain PDZ domains. For example, five ligands bind significantly in both the "G" and the "A" assays to 41.8 kD protein, a previously unstudied PDZ domain-containing protein.

All of these ligands terminate in A, V, I, or L, and four of five have serine (S) at the −2 position, defining the C-terminal ligand motif S-X-A/V/I/L for this PDZ domain. Similarly, two of three ligands that bind specifically to KIAA0561 fit the C-terminal motif X* -S/T-D/E-V/I/L where X* is any non-aromatic amino acid. Interestingly, one of these ligands also binds to KIAA 0561's closest relative, TAX2. Likewise, the two ligands that bind to prIL16 both have a charged amino acid at the −3 position, a hydrophobic amino acid at the −2 position, and valine at the terminal position. A final interesting example of defining the ligand specificity of a PDZ domain involves PTN-4. Although the two ligands that bind significantly to PTN-4 are not closely related at their C-terminal 2 residues, both fit the C-terminal motif D/E-S-X-V/I/L/F/Y. These motifs characterizing the ligand specificity of particular PDZ proteins are summarized in TABLE 5B. Such motifs allow searches of databases for novel ligands (PL proteins) binding to these particular PDZ proteins. Knowledge of the PL proteins that bind to these PDZ proteins allows the design of inhibitors of these interactions, using the methods described herein, infra. In addition, knowledge of the set of PL proteins that bind to a particular PDZ protein can be used to predict the utility and the side effects of compounds that target this PDZ protein.

TABLE 5B

| PDZ | −3 | −2 | −1 | 0 |
|---|---|---|---|---|
| 41.8 kD | X | X | X | A/V/I/L |
| KIAA 0561 | X* | S/T | D/E | V/I/L |
| TAX 2 | X | S | D/E | V |
| PRIL16 | D/E/K/R | V/I/L/F/Y | X | V |
| PTN4 | D/E | S | X | V/I/L/F/Y |

X* is any non-aromatic amino acid.

6.3 Measurement of PDZ-Ligand Binding Affinity

The "A" and "G" assays of the invention can be used to determine the "apparent affinity" of binding of a PDZ ligand peptide to a PDZ-domain polypeptide. Apparent affinity is determined based on the concentration of one molecule required to saturate the binding of a second molecule (e.g., the binding of a ligand to a receptor). Two particularly useful approaches for quantitation of apparent affinity of PDZ-ligand binding are provided infra.

(1) A GST/PDZ fusion protein, as well as GST alone as a negative control, are bound to a surface (e.g., a 96-well plate) and the surface blocked and washed as described supra for the "G" assay.

(2) 50 uL per well of a solution of biotinylated PL peptide (e.g. as shown in TABLE 4) is added to the surface in increasing concentrations in PBS/BSA (e.g. at 0.1 uM, 0.33 uM, 1 uM, 3.3 uM, 10 uM, 33 uM, and 100 uM). In one embodiment, the PL peptide is allowed to react with the bound GST/PDZ fusion protein (as well as the GST alone negative control) for 10 minutes at 4 C followed by 20 minutes at 25 C. The plate is washed 3 times with ice cold PBS to remove unbound labeled peptide.

(3) The binding of the PL peptide to the immobilized PDZ-domain polypeptide is detected as described supra for the "G" assay.

(4) For each concentration of peptide, the net binding signal is determined by subtracting the binding of the peptide to GST alone from the binding of the peptide to the GST/PDZ fusion protein. The net binding signal is then plotted as a function of ligand concentration and the plot is fit (e.g. by using the Kaleidagraph software package curve fitting algorithm) to the following equation, where "Signal$_{[ligand]}$" is the net binding signal at PL peptide concentration "[ligand]," "Kd" is the apparent affinity of the binding event, and "Saturation Binding" is a constant determined by the curve fitting algorithm to optimize the fit to the experimental data:

$$\text{Signal}_{[Ligand]} = \text{Saturation Binding} \times ([\text{ligand}]/([\text{ligand}]+Kd))$$

For reliable application of the above equation it is necessary that the highest peptide ligand concentration successfully tested experimentally be greater than, or at least similar to, the calculated Kd (equivalently, the maximum observed binding should be similar to the calculated saturation binding). In cases where satisfying the above criteria proves difficult, an alternative approach (infra) can be used.

The results obtained when using approach 1 are demonstrated in FIGS. 2A and 2B. FIG. 2 shows varying concentrations of biotinylated CLASP-2 (FIG. 2A) or Fas (FIG. 2B). C-terminal peptides reacted with immobilized (plate bound) GST polypeptide or GST/PDZ fusion proteins (GST/DLG1, GST/NeDLG, and GDT/PSD95) in duplicate. The signals were normalized, plotted and fit to a saturation binding curve, yielding an apparent affinity of 21 uM for DLG1-CLASP-2 interaction, 7.5 uM for NeDLG-CLASP-2 interaction, 45 uM for PSD95-CLASP-2 interaction, and 54 uM for DLG1-Fas interaction, 54 uM for NeDLG-Fas interaction, and 85 uM for PSD95-Fas interaction.

Approach 2:

(1) A fixed concentration of a PDZ-domain polypeptide and increasing concentrations of a labeled PL peptide (labeled with, for example, biotin or fluorescein, see TABLE 4 for representative peptide amino acid sequences) are mixed together in solution and allowed to react. In one embodiment, preferred peptide concentrations are 0.1 uM, 1 uM, 10 uM, 100 uM, 1 mM. In various embodiments, appropriate reaction times can range from 10 minutes to 2 days at temperatures ranging from 4 C to 37 C. In some embodiments, the identical reaction can also be carried out using a non-PDZ domain-containing protein as a control (e.g., if the PDZ-domain polypeptide is fusion protein, the fusion partner can be used).

(2) PDZ-ligand complexes can be separated from unbound labeled peptide using a variety of methods known in the art. For example, the complexes can be separated using high performance size-exclusion chromatography (HPSEC, gel filtration) (Rabinowitz et al., 1998, Immunity 9:699), affinity chromatography (e.g. using glutathione sepharose beads), and affinity absorption (e.g., by binding to an anti-GST-coated plate as described supra).

(3) The PDZ-ligand complex is detected based on presence of the label on the peptide ligand using a variety of methods and detectors known to one of skill in the art. For example, if the label is fluorescein and the separation is achieved using HPSEC, an in-line fluorescence detector can be used. The binding can also be detected as described supra for the G assay.

(4) The PDZ-ligand binding signal is plotted as a function of ligand concentration and the plot is fit. (e.g., by using the Kaleidagraph software package curve fitting algorithm) to the following equation, where "Signal$_{[ligand]}$" is the binding signal at PL peptide concentration "[ligand]," "Kd" is the apparent affinity of the binding event, and "Saturation Binding" is a constant determined by the curve fining algorithm to optimize the fit to the experimental data:

$$\text{Signal}_{[Ligand]} = \text{Saturation Binding} \times ([\text{ligand}]/([\text{ligand}]+Kd])$$

Measurement of the affinity of a labeled peptide ligand binding to a PDZ-domain polypeptide n is useful because knowledge of the affinity (or apparent affinity) of this interaction allows rational design of inhibitors of the interaction with known potency (See EXAMPLE 2). The potency of inhibitors in inhibition would be similar to (i.e. within one-order of magnitude of) the apparent affinity of the labeled peptide ligand binding to the PDZ-domain.

Thus, in one aspect, the invention provides a method of determining the apparent affinity of binding between a PDZ domain and a ligand by immobilizing a polypeptide comprising the PDZ domain and a non-PDZ domain on a surface, contacting the immobilized polypeptide with a plurality of different concentrations of the ligand, determining the amount of binding of the ligand to the immobilized polypeptide at each of the concentrations of ligand, and calculating the apparent affinity of the binding based on that data. Typically, the polypeptide comprising the PDZ domain and a non-PDZ domain is a fusion protein. In one embodiment, the e.g., fusion protein is GST-PDZ fusion protein, but other polypeptides can also be used (e.g., a fusion protein including a PDZ domain and any of a variety of epitope tags, biotinylation signals and the like) so long as the polypeptide can be immobilized in an orientation that does not abolish the ligand binding properties of the PDZ domain, e.g, by tethering the polypeptide to the surface via the non-PDZ domain via an anti-domain antibody and leaving the PDZ domain as the free end. It was discovered, for example, reacting a PDZ-GST fusion polypeptide directly to a plastic plate provided suboptimal results. The calculation of binding affinity itself can be determined using any suitable equation (e.g., as shown supra; also see Cantor and Schimmel (1980) BIOPHYSICAL CHEMISTRY WH Freeman & Co., San Francisco) or software.

Thus, in a preferred embodiment, the polypeptide is immobilized by binding the polypeptide to an immobilized immunoglobulin that binds the non-PDZ domain (e.g., an anti-GST antibody when a GST-PDZ fusion polypeptide is used). In a preferred embodiment, the step of contacting the ligand and PDZ-domain polypeptide is carried out under the conditions provided supra in the description of the "G" assay. It will be appreciated that binding assays are conveniently carried out in multiwell plates (e.g., 24-well, 96-well plates, or 384 well plates).

The present method has considerable advantages over other methods for measuring binding affinities PDZ-PL affinities; which typically involve contacting varying concentrations of a GST-PDZ fusion protein to a ligand-coated surface. For example, some previously described methods for determining affinity (e.g., using immobilized ligand and GST-PDZ protein in solution) did not account for oligomerization state of the fusion proteins used, resulting in potential errors of more than an order of magnitude.

6.4 Assays to Identity Novel PDZ Domain Binding Moieties and to Identify Inhibitors of PDZ Protein-PL Protein Binding Although described supra primarily in terms of identifying interactions between PDZ-domain polypeptides and PL proteins, the assays described supra and other assays can also be used to identify the binding of other molecules (e.g., peptide mimetics, small molecules, and the like) to PDZ domain sequences. For example, using the assays disclosed herein, combinatorial and other libraries of compounds can be screened, e.g., for molecules that specifically bind to PDZ domains in hematopoietic cells. Screening of libraries can be accomplished by any of a variety of commonly known methods. See, e.g., the following references, which disclose screening of peptide libraries: Parmley and Smith, 1989, *Adv. Exp. Med. Biol.* 251:215–218; Scott and Smith, 1990, *Science* 249:386–390; Fowlkes et al., 1992; *BioTechniques* 13:422–427; Oldenburg et al., 1992, *Proc. Natl. Acad. Sci. USA* 89:5393–5397; Yu et al., 1994, *Cell* 76:933–945; Staudt et al., 1988, *Science* 241:577–580; Bock et al., 1992, *Nature* 355:564–566; Tuerk et al., 1992, *Proc. Natl. Acad. Sci. USA* 89:6988–6992; Ellington et al., 1992, *Nature* 355:850–852; U.S. Pat. No. 5,096,815, U.S. Pat. No. 5,223,409, and U.S. Pat. No. 5,198,346, all to Ladner et al.; Rebar and Pabo, 1993, *Science* 263:671–673; and PCT Publication No. WO 94/18318.

In a specific embodiment, screening can be carried out by contacting the library members with a hematopoietic cell PDZ-domain polypeptide immobilized on a solid support (e.g. as described supra in the "G" assay) and harvesting those library members that bind to the protein. Examples of such screening methods, termed "panning" techniques are described by way of example in Parmley and Smith, 1988, *Gene* 73:305–318; Fowlkes et al., 1992, *BioTechniques* 13:422–427; PCT Publication No. WO 94/18318; and in references cited hereinabove.

In another embodiment, the two-hybrid system for selecting interacting proteins in yeast (Fields and Song, 1989, *Nature* 340:245–246; Chien et al., 1991, *Proc. Natl. Acad. Sci. USA* 88:9578–9582) can be used to identify molecules that specifically bind to a PDZ domain-containing protein. Furthermore, the identified molecules are further tested for their ability to inhibit transmembrane receptor interactions with a PDZ domain.

In one aspect of the invention, antagonists of an interaction between a PDZ protein and a PL protein are identified. In one embodiment, a modification of the "A" assay described supra is used to identify antagonists. In one embodiment, a modification of the "G" assay described supra is used to identify antagonists.

In one embodiment, screening assays are used to detect molecules that specifically bind to PDZ domains in hematopoietic cells. Such molecules are useful as agonists or antagonists of PDZ-protein-mediated cell function (e.g., cell activation, e.g., T cell activation, vesicle transport, cytokine release, growth factors, transcriptional changes, cytoskeletin rearrangement, cell movement, chemotaxis, and the like). In one embodiment, such assays are performed to screen for leukocyte activation inhibitors for drug development. The invention thus provides assays to detect molecules that specifically bind to PDZ domain-containing proteins in hematopoietic cells. For example, recombinant cells expressing PDZ domain-encoding nucleic acids can be used to produce PDZ domains in these assays and to screen for molecules that bind to the domains. Molecules are contacted with the PDZ domain (or fragment thereof) under conditions conducive to binding, and then molecules that specifically bind to such domains are identified. Methods that can be used to carry out the foregoing are commonly known in the art.

It will be appreciated by the ordinarily skilled practitioner that, in one embodiment, antagonists are identified by conducting the A or G assays in the presence and absence of a known or candidate antagonist. When decreased binding is observed in the presence of a compound, that compound is identified as an antagonist. Increased binding in the presence of a compound signifies that the compound is an agonist.

For example, in one assay, a test compound can be identified as an inhibitor (antagonist) of binding between a PDZ protein and a PL protein by contacting a PDZ domain polypeptide and a PL peptide in the presence and absence of the test compound, under conditions in which they would (but for the presence of the test compound) form a complex, and detecting the formation of the complex in the presence and absence of the test compound. It will be appreciated that less complex formation in the presence of the test compound than in the absence of the compound indicates that the test compound is an inhibitor of a PDZ protein-PL protein binding. In various embodiments, the PL peptide comprises an amino acid sequence substantially identical to the C-terminal sequence of a PL protein (e.g., CD6, CD49E, CD49F, CD138, Clasp-1, Clasp-4, VCAM1, Clasp-2, CD95, DNAM-1, CD83, CD44, CD4, CD97, Neurexin, CD3n, DOCK2, CD34, FceRIb, or FasLigand).

In one embodiment, the "G" assay is used in the presence or absence of an candidate inhibitor. In one embodiment, the "A" assay is used in the presense or absence of a candiate inhibitor.

In one embodiment (in which a G assay is used), one or more PDZ domain-containing GST-fusion proteins are bound to the surface of wells of a 96-well plate as described supra (with appropriate controls including nonfusion GST protein). All fusion proteins are bound in multiple wells so that appropriate controls and statistical analysis can be done. A test compound in BSA/PBS (typically at multiple different concentrations) is added to wells. Immediately thereafter, 30 uL of a detectably labeled (e.g., biotinylated) peptide known to bind to the relevant PDZ domain (see, e.g., TABLE 2) is added in each of the wells at a final concentration of, e.g., between about 2 uM and about 40 uM, typically 5 uM, 15 uM, or 25 uM. This mixture is then allowed to react with the PDZ fusion protein bound to the surface for 10 minutes at 4° C. followed by 20 minutes at 25° C. The surface is washed free of unbound peptide three times with ice cold PBS and the amount of binding of the peptide in the presence and absence of the test compound is determined. Usually, the level of binding is measured for each set of replica wells (e.g. duplicates) by subtracting the mean GST alone background from the mean of the raw measurement of peptide binding in these wells.

In an alternative embodiment, the A assay is carried out in the presence or absence of an test candidate to identify inhibitors of PL-PDZ interactions.

In one embodiment, a test compound is determined to be a specific inhibitor of the binding of the PDZ domain (P) and a PL (L) sequence when, at a test compound concentration of less than or equal to 1 mM (e.g., less than or equal to: 500 uM, 100 uM, 10 uM, 1 uM, 100 nM or 1 nM) the binding of P to L in the presence of the test compound less than about 50% of the binding in the absence of the test compound. (in various embodiments, less than about 25%, less than about 10%, or less than about 1%). Preferably, the net signal of binding of P to L in the presence of the test compound plus six (6) times the standard error of the signal in the presence of the test compound is less than the binding signal in the absence of the test compound.

In one embodiment, assays for an inhibitor are carried out using a single PDZ protein-PL protein pair (e.g., a PDZ domain fusion protein and a PL peptide). In a related embodiment, the assays are carried out using a plurality of pairs, such as a plurality of different pairs listed in TABLE 2.

In some embodiments, it is desirable to identify compounds that, at a given concentration, inhibit the binding of one PL-PDZ pair, but do not inhibit (or inhibit to a lesser degree) the binding of a specified second PL-PDZ pair. These antagonists can be identified by carrying out a series of assays using a candidate inhibitor and different PL-PDZ pairs (e.g., as shown in the matrix of TABLE 2) and comparing the results of the assays. All such pairwise combinations are contemplated by the invention (e.g., test compound inhibits binding of $PL_1$ to $PDZ_1$ to a greater degree than it inhibits binding of $PL_1$ to $PDZ_2$ or $PL_2$ to $PDZ_2$). Importantly, it will be appreciated that, based on the data provided in TABLE 2 and disclosed herein (and additional data that can be generated using the methods described herein) inhibitors with different specificities can readily be designed.

For example, according to the invention, the Ki ("potency") of an inhibitor of a PDZ-PL interaction can be determined. Ki is a measure of the concentration of an inhibitor required to have a biological effect. For example, administration of an inhibitor of a PDZ-PL interaction in an amount sufficient to result in an intracellular inhibitor concentration of at least between about 1 and about 100 Ki is expected to inhibit the biological response mediated by the target PDZ-PL interaction. In one aspect of the invention, the Kd measurement of PDZ-PL binding as determined using the methods supra is used in determining Ki.

Thus, in one aspect, the invention provides a method of determining the potency (Ki) of an inhibitor or suspected inhibitor of binding between a PDZ domain and a ligand by immobilizing a polypeptide comprising the PDZ domain and a non-PDZ domain on a surface, contacting the immobilized polypeptide with a plurality of different mixtures of the ligand and inhibitor, wherein the different mixtures comprise a fixed amount of ligand and different concentrations of the inhibitor, determining the amount of ligand bound at the different concentrations of inhibitor, and calculating the Ki of the binding based on the amount of ligand bound in the presence of different concentrations of the inhibitor. In an embodiment, the polypeptide is immobilized by binding the polypeptide to an immobilized immunoglobulin that binds the non-PDZ domain. This method, which is based on the "G" assay described supra, is particularly suited for high-throughput analysis of the Ki for inhibitors of PDZ-ligand interactions. Further, using this method, the inhibition of the PDZ-ligand interaction itself is measured, without distortion of measurements by avidity effects.

Typically, at least a portion of the ligand is detectably labeled to permit easy quantitation of ligand binding.

It will be appreciated that the concentration of ligand and concentrations of inhibitor are selected to allow meaningful detection of inhibition. Thus, the concentration of the ligand whose binding is to be blocked is close to or less than its binding affinity (e.g., preferably less than the 5× Kd of the interaction, more preferably less than 2× Kd, most preferably less than 1× Kd). Thus, the ligand is typically present at a concentration of less than 2 Kd (e.g., between about 0.01 Kd and about 2 Kd) and the concentrations of the test inhibitor typically range from 1 nM to 100 uM (e.g. a 4-fold dilution series with highest concentration 10 uM or 1 mM). In a preferred embodiment, the Kd is determined using the assay disclosed supra.

The Ki of the binding can be calculated by any of a variety of methods routinely used in the art, based on the amount of ligand bound in the presence of different concentrations of the inhibitor. in an illustrative embodiment, for example, a plot of labeled ligand binding versus inhibitor concentration is fit to the equation:

$$S_{inhibitor} = S_0 * Ki/([I]+Ki)$$

where $S_{inhibitor}$ is the signal of labeled ligand binding to immobilized PDZ domain in the presence of inhibitor at concentration [I] and $S_0$ is the signal in the absence of inhibitor (i.e., [I]=0). Typically [I] is expressed as a molar concentration.

In another aspect of the invention, an enhancer (sometimes referred to as, augmentor or agonist) of binding between a PDZ domain and a ligand is identified by immobilizing a polypeptide comprising the PDZ domain and a non-PDZ domain on a surface, contacting the immobilized polypeptide with the ligand in the presence of a test agent and determining the amount of ligand bound, and comparing the amount of ligand bound in the presence of the test agent with the amount of ligand bound by the polypeptide in the absence of the test agent. At least two-fold (often at least 5-fold) greater binding in the presence of the test agent compared to the absence of the test agent indicates that the test agent is an agent that enhances the binding of the PDZ domain to the ligand. As noted supra, agents that enhance PDZ-ligand interactions are useful for disruption (dysregulation) of biological events requiring normal PDZ-ligand function (e.g., cancer cell division and metastasis, and activation and migration of immune cells).

The invention also provides methods for determining the "potency" or "$K_{enhancer}$" of an enhancer of a PDZ-ligand interaction. For example, according to the invention, the $K_{enhancer}$ of an enhancer of a PDZ-PL interaction can be determined, e.g., using the Kd of PDZ-PL binding as determined using the methods described supra. $K_{enhancer}$ is a measure of the concentration of an enhancer expected to have a biological effect. For example, administration of an enhancer of a PDZ-PL interaction in an amount sufficient to result in an intracellular inhibitor concentration of at least between about 0.1 and about 100 $K_{enhancer}$ (e.g., between about 0.5 and about 50 $K_{enhancer}$) is expected to disrupt the biological response mediated by the target PDZ-PL interaction.

Thus, in one aspect the invention provides a method of determining the potency ($K_{enhancer}$) of an enhancer or suspected enhancer of binding between a PDZ domain and a ligand by immobilizing a polypeptide comprising the PDZ domain and a non-PDZ domain on a surface, contacting the immobilized polypeptide with a plurality of different mixtures of the ligand and enhancer, wherein the different mixtures comprise a fixed amount of ligand, at least a portion of which is detectably labeled, and different concentrations of the enhancer, determining the amount of ligand bound at the different concentrations of enhancer, and calculating the potency ($K_{enhancer}$) of the enhancer from the binding based on the amount of ligand bound in the presence of different concentrations of the enhancer. Typically, at least a portion of the ligand is detectably labeled to permit easy quantitation of ligand binding. This method, which is based on the "G" assay described supra, is particularly suited for high-throughput analysis of the $K_{enhancer}$ for enhancers of PDZ-ligand interactions.

It will be appreciated that the concentration of ligand and concentrations of enhancer are selected to allow meaningful detection of enhanced binding. Thus, the ligand is typically present at a concentration of between about 0.01 Kd and about 0.5 Kd and the concentrations of the test agent/enhancer typically range from 1 nM to 1 mM (e.g. a 4-fold dilution series with highest concentration 10 uM or 1 mM). In a preferred embodiment, the Kd is determined using the assay disclosed supra.

The potency of the binding can be determined by a variety of standard methods based on the amount of ligand bound in the presence of different concentrations of the enhancer or augmentor. For example, a plot of labeled ligand binding versus enhancer concentration can be fit to the equation:

$$S([E])=S(0)+(S(0)*(D_{enhancer})*[E])/([E]+K_{enhancer})$$

where "$K_{enhancer}$" is the potency of the augmenting compound, and "$D_{enhancer}$" is the fold-increase in binding of the labeled ligand obtained with addition of saturating amounts of the enhancing compound, [E] is the concentration of the enhancer. It will be understood that saturating amounts are the amount of enhancer such that further addition does not significantly increase the binding signal. Knowledge of "$K_{enhancer}$" is useful because it describes a concentration of the augmenting compound in a target cell that will result in a biological effect due to dysregulation of the PDZ-PL interaction. Typical therapeutic concentrations are between about 0.1 and about 100 $K_{enhancer}$.

Global Analysis of PDZ-PL Interactions

As described supra, the present invention provides powerful methods for analysis of PDZ-ligand interactions, including high-throughput methods such as the "G" assay and affinity assays described supra. In one embodiment of the invention, the affinity is determined for a particular ligand and a plurality of PDZ proteins. Typically the plurality is at least 5, and often at least 25, or at least 40 different PDZ proteins. In a preferred embodiment, the plurality of different PDZ proteins are from a particular tissue (e.g., central nervous system, spleen, cardiac muscle, kidney) or a particular class or type of cell, (e.g., a hematopoietic cell, a lymphocyte, a neuron) and the like. In a most preferred embodiment, the plurality of different PDZ proteins represents a substantial fraction (e.g., typically a majority, more often at least 80%) of all of the PDZ proteins known to be, or suspected of being, expressed in the tissue or cell(s), e.g., all of the PDZ proteins known to be present in lymphocytes. In an embodiment, the plurality is at least 50%, usually at least 80%, at least 90% or all of the PDZ proteins disclosed herein as being expressed in hematopoietic cells (see Table 6).

In one embodiment of the invention, the binding of a ligand to the plurality of PDZ proteins is determined. Using this method, it is possible to identify a particular PDZ domain bound with particular specificity by the ligand. The binding may be designated as "specific" if the affinity of the ligand to the particular PDZ domain is at least 2-fold that of the binding to other PDZ domains in the plurality (e.g., present in that cell type). The binding is deemed "very specific" if the affinity is at least 10-fold higher than to any other PDZ in the plurality or, alternatively, at least 10-fold higher than to at least 90%, more often 95% of the other PDZs in a defined plurality. Similarly, the binding is deemed "exceedingly specific" if it is at least 100-fold higher. For example, a ligand cound bind to 2 different PDZs with an affinity of 1 uM and to no other PDZs out of a set 40 with an affinty of less than 100 uM. This would constitute specific binding to those 2 PDZs. Similar measures of specifity are used to describe binding of a PDZ to a plurality of PLs.

It will be recognized that high specificity PDZ-PL interactions represent potentially more valuable targets for achieving a desired biological effect the ability of an inhibitor or enhancer to act with high specificity is often desirable. In particular, the most specific PDZ-ligand interactions are also the best therapeutic targets, allowing specific inhibition of the interaction.

In an embodiment an interaction between a PDZ and a PL is deemed.

Thus, in one embodiment, the invention provides a method of identifying a high specificity interaction between a particular PDZ domain and a ligand known or suspected of binding at least one PDZ domain, by providing a plurality of different immobilized polypeptides, each of said polypeptides comprising a PDZ domain and a non-PDZ domain; determining the affinity of the ligand for each of said polypeptides, and comparing the affinity of binding of the ligand to each of said polypeptides, wherein an interaction between the ligand and a particular PDZ domain is deemed to have high specificity when the ligand binds an immobilized polypeptide comprising the particular PDZ domain with at least 2-fold higher affinity than to immobilized polypeptides not comprising the particular PDZ domain.

In a related aspect, the affinity of binding of a specific PDZ domain to a plurality of ligands (or suspected ligands) is determined. For example, in one embodiment, the invention provides a method of identifying a high specificity interaction between a PDZ domain and a particular ligand known or suspected of binding at least one PDZ domain, by providing an immobilized polypeptide comprising the PDZ domain and a non-PDZ domain; determining the affinity of each of a plurality of ligands for the polypeptide, and comparing the affinity of binding of each of the ligands to the polypeptide, wherein an interaction between a particular ligand and the PDZ domain is deemed to have high specificity when the ligand binds an immobilized polypeptide comprising the PDZ domain with at least 2-fold higher affinity than other ligands tested. Thus, the binding may be designated as "specific" if the affinity of the PDZ to the particular PL is at least 2-fold that of the binding to other PLs in the plurality (e.g., present in that cell type). The binding is deemed "very specific" if the affinity is at least 10-fold higher than to any other PL in the plurality or, alternatively, at least 10-fold higher than to at least 90%, more often 95% of the other PLs in a defined plurality. Similarly, the binding is deemed "exceedingly specific" if it is at least 100-fold higher. Typically the plurality is at least 5 different ligands, more often at lease 10.

TABLE 6

PDZ Domain-Containing Genes Expressed in T Cells and B Cells

| PDZ gen name | Expressed in T/B cells | Gen bank acc. # |
| --- | --- | --- |
| AF6 | T-/B-cells | 430993 |
| BAII associated prot. | T-/B-cells | 3370997 |
| CASK (mouse) | T-/B-cells | 3087815 |
| Connector enhancer | B-cells | 3930780 |
| Cytohesin bind. Prot. | T-/B-cells | 3192908 |
| DLG1 | T-/B-cells | 475816 |
| DLG5 (pdlg) | T-/B-cells | 3650451 |
| DVL1 | T-/B-cells | 2291005 |
| DVL3 | T-/B-cells | 6806886 |
| GTPase | T-/B-cells | 3004860 |
| Guanin-exchange factor 1 | T-/B-cells | 6650765 |
| hypoth. 41.8 kd | T-/B-cells | 3882222 |
| PDZ domain containing prot. | T cells only | 2370148 |
| KIAA147 | T-/B-cells | 1469875 |
| KIAA0300 | T-/B-cells | 2224540 |
| KIAA0303 | T-/B-cells | 2224546 |
| KIAA0316 | T-cells | 6683123 |
| KIAA0380 | T-/B-cells | 2224700 |
| KIAA0440 | T-/B-cells | 2662160 |
| KIAA0545 | T-/B-cells | 303617 |
| KIAA0561 | T-/B-cells | 3043645 |
| KIAA0559 | B-cells | 3043641 |
| KIAA0807 | T-/B-cells | 3882334 |
| KIAA0858 | T-/B-cells | 42402004 |
| KIAA0902 | T-/B-cells | 4240304 |
| LIMK1 | T-/B-cells | 4587498 |
| LIMK2 | T-/B-cells | 1805593 |
| LIM domain prot | T-/B-cells | 2957144 |
| LIM protein | T-/B-cells | 3108092 |
| MINT1 | T-/B-cells | 2625024 |
| MINT3 | T-/B-cells | 3169808 |
| MPP1 | T-/B-cells | 189785 |
| MPP2 | T-/B-cells | 939884 |
| NE-DLG | T-/B-cells | 1515354 |
| NOS1 | T-/B-cells | 642525 |
| novel serine protease | T-/B-cells | 1621243 |
| PDZK1 | T-/B-cells | 2944188 |
| PICK8 | T-/B-cells | 4678411 |
| PTN-3 | T-/B-cells | 179912 |
| PTN-4 | B cells | 190747 |
| prIL16 | T-/B-cells | 1478492 |
| PSD95 | T-/B-cells | 3318652 |
| RPIP8 | T-/B-cells | 5730014 |
| RGS12 | T-/B-cells | 3290015 |
| serine protease | T-/B-cells | 2738914 |
| 26s subunit p27 | T-cells | 9184389 |
| hSYNTENIN | T-/B-cells | 2795862 |
| SYNTR. 1 alpha | T-/B-cells | 1145727 |
| TAX1-IP | T-/B-cells | 2613001 |
| TAX2-IP | T-/B-cells | 2613003 |

TABLE 6-continued

PDZ Domain-Containing Genes Expressed in T Cells and B Cells

| PDZ gen name | Expressed in T/B cells | Gen bank acc. # |
| --- | --- | --- |
| TAX2-like protein | T-/B-cells | 3253116 |
| TAX33-IP | T-/B-cells | 2613007 |
| TAX40-IP (PAR-6) | T-/B-cells | 2613011 |
| Tax43-IP (SYN. Beta1) | T-/B-cells | 2613011 |
| TIAM | T-/B-cells | 4507500 |
| wwp3 | T-/B-cells | 2695619 |
| X11 prot. beta | T-/B-cells | 3005559 |
| ZO1 | T-/B-cells | 292937 |

Use of Array for Global Predictions

One discovery of the present inventors relates to the important and extensive roles played by interactions between PDZ proteins and PL proteins, particularly in the biological function of hematopoietic cells and other cells involved in the immune response. Further, it has been discovered that valuable information can be ascertained by analysis (e.g., simultaneous analysis) of a large number of PDZ-PL interactions. In a most preferred embodiment, the analysis encompasses all of the PDZ proteins expressed in a particular tissue (e.g., spleen) or type or class of cell (e.g., hematopoietic cell, neuron, lymphocyte, B cell, T cell and the like). Alternatively, the analysis encompasses at least about 5, or at least about 10, or at least about 12, or at least about 15 and often at least 50 different polypeptides; or a substantial fraction (e.g., typically a majority, more often at least 80%) of all of the PDZ proteins known to be, or suspected of being, expressed in the tissue or cell(s), e.g., all of the PDZ proteins known to be present in lymphocytes. In an embodiment, the plurality is at least 50%, usually at least 80%, at least 90% or all of the PDZ proteins disclosed herein as being expressed in hematopoietic cells (see Table 6).

In an embodiment the array includes at least one, preferably at least 5 or at least and sometimes all of the following PDZ proteins present in lymphocytes: BAI I associated prot., Connector enhancer, DLG5 (pdlg), DVL3, GTPase, Guanin-exchange factor 1, PDZ domain containing prot., KIAA147, KIAA0300, KIAA0380, KIAA0440, KIAA0545, KIAA0807, KIAA0858, KIAA0902, novel serine protease, PDZK1, PICK8, PTN-3, RPIP8, serine protease, 26s subunit p27, hSYNTENIN, TAX1-IP, TAX2-like protein, wwp3, X11 prot. beta, ZO1.

It will be apparent from this disclosure that analysis of the relatively large number of different interactions preferably takes place simultaneously. In this context, "simultaneously" means that the analysis of several different PDZ-PL interactions (or the effect of a test agent on such interactions) is assessed means together (e.g., the same day or same hour). Typically the analysis is carried out in a highthroughput (e.g., robotic) fashion. One advantage of this method of simultaneous analysis is that it permits rigorous comparison of multiple different PDZ-PL interactions. For example, as explained in detail elsewhere herein, simultaneous analysis (and use of the arrays described infra) facilitates, for example, the direct comparison of the effect of an agent (e.g., an potential interaction inhibitor) on the interactions between a substantial portion of PDZs and/or PLs in a tissue or cell.

Accordingly, in one aspect, the invention provides an array of immobilized polypeptide comprising the PDZ domain and a non-PDZ domain on a surface. Typically, the array comprises at least about 5, or at least about 10, or at least about 12, or at least about 15 and often at least 50 different polypeptides. In one preferred embodiment, the different PDZ proteins are from a particular tissue (e.g., central nervous system, speen, cardiac muscle, kidney) or a particular class or type of cell, (e.g., a hematopoietic cell, a lymphocyte, a neuron) and the like. In a most preferred embodiment, the plurality of different PDZ proteins represents a substantial fraction (e.g., typically a majority, more often at least 80%) of all of the PDZ proteins known to be, or suspected of being, expressed in the tissue or cell(s), e.g., all of the PDZ proteins known to be present in lymphocytes. In an embodiment, the plurality is at least 50%, usually at least 80%, at least 90% or all of the PDZ proteins disclosed herein as being expressed in hematopoietic cells (see Table 6) all of the PDZ proteins known to be present in lymphocytes. In an embodiment, the plurality is at least 50%, usually at least 80%, at least 90% or all of the PDZ proteins disclosed herein as being expressed in hematopoietic cells (see Table 6).

In an embodiment the array includes at least one, preferably at least 5 and sometimes all of the following PDZ proteins present in lymphocytes: BAI I associated prot., Connector enhancer, DLG5 (pdlg), DVL3, GTPase, Guanin-exchange factor 1, PDZ domain containing prot., KIAA147, KIAA0300, KIAA0380, KIAA0440, KIAA0545, KIAA0807, KIAA0858, KIAA0902, novel serine protease, PDZK1, PICK8, PTN-3, RPIP8, serine protease, 26s subunit p27, hSYNTENIN, TAX1-IP, TAX2-like protein, wwp3, X11 prot. beta, ZO1. In this context, "array" refers to an ordered series of of immobilized polypeptides in which the identity of each polypeptide is associated with its location. In some embodiments the plurality of polypeptides are arrayed in a "common" area such that they can be simultaneously exposed to a solution (e.g., containing a ligand or test agent). For example, the plurality of polypeptides can be on a slide, plate or similar surface, which may be plastic, glass, metal, silica, beads or other surface to which proteins can be immobilized. In a different embodiment, the different immobilized polypeptides are situated in separate areas, such as different wells of multi-well plate (e.g., a 24-well plate, a 96-well plate, a 384 well plate, and the like). It will be recognized that a similar advantage can be obtained by using multiple arrays in tandem.

a) Analysis of PDZ-PL Inhibition Profile

In one aspect, the invention provides a method for determining if a test compound inhibits any PDZ-ligand interaction in large set of PDZ-ligand interaction (e.g., some or all of the PDZ-ligands interactions described in Table 2; a majority of the PDZ-ligands identified in a particular cell or tissue as described supra (e.g., lymphocytes) and the like. in one embodiment, the PDZ domains of interest are expressed as GST-PDZ fusion proteins and immobilized as described herein. For each PDZ domain, a labeled ligand that binds to the domain with a known affinity is identified as described herein.

As disclosed herein, numerous PDZ-PL interactions occur in cells of the hematopoietic system. For any known or suspected modulator (e.g., inhibitor) of a PDL-PL interaction(s), it is useful to know which interactions are inhibited (or augmented). For example, an agent that inhibits all PDZ-PL interactions in a cell (e.g., a lymphocyte) will have different uses than an agent that inhibits only one, or a small number, of specific PDZ-PL interactions. The profile of PDZ interactions inhibited by a particular agent is referred to as the "inhibition profile" for the agent, and is described in detail below. The profile of PDZ interactions enhanced by a particular agent is referred to as the "enhancement profile" for the agent. It will be readily apparent to one of skill guided by the description of the inhibition profile how to determine the enhancement profile for an agent. The present invention provides methods for determining the PDZ interaction (inhibition/enhancement) profile of an agent in a single assay.

In one aspect, the invention provides a method for determining the PDZ-PL inhibition profile of a compound by providing (i) a plurality of different immobilized polypeptides, each of said polypeptides comprising a PDZ domain and a non-PDZ domain and (ii) a plurality of corresponding ligands, wherein each ligand binds at least one PDZ domain in (i), then contacting each of said immobilized polypeptides in (i) with a corresponding ligand in (ii) in the presence and absence of a test compound, and determining for each polypeptide-ligand pair whether the test compound inhibits binding between the immobilized polypeptide and the corresponding ligand.

Typically the plurality is at least 5, and often at least 25, or at least 40 different PDZ proteins. In a preferred embodiment, the plurality of different ligands and the plurality of different PDZ proteins are from the same tissue or a particular class or type of cell, e.g., a hematopoietic cell, a lymphocyte, a neuron and the like. In a most preferred embodiment, the plurality of different PDZs represents a substantial fraction (e.g., at least 80%) of all of the PDZs known to be, or suspected of being, expressed in the tissue or cell(s), e.g., all of the PDZs known to be present in lymphocytes (for example, at least 80%, at least 90% or all of the PDZs disclosed herein as being expressed in hematopoietic cells).

In one embodiment, the inhibition profile is determined as follows: A plurality (e.g., all known) PDZ domains expressed in a cell (e.g., lymphocytes) are expressed as GST-fusion proteins and immobilized without altering their ligand binding properties as described supra. For each PDZ domain, a labeled ligand that binds to this domain with a known affinity is identified. If the set of PDZ domains expressed in lymphocytes is denoted by {P1 . . . Pn}, any given PDZ domain Pi binds a (labeled) ligand Li with affinity $K_d i$. To determine the inhibition profile for a test agent "compound X" the "G" assay (supra) can be performed as follows in 96-well plates with rows A–H and columns 1–12. Column 1 is coated with P1 and washed. The corresponding ligand L1 is added to each washed coated well of column 1 at a concentration 0.5 $K_d 1$ with (rows B, D, F, H) or without (rows A, C, E, F) between about 1 and about 1000 uM) of test compound X. Column 2 is coated with P2, and L2 (at a concentration 0.5 $K_d 2$) is added with or without inhibitor X. Additional PDZ domains and ligands are similarly tested.

Compound X is considered to inhibit the binding of Li to Pi if the average signal in the wells of column i containing X is less than half the signal in the equivalent wells of the column lacking X. Thus, in this single assay one determines the fill set of lymphocyte PDZs that are inhibited by compound X.

In some embodiments, the test compound X is a mixture of compounds, such as the product of a combinatorial chemistry synthesis as described supra. In some embodiments, the test compound is known to have a desired biological effect, and the assay is used to determine the mechanism of action (i.e., if the biological effect is due to modulating a PDZ-PL interaction).

It will be apparent that an agent that modulates only one, or a few PDZ-PL interactions, in a panel (e.g., a panel of all known PDZs lymphocytes, a panel of at least 10, at least 20 or at least 50 PDZ domains) is a more specific modulator than an agent that modulate many or most interactions. Typically, an agent that modulates less than 20% of PDZ domains in a panel (e.g., Table 2) is deemed a "specific" inhibitor, less than 6% a "very specific" inhibitor, and a single PDZ domain a "maximally specific" inhibitor.

It will also be appreciated that "compound X" may be a composition containing mixture of compounds (e.g., generated using combinatorial chemistry methods) rather than a single compound.

Several variations of this assay are contemplated:

In some alternative embodiments, the assay above is performed using varying concentrations of the test compound X, rather than fixed concentration. This allows determination of the Ki of the X for each PDZ as described above.

In an alternative embodiment, instead of pairing each PDZ Pi with a specific labeled ligand Li, a mixture of different labeled ligands is created that such that for every PDZ at least one of the ligands in the mixture binds to this PDZ sufficiently to detect the binding in the "G" assay. This mixture is then used for every PDZ domain.

In one embodiment, compound X is known to have a desired biological effect, but the chemical mechanism by which it has that effect is unknown. The assays of the invention can then be used to determine if compound X has its effect by binding to a PDZ domain.

In one embodiment, PDZ-domain containing proteins are classified in to groups based on their biological function, e.g. into those that regulate chemotaxis versus those that regulate transcription. An optimal inhibitor of a particular function (e.g., including but not limited to an anti-chemotactic agent, an anti-T cell activation agent, cell-cycle control, vesicle transport, apoptosis, etc.) will inhibit multiple PDZ-ligand interactions involved in the function (e.g., chemotaxis, activation) but few other interactions. Thus, the assay is used in one embodiment in screening and design of a drug that specifically blocks a particular function. For example, an agent designed to block chemotaxis might be identified because, at a given concentration, the agent inhibits 2 or more PDZs involved in chemotaxis but fewer than 3 other PDZs, or that inhibits PDZs involved in chemotaxis with a Ki>10-fold better than for other PDZs. Thus, the invention provides a method for identifying an agent that inhibits a first selected PDZ-PL interaction or plurality of interactions but does not inhibit a second selected PDZ-PL interaction or plurality of interactions. The two (or more) sets of interactions can be selected on the basis of the known biological function of the PDZ proteins, the tissue specificity of the PDZ proteins, or any other criteria. Moreover, the assay can be used to determine effective doses (i.e., drug concentrations) that result in desired biological effects while avoiding undesirable effects.

b) Side Effects of PDZ-PL Modulator Interactions

In a related embodiment, the invention provides a method for determining likely side effects of a therapeutic that inhibits PDZ-ligand interactions. The method entails identifying those target tissues, organs or cell types that express PDZ proteins and ligands that are disrupted by a specified inhibitor. If, at a therapeutic dosage, a drug intended to have an effect in one organ system (e.g., hematopoietic system) disrupts PDZ-PL interactions in a different system (e.g., CNS) it can be predicted that the drug will have effects ("side effects") on the second system. It will be apparent that the information obtained from this assay will be useful in the rational design and selection of drugs that do not have the side-effect.

In one embodiment, for example, a comprehensive PDZ protein set is obtained. A "perfectly comprehensive" PDZ protein set is defined as the set of all PDZ proteins expressed in the subject animal (e.g., humans). A comprehensive set may be obtained by analysis of, for example, the human genome sequence. However, a "perfectly comprehensive" set is not required and any reasonably large set of PDZ domain proteins (e.g., the set of all known PDZ proteins; or the set listed in Table 6) will provide valuable information.

In one embodiment, the method involves some of all of the following steps:

a) For each PDZ protein, determine the tissues in which it is highly expressed. This can be done experimentally although the information generally will be available in the scientific literature;

b) For each PDZ protein (or as many as possible), identify the cognate PL(s) bound by the PDZ protein;

c) Determine the Ki at which the test agent inhibits each PDZ-PL interaction, using the methods described supra;

d) From this information it is possible to calculate the pattern of PDZ-PL interactions disrupted at various concentrations of the test agent.

By correlating the set of PDZ-PL interactions disrupted with the expression pattern of the members of that set, it will be possible to identify the tissues likely affected by the agent.

Additional steps can also be carried out, including determining whether a specified tissue or cell type is exposed to an agent following a particular route of administration. This can be determined using basis pharmacokinetic methods and principles.

Modulation of Activities

The PDZ binding moieties and PDZ protein-PL protein binding antagonists of the invention are used to modulate biological activities or functions of cells (e.g., hematopoietic cells, such as T cells and B cells and the like), endothelial cells, and other immune system cells, as described herein, and for treatment of diseases and conditions in human and nonhuman animals (e.g., experimental models). Exemplary biological acitivities are listed supra.

When administered to patients, the compounds of the invention (e.g., PL-PDZ interaction inhibitors) are useful for treating (ameliorating symptoms of) a variety of diseases and conditions, including diseases characterized by inflammatory and humoral immune responses, e.g., inflammation, allergy (e.g., systemic anaphylaxis, hypersensitivity responses, drug allergies, insect sting allergies; inflammatory bowel diseases, ulcerative colitis, ileitis and enteritis; psoriasis and inflammatory dermatoses, scleroderma; respiratory allergic diseases such as asthma, allergic rhinitis, hypersensitivity lung diseases, and the like vasculitis, rh incompatibility, transfusion reactions, drug sensitivities, PIH, atopic dermatitis, eczema, rhinnitis; autoimmune diseases, such as arthritis (rheumatoid and psoriatic), multiple sclerosis, systemic lupus erythematosus, insulin-dependent diabetes, glomerulonephritis, scleroderma, MCTD, IDDM, Hashimoto thyroiditis, Goodpasture syndrome, psoriasis and the like, osteoarthritis, polyarthritis, graft rejection (e.g., allograft rejection, e.g., renal allograft rejection, graft-vs-host disease, transplantation rejection (cardiac, kidney, lung, liver, small bowel, cornea, pancreas, cadaver, autologous, bone marrow, xenotransplantation)), atherosclerosis, angiogenesis-dependent disorders, cancers (e.g., melanomas and breast cancer, prostrate cancer, leukemias, lymphomas, metastatic disease), infectious diseases (e.g., viral infection, such as HIV, measles, parainfluenza, virus-mediated cell fusion), ischemia (e.g., post-myocardial infarction complications, joint injury, kidney, scleroderma).

The PL proteins and PDZ proteins listed in TABLE 2 are well characterized, and one of skill, guided by this disclosure (including the discovery of the interactions between PL proteins and PDZ proteins described herein), will recognize many uses for modulators (e.g., enhancers or inhibitors) of PDZ-PL interactions such as those described in TABLE 2. To further assist the reader, a discussion of the characteristics of selected PL proteins (and their function) is provided infra. It will be recognized that this discussion is not comprehensive and is not intended to limit the invention in any way. Moreover, nothing in this section should be construed as an intention by the inventors to be limited to a particular mechanism of action.

A. CD6

As shown supra, CD6 binds PDZ protein 41.8. CD6 is expressed on thymocytes, T cells, and B cell chronic lymphocytic leukemias. CD6 plays a role in T cell co-stimulation and CD6 negative T cells are less autoreactive than CD6 positive T cells. Inhibition of CD6 and CD6/41.8 interactions is predicted to reduce the symptoms of graft-versus-host disease (GVHD) or psoriasis. Thus, in one embodiment of the invention, GVHD is reduced in a patient receiving donor bone marrow cells by pre-treating the cells with an effective amount of an antagonist. In combination with post-transplantation immunosuppressive therapy such as FK506, Cellcept, or cyclosporin, CD6-PDZ interaction inhibitors will improve overall survival of transplantation patients (e.g., leukemia patients).

B. CD49e (ALPHA-4)

As shown by the experiments reported herein, the C-terminal end of CD49e binds to the PDZ-domain-containing protein41.8 kD. CD49e is a 110 kD transmembrane membrane protein of the integrin alpha family (integrin alpha 5). Paired with the integrin beta-1 subunit it forms VLA-5. VLA-5 is expressed predominantly on hematopoietic and lymphoid lineage cells including monocytes, basophils, T cells, and activated B cells. VLA-5 is the receptor for the ubiquitously-expressed adhesion molecule fibronectin. Tissue injury such as myocardial infarction releases soluble fragments of fibronectin. Binding of these soluble fragments to VLA-5 results in chemotaxis of immune cells including monocytes to the source of fibronectin, as well as down-modulation of VLA-5 expression on these cells. Such ligand-induced down-modulation is a common and required feature of chemotaxic receptors. Once immune cells migrate fully to the source of fibronectin, adhesion to the fibronectin surface is enhanced by fibronectin-VLA-5 interaction. Without intending to be bound by a particular mechanism, the 41.8/CD49e interaction is believed to be necessary for proper membrane distribution of CD49e and/or recycling of CD49e such that when it is disrupted, the migration and adherence to fibronectin-containing surfaces is similarly disrupted, resulting in an inability of immune system cells to effectively migrate toward a fibronectin source and adhere to fibronectin-containing surfaces. Such disruption would therefore result in desirable reduced inflammatory processes, including reduced post-myocardial infarction inflammation. Other diseases to be treated include but are not limited to joint inflammation, psoriasis, contact allergy, Crohn's Disease, inflammatory bowel disease, eczema, atopic dermatitis.

C. CD49F (VLA-6 α Subunit)

As shown supra, CD49F binds PDZ protein 41.8. CD49f is known as an integrin subunit that pairs either with the β1 integrin subunit (CD29), forming VLA-6, or with CD104 (β4 integrin subunit). The integrin supergene family consists of a number of cell surface αβ heterodimers important for many different physiologic processes, including embryogenesis, thrombosis, wound healing, tumorigenesis and immune responses. Each β chain can pair with various α chains. Both VLA-6 and CD49f/CD104 are widely expressed on epithelia in non-lymphoid tissues. VLA-6 is also expressed on platelets, monocytes, thymocytes and T lymphocytes, with an increased expression on activated and resting memory T cells.

Inhibition of interactions between VLA-6 and 41.8 has a number of therapeutic functions such as the prevention and treatment of metastatic cancers, and treatment of overactive immunity. For example, VLA-6 is associated with invasivion of prostate carcinoma and plays a role in the metastasis of breast cancer. Blockage of VLA-6 function combined with conventional treatment for prostrate cancer, would be a more effective treatment by preventing metastatic disease (see, Cress et al., 1995, Cancer Metastasis R). Blockage of CD49f through PDZ interaction may also treat Rh incompatibility by blunting memory response or in the treatment of keloids.

D. CD138 (Syndecan-1)

CD 138 is a transmembrane proteoglycan receptor with the extracellular domain functioning as a ligand binding domain for various extracellular matrix components and the intracellular portion functioning to alter cytoskeleton and transduce intracellular signals. CD138 also binds FGF2 and may be a co-receptor for FGF receptor (Yayon et al., 1991).

As shown supra, CD138 interacts with 41.8 kD protein and TIAM1. The c-terminus of CD138 has also been reported to bind the PDZ domains of syntenin and human CASK (Cohen et al., 1998, J. Cell. Biol. 142:129–138; Grootjans et al., 1997, PNAS 94:13683–13688; Hsueh et al., 1998, J. Cell. Biol. 142:139–151). CD138 is expressed in pre-B cells, immature B cells, plasma cells, neural cells, the basolateral surface of epithelial cells, embryonic mesenchymal cells, vascular smooth muscle cells, endothelial cells and neural cells but not mature circulating B cells. The interaction between CD138 and the PDZ domains of the 41.8 kD protein and TIAM1 proteins is believed to be necessary for the proper distribution of CD138 on the cell surface. Disruption of the interaction by administration of an effective amount of an antagonist is expected to interfere with the migration and adherence of cells to the extracellular matrix, resulting in reduced inflammatory and humoral immune responses. Inhibition of CD138 may be used to treat without limitation diseases such as post-myocardial infarction inflamatory damage, joint injury, rheumatoid arthritis, vasculitis, drug reaction, scleraderma, SLE, Hashimoto thyroiditis, Goodpasture's syndrome, juvenile insulin-dependent diabetes, psoriasis.

E. CD98

As shown supra, CD98 interacts with MPP2. CD98 is expressed at high levels on monocytes and at low levels on T cells, B cells, splenocytes, NK cells, and granulocytes. CD98 plays roles in adhesion, fusion and is a L-type amino acid transporter. CD98 is also involved in virus-mediated cell fusion (e.g. paramyoviruses: parainfluenza virus type 2, Newcastle disease virus, and rubulaviruses) and antagonism of CD98 function is expected to treat) viral infections and limit viral spread. CD98 inhibitors can be an antiviral agent for, but not limited to paramyovirus, parainfluenza, Newcastle disease and rubula. Other roles include treatment for acute leukemias.

F. CLASP-1

As shown supra, CLASP-1 interacts with DLG1, PSD95, and NeDLG. CLASP-1 is a member of a superfamily of immune-cell associated proteins with similar motifs (see PCT/US99/22996 published as WO 00/20434). CLASP-1 functions in the maintenance of the immune synapse. The CLASP-1 transcript is present in lymphoid organs and neural tissue, and the protein is expressed by T and B lymphocytes and macrophages in the MOMA-1 subregion of the marginal zone of the spleen, an area known to be important in T:B cell interaction. CLASP-1 staining of individual T and B cells exhibits a preactivation structural polarity, being organized as a "ball" or "cap" structure in B cells, and forming a "ring", "ball" or "cap" structure in T cells. The placement of these structures is adjacent to the microtubule-organizing center ("MTOC"). CLASP-1 antibody staining indicates that CLASP-1 is at the interface of T-B cell conjugates that are fully committed to differentiation. Antibodies to the extracellular domain of CLASP-1 also block T-B cell conjugate formation and T cell activation.

Antagonism of CLASP-1 function is expected to interfere with immune responses (e.g., T and B cell activation), signal transduction, cell—cell interactions, and membrane organization. Diseases to be treatment by CLASP-1 agonists/antagonists include, but is not limited to, rheumaotoid arthritis, juvenile diabetes, organ rejection, graft-versus-host disease, scleroderma, multiple sclerosis.

G. CLASP-4

As shown supra, CLASP-4 interacts with DLG1, PSD95, NeDLG, LDP, AF6, 41.8, and MINT1. CLASP-4 is a member of a superfamily of immune-cell associated proteins with similar motifs (see copending U.S. Pat. Application 60/196,527 filed Apr. 11, 2000). The CLASP-4 protein is expressed primarily in peripheral blood lymphocytes. Inhibition of the interaction of CLASP-4 and PDZ domains will interfere with immune responses (e.g., T and B cell activation), signal transduction, cell—cell interactions, and membrane organization. Diesease to be treated bu CLASP-4 agonists/antagonists include, but is not limited to, rheumaotoid arthritis, juvenile diabetes, organ rejection, graft-versus-host disease, scleroderma, multiple sclerosis, acute leukemias, leukemic blast crisis, post-infarction inflamation (cardiac, etc.), atherosclerosis.

H. VCAM1

The vascular cell adhesion molecule-1 (VCAM-1, CD106) is predominantly expressed by vascular endothelium (i.e., endothelial cells) but has been detected in macrophages, dendritic cells, bone marrow-derived cells, fibroblasts, cortical thymic epithelial cells, vascular smooth muscle cells, myoblasts and myotubes. VCAM-1 mediates adhesion through interacting with an integrin ligand, VLA-4, which is expressed by lymphocytes, monocytes and eosinophils. The interaction between VCAM-1 and VLA-4 is important for activation, flattening and extravasation of VLA-4 expressing cells when the endothelium itself has become activated due to inflammation or injury (Salomon et al., 1997, *Blood* 89:2461–2471; St-Pierre et al., 1996, *Eur. J. Immunol.* 26:2050–2055; Bell et al., 1995, *Int. Immunol.* 7:1861–1871).

As discussed supra, the C-terminal region of VCAM-1 is a ligand for the PDZ domains of MPP1, DLG1, NeDLG1, LDP, 41.8 protein, TIAM1 and K303. These interactions are believed to mediate the function of endothelial cell interactions with integrin expressing leukocytes. When the PDZ-PL interactions are disrupted, the adherence of leukocytes to the endothelium will similarly be disrupted, resulting in, e.g., reduction of inflammation. Thus, inhibition of VCAM-1 binding to PDZ proteins is useful for reducing abnormal VCAM-1 inflammatory responses and associated pathologies such as (but not limited to) renal allograft rejection, insulin-dependent diabetes, rheumatoid arthritis, post-myocardial infarction complications and systemic lupus erythematosus (Pasloske et al., 1994, *Ann Rev Med* 45:283; Ockenhouse et al., 1992, *J. Exp. Med.* 176:1183; Solezk et al., 1997, *Kidney Int.* 51:1476; Tedla, et al., 1999, *Clin. Exp. Immunol.* 117:92–99; Kusterer et al., 1999, *Exp Clin Endocrinol Diabetes* 107:S 102–107; Bonomini et al., 1998, *Nephron* 79:399; Suassuna et al., 1994, *Kidney Int.* 46:443; Ferri et al., 1999, *Hypertension* 34:568).

I. CLASP-2

As shown supra, CLASP-2 interacts with PSD-95, NeDLG, and DLG1. CLASP-2 is a member of a superfamily of immune-cell associated proteins with similar motifs (see copending U.S. patent Ser. No. 09/547,276 filed Apr. 11, 2000; WO 00/10158 filed Apr. 11, 2000; WO 00/10156 filed Apr. 11, 2000). The CLASP-2 transcript is present most strongly in placenta followed by lung, kidney and heart and the protein is expressed in T and B cells, and kidney epithelial cells.

Inhibition of the interaction of CLASP-2 and PDZ domains will interfere with CLASP-2 function resulting in interference with T and B cell function (e.g., T and B cell activation), signal transduction, cell—cell interactions, and membrane organization. In addition, since CLASP-2 is present in heart, blocking CLASP-2 function or expression can selectively block immune responses in the heart (for example, to selectively stop immune response in the heart compartment, e.g., following cardiac transplant rejection or post-MI inflammation, without compromising immunity elsewhere). Other diseases to be treatment by CLASP-1 agonists/antagonists include, but is not limited to, rheumaotoid arthritis, juvenile diabetes, organ rejection, graft-versus-host disease, scleroderma, multiple sclerosis.

J. CD95 (Apo-1/Fas)

CD95 (Fas/Apo-1) and Fas ligand (FasL) are a receptor-ligand pair involved in lymphocyte homeostasis and peripheral tolerance. Binding of Fas by its ligand results in apoptotic cell death, an important major mechanism for safe clearance of unwanted cell during resolution of the acute inflammatory response. As is shown supra, CD95 binds the PDZ domains DLG1, PSD95, NeDLG, and 41.8. Inhibition of the interaction of CD95 and PDZ domains.

K. KV1.3 (Shaker Type Kv1.3 Potassium Channel)

As shown supra, Kv1.3 binds DLG1, PSD95, NeDLG, LIMK, 41.8, RGS12, DVL1, and MINT1. Kv1.3 is a Shaker-related channel protein that is involved in modulating the membrane potential of T lymphocytes (Lewis and Cahalan, 1995, *Ann. Rev. Immunol.* 13:623). Inhibition of the Kv1.3 channel chronically depolarizes the T cell membrane, reduces calcium entry via calcium-activated release calcium channels in the plasma membrane, and consequently inhibits the calcium-signaling pathway essential for lymphocyte activation. Hanada et al., reported that Kv1.3 is associated with DLG1 and PSD95 in Jurkat T cells (*J. Biol. Chem.* 1997, 272:26899). Administration of Kv1.3-PDZ protein agonist/antagonists will disrupt T cell signaling and can be a useful therapeutic drug to treat, but not limited to, organ transplantation, graft-versus-host disease, Crohn's Disease, Ulcerative colitis, inflammatory bowel disease, rheumatoid arthritis, osteoarthritis, multiple sclerosis, scleroderma, mixed connective tissue disease.

L. DNAM-1

As shown supra, DNAM-1 binds several PDZ proteins, including MPP2, DLG1, PSD95, NeDLG, LIM, AF6, 41.8 and RGS12. DNAM-1 is associated with Fyn constitutively but required the presence of pervanadate (a tyrosine phosphatase inhibitor) (see Shibuya, et al. 1999, Immunity. 11:615–623). Upon stimulation with anti-CD3 (or DNAM-1), DNAM-1 is phosphorylated at Serine 329 (Shibuya, et al. 1998, J. Immun. 161:1671–1676.) and associates with LFA-1. Furthermore, Fyn becomes associated with DNAM-1 independent of pervanadate. Fyn phosphorylates DNAM-1 at Y 322, but does not require Y322 to continue binding to DNAM-1.

Since DNAM-1 itself does not have a SH3 binding domain but only has the Src phosphorylation site at Y322, an adaptor molecule must be present to bridge DNAM-1 and Fyn. DLG1 has been described in the literature to be present in T cells (Hanada, et al. 1997. J Biol Chem 272:26899), but does not bind Fyn. PSD95 does not have a SH3 binding site. However, several of the other PDZ proteins do have SH3 binding domains including but not limited to NeDLG, RGS12, MPP2 and can fulfill this function. These adaptor PDZ listed supra binds to DNAM-1 through its PDZ domain and simultaneously binds to the SH3 domain of Fyn through its proline-rich sequences just N-terminal to the PDZ domain. The Y139 is a candidate phosphorylation site to control association of Fyn to DNAM-1 and the adaptor PDZ.

Based on this analysis, inhibition of PDZ association with DNAM-1 using the reagents of the invention will inhibit Fyn association with DNAM-1 and the subsequent Y322 phosphorylation and activation of cytotoxic T cells. Diseases that can be treated include but are not limited to Crohn's Disease, multiple sclerosis, ulcerative colitis, inflammatory bowel disease, graft-versus-host, juvenile diabetes, Hashimoto's disease.

M. CD83 (HB15)

CD83 is a transmembrane glycoprotein, expressed predominantly on activated dendritic cells (DCs), Langerhans cells in the skin, with some weak expression detected on activated peripheral lymphocytes, and interdigitating reticulum cells within the T cell zones of lymphoid organs (Zhou and Tedder, 1995, J. Immunol. 154:3821–3835; Zhou et al., 1992, J. Immunol. 149:735–742). CD83 is up-regulated de novo upon activation of an immature DCs, and is the major discriminating marker and characteristic for activated, mature DCs (Czerniecki et al., 1997, J. Immunol. 159:3823–3837). DCs function as antigen presenting cells (APCs). Upregulation and expression of CD83 thus appears to be required for DCs to mature and function as APCs.

As shown by experiments described supra, the CD83 binds to the PDZ domains of DLG1, PSD95, and NeDLG. These interactions between CD83 and PDZ domains, and between CD83 and DLG1, PSD95, and NeDLG are believed to be important for proper distribution and recycling of CD83. Disruption of CD83 and PDZ proteins with agonists and antagonist can be used to treat, but not limited to, psoriasis, cancers, allergies, autoimmune diseases such as multiple sclerosis, system lupus erythematosis.

N. CD44 (Phagocytic Glycoprotein 1, Lymphocyte Homing Receptor, p85 and HCAM)

CD44 is single pass transmembrane protein that has several different isoforms due to alternative splicing. It has a broad pattern of expression being detected on both hematopoietic and non-hematopoietic cell types including epithelial, endothelial, mesenchymal and neuronal cells. CD44H is a major isoform that is expressed in lymphoid, myeloid and erythroid cells (reviewed in Barclay et al., 1997, The Leukocyte Antigen Facts Book, 2ed, Academic Press). CD44 is a receptor for hyaluronate (HA), which is a constituent of the extracellular matrix (ECM). In the immune system, CD44 functions as an adhesion molecule on the surface of leukocytes and erythrocytes that binds HA polymers in the ECM, and it can also act as a signaling receptor when HA becomes soluble during inflammatory reactions or tissue damage. The cytoplasmic region of CD44 has been shown to bind or be associated with the actin cytoskeleton through interactions with spectrin and members of the ERM (ezrin, radixin, and meosin) family (reviewed in Lesley et al., 1993; Bajorath, 2000, Proteins 39:103–111). Additionally, CD44 is associated with the non-receptor tyrosine kinase p56Lck (Taher et al., 1996, J. Biol. Chem. 271:2863–2867. CD44 has been shown to be a co-stimulatory molecule with CD3/TCR engagement to activate T cells (reviewed in Aruffo, 1996, J. Clin. Invest. 98:2191–2192).

As described supra by experiments reported herein, the C-terminus of CD44 is a ligand for the PDZ domain contained in MPP1, prIL-16 and MINT1. It is believed that the interactions of CD44 with PDZ domains, and between CD44 with MPP1, prIL-16 and MINT1 function in maintenance of leukocyte structure and in leukocyte signaling. Thus, when a CD44-PDZ interaction is disrupted, CD44 will fail to transduce proper intracellular signals, and maintain proper distribution of CD44 on the surface, which will prevent adhesion of leukocytes to the endothelium during inflammation and tissue damage. Administration of agonists/antagonists of this interaction will thus result in, but not limited to, reduced inflammatory responses during tissue ischemia and cell lysis (e.g., rhabdomyosis), vascular insufficiencies (e.g. frostbite), psoriasis, eczema, graft-versus-host disease, granuloma annulare, scleroderma.

O. CD97 (CD55)

As discussed supra, CD97 binds the PDZ domains of DLG1 and 41.8. CD97 is a 79.7 kD seven-span transmembrane protein expressed on granulocytes and monocytes and at low levels on resting T cells and B cells. Upon T or B cell activation expression levels of CD97 in T cells and B cells increases rapidly (Eichler et al., 1994, Scand. J. Immunol. 39, 111–115; Pickl et al., 1995, Leukocyte Typing V: 1151–1153). When expressed on COS cells, CD97 confers adhesion to lymphocytes and to erythrocytes.

According to the present invention, the interaction of CD97 with DLG1 and the 41.8 kd protein can be altered to interfere with proper membrane distribution of CD97 and/or recycling of CD97. Such modulation will affect CD97 dependent adherence of cells with therapeutic benefit. Without being limited, agonists and antagonists of CD97-PDZ protein interaction can be used to treat rheumatoid arthritis, osteoarthritis, Crohn's Disease, Ulcerative colitis, psoriasis.

P. Glycophorin C (GC)

As is shown supra, the c-terminus of Glycophorin C (GC) interacts with the PDZ domains of human DLG, PSD95, NeDLG, MMP2, AF6, 41.8, and MINT1 (with Mint-1 described previously). Glycophorin C is an integral membrane protein expressed in erythroid cells, thymus, stomach, breast, adult and fetal liver, monocytes, T and B cells (Le Van Kim et al., 1989, J. Biol. Chem. 264:20407–20414) and is known for its role in human erythrocytes where it interacts with MPP1 and protein 4.1 to regulate the shape, integrity and mechanical stability of red cells (Marfatia et al., 1997, J. Biol. Chem. 272:24191–24197; Reid et al., 1987, Blood 69:1068–1072.).

Interactions between Glycophorin C and PDZ proteins DLG, PSD95, NeDLG, MMP2, AF6, 41.8, and MINT1 are believed necessary for maintenance of the physical integrity of cells in which they are expressed. Modulation of GC-PDZ interactions will alter with the function of these and can be utilized to treat, but not limited to, polycythemia vera, spherocytosis.

Q. CDw128A (IL8RA)

As is described supra, CDW128A binds to the PDZ domains of DLG1 and NeDLG. There are two forms for the IL-8 receptor, IL-8RA (CDw128A) and IL-8RB (CDw128B) both of which are members of the G protein-coupled receptor superfamily and chemokine receptor branch of rhodopsin family. CDw128A and CDw128B both bind IL-8 with the same affinity but only CDw128B, binds three other IL-8-related CXC chemokines: melanoma growth-stimulating activity (GRO/MGSA), neutrophil-activating peptide 2 (NAP-2) and ENA-78. See, e.g., Ahuja, SK. And Murphy, PM. 1996. J Biol Chem 271:20545–50.

CDw128A is expressed on all granulocytes, a subset of T cells, monocytes, endothelial cells, keratinocytes, erythrocytes, and melanoma cells. IL-8 induces chemotaxis of neutrophils, basophils, and T lymphocytes and increases neutrophil and monocyte adhesion to endothelial cells. The binding of IL-8 to IL8RA induces a transient increase in intracellular calcium levels, activation of phospholipase D, a respiratory burst of neutrophils and chemotaxis. This pro-inflammatory response is effective in normal immune responses. Inhibitors of CDw128A are useful for treatment of psoriasis, rheumatoid arthritis, polyarthritis, and for control of angiogenesis-dependent disorders such as melanomas and breast cancer.

R. CD3-eta(η)

CD3-η is a splice variant of CD3 zeta and a component of the CD3/TCR complex, which is required for antigen recognition, signal transduction and activation of T cells (Weiss and Littman, 1994, Cell 76:263–274.). See, Barclay et al., 1997, The Leucocyte antigen facts book, 2nd Ed, Academic Press. As shown by experiments reported herein, the C-terminal region of CD3-η is a ligand for the PDZ domains of MINT1, 41.8 protein, DLG1, and PSD95. The interactions of CD3-η with PDZ domains, and of CD3-η with MINT1, 41.8 protein, DLG1, and PSD95 are believed to be important activation of T cells, which is required for all cellular immune responses. Modulation of this interaction by agonists and antagonists can be used to treat, but is not limited to, acute and chronic allograft rejection, multiple sclerosis, graft-versus-host disease, rheumatoid arthritis.

S. LPAP (CD45-AP, LSM-1)

LPAP is a transmembrane protein expressed on resting and activated T- and B-cells. LPAP has been shown to bind to CD45, a protein that is part of the T-cell receptor complex and has been found to co-localize with CD4, CD2 and Thy-1. LPAP has also been co-immune precipitated with p56(lck) and ZAP-70. The actual function of LPAP is unknown, but it has been suggested that it is an assembly molecule for the CD45 complex.

As shown supra, LPAP binds to DLG-1 and MINT-1. Notably, DLG-1 and MINT-1 are both expressed in T-cells. It has also been shown that DLG-1 co-precipitates with p56(lck) in T-cells. The assays described herein also demonstrated that DLG-1 binds to CD95 and KV1.3, and binding of MINT-1 to KV1.3. All of these molecules are involved in signaling by the TCR. LPAP is believed to function in organizing the signaling by CD45 in T-cell activation, possibly by recruiting p56(lck) as a substrate for CD45. Blocking the function of CD45 has been shown to severely impair the T-cell response. Inhibiting the interaction between LPAP and PDZ proteins is expected to alter the CD45-mediated path from the rest of the immune response. Agonists and antagonists of PL-PDZ binding can be used to treat, but is not limited to, rheumatoid arthritis, transplant rejection, multiple sclerosis, scleroderma, graft-versus-host disease.

T. CD46 (Complement Membrane Cofactor Protein (MCP))

CD46 is a membrane protein expressed on all nucleated cells, but not on erythrocytes. CD46 is a member of the regulator of complement activation protein family. Its primary function is the protection of cells from complement attack by inactivating membrane deposited C3b/C4b complement (Liszewski, et al., 1999, Adv. Immunol. 61:201–283). CD46 exists in more than 8 isoforms that are generated by differential splicing, with molecular weights ranging from 45 to 70 kD. In addition to the above function, CD46 also serves as the receptor for the measles virus and for other pathogenic microorganisms (e.g. Streptococcus pyogenes) (Manchester et al, 1994, Proc. Natl Acad. Sci. USA 91:2161; Okada et al., 1995, Proc. Natl Acad. Sci. USA 92:2489–2493.). CD46 also appears to be over-expressed on certain tumors (Jurianz et al., 1999, Mol Immunol 36:929–939) thus rendering tumor cells insensitive to the action of complement. See, Barclay et al., (1997) The Leucocyte antigen facts book, 2ed, Academic Press.

As shown supra, CD46 binds DLG1, PSD95 and Ne-DLG. This interaction is believed to be necessary for proper membrane distribution of CD46 and/or recycling of CD46. Alteration of the CD46-PDZ interaction can reduce the ability of measles virus and other pathogens to enter cells, renders CD46-expressing tumors susceptible to attack by complement The administration of CD46-PDZ interaction agonists and antagonists is useful for the treatment of, but not limited to, cancers and viral infectious diseases.

U. CDw128B

As is described supra, CDw128B binds to the PDZ domains of DLG1, NeDLG, PSD95, and 41.8 in the assays described supra. There are two forms for the IL-8 receptor, IL-8RA (CDw128A) and IL-8RB (CDw128B) both of which are members of the G protein-coupled receptor superfamily and chemokine receptor branch of rhodopsin family. CDw128A and CDw128B both binds IL-8 with equal affinity but only CDw128B, also binds three other IL-8-related CXC chemokines: melanoma growth-stimulating activity (GRO/MGSA), neutrophil-activating peptide 2 (NAP-2) and ENA-78. See, e.g., Ahuja, S K and Murphy, P M. 1996. J Biol Chem 271:20545–50.

CDw128B is expressed on all granulocytes, a subset of T cells, monocytes, endothelial cells, keratinocytes, erythrocytes, and melanoma cells. IL-8 induces chemotaxis of neutrophils, basophils, and T lymphocytes but diminished relative to IL8RA and increases neutrophil and monocyte adhesion to endothelial cells. The binding of IL-8A to its receptor induces a transient increase in intracellular calcium levelsand granule release but does not induce activation of phospholipase D or a respiratory burst in neutrophils. This pro-inflammatory response is effective in normal immune responses. Inhibitors of CDw128B are useful for treatment of psoriasis, rheumatoid arthritis, polyarthritis, and for control of angiogenesis-dependent disorders such as melanomas and breast cancer.

V. DOCK2

The DOCK family are a group of morphogenetic transmembrane proteins that interacts with cytoskeleton to affect cell shape changes. Members of this new family include Drosophila myoblast city (mbc), DOCK180, DOCK2, DOCK3, CED5, KIAA0209 and CLASP. The prototypical molecule, DOCK1 or DOCK180 is the human homolog of C. elegans gene, CED5 which is involved in the engulfment and phagocytosis by macrophages of apoptotic cells. DOCK2 is found in peripheral blood lymphocytes and can convert a flatten cell into a rounded morphology upon transfection (Nagase, et. al. 1996. DNA Res 3:321–329, Nishihara, H. 1999. Hokkaido Igaku Zasshi 74:157).

As shown supra, DOCK2 is a PL and binds to PDZ proteins. Using PDZ proteins as an adaptor, DOCK2 complexes with A, B, C to control cell shape in preparation for transit of lymphocytes for vascular circulation. Modulation of DOCK2 by agonists and antagonists of its PDZ protein interaction can be used to treat, but is not limited to, acute leukemia, blast crisis, post-myocardial infarction inflammation, post-traumatic inflammation.

W. CD34

As is shown supra, CD34 binds DLG1, PSD95, and NeDLG. CD34 is expressed on a small subpopulation of bone marrow cells which includes hematopoietic stem cells. CD34 is also present on bone marrow stomal cells and on endothelial cells. The selectins CD62L (L-selectin) and CD62E (E-selectin) bind CD34. CD34 mediates attachment and rolling of leukocytes. The hematopoietic stem cell properties of CD34 include myeloid differentiation of stem cells. Modulation of the CD34-PDZ interaction with agonists and/or antagonists can be used to treat, but is not limited to, myelodysplasia, leukemias, post-traumatic inflammation, post-myocardial infarction inflammation.

X. Fc epsilon receptor beta I chain (FcεRβI)

The high affinity receptor for human IgE, FcεRI, is composed of an α, β, and disulfide-linked γ homodimer. The α-chain binds the Fc portion of IgE, whereas the β-chain serves to amplify signals that are transduced through the γ-chain homodimer. Both αβγ2 tetramer and αγ2 trimer complexes exist, but the β-chain amplifies the signal 5- to 7-fold, as measured by Syk activation and calcium mobilization. Additionally, the FcεRβI is a PDZ ligand and is a member of the CD20/FcεRβI receptor family. As is shown supra, FcεRβI binds MINT1.

As the high-affinity receptor for IgE, FcβRI on basophils and mast cells plays a central role in the initiation of allergic responses. Signaling through the FcβRI begins by crosslinking of a multivalent allergen bound to IgE. The result is vesicular degranulation, release of histamine, leukotrienes and pro-inflammatory cytokines (IL-6 and TNFα), factors responsible for the symptoms of immediate hypersensitivity. Alteration of signaling by targeting PL/PDZ interaction with agonists and antagonists can be used to treat, but is not limited to, asthma, atopic dermatitis, eczema, drug reaction, mastocytosis, urticaria, eosinophilia myalgia syndrome (Turner, H., et. al., 1999, *Nature* 402 SUPP:B24).

Y. FAS Ligand (FasL)

CD95 (Fas/Apo-1) and Fas ligand (FasL) are a receptor-ligand pair critically involved in lymphocyte homeostasis and peripheral tolerance. Binding of Fas by its ligand results in apoptotic cell death, an important major mechanism for safe clearance of unwanted cell during resolution of the acute inflammatory response. FasL is mainly restricted to activated T lymphocytes and is rapidly induced. Fas ligand is frequently up-regulated in breast cancer, as compared with normal breast epithelial cells and benign breast disease. As is shown supra, FasL binds the KIAA0561 PDZ domain. The PDZ-PL modifiers are useful for treatment of, but not limited to, tumors, e.g., tumors unresponsive to conventional chemotherapy.

Z. CDW125 (IL5R)

As is shown supra, CDW125 binds PTN-4 and RGS12. CDW125 is an IL-5 receptor expressed on eosinophils and basophils. IL5 promotes growth and differentiation of eosinophil precursors and actives mature eosinophils (Takatsu et al 1994, *Adv. Immunol.* 57:145–190). The secreted form of CDw125 has antagonistic properties and is able to inhibit IL-5-induced eosinophil proliferation and differentiation. Modulation of CDW125 binding to PDZ domains may be used to treat, but is not limited to, asthma, atopic dermatitis, eczema, drug reaction, urticaria, mastocytosis, eosinophilia.

AA. Burkitt's Lymphoma Receptor-1 (BLR-1; CXCR5)

BLR-1 is a transmembrane receptor detected primarily on B cells, and shown to be upregulated in stimulated T cells (Dobner et al., 1992, *Eur J. Immunol.* 22:2795–2799; Flynn et al., 1998, *J. Exp. Med.* 188:297–304). BLR-1 functions in chemotaxis of B and T cells into follicles of secondary lymphoid organs (e.g. spleen) for proper development and selection toward antigens (Forster et al., 1996, *Cell* 87:1037–1047. Its ligand is B-lymphocyte chemoattractant (BLC), which is strongly expressed in the follicles of Peyer's patches, spleen and lymph nodes (Gunn et al., 1998, *Nature* 391:799–803). Consistent with its chemotactic role is the demonstration that BLR-1 expression is downregulated in developed, activated B cells (plasma cells) to prevent them from being retained in follicles (Forster et al., 1994, *Cell Mol Biol* 40:381–387), and blr –/– B cells fail to migrate to B cell follicles (Forster et al., 1996).

As shown by experiments reported herein, the C-terminal end of BLR-1 binds to the PDZ domain containing protein MINT1. Without intending to be bound by a particular mechanism, the interaction between BLR-1 and MINT1, and BLR-1 and PDZ domains is necessary for the proper distribution and signaling of BLR-1 on the cell surface. When this interaction is disrupted, the chemotactic abilities of lymphoid cells expressing BLR-1 is similarly disrupted. Such a disruption results in a reduced immune response, interference with the ability of lymphocytes to properly circulate and develop responses to antigen. Agonists and antagonists of this interaction can be used to treat, but is not limited to, systemic lupus erythematosus, scleroderma and other autoimmune diseases.

BB. CD4

CD4 is a co-receptor with the T cell receptor (TCR) involved in antigen recognition. Both CD4 and TCR belong to the immunoglobulin supergene family. T cell activation is enhanced by increasing the avidity of T cells for effector and target cells. The cytoplasmic domain is involved in signal transduction and association with the tyrosine kinase p56$^{kk}$. CD4 is expressed on most thymocytes, two-thirds of peripheral blood T lymphocytes, monocytes and macrophages.

Human immunodeficiency virus type-1 (HIV-1) infects cells by membrane fusion mediated by its envelope glycoproteins (gp120-gp4) and is triggered by the interaction of CD4 and a chemokine co-receptor, CCR5 or CXCR4. Modulation of CD4-PDZ inhibitors with agonists and antagonists can be used to treat, but is not limited to, HIV infection immediately after exposure to HIV, rheumatoid arthritis, multiple sclerosis, scleroderma, systemic lupus erythematosis, psoriasis.

6.5 Agonists and Antagonists of PDZ-PL Interactions

As described herein, interactions between PDZ proteins and PL proteins in cells (e.g., hematopoietic cells, e.g., T cells and B cells) may be disrupted or inhibited by the administration of inhibitors or antagonists. Inhibitors can be identified using screening assays described herein. In embodiment, the motifs disclosed herein are used to design inhibitors. In some embodiments, the antagonists of the invention have a structure (e.g., peptide sequence) based on the C-terminal residues of PL-domain proteins listed in TABLE 2. In some embodiments, the antagonists of the invention have a structure (e.g., peptide sequence) based on a PL motif disclosed herein.

The PDZ/PL antagonists and antagonists of the invention may be any of a large variety of compounds, both naturally occurring and synthetic, organic and inorganic, and including polymers (e.g., oligopeptides, polypeptides, oligonucleotides, and polynucleotides), small molecules, antibodies, sugars, fatty acids, nucleotides and nucleotide analogs, analogs of naturally occurring structures (e.g., peptide mimetics, nucleic acid analogs, and the like), and numerous other compounds. Although, for convenience, the present discussion primarily refers antagonists of PDZ-PL interactions, it will be recognized that PDZ-PL interaction agonists can also be use in the methods disclosed herein.

In one aspect, the peptides and peptide mimetics or analogues of the invention contain an amino acid sequence that binds a PDZ domain in hematopoietic cells such as T cells and B cells, or otherwise inhibits the association of PL proteins and PDZ proteins. In one embodiment, the antagonists comprise a peptide that has a sequence corresponding to the carboxy-terminal sequence of a PL protein listed in TABLE 2, e.g., a peptide listed TABLE 4. Typically, the peptide comprises at least the C-terminal four (4) residues of the PL protein, and often the inhibitory peptide comprises more than four residues (e.g., at least five, six, seven, eight, nine, ten, twelve or fifteen residues) from the PL protein C-terminus. See, e.g. Section 6.5.1, infra. Moreover, the C-terminal domains of specific surface receptors expressed by hematopoietic system and endothelial cells may themselves be used as inhibitors, and may be used as the basis for rational design of non-peptide inhibitors. See Section 6.6, infra.

In some embodiments, the antagonist is a fusion protein comprising such a sequence. Fusion proteins containing a transmembrane transporter amino acid sequence are particularly useful. See, e.g. Section 6.5.2, infra.

In some embodiments, the inhibitor is conserved variant of the PL C-terminal protein sequence having inhibitory activity. See, e.g. Section 6.5.3, infra.

In some embodiments, the antagonist is a peptide mimetic of a PL C-terminal sequence. See, e.g. Section 6.5.4, infra.

In some embodiments, the inhibitor is a small molecule (i.e., having a molecular weight less than 1 kD). See, e.g. Section 6.5.5, infra 6.5.1 Peptide Antagonists In one embodiment, the antagonists comprise a peptide that has a sequence of a PL protein carboxy-terminus listed in TABLE 2. The peptide comprises at least the C-terminal two (2) residues of the PL protein, and typically, the inhibitory peptide comprises more than two residues (e.g, at least three, four, five, six, seven, eight, nine, ten, twelve or fifteen residues) from the PL protein C-terminus. Most often, the residues shared by the inhibitory peptide with the PL protein are found at the C-terminus of the peptide. However, in some embodiments, the sequence is internal. Similarly, in some cases, the inhibitory peptide comprises residues from a PL sequence that is near, but not at the c-terminus of a PL protein (see, Gee et al., 1998, *J Biological Chem.* 273:21980–87).

For example, the "core PDZ motif sequence" of a hematopoietic cell surface receptor at its C-terminus contains the last four amino acids, this sequence may be used to target PDZ domains in hematopoietic cells. The four amino acid core of a PDZ motif sequence may contain additional amino acids at its amino terminus to further increase its binding affinity and/or stability. In one embodiment, the PDZ motif sequence peptide can be from four amino acids up to 15 amino acids. It is preferred that the length of the sequence to be 6–10 amino acids. More preferably, the PDZ motif sequence contains 8 amino acids. Additional amino acids at the amino terminal end of the core sequence may be derived from the natural sequence in each hematopoietic cell surface receptor or a synthetic linker. The additional amino acids may also be conservatively substituted. When the third residue from the C-terminus is S, T or Y, this residue may be phosphorylated prior to the use of the peptide.

In some embodiments, the peptide and nonpeptide inhibitors of the are small, e.g., fewer than ten amino acid residues in length if a peptide. Further, it is reported that a limited number of ligand amino acids directly contact the PDZ domain (generally less than eight) (Kozlov et al., 2000, Biochemistry 39, 2572; Doyle et al., 1996, Cell 85, 1067) and that peptides as short as the C-terminal three amino acids often retain similar binding properties to longer (>15) amino acids peptides (Yanagisawa et al., 1997, J. Biol. Chem. 272, 8539).

FIGS. 3A–H show the use of peptides to inhibit PL-PDZ interactions using the G assay described supra. In FIGS. 3A and B, the inhibiton assays were carried out using GST fusion proteins containing PDZ domains from DLG1 or PSD95 (see supra and TABLE 3). Binding of biotinylated PL peptides for CLASP-2, CD46, Fas, or KV1.3 (as listed in TABLE 4) was determined in the presence of various competitor peptides (at a concentration of 100 uM) or in the absence of a competitor (equalized as 100% binding). The competitor peptides were 8-mers peptides having the sequence of C-terminus of CLASP-2 (MTSSSSVV; SEQ ID NO:227), CD46 (REVKFTSL; SEQ ID NO:113), or Fas (TFFGLYKL; SEQ ID NO:83), a unlabeled 19-mer having the sequence of c-terminus of KV1.3 (i.e., non-biotinylated AA33L as listed in TABLE 4), or a peptide having the sequence of residues 64–76 of hemoglobin (Vidal et al., 1999, *J. Immunol.* 163, 4811), i.e., an unrelated competitor. The binding of biotinylated peptide (10 uM for Fas and KV1.3, 20 uM for CLASP-2 and CD46) to GST alone was subtracted from the binding to the fusion proteins to obtain the net signal for each experimental condition. This net signal was then normalized by dividing by the signal in the absence of competitor peptide and the data were plotted. Error bars indicated the standard deviation of duplicate measurements. Specific inhibition of CLASP-2 PL-DLG PDZ binding was observed with the CLASP-2 8-mer, the CD46 8-mer, the Fas 8-mer, and the KV1.3 peptide, but not in the absence of peptide or using an unrelated peptide.

Figure 3E:
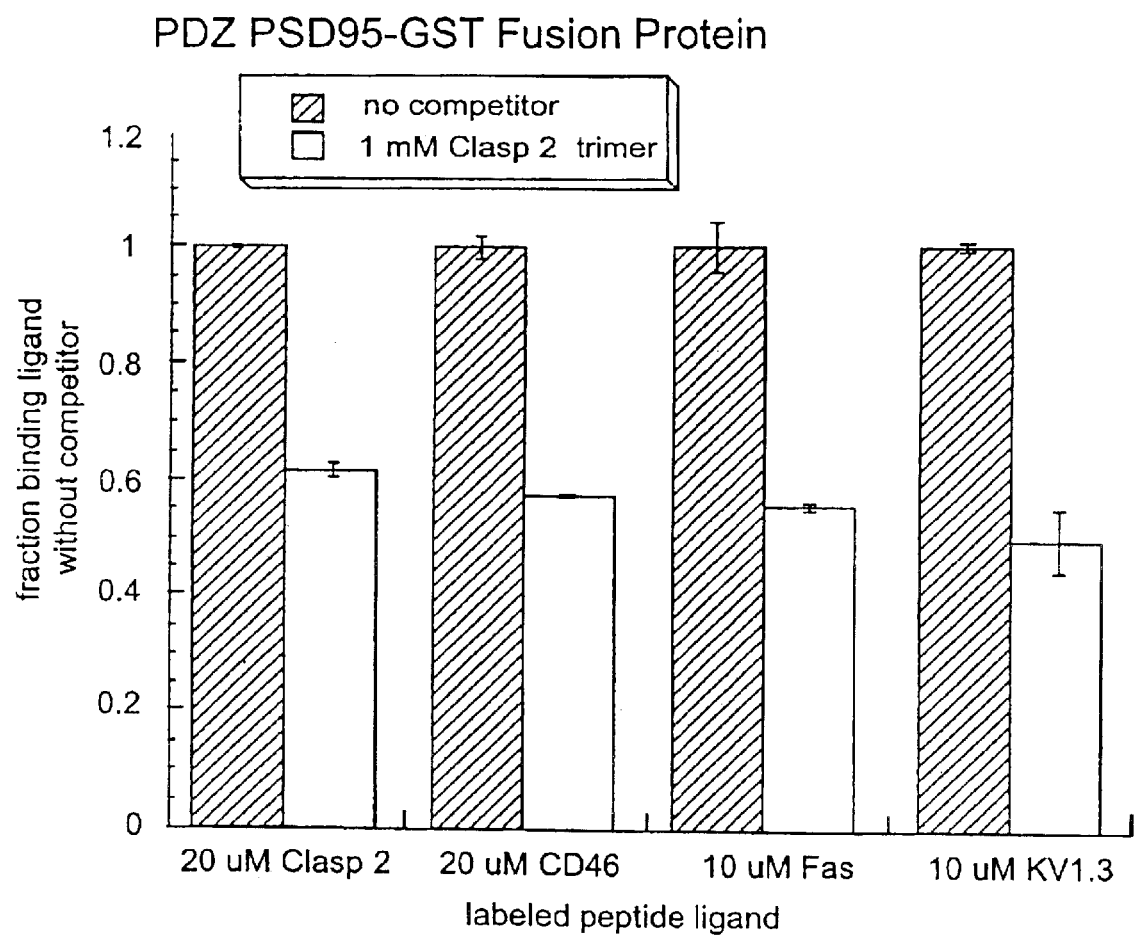
Figure 3F:
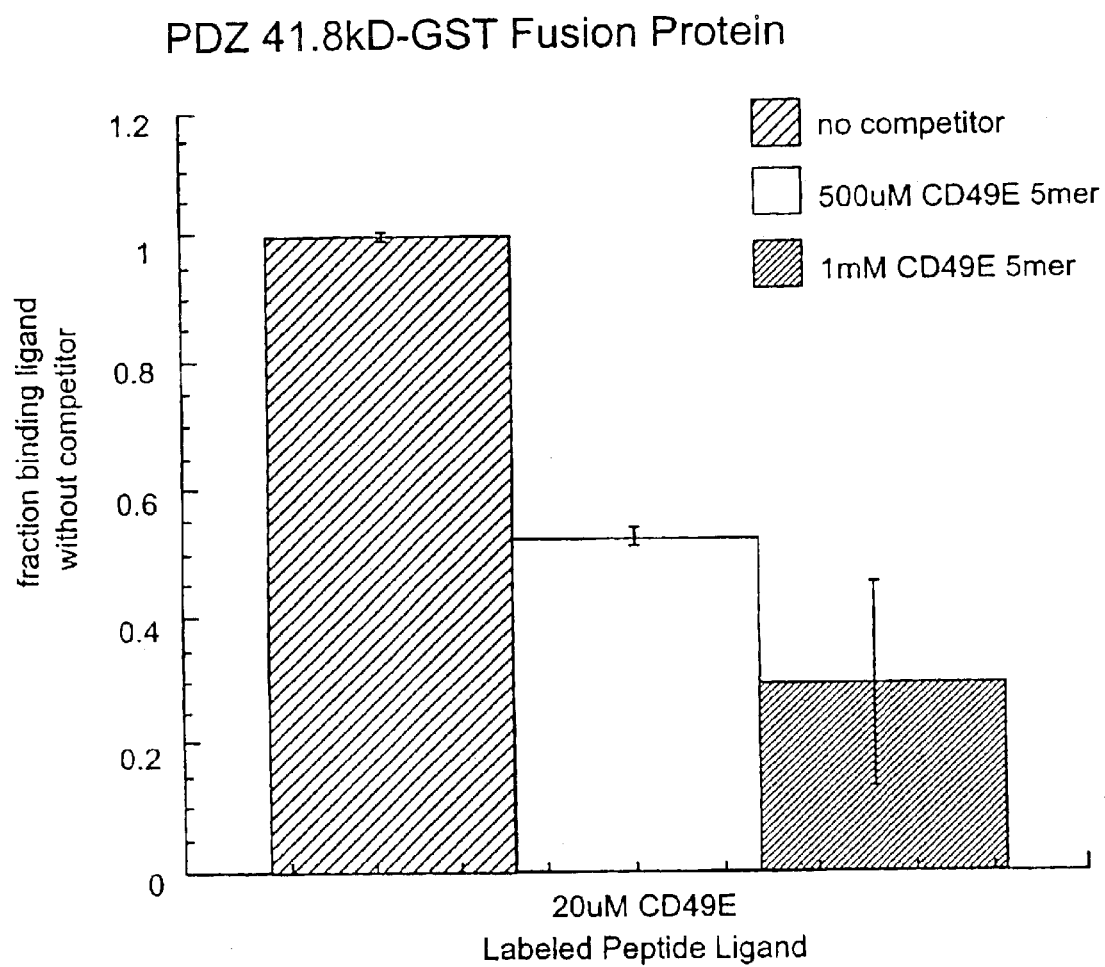

FIGS. 3C–F show similar assays using shorter peptides to inhibit (e.g., a 3-mer and a 5-mer). FIGS. 3C–E show binding of biotinylated PL peptides for CLASP-2, CD46, Fas, or KV1.3, at the indicated concentration (as listed in TABLE 3) to GST fusion proteins containing PDZ domains from NeDLG, DLG1, or PSD95 in the absence or presence of 1 mM 3-mer peptide having the sequence of the C-terminus of Clasp 2 (SVV) (TABLE 3). FIG. 3F shows the effect on binding of a 5-mer CD49E peptide (ATSDA; SEQ ID NO:25) to GST fusion proteins containing a PDZ domain from 41.8 Kd.

6.5.2 Peptide Variants

Having identified PDZ binding peptides and PDZ-PL interaction inhibitory sequences, variations of these sequences can be made and the resulting peptide variants can be tested for PDZ domain binding or PDZ-PL inhibitory activity. In embodiments, the variants have the same or a different ability to bind a PDZ domain as the parent peptide. Typically, such amino acid substitutions are conservative, i.e., the amino acid residues are replaced with other amino acid residues having physical and/or chemical properties similar to the residues they are replacing. Preferably, conservative amino acid substitutions are those wherein an amino acid is replaced with another amino acid encompassed within the same designated class.

6.5.3 Peptide Mimetics

Having identified PDZ binding peptides and PDZ-PL interaction inhibitory sequences, peptide mimetics can be prepared using routine methods, and the inhibitory activity of the mimetics can be confirmed using the assays of the invention. Thus, in some embodiments, the antagonist is a peptide mimetic of a PL C-terminal sequence. The skilled artisan will recognize that individual synthetic residues and polypeptides incorporating mimetics can be synthesized using a variety of procedures and methodologies, which are well described in the scientific and patent literature, e.g., Organic Syntheses Collective Volumes, Gilman et al. (Eds) John Wiley & Sons, Inc., NY. Polypeptides incorporating mimetics can also be made using solid phase synthetic procedures, as described, e.g., by Di Marchi, et al., U.S. Pat. No. 5,422,426. Mimetics of the invention can also be synthesized using combinatorial methodologies. Various techniques for generation of peptide and peptidomimetic libraries are well known, and include, e.g., multipin, tea bag, and split-couple-mix techniques; see, e.g., al-Obeidi (1998) Mol. Biotechnol. 9:205–223; Hruby (1997) Curr. Opin. Chem. Biol. 1:114–119; Ostergaard (1997) Mol. Divers. 3:17–27; Ostresh (1996) Methods Enzymol. 267:220–234.

6.5.4 Small Molecules

In some embodiments, the inhibitor is a small molecule (i.e., having a molecular weight less than 1 kD). Methods for screening small molecules are well known in the art and include those described supra at Section 6.4.

6.6 Cell Surface Receptors and PDZ-Domain Binding Sequences

The following sections describe specific surface receptors expressed by different cell types in the hematopoietic and immune response system. The C-termini of these receptors are used as inhibitors, or serve as the basis for designing PDZ motif sequence peptides, variants, fusion proteins, peptidomimetics, and small molecules for use in inhibiting PDZ-PL interactions. In a preferred embodiment, the peptides are tested in an assay of the invention for inhibitory or modulatory activity (also see, TABLE 4, and discussion supra).

6.6.1 PDZ Motif Sequences of T Cell Surface Receptors

A number of surface receptors expressed by T cells contain a PDZ motif sequence (PL sequence). These molecules include CD31η, CD4, CD6, CD38, CD49e, CD49f, CD53, CD83, CD90, CD95, CD97, CD98, CDw137 (41BB), CD166, CDw128 (IL8 R), DNAM-1, Fas ligand (FasL) and LPAP (Barclay et al., 1997, The Leucocyte Antigen Facts Book, second edition, Academic Press), CLASP-1, CLASP-2, CLASP-4, KV1.3, and DOCK2.

The C-terminal core sequence of CD3 is SSQL (SEQ ID NO:4). When naturally-occurring residues are added to the core sequence, SSSQL (SEQ ID NO:5), SSSSQL (SEQ ID NO:6), PSSSSQL (SEQ ID NO:7), and PPSSSSQL (SEQ ID NO:8) may also be used to target a PDZ domain-containing protein in T cells.

The C-terminal core sequence of CD4 is CSPI (SEQ ID NO:9). When naturally-occurring residues are added to the core sequence, TCSPI (SEQ ID NO:10), KTCSPI (SEQ ID NO:11), QKTCSPI (SEQ ID NO:12), and FQKTCSPI (SEQ ID NO:13) may also be used to target a PDZ domain-containing protein in T cells.

The C-terminal core sequence of CD6 is ISAA (SEQ ID NO:14). When naturally-occurring residues are added to the core sequence, DISAA (SEQ ID NO:15), DDISAA (SEQ ID NO:16), YDDISAA (SEQ ID NO:17), and DYDDISAA (SEQ ID NO:18) may also be used to target a PDZ domain-containing protein in T cells.

The C-terminal core sequence of CD38 is TSEI (SEQ ID NO:19). When naturally-occurring residues are added to the core sequence, CTSEI (SEQ ID NO:20), SCTSEI (SEQ ID NO:21), SSCTSEI (SEQ ID NO:22), and DSSCTSEI (SEQ ID NO:23) may also be used to target a PDZ domain-containing protein in T cells.

The C-terminal core sequence of CD49e is TSDA (SEQ ID NO:24). When naturally-occurring residues are added to the core sequence, ATSDA (SEQ ID NO:25), PATSDA (SEQ ID NO:26), PPATSDA (SEQ ID NO:27), and KPPATSDA (SEQ ID NO:28) may also be used to target a PDZ domain-containing protein in T cells.

The C-terminal core sequence of CD49f is TSDA (SEQ ID NO:24). When naturally-occurring residues are added to the core sequence, LTSDA (SEQ ID NO:30), RLTSDA (SEQ ID NO:31), ERLTSDA (SEQ ID NO:32), and KERLTSDA (SEQ ID NO:33) may also be used to target a PDZ domain-containing protein in T cells.

The C-terminal core sequence of CD53 is TIGL (SEQ ID NO:34). When naturally-occurring residues are added to the core sequence, QTIGL (SEQ ID NO:35), SQTIGL (SEQ ID NO:36), TSQTIGL (SEQ ID NO:37), and KTSQTIGL (SEQ ID NO:38) may also be used to target a PDZ domain-containing protein in T cells.

The C-terminal core sequence of CD83 is TELV (SEQ ID NO:248). When naturally-occurring residues are added to the core sequence, KTELV (SEQ ID NO:249), HKTELV (SEQ ID NO:250), PHKTELV (SEQ ID NO:251), and TPHKTELV (SEQ ID NO:252) may also be used to target a PDZ domain-containing protein in T cells.

The C-terminal core sequence of CD90 is FMSL (SEQ ID NO:39). When naturally-occurring residues are added to the core sequence, DFMSL (SEQ ID NO:40), TDFMSL (SEQ ID NO:41), ATDFMSL (SEQ ID NO:42), and QATDFMSL (SEQ ID NO:43) may also be used to target a PDZ domain-containing protein in T cells.

The C-terminal core sequence of CD95 is QSLV (SEQ ID NO:44). When naturally-occurring residues are added to the core sequence, IQSLV (SEQ ID NO:45), EIQSLV (SEQ ID NO:46), NEIQSLV (SEQ ID NO:47), and RNEIQSLV (SEQ ID NO:48) may also be used to target a PDZ domain-containing protein in T cells.

The C-terminal core sequence of CD97 is ESGI (SEQ ID NO:49). When naturally-occurring residues are added to the core sequence, SESGI (SEQ ID NO:50), ASESGI (SEQ ID NO:51), RASESGI (SEQ ID NO:52), and LRASESGI (SEQ ID NO:53) may also be used to target a PDZ domain-containing protein in T cells.

The C-terminal core sequence of CD98 is PYAA (SEQ ID NO:54). When naturally-occurring residues are added to the core sequence, FPYAA (SEQ ID NO:55), RFPYAA (SEQ ID NO:56), LRFPYAA (SEQ ID NO:57), and LLRFPYAA (SEQ ID NO:58) may also be used to target a PDZ domain-containing protein in T cells.

The C-terminal core sequence of CDw137 is GCEL (SEQ ID NO:59). When naturally-occurring residues are added to the core sequence, GGCEL (SEQ ID NO:60), EGGCEL (SEQ ID NO:61), EEGGCEL (SEQ ID NO:62), and EEEGGCEL (SEQ ID NO:63) may also be used to target a PDZ domain-containing protein in T cells.

The C-terminal core sequence of CD166 is KTEA (SEQ ID NO:64). When naturally-occurring residues are added to the core sequence, HKTEA (SEQ ID NO:65), NHKTEA (SEQ ID NO:66), NNHKTEA (SEQ ID NO:67), and ENNHKTEA (SEQ ID NO:68) may also be used to target a PDZ domain-containing protein in T cells.

The C-terminal core sequence of CDw128 is SSNL (SEQ ID NO:69). When naturally-occurring residues are added to the core sequence, VSSNL (SEQ ID. NO:70), NVSSNL (SEQ ID NO:71), VNVSSNL (SEQ ID NO:72), and SVNVSSNL (SEQ ID NO:73) may also be used to target a PDZ domain-containing protein in T cells.

The C-terminal core sequence of DNAM-1 is KTRV (SEQ ID NO:74). When naturally-occurring residues are added to the core sequence, PKTRV (SEQ ID NO:75), RPKTRV (SEQ ID NO:76), RRPKTRV (SEQ ID NO:77), and SRRPKTRV (SEQ ID NO:78) may also be used to target a PDZ domain-containing protein in T cells.

The C-terminal core sequence of FasL is LYKL (SEQ ID NO:79). When naturally-occurring residues are added to the core sequence, GLYKL (SEQ ID NO:80), FGLYKL (SEQ ID NO:81), FFGLYKL (SEQ ID NO:82), and TFFGLYKL (SEQ ID NO:83) may also be used to target a PDZ domain-containing protein in T cells.

The C-terminal core sequence of LPAP is VTAL (SEQ ID NO:84). When naturally-occurring residues are added to the core sequence, HVTAL (SEQ ID NO:85), LHVTAL (SEQ ID NO:86), GLHVTAL (SEQ ID NO:87), and QGLHVTAL (SEQ ID NO:88) may also be used to target a PDZ domain-containing protein in T cells.

The C-terminal core sequence of CLASP-1 is SAQV (SEQ ID NO:218). When naturally-occurring residues are added to the core sequence, SSAQV (SEQ ID NO:219), SSSAQV (SEQ ID NO:220), ISSSAQV (SEQ ID NO:221), and SISSSAQV (SEQ ID NO:222) may also be used to target a PDZ domain-containing protein in T cells.

The C-terminal core sequence of CLASP-2 is SSVV (SEQ ID NO:223). When naturally-occurring residues are added to the core sequence, SSSVV (SEQ ID NO:224), SSSSVV (SEQ ID NO:225), TSSSSVV (SEQ ID NO:226), and MTSSSSVV (SEQ ID NO:227) may also be used to target a PDZ domain-containing protein in T cells.

The C-terminal core sequence of CLASP-4 is YAEV (SEQ ID NO:228). When naturally-occurring residues are added to the core sequence, RYAEV (SEQ ID NO:229), PRYAEV (SEQ ID NO:230), SPRYAEV (SEQ ID NO:231), and GSPRYAEV (SEQ ID NO:232) may also be used to target a PDZ domain-containing protein in T cells.

The C-terminal core sequence of KV1.3 is FTDV (SEQ ID NO:238). When naturally-occurring residues are added to the core sequence, IFTDV (SEQ ID NO:239), KIFTDV (SEQ ID NO:240), KKIFTDV (SEQ ID NO:241), and IKKIFTDV (SEQ ID NO:242) may also be used to target a PDZ domain-containing protein in T cells.

The C-terminal core sequence of DOCK2 is STDL (SEQ ID NO:243). When naturally-occurring residues are added to the core sequence, LSTDL (SEQ ID NO:244), SLSTDL (SEQ ID NO:245), DSLSTDL (SEQ ID NO:246), and PDSLSTDL (SEQ ID NO:247) may also be used to target a PDZ domain-containing protein in T cells.

6.6.2 PDZ Motif Sequences of B Cell Surface Receptors

A number of surface receptors expressed by B cells contain a PDZ domain motif sequence. These molecules include, but are not limited to, CD38, CD53, CD95, CD97, CD98, CDw137, CD138, CDw125 (IL5R), DNAM-1, LPAP, Syndecan-2 (Barclay et al., 1997, The Leucocyte Antigen Facts Book, second edition, Academic Press) and BLR-1. The specific motif sequences of CD38, CD53, CD83, CD95, CD97, CD98, CDw137, DNAM-1, DOCK2, LPAP, CLASP-1, CLASP-2 and CLASP-4 have been described in the preceding paragraphs.

The C-terminal core sequence of CD138 is EFYA (SEQ ID NO:89). When naturally-occurring residues are added to the core sequence, EEFYA (SEQ ID NO:90), QEEFYA (SEQ ID NO:91), KQEEFYA (SEQ ID NO:92), and TKQEEFYA (SEQ ID NO:93) may also be used to target a PDZ domain-containing protein in B cells.

The C-terminal core sequence of CDw125 is DSVF (SEQ ID NO:94). When naturally-occurring residues are added to the core sequence, EDSVF (SEQ ID NO:95), LEDSVF (SEQ ID NO:96), TLEDSVF (SEQ ID NO:97), and ETLEDSVF (SEQ ID NO:98) may also be used to target a PDZ domain-containing protein in B cells.

The C-terminal core sequence of Syndecan-2 is EFYA (SEQ ID NO:89). When naturally-occurring residues are added to the core sequence, KEFYA (SEQ ID NO:259), TKEFYA (SEQ ID NO:260), PTKEFYA (SEQ ID NO:261), and APTKEFYA (SEQ ID NO:262) may also be used to target a PDZ domain-containing protein in B cells.

The C-terminal core sequence of BLR-1 is LTTF (SEQ ID NO:253). When naturally-occurring residues are added to the core sequence, SLTTF (SEQ ID NO:254), TSLTTF (SEQ ID NO:255), ATSLTTF (SEQ ID NO:256), and NATSLTTF (SEQ ID NO:257) may also be used to target a PDZ domain-containing protein in B cells.

6.6.3 PDZ Motif Sequences of Natural Killer Cell Surface Receptors

A number of surface receptors expressed by NK cells contain a PDZ domain motif sequence. These molecules include, but are not limited to CD38, CD56, CD98 and DNAM-1. The specific motif sequences of CD38, CD98 and DNAM-1 have been described in the preceding paragraphs.

The C-terminal core sequence of CD56 is ESKA (SEQ ID NO:99). When naturally-occurring residues are added to the core sequence, NESKA (SEQ ID NO:100), ENESKA (SEQ ID NO:101), KENESKA (SEQ ID NO:102), and TKENESKA (SEQ ID NO:103) may also be used to target a PDZ domain-containing protein in NK cells.

6.6.4 PDZ Motif Sequences of Monocyte Surface Receptors

A number of surface receptors expressed by cells of the monocytic lineage (monocytes and macrophages) contain a PDZ domain motif sequence. These molecules include, but are not limited to, CD38, CD44, CD46, CD49e, CD49f, CD53, CD61, CD95, CD97, CD98, CD148, CDw128, CDw137, Ly-6, DNAM-1 and FcεRIβ. The specific motif sequences of CD38, CD49e, CD49f, CD53, CD95, CD97, CD98, CDw128, CDw137, DNAM-1, Galectin 3 (Mac-2) and Mannose receptor have been described in the preceding paragraphs.

The C-terminal core sequence of CD44 is KIGV (SEQ ID NO:104). When naturally-occurring residues are added to the core sequence, MKIGV (SEQ ID NO:105), DMKIGV (SEQ ID NO:106), VDMKIGV (SEQ ID NO:107) and NVDMKIGV (SEQ ID NO:108) may also be used to target a PDZ domain-containing protein in monocytes.

The C-terminal core sequence of CD46 is FTSL (SEQ ID NO:109). When naturally-occurring residues are added to the core sequence, KFTSL (SEQ ID NO:110), VKFTSL (SEQ ID NO:11), EVKFRSL (SEQ ID NO:112) and REVKFTSL (SEQ ID NO:113) may also be used to target a PDZ domain-containing protein in monocytes.

The C-terminal core sequence of CD61 is KSLV (SEQ ID NO:114). When naturally-occurring residues are added to the core sequence, LKSLV (SEQ ID NO:115), FLKSLV (SEQ ID NO:116), RFLKSLV (SEQ ID NO:117) and GRFLKSLV (SEQ ID NO:118) may also be used to target a PDZ domain-containing protein in monocytes.

The C-terminal core sequence of CD148 is GYIA (SEQ ID NO:119). When naturally-occurring residues are added to the core sequence, NGYIA (SEQ ID NO:120), TNGYIA (SEQ ID NO:121), KTNGYIA (SEQ ID NO:122) and GKTNGYIA (SEQ ID NO:123) may also be used to target a PDZ domain-containing protein in monocytes.

The C-terminal core sequence of Ly-6 is QTLL (SEQ ID NO:124). When naturally-occurring residues are added to the core sequence, LQTLL (SEQ ID NO:125), LLQTLL (SEQ ID NO:126), VLLQTLL (SEQ ID NO:127) and SVLLQTLL (SEQ ID NO:128) may also be used to target a PDZ domain-containing protein in monocytes.

The C-terminal core sequence of FcεRIβ is PIDL (SEQ ID NO:129). When naturally-occurring residues are added to the core sequence, PPIDL (SEQ ID NO:130), SPPIDL (SEQ ID NO:131), MSPPIDL (SEQ ID NO:132) and EMSPPIDL (SEQ ID NO:133) may also be used to target a PDZ domain-containing protein in monocytes.

The C-terminal core sequence of Galectin 3 is YTMI (SEQ ID NO:134). When naturally-occurring residues are added to the core sequence, SYTMI (SEQ ID NO:135), ASYTMI (SEQ ID NO:136), SASYTMI (SEQ ID NO:137) and TSASYTMI (SEQ ID NO:138) may also be used to target a PDZ domain-containing protein in monocytes.

The C-terminal core sequence of mannose receptor is HSVI (SEQ ID NO:139). When naturally-occurring residues are added to the core sequence, EHSVI (SEQ ID NO:140), NEHSVI (SEQ ID NO:141), QNEHSVI (SEQ ID NO:142) and EQNEHSVI (SEQ ID NO:143) may also be used to target a PDZ domain-containing protein in monocytes.

6.6.5 PDZ Motif Sequences of Granulocyte Surface Receptors

A number of surface receptors expressed by granulocytes contain a PDZ domain motif sequence. These molecules include, but are not limited to CD53, CD95, CD97, CD98, CD148, CDw125, CDw128, FcεRIβ and G-CSFR. The specific motif sequences of most of these molecules have been described in the preceding paragraphs.

The C-terminal core sequence of G-CSFR is TSVL (SEQ ID NO:144). When naturally-occurring residues are added to the core sequence, ITSVL (SEQ ID NO:145), PITSVL (SEQ ID NO:146), FPITSVL (SEQ ID NO:147) and LFPITSVL (SEQ ID NO:148) may also be used to target a PDZ domain-containing protein in monocytes.

6.6.6 PDZ Motif Sequences of Endothelial Cell Surface Receptors

While endothelial cells are not hematopoietic cells, they closely interact with the hematopoietic system as they form the lining of blood vessels. As such, endothelial cells come in contact with the cells of the hematopoietic system. Thus, the ability to regulate endothelial cell function provides for indirect regulation of hematopoietic cells.

A number of surface receptors expressed by endothelial cells contain a PDZ domain motif sequence. These molecules include, but are not limited to CD34, CD46, CD66b, CD66c, CD105, CD106, CD62e (E-selectin) and VCAM1.

The C-terminal core sequence of CD34 is DTEL (SEQ ID NO:149). When naturally-occurring residues are added to the core sequence, ADTEL (SEQ ID NO:150), VADTEL (SEQ ID NO:151), VVADTEL (SEQ ID NO:152) and HVVADTEL (SEQ ID NO:153) may also be used to target a PDZ domain-containing protein in endothelial cells.

The C-terminal core sequence of CD66b and CD66c is VALI (SEQ ID NO:154). When naturally-occurring residues are added to the core sequence, RVALI (SEQ ID NO:155), ARVALI (SEQ ID NO:156), LARVALI (SEQ ID NO:157) and VLARVALI (SEQ ID NO:158) may also be used to target a PDZ domain-containing protein in endothelial cells.

The C-terminal core sequence of CD105 is SSMA (SEQ ID NO:159). When naturally-occurring residues are added to the core sequence, TSSMA (SEQ ID NO:160), STSSMA (SEQ ID NO:161), CSTSSMA (SEQ ID NO:291) and PCSTSSMA (SEQ ID NO:162) may also be used to target a PDZ domain-containing protein in endothelial cells.

The C-terminal core sequence of CD106 is KSKV (SEQ ID NO:163). When naturally-occurring residues are added to the core sequence, QKSKV (SEQ ID NO:164), AQKSKV (SEQ ID NO:165), EAQKSKV (SEQ ID NO:166) and VEAQKSKV (SEQ ID NO:167) may also be used to target a PDZ domain-containing protein in endothelial cells.

The C-terminal core sequence of CD62e is SYIL (SEQ ID NO:168). When naturally-occurring residues are added to the core sequence, PSYIL (SEQ ID NO:169), KPSYIL (SEQ ID NO:170), QKPSYIL (SEQ ID NO:171) and YQKPSYIL (SEQ ID NO:172) may also be used to target a PDZ domain-containing protein in endothelial cells.

The C-terminal core sequence of VCAM1 is KSKV (SEQ ID NO:163). When naturally-occurring residues are added to the core sequence, QKSKV (SEQ ID NO:164), AQKSKV (SEQ ID NO:165), EAQKSKV (SEQ ID NO:166), and VEAQKSKV (SEQ ID NO:167) may also be used to target a PDZ domain-containing protein in endothelial cells.

6.6.7 Mast Cell, Basophils and Eosinophil Cell Surface Receptors

FcεRIβ, CDw125, CDw128 and IL-8RB are transmembrane receptors expressed by mast cells, basophils and eosinophils. These receptors play a role in the activation of these cells to result in degranulation and histamine release in allergic reactions. The C-terminal core sequence of FcεRIβ is PIDL (SEQ ID NO:129). When naturally-occurring residues are added to the core sequence, PPIDL (SEQ ID NO:130), SPPIDL (SEQ ID NO:131), MSPPIDL (SEQ ID NO:132) and EMSPPIDL (SEQ ID NO:133) may also be used to target a PDZ domain-containing protein in mast cells. In addition, the residue E may be substituted with G to increase its binding affinity.

The C-terminal core sequence of CDw125 is DSVF (SEQ ID NO:94). When naturally-occurring residues are added to the core sequence, EDSVF (SEQ ID NO:95), LEDSVF (SEQ ID NO:96), TLEDSVF (SEQ ID NO:97), and ETLEDSVF (SEQ ID NO:98) may also be used to target a PDZ domain-containing protein in mast cells.

The C-terminal core sequence of CDw128 is SSNL (SEQ ID NO:69). When naturally-occurring residues are added to the core sequence, VSSNL (SEQ ID NO:70), NVSSNL (SEQ ID NO:71), VNVSSNL (SEQ ID NO:72), and SVNVSSNL (SEQ ID NO:73) may also be used to target a PDZ domain-containing protein in mast cells.

The C-terminal core sequence of IL-8RB is STTL (SEQ ID NO:233). When naturally-occurring residues are added to the core sequence TSTTL (SEQ ID NO:234), HTSTTL (SEQ ID NO:235), GHTSTTL (SEQ ID NO:236) and SGHTSTTL (SEQ ID NO:237) may also be used to target a PDZ domain-containing protein in mast cells.

6.6.8 Other PDZ Motif Sequences

The C-terminal core sequence of NMDA is ESDV (SEQ ID NO:263). When naturally-occurring residues are added to the core sequence, IESDV (SEQ ID NO:264), SIESDV (SEQ ID NO:265), PSIESDV (SEQ ID NO:266), and MPSIESDV (SEQ ID NO:267) may also be used to target a PDZ domain-containing protein in neuronal cells.

The C-terminal core sequence of neurexin is EYYV (SEQ ID NO:268). When naturally-occurring residues are added to the core sequence, KEYYV (SEQ ID NO:269), DKEYYV (SEQ ID NO:270), KDKEYYV (SEQ ID NO:271), and NKDKEYYV (SEQ ID NO:272) may also be used to target a PDZ domain-containing protein in neuronal cells.

The C-terminal core sequence of Glycophorin C is EYFI (SEQ ID NO:273). When naturally-occurring residues are added to the core sequence, KEYFI (SEQ ID NO:274), RKEYFI (SEQ ID NO:275), SRKEYFI (SEQ ID NO:276), and SSRKEYFI (SEQ ID NO:277) may also be used to target a PDZ domain-containing protein.

The C-terminal core sequence of CD148 is KTIA (SEQ ID NO:278). When naturally-occurring residues are added to the core sequence, GKTIA (SEQ ID NO:279), FGKTIA (SEQ ID NO:280), TFGKTIA (SEQ ID NO:281), and TTF-GKTIA (SEQ ID NO:282) may also be used to target a PDZ domain-containing protein in epithelial or myeloid cells.

6.7. Preparation of Peptides 6.7.1. Chemical Synthesis

The peptides of the invention or analogues thereof, may be prepared using virtually any art-known technique for the preparation of peptides and peptide analogues. For example, the peptides may be prepared in linear form using conventional solution or solid phase peptide syntheses and cleaved from the resin followed by purification procedures (Creighton, 1983, Protein Structures And Molecular Principles, W.H. Freeman and Co., N.Y.). Suitable procedures for synthesizing the peptides described herein are well known in the art. The composition of the synthetic peptides may be confirmed by amino acid analysis or sequencing (e.g., the Edman degradation procedure and mass spectroscopy).

In addition, analogues and derivatives of the peptides can be chemically synthesized. The linkage between each amino acid of the peptides of the invention may be an amide, a substituted amide or an isostere of amide. Nonclassical amino acids or chemical amino acid analogues can be introduced as a substitution or addition into the sequence. Non-classical amino acids include, but are not limited to, the D-isomers of the common amino acids, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosine, citrulline, cysteic acid, t-butylglycine, t-butylalanine, phenylglycine, cyclohexylalanine, β-alanine, fluoro-amino acids, designer amino acids such as β-methyl amino acids, Cα-methyl amino acids, Nα-methyl amino acids, and amino acid analogues in general. Furthermore, the amino acid can be D (dextrorotary) or L (levorotary).

6.7.2. Recombinant Synthesis

If the peptide is composed entirely of gene-encoded amino acids, or a portion of it is so composed, the peptide or the relevant portion may also be synthesized using conventional recombinant genetic engineering techniques. For recombinant production, a polynucleotide sequence encoding a linear form of the peptide is inserted into an appropriate expression vehicle, i.e., a vector which contains the necessary elements for the transcription and translation of the inserted coding sequence, or in the case of an RNA viral vector, the necessary elements for replication and translation. The expression vehicle is then transfected into a suitable target cell which will express the peptide. Depending on the expression system used, the expressed peptide is then isolated by procedures well-established in the art. Methods for recombinant protein and peptide production are well known in the art (see, e.g., Maniatis et al., 1989, Molecular Cloning A Laboratory Manual, Cold Spring Harbor Laboratory, N.Y.; and Ausubel et al., 1989, Current Protocols in Molecular Biology, Greene Publishing Associates and Wiley Interscience, N.Y.).

A variety of host-expression vector systems may be utilized to express the peptides described herein. These include, but are not limited to, microorganisms such as bacteria transformed with recombinant bacteriophage DNA or plasmid DNA expression vectors containing an appropriate coding sequence; yeast or filamentous fungi transformed with recombinant yeast or fungi expression vectors containing an appropriate coding sequence; insect cell systems infected with recombinant virus expression vectors (e.g., baculovirus) containing an appropriate coding sequence; plant cell systems infected with recombinant virus expression vectors (e.g., cauliflower mosaic virus or tobacco mosaic virus) or transformed with recombinant plasmid expression vectors (e.g., Ti plasmid) containing an appropriate coding sequence; or animal cell systems.

The expression elements of the expression systems vary in their strength and specificities. Depending on the host/vector system utilized, any of a number of suitable transcription and translation elements, including constitutive and inducible promoters, may be used in the expression vector. For example, when cloning in bacterial systems, inducible promoters such as pL of bacteriophage λ, plac, ptrp, ptac (ptrp-lac hybrid promoter) and the like may be used; when cloning in insect cell systems, promoters such as the baculovirus polyhedron promoter may be used; when cloning in plant cell systems, promoters derived from the genome of plant cells (e.g., heat shock promoters; the promoter for the small subunit of RUBISCO; the promoter for the chlorophyll a/b binding protein) or from plant viruses (e.g., the 35S RNA promoter of CaMV; the coat protein promoter of TMV) may be used; when cloning in mammalian cell systems, promoters derived from the genome of mammalian cells (e.g., metallothionein promoter) or from mammalian viruses (e.g., the adenovirus late promoter; the vaccinia virus 7.5 K promoter) may be used; when generating cell lines that contain multiple copies of expression product, SV40-, BPV- and EBV-based vectors may be used with an appropriate selectable marker.

In cases where plant expression vectors are used, the expression of sequences encoding the peptides of the invention may be driven by any of a number of promoters. For example, viral promoters such as the 35S RNA and 19S RNA promoters of CaMV (Brisson et al., 1984, Nature 310:511–514), or the coat protein promoter of TMV (Takamatsu et al., 1987, EMBO J. 6:307–311) may be used; alternatively, plant promoters such as the small subunit of RUBISCO (Coruzzi et al., 1984, EMBO J. 3:1671–1680; Broglie et al., 1984, Science 224:838–843) or heat shock promoters, e.g., soybean hsp17.5-E or hsp17.3-B (Gurley et al., 1986, Mol. Cell. Biol. 6:559–565) may be used. These constructs can be introduced into planleukocytes using Ti plasmids, Ri plasmids, plant virus vectors, direct DNA transformation, microinjection, electroporation, etc. For reviews of such techniques see, e.g., Weissbach & Weissbach, 1988, Methods for Plant Molecular Biology, Academic Press, NY, Section VIII, pp. 421–463; and Grierson & Corey, 1988, Plant Molecular Biology, 2d Ed., Blackie, London, Ch. 7–9.

In one insect expression system that may be used to produce the peptides of the invention, *Autographa californica* nuclear polyhidrosis virus (AcNPV) is used as a vector to express the foreign genes. The virus grows in *Spodoptera frugiperda* cells. A coding sequence may be cloned into non-essential regions (for example the polyhedron gene) of the virus and placed under control of an AcNPV promoter (for example, the polyhedron promoter). Successful insertion of a coding sequence will result in inactivation of the polyhedron gene and production of non-occluded recombinant virus (i.e., virus lacking the proteinaceous coat coded for by the polyhedron gene). These recombinant viruses are then used to infect *Spodoptera frugiperda* cells in which the inserted gene is expressed. (e.g., see Smith et al., 1983, J. Virol. 46:584; Smith, U.S. Pat. No. 4,215,051). Further examples of this expression system may be found in Current Protocols in Molecular Biology, Vol. 2, Ausubel et al., eds., Greene Publish. Assoc. & Wiley Interscience.

In mammalian host cells, a number of viral based expression systems may be utilized. In cases where an adenovirus is used as an expression vector, a coding sequence may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing peptide in infected hosts. (e.g., See Logan & Shenk, 1984, Proc. Natl. Acad. Sci. USA 81:3655–3659). Alternatively, the vaccinia 7.5 K promoter may be used, (see, e.g., Mackett et al., 1982, Proc. Natl. Acad. Sci. USA 79:7415–7419; Mackett et al., 1984, J. Virol. 49:857–864; Panicali et al., 1982, Proc. Natl. Acad. Sci. USA 79:4927–4931).

Other expression systems for producing linear peptides of the invention will be apparent to those having skill in the art.

6.7.3. Purification of the Peptides and Peptide Analogues

The peptides and peptide analogues of the invention can be purified by art-known techniques such as high performance liquid chromatography, ion exchange chromatography, gel electrophoresis, affinity chromatography and the like. The actual conditions used to purify a particular peptide or analogue will depend, in part, on factors such as net charge, hydrophobicity, hydrophilicity, etc., and will be apparent to those having skill in the art. The purified peptides can be identified by assays based on their physical or functional properties, including radioactive labeling followed by gel electrophoresis, radioimmunoassays, ELISA, bioassays, and the like.

For affinity chromatography purification, any antibody which specifically binds the peptides or peptide analogues may be used. For the production of antibodies, various host animals, including but not limited to rabbits, mice, rats, etc., may be immunized by injection with a peptide. The peptide may be attached to a suitable carrier, such as BSA or KLH, by means of a side chain functional group or linkers attached to a side chain functional group. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacilli Calmette-Guerin) and *Corynebacterium parvum*.

Monoclonal antibodies to a peptide may be prepared using any technique which provides for the production of antibody molecules by continuous cell lines in culture. These include but are not limited to the hybridoma technique originally described by Koehler and Milstein, 1975, Nature 256:495–497, the human B-cell hybridoma technique, Kosbor et al., 1983, Immunology Today 4:72; Cote e al., 1983, Proc. Natl. Acad. Sci. U.S.A. 80:2026–2030 and the EBV-hybridoma technique (Cole et al., 1985, Monoclonal Antibodies and Cancer Therapy, Alan R. Liss, Inc., pp. 77–96 (1985)). In addition, techniques developed for the production of "chimeric antibodies" (Morrison et al., 1984, Proc. Natl. Acad. Sci. U.S.A. 81:6851–6855; Neuberger et al., 1984, Nature 312:604–608; Takeda et al., 1985, Nature 314:452–454) by splicing the genes from a mouse antibody molecule of appropriate antigen specificity together with genes from a human antibody molecule of appropriate biological activity can be used. Alternatively, techniques described for the production of single chain antibodies (U.S. Pat. No. 4,946,778) can be adapted to produce peptide-specific single chain antibodies.

Antibody fragments which contain deletions of specific binding sites may be generated by known techniques. For example, such fragments include but are not limited to $F(ab')_2$ fragments, which can be produced by pepsin digestion of the antibody molecule and Fab fragments, which can be generated by reducing the disulfide bridges of the $F(ab')_2$ fragments. Alternatively, Fab expression libraries may be constructed (Huse et al., 1989, Science 246:1275–1281) to allow rapid and easy identification of monoclonal Fab fragments with the desired specificity for the peptide of interest.

The antibody or antibody fragment specific for the desired peptide can be attached, for example, to agarose, and the antibody-agarose complex is used in immunochromatography to purify peptides of the invention. See, Scopes, 1984, Protein Purification: Principles and Practice, Springer-Verlag N.Y., Inc., NY, Livingstone, 1974, Methods Enzymology: Immunoaffinity Chromatography of Proteins 34:723–731.

6.8. Uses of PDZ Domain Binding and Antagonist Compounds

In one aspect of the invention, the PDZ domain binding and PDZ-PL inhibitory compounds of the present invention are useful in regulating diverse activities of hematopoietic cells (e.g., T cells and B cells) and other cells involved in the immune response.

In one embodiment of the invention, the compounds of the invention are used to inhibit leukocyte activation, which is manifested in measurable events including but not limited to, cytokine production, cell adhesion, expansion of cell numbers, apoptosis and cytotoxicity. As a corollary, the compounds of the invention may be used to treat diverse conditions associated with undesirable leukocyte activation, including but not limited to, acute and chronic inflammation, graft-versus-host disease, transplantation rejections hypersensitivities and autoimmunity such as multiple sclerosis, rheumatoid arthritis, peridontal disease, systemic lupus erythematosis, juvenile diabetes mellitis, non-insulin-dependent diabetes, and allergies, and other conditions listed herein (see, e.g., Section 6.4, supra).

Thus, the invention also relates to methods of using such compositions in modulating leukocyte activation as measured by, for example, cytotoxicity, cytokine production, cell proliferation, and apoptosis. Assays for activation are well known. For example, PDZ/PL interaction antagonists can be evaluated in the following: (1) cytotoxic T lymphocytes can be incubated with radioactively labeled target cells and the antigen-specific lysis of these target cells detected by the release of radioactivity, (2) helper T lymphocytes can be incubated with antigens and antigen presenting cells and the synthesis and secretion of cytokines measured by standard methods (Windhagen A; et al., 1995, Immunity 2(4): 373–80), (3) antigen presenting cells can be incubated with whole protein antigen and the presentation of that antigen on MHC detected by either T lymphocyte activation assays or biophysical methods (Harding et al., 1989, Proc. Natl. Acad. Sci., 86: 4230–4), (4) mast cells can be incubated with reagents that cross-link their Fc-epsilon receptors and histamine release measured by enzyme immunoassay (Siraganian, et al., 1983, TIPS 4: 432–437).

Similarly, the effect of PDZ/PL interaction antagonists on products of leukocyte activation in either a model organism (e.g., mouse) or a human patient can also be evaluated by various methods that are well known. For example, (1) the production of antibodies in response to vaccination can be readily detected by standard methods currently used in clinical laboratories, e.g., an ELISA; (2) the migration of immune cells to sites of inflammation can be detected by scratching the surface of skin and placing a sterile container to capture the migrating cells over scratch site (Peters et al., 1988, Blood 72: 1310–5); (3) the proliferation of peripheral blood mononuclear cells in response to mitogens or mixed lymphocyte reaction can be measured using $^3$H-thymidine; (4) the phagocytic capacity of granulocytes, macrophages, and other phagocytes in PBMCs can be measured by placing PMBCs in wells together with labeled particles (Peters et al., 1988); and (5) the differentiation of immune system cells can be measured by labeling PBMCs with antibodies to CD molecules such as CD4 and CD8 and measuring the fraction of the PBMCs expressing these markers.

In one exemplary assay, human peripheral blood mononuclear cells (PBMC), human T cell clones (e.g., Jurkat E6, ATCC TIB-152), EBV-transformed B cell clones (e.g., 9D10, ATCC CRL-8752), antigen-specific T cell clones or lines can be used to examine PDZ/PL interaction antagonists in vitro. Inhibition of activation of these cells or cell lines can be used for the evaluation of potential PDZ/PL interaction antagonists.

Standard methods by which hematopoietic cells are stimulated to undergo activation characteristic of an immune response are, for example:

A) Antigen specific stimulation of immune responses. Either pre-immunized or naive mouse splenocytes can be generated by standard procedures. In addition, antigen-specific T cell clones and hybridomas (e.g., MBP-specific), and numerous B cell lymphoma cell lines (e.g., CH27), have been previously characterized and are available for the assays discussed below. Antigen specific splenocytes or B-cells can be mixed with antigen specific T-cells in the presence of antigen to generate an immune response. This can be performed in the presence or absence of PDZ/PL interaction antagonists to assay whether PDZ/PL interaction antagonists modulate the immune response infra.

B) Non-specific T cell activation. The following methods can be used to activate T cells in the absence of antigen: 1) cross-linking T cell receptor (TCR) by addition of antibodies against receptor activation molecules (e.g., TCR, CD3, or CD2) together with antibodies against co-stimulator molecules, for example anti-CD28; 2) activating cell surface receptors in a non-specific fashion using lectins such as concanavalin A (con A) and phytohemagglutinin (PHA); 3) mimicking cell surface receptor-mediated activation using pharmacological agents that activate protein kinase C (e.g., phorbol esters) and increase cytoplasmic $Ca^{2+}$ (e.g., ionomycin).

C) Non-specific B cell activation: 1) application of antibodies against cell surface molecules such as IgM, CD20, or CD21. 2) Lipopolysaccharide (LPS), phorbol esters, calcium ionophores and ionomycin can also be used to by-pass receptor triggering.

D) Mixed lymphocyte reaction (MLR). Mix donor PBMC with recipient PBMC to activate lymphocytes by presentation of mismatched tissue antigens, which occurs in all cases except identical twins.

E) Generation of a specific T cell clone or line that recognizes a particular antigen. A standard approach is to generate tetanus toxin-specific T cells from a donor that has recently been boosted with tetanus toxin. Major histocompatibility complex- (MHC-) matched antigen presenting cells and a source of tetanus toxin are used to maintain antigen specificity of the cell line or T cell clone (Lanzavecchia, A., et al., 1983, Eur. J. Immun. 13: 733–738).

Assay Quantitation

The assays described above can be quantitated by a variety of well known quantitation methods. For example:

(A) Tyrosine Phosphorylation

Tyrosine phosphorylation of early response proteins such as HS 1, PLC-r, ZAP-76, and Vav is an early biochemical event following leukocyte activation. The tyrosine phosphorylated proteins can be detected by Western blot using antibodies against phosphorylated tyrosine residues. Tyrosine phosphorylation of these early response proteins can be used as a standard assay for leukocyte activation (J. Biol. Chem., 1997, 272(23): 14562–14570). Any change in the phosphorylation pattern of these or related proteins when immune responses are generated in the presence of potential PDZ/PL interaction antagonists is indicative of a potential PDZ/PL interaction antagonists.

(B) Intracellular Calcium Flux

The kinetics of intracellular $Ca^{2+}$ concentrations are measured over time after stimulation of cells preloaded with a calcium sensitive dye. Upon binding $Ca^{2+}$ the indicator dye (e.g., Fluor-4 (Molecular Probes)), exhibits an increase in fluorescence level using flow cytometry, solution fluorometry, and confocal microscopy. Any change in the level or timing of calcium flux when immune responses are generated in the presence of PDZ/PL interaction antagonists is indicative of an inhibition of this response.

(C) Regulation of Early Activation Markers

Increased and diminished expression/regulation of early lymphocyte activation marker levels such as CD69, IL-2R, MHC class II, B7, and TCR are commonly measured with fluorescently labeled antibodies using flow cytometry. All antibodies are commercially available. Any change in the expression levels of lymphocyte activation markers when immune responses are generated in the presence of the PDZ/PL interaction antagonists is indicative of an inhibition of this response.

(D) Increased Metabolic Activity/Acid Release

Activation of most known signal transduction pathways trigger increases in acidic metabolites. This reproducible biological event is measured as the rate of acid release using a microphysiometer (Molecular Devices), and is used as an early activation marker when comparing the treatment of cells with potential biological therapeutics (McConnell, H. M. et al., 1992, Science 257: 1906–1912 and McConnell, H. M., 1995, Proc. Natl. Acad. Sci. 92: 2750–2754). Any statistically significant increase or decrease in acid release of the PDZ/PL interaction antagonist-treated sample, as compared to control sample (no treatment), suggest an effect of the PDZ/PL interaction antagonist on biological function.

(E) Cell Proliferation/Cell Viability Assays (1) $^3$H-thimidine Incorporation

Exposure of lymphocytes to antigen or mitogen in vitro induces DNA synthesis and cellular proliferation. The measurement of mitotic activity by $^3$H-thimidine incorporation into newly synthesized DNA is one of the most frequently used assays to quantitative T cell activation. Depending on the cell population and form of stimulation used to activate the T cells, mitotic activity can be measured within 24–72 hrs. in vitro, post 3H-thimidine pulse (Mishell, B. B. and S. M. Shiigi, 1980, Selected Methods in Cellular Immunology, W. H. Freeman and Company and Dutton, R. W. and Pearce, J. D., 1962, Nature 194: 93). Any statistically significant increase or decrease in CPM of the PDZ/PL interaction antagonist-treated sample, as compared to control sample (no treatment), suggest and effect of the PDZ/PL interaction antagonist on biological function.

(2) MTS [5-(3-carboxymethoxyphenyl)-2-(4,5-dimethylthiazolyl)-3(4-sulfophenyl)tetrazolium, inner salt] is a colorimetric method for determining the number of viable cells in proliferation or cytotoxicity assays (Barltrop, J. A. et al., 1991, Bioorg. & Med. Chem. Lett. 1: 611). 1–5 days after lymphocyte activation, MTS tetrazolium compound, Owen's reagent, is bioreduced by cells into a colored formazan product that is soluble in tissue culture media. Color intensity is read at 490 nm minus 650 nm using a microplate reader. Any statistically significant increase or decrease in color intensity of the PDZ/PL interaction antagonist-treated sample, as compared to control sample (no treatment), can suggest an effect of the PDZ/PL interaction antagonist on biological function (Mosmann, T., 1983, J. Immunol. Methods 65: 55 and Barltrop, J. A. et al. (1991)).

(3) Bromodeoxyuridine (BrdU), a thymidine analogue, readily incorporates into cells undergoing DNA synthesis. BrdU-pulsed cells are labeled with an enzyme-conjugated anti-BrdU antibody (Gratzner, H. G., 1982, Science 218: 474–475). A colorimetric, soluble substrate is used to visualize proliferating cells that have incorporated BrdU. Reaction is stopped with sulfuric acid and plate is read at 450 nm using a microplate reader. Any statistically significant increase or decrease in color intensity of the PDZ/PL interaction antagonist-treated sample, as compared to control sample (no treatment), suggest an effect of the PDZ/PL interaction antagonist on biological function.

(F) Apoptosis by Annexin V

Programmed cell death or apoptosis is an early event in a cascade of catabolic reactions leading to cell death. A lose in the integrity of the cell membrane allows for the binding of fluorescently conjugated phosphatidylserine. Stained cells can be measured by fluorescence microscopy and flow cytometry (Vermes, I., 1995, J. Immunol. Methods. 180: 39–52). In one embodiment, any statistically significant increase or decrease in apoptotic cell number of the PDZ/PL interaction antagonist-treated sample, as compared to control sample (no treatment), suggest an effect of the PDZ/PL interaction antagonist on biological function. For evaluating apoptosis in situ, assays for evaluating cell death in tissue samples can also be used in vivo studies.

(G) Quantitation of Cytokine Production

Cell supernatants harvested after cell stimulation for 16–48 hrs are stored at −80° C. until assayed or directly tested for cytokine production. Multiple cytokine assays can be performed on each sample. IL-2, IL-3, IFN-γ and other cytokine ELISA Assays are available for mouse, rat, and human (Endogen, Inc. and BioSource). Cytokine production is measured using a standard two-antibody sandwich ELISA protocol as described by the manufacturer. The presence of horseradish peroxidase is detected with 3, 3'5, 5' tertamethyl benziidine (TMB) substrate and the reaction is stopped with sulfuric acid. The absorbency at 450 nm is measured using a microplate reader. Any statistically significant increase or decrease in color intensity of the PDZ/PL interaction antagonist-treated sample, as compared to control sample (no treatment), suggest an effect of the PDZ/PL interaction antagonist on biological function. See also Example 1, infra. Detection of intracellular cytokines using anti-cytokine antibodies provides the additional advantage of measuring cytokines fore mixed cell populations. This allows for phenotyping measuring frequency of cytokine producing cell types in suspension or in tissues.

(H) NF-AT can be Visualized by Immunostaining

T cell activation requires the import of nuclear factor of activated T cells (NF-AT) to the nucleus. This translocation of NF-AT can be visualized by immunostaining with anti-NF-AT antibody (Cell 1998, 93: 851–861). Therefore, NF-AT nuclear translocation has been used to assay T cell activation. Similarly, NF-AT/luciferase reporter assays have been used as a standard measurement of T cell activation (MCB 1996, 12: 7151–7160). Any statistically significant increase or decrease in the nuclear translocation of NF-AT brought about by the PDZ/PL interaction antagonist-treated sample, as compared to control sample (no treatment), suggest an effect of the PDZ/PL interaction antagonist on biological function. In order to optimize the use of the peptides and peptide analogues disclosed herein in a human subject, various animal models may be used to define certain clinical parameters. For example, the compounds of the invention may be tested in different dosages, formulations and route of administration in a cardiac transplant mouse model to optimize their ability to inhibit rejection responses to solid organ transplants (Fulmer et al., 1963, Am. J. Anat. 113:273; Jockusch et al., 1983, Exp. Neurol. 81:749).

In situations where inhibition of a T cell response is desired, the compounds of the inventions may be used to inhibit PDZ domain interactions with CD3, CD4, CD6 and CDw137. In addition, the compounds of the invention may be used to inhibit PDZ domain interactions with CD53 and CD138 in B cells. In order to inhibit IgE-mediated allergic reactions, the compounds of the invention may be used to inhibit PDZ domain interactions with FcεRIβ, CDw125 and CDw128. Furthermore, a PDZ motif sequence (PL sequence) of CD95 may be used to induce apoptosis of lymphomas.

(I) Inflammatory Mediator Release Assays

Assays are well known in the art for inflammatory mediator release to access the effect of compounds or treatments IgE-mediated degranulation. See, e.g. Berger et al., 1997, Measuring Cell Degranulation e.g., Ch 19.6 Immunology Method Manual. Academic Press, Ltd. 1436–1440 and Siraganian, 1983, Histamine Secretion from Mast Cells and Basophil. TIPS 4:432–437, both incorporated by reference herein.

6.9. Formulation and Route of Administration 6.9.1 Introduction of Agonists or Antagonists (e.g., Peptides and Fusion Proteins) into Cells In one aspect, the PDZ-PL antagonists of the invention are introduced into a cell to modulate (i.e., increase or decrease) a biological function or activity of the cell. Many small organic molecules readily cross the cell membranes (or can be modified by one of skill using routine methods to increase the ability of compounds to enter cells, e.g., by reducing or eliminating charge, increasing lipophilicity, conjugating the molecule to a moiety targeting a cell surface receptor such that after interacting with the receptor). Methods for introducing larger molecules, e.g., peptides and fusion proteins are also well known, including, e.g., injection, liposome-mediated fusion, application of a hydrogel, conjugation to a targeting moiety conjugate endocytozed by the cell, electroporation, and the like).

In one embodiment, the antagonist or agent is a fusion polypeptide or derivatized polypeptide. A fusion or derivatized protein may include a targeting moiety that increases the ability of the polypeptide to traverse a cell membrane or causes the polypeptide to be delivered to a specified cell type (e.g., liver cells or tumor cells) preferentially or cell compartment (e.g., nuclear compartment) preferentially. Examples of targeting moieties include lipid tails, amino acid sequences such as antennapoedia peptide or a nuclear localization signal (NLS; e.g., Xenopus nucleoplasmin Robbins et al., 1991, Cell 64:615).

In one embodiment of the invention, a peptide sequence or peptide analog determined to inhibit a PDZ domain-PL protein binding, in an assay of the invention is introduced into a cell by linking the sequence to an amino acid sequence that facilitates its transport through the plasma membrane (a "transmembrane transporter sequence"). The peptides of the invention may be used directly or fused to a transmembrane transporter sequence to facilitate their entry into cells. In the case of such a fusion peptide, each peptide may be fused with a heterologous peptide at its amino terminus directly or by using a flexible polylinker such as the pentamer G—G—G—G-S (SEQ ID NO:1) repeated 1 to 3 times. Such linker has been used in constructing single chain antibodies (scFv) by being inserted between $V_H$ and $V_L$ (Bird et al., 1988, Science 242:423–426; Huston et al., 1988, Proc. Natl. Acad. Sci. U.S.A. 85:5979–5883). The linker is designed to enable the correct interaction between two beta-sheets forming the variable region of the single chain antibody. Other linkers which may be used include Glu-Gly-Lys-Ser—Ser-Gly-Ser-Gly-Ser-Glu-Ser-Lys-Val-Asp (SEQ ID NO:2) (Chaudhary et al., 1990, Proc. Natl. Acad. Sci. U.S.A. 87:1066–1070) and Lys-Glu-Ser-Gly-Ser-Val-Ser—Ser-Glu-Gln-Leu-Ala-Gln-Phe-Arg-Ser-Leu-Asp (SEQ ID NO:3) (Bird et al., 1988, Science 242:423–426).

A number of peptide sequences have been described in the art as capable of facilitating the entry of a peptide linked to these sequences into a cell through the plasma membrane (Derossi et al., 1998, Trends in Cell Biol. 8:84). For the purpose of this invention, such peptides are collectively referred to as transmembrane transporter peptides. Examples of these peptide include, but are not limited to, tat derived from HIV (Vives et al., 1997, J. Biol. Chem. 272:16010; Nagahara et al., 1998, Nat. Med. 4:1449), antennapedia from Drosophila (Derossi et al., 1994, J. Biol. Chem. 261:10444), VP22 from herpes simplex virus (Elliot and D'Hare, 1997, Cell 88:223–233), complementarity-determining regions (CDR) 2 and 3 of anti-DNA antibodies (Avrameas et al., 1998, Proc. Natl. Acad Sci. U.S.A., 95:560 1–5606), 70 KDa heat shock protein (Fujihara, 1999, EMBO J. 18:411–419) and transportan (Pooga et al., 1998, FASEB J. 12:67–77). In a preferred embodiment of the invention, a truncated HIV tat peptide having the sequence of GYGRKKRRQRRRG (SEQ ID NO:173) is used.

It is preferred that a transmembrane transporter sequence is fused to a hematopoietic cell surface receptor carboxyl terminal sequence at its amino-terminus with or without a linker. Generally, the C-terminus of a PDZ motif sequence (PL sequence) must be free in order to interact with a PDZ domain. The transmembrane transporter sequence may be used in whole or in part as long as it is capable of facilitating entry of the peptide into a cell.

In an alternate embodiment of the invention, a hematopoietic cell surface receptor C-terminal sequence may be used alone when it is delivered in a manner that allows its entry into cells in the absence of a transmembrane transporter sequence. For example, the peptide may be delivered in a liposome formulation or using a gene therapy approach by delivering a coding sequence for the PDZ motif alone or as a fusion molecule into a target cell.

The compounds of the of the invention may also be administered via liposomes, which serve to target the conjugates to a particular tissue, such as lymphoid tissue, or targeted selectively to infected cells, as well as increase the half-life of the peptide composition. Liposomes include emulsions, foams, micelles, insoluble monolayers, liquid crystals, phospholipid dispersions, lamellar layers and the like. In these preparations the peptide to be delivered is incorporated as part of a liposome, alone or in conjunction with a molecule which binds to, e.g., a receptor prevalent among lymphoid cells, such as monoclonal antibodies which bind to the CD45 antigen, or with other therapeutic or immunogenic compositions. Thus, liposomes filled with a desired peptide or conjugate of the invention can be directed to the site of lymphoid cells, where the liposomes then deliver the selected inhibitor compositions. Liposomes for use in the invention are formed from standard vesicle-forming lipids, which generally include neutral and negatively charged phospholipids and a sterol, such as cholesterol. The selection of lipids is generally guided by consideration of, e.g., liposome size, acid lability and stability of the liposomes in the blood stream. A variety of methods are available for preparing liposomes, as described in, e.g., Szoka et al., Ann. Rev. Biophys. Bioeng. 9:467 (1980), U.S. Pat. Nos. 4,235,871, 4,501,728 and 4,837,028.

The targeting of liposomes using a variety of targeting agents is well known in the art (see, e.g., U.S. Pat. Nos. 4,957,773 and 4,603,044). For targeting to the immune cells, a ligand to be incorporated into the liposome can include, e.g., antibodies or fragments thereof specific for cell surface determinants of the desired immune system cells. A liposome suspension containing a peptide or conjugate may be administered intravenously, locally, topically, etc. in a dose which varies according to, inter alia, the manner of administration, the conjugate being delivered, and the stage of the disease being treated.

In order to specifically deliver a PDZ motif sequence (PL sequence) peptide into a specific cell type, the peptide may be linked to a cell-specific targeting moiety, which include but are not limited to, ligands for diverse leukocyte surface molecules such as growth factors, hormones and cytokines, as well as antibodies or antigen-binding fragments thereof. Since a large number of cell surface receptors have been identified in leukocytes, ligands or antibodies specific for these receptors may be used as cell-specific targeting moieties. For example, interleukin-2, B7-1 (CD80), B7-2 (CD86) and CD40 or peptide fragments thereof may be used to specifically target activated T cells (The Leucocyte Antigen Facts Book, 1997, Barclay et al. (eds.), Academic Press). CD28, CTLA-4 and CD40L or peptide fragments thereof may be used to specifically target B cells. Furthermore, Fc domains may be used to target certain Fc receptor-expressing cells such as monocytes.

Antibodies are the most versatile cell-specific targeting moieties because they can be generated against any cell surface antigen. Monoclonal antibodies have been generated against leukocyte lineage-specific markers such as certain CD antigens. Antibody variable region genes can be readily isolated from hybridoma cells by methods well known in the art. However, since antibodies are assembled between two heavy chains and two light chains, it is preferred that a scFv be used as a cell-specific targeting moiety in the present invention. Such scFv are comprised of $V_H$ and $V_L$ domains linked into a single polypeptide chain by a flexible linker peptide.

The PDZ motif sequence (PL sequence) may be linked to a transmembrane transporter sequence and a cell-specific targeting moiety to produce a tri-fusion molecule. This molecule can bind to a leukocyte surface molecule, passes through the membrane and targets PDZ domains.

Alternatively, a PDZ motif sequence (PL sequence) may be linked to a cell-specific targeting moiety that binds to a surface molecule that internalizes the fusion peptide.

In an other approach, microspheres of artificial polymers of mixed amino acids (proteinoids) have been used to deliver pharmaceuticals. For example, U.S. Pat. No. 4,925,673 describes drug-containing proteinoid microsphere carriers as well as methods for their preparation and use. These proteinoid microspheres are useful for the delivery of a number of active agents. Also see, U.S. Pat. Nos. 5,907,030 and 6,033,884, which are incorporated herein by reference.

6.9.2 Introduction of Polynucleotides into Cells

A polynucleotide encoding a surface receptor C-terminal peptide may be useful in the treatment of various leukocyte activation-associated abnormal conditions. By introducing gene sequences into cells, gene therapy can be used to treat conditions in which leukocytes are activated to result in deleterious consequences. In one embodiment, a polynucleotide that encodes a PL sequence peptide of the invention is introduced into a cell where it is expressed. The expressed peptide then inhibits the interaction of PDZ proteins and PL proteins in the cell.

Thus, in one embodiment, the polypeptides of the invention are expressed in a cell by introducing a nucleic acid (e.g., a DNA expression vector or mRNA) encoding the desired protein or peptide into the cell. Expression may be either constitutive or inducible depending on the vector and choice of promoter. Methods for introduction and expression of nucleic acids into a cell are well known in the art and described herein.

In a specific embodiment, nucleic acids comprising a sequence encoding a peptide disclosed herein, are administered to a human subject. In this embodiment of the invention, the nucleic acid produces its encoded product that mediates a therapeutic effect by inhibiting leukocyte activation. Any of the methods for gene therapy available in the art can be used according to the present invention. Exemplary methods are described below.

For general reviews of the methods of gene therapy, see Goldspiel et al., 1993, Clinical Pharmacy 12:488–505; Wu and Wu, 1991, Biotherapy 3:87–95; Tolstoshev, 1993, Ann. Rev. Pharmacol. Toxicol. 32:573–596; Mulligan, 1993, Science 260:926–932; and Morgan and Anderson, 1993, Ann. Rev. Biochem. 62:191–217; May, 1993, TIBTECH 11(5):155–215. Methods commonly known in the art of recombinant DNA technology which can be used are described in Ausubel et al. (eds.), 1993, Current Protocols in Molecular Biology, John Wiley & Sons, NY; and Kriegler, 1990, Gene Transfer and Expression, A Laboratory Manual, Stockton Press, NY.

In a preferred embodiment of the invention, the therapeutic composition comprises a coding sequence that is part of an expression vector. In particular, such a nucleic acid has a promoter operably linked to the coding sequence, said promoter being inducible or constitutive, and, optionally, tissue-specific. In another specific embodiment, a nucleic acid molecule is used in which the coding sequence and any other desired sequences are flanked by regions that promote homologous recombination at a desired site in the genome, thus providing for intrachromosomal expression of the nucleic acid (Koller and Smithies, 1989, Proc. Natl. Acad. Sci. USA 86:8932–8935; Zijlstra et al., 1989, Nature 342:435–438).

Delivery of the nucleic acid into a patient may be either direct, in which case the patient is directly exposed to the nucleic acid or nucleic acid-carrying vector, or indirect, in which case, cells are first transformed with the nucleic acid in vitro, then transplanted into the patient. These two approaches are known, respectively, as in vivo or ex vivo gene therapy.

In a specific embodiment, the nucleic acid is directly administered in vivo, where it is expressed to produce the encoded product. This can be accomplished by any methods known in the art, e.g., by constructing it as part of an appropriate nucleic acid expression vector and administering it so that it becomes intracellular, e.g., by infection using a defective or attenuated retroviral or other viral vector (see U.S. Pat. No. 4,980,286), by direct injection of naked DNA, by use of microparticle bombardment (e.g., a gene gun; Biolistic, Dupont), by coating with lipids or cell-surface receptors or transfecting agents, by encapsulation in liposomes, microparticles, or microcapsules, by administering it in linkage to a peptide which is known to enter the nucleus, or by administering it in linkage to a ligand subject to receptor-mediated endocytosis (see e.g., Wu and. Wu, 1987, J. Biol. Chem. 262:4429–4432) which can be used to target cell types specifically expressing the receptors. In another embodiment, a nucleic acid-ligand complex can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180 dated Apr. 16, 1992; WO 92/22635 dated Dec. 23, 1992; WO92/20316 dated Nov. 26, 1992; WO93/14188 dated Jul. 22, 1993; WO 93/20221 dated Oct. 14, 1993). Alternatively, the nucleic acid can be introduced intracellularly and incorporated within host cell DNA for expression, by homologous recombination (Koller and Smithies, 1989, Proc. Natl. Acad. Sci. USA 86:8932–8935; Zijlstra et al., 1989, Nature 342:435–438).

In a preferred embodiment of the invention, adenoviruses as viral vectors can be used in gene therapy. Adenoviruses have the advantage of being capable of infecting non-dividing cells (Kozarsky and Wilson, 1993, Current Opinion in Genetics and Development 3:499–503). Other instances of the use of adenoviruses in gene therapy can be found in Rosenfeld et al., 1991, Science 252:431–434; Rosenfeld et al., 1992, Cell 68:143–155; and Mastrangeli et al., 1993, J. Clin. Invest. 91:225–234. Furthermore, adenoviral vectors with modified tropism may be used for cell specific targeting (WO98/40508). Adeno-associated virus (AAV) has also been proposed for use in gene therapy (Walsh et al., 1993, Proc. Soc. Exp. Biol. Med. 204:289–300).

In addition, retroviral vectors (see Miller et al., 1993, Meth. Enzymol. 217:581–599) have been modified to delete retroviral sequences that are not necessary for packaging of the viral genome and integration into host cell DNA. The coding sequence to be used in gene therapy is cloned into the vector, which facilitates delivery of the gene into a patient. More detail about retroviral vectors can be found in Boesen et al., 1994, Biotherapy 6:291–302, which describes the use of a retroviral vector to deliver the mdr 1 gene to hematopoietic stem cells in order to make the stem cells more resistant to chemotherapy. Other references illustrating the use of retroviral vectors in gene therapy are: Clowes et al., 1994, J. Clin. Invest. 93:644–651; Kiem et al., 1994, Blood 83:1467–1473; Salmons and Gunzberg, 1993, Human Gene Therapy 4:129–141; and Grossman and Wilson, 1993, Curr. Opin. in Genetics and Devel. 3:110–114.

Another approach to gene therapy involves transferring a gene to cells in tissue culture. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, lipofection, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see e.g., Loeffler and Behr, 1993, Meth. Enzymol. 217:599–618; Cohen et al., 1993, Meth. Enzymol. 217:618–644; Cline, 1985, Pharmac. Ther. 29:69–92) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny. In a preferred embodiment, the cell used for gene therapy is autologous to the patient.

In a specific embodiment, the nucleic acid to be introduced for purposes of gene therapy comprises an inducible promoter operably linked to the coding sequence, such that expression of the nucleic acid is controllable by controlling the presence or absence of the appropriate inducer of transcription.

Oligonucleotides such as anti-sense RNA and DNA molecules, and ribozymes that function to inhibit the translation of a leukocyte surface receptor mRNA, especially its C-terminus are also within the scope of the invention. Anti-sense RNA and DNA molecules act to directly block the translation of mRNA by binding to targeted mRNA and preventing protein translation. In regard to antisense DNA, oligodeoxyribonucleotides derived from the translation initiation site, e.g., between −10 and +10 regions of a nucleotide sequence, are preferred.

The antisense oligonucleotide may comprise at least one modified base moiety which is selected from the group including, but not limited to, 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

Ribozymes are enzymatic RNA molecules capable of catalyzing the specific cleavage of RNA. The mechanism of ribozyme action involves sequence specific hybridization of the ribozyme molecule to complementary target RNA, followed by endonucleolytic cleavage. Within the scope of the invention are engineered hammerhead motif ribozyme molecules that specifically and efficiently catalyze endonucleolytic cleavage of leukocyte surface receptor RNA sequences.

Specific ribozyme cleavage sites within any potential RNA target are initially identified by scanning the target molecule for ribozyme cleavage sites which include the following sequences, GUA, GUU and GUC. Once identified, short RNA sequences of between 15 and 20 ribonucleotides corresponding to the region of the target gene containing the cleavage site may be evaluated for predicted structural features such as secondary structure that may render the oligonucleotide sequence unsuitable. The suitability of candidate targets may also be evaluated by testing their accessibility to hybridization with complementary oligonucleotides, using ribonuclease protection assays.

The anti-sense RNA and DNA molecules and ribozymes of the invention may be prepared by any method known in the art for the synthesis of nucleic acid molecules. These include techniques for chemically synthesizing oligodeoxyribonucleotides well known in the art such as for example solid phase phosphoramidite chemical synthesis. Alternatively, RNA molecules may be generated by in vitro and in vivo transcription of DNA sequences encoding the RNA molecule. Such DNA sequences may be incorporated into a wide variety of vectors which contain suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Various modifications to the DNA molecules may be introduced as a means of increasing intracellular stability and half-life. Possible modifications include, but are not limited to, the addition of flanking sequences of ribo- or deoxy-nucleotides to the 5' and/or 3' ends of the molecule or the use of phosphorothioate or 2' O-methyl rather than phosphodiesterase linkages within the oligodeoxyribonucleotide backbone.

6.9.3 Other Pharmaceutical Compositions

The compounds of the invention, may be administered to a subject per se or in the form of a sterile composition or a pharmaceutical composition. Pharmaceutical compositions comprising the compounds of the invention may be manufactured by means of conventional mixing, dissolving, granulating, dragee-making, levigating, emulsifying, encapsulating, entrapping or lyophilizing processes. Pharmaceutical compositions may be formulated in conventional manner using one or more physiologically acceptable carriers, diluents, excipients or auxiliaries that facilitate processing of the active peptides or peptide analogues into preparations which can be used pharmaceutically. Proper formulation is dependent upon the route of administration chosen.

For topical administration the compounds of the invention may be formulated as solutions, gels, ointments, creams, suspensions, etc. as are well-known in the art.

Systemic formulations include those designed for administration by injection, e.g. subcutaneous, intravenous, intramuscular, intrathecal or intraperitoneal injection, as well as those designed for transdermal, transmucosal, oral or pulmonary administration.

For injection, the compounds of the invention may be formulated in aqueous solutions, preferably in physiologically compatible buffers such as Hanks's solution, Ringer's solution, or physiological saline buffer. The solution may contain formulatory agents such as suspending, stabilizing and/or dispersing agents.

Alternatively, the compounds may be in powder form for constitution with a suitable vehicle, e.g., sterile pyrogen-free water, before use.

For transmucosal administration, penetrants appropriate to the barrier to be permeated are used in the formulation. Such penetrants are generally known in the art. This route of administration may be used to deliver the compounds to the nasal cavity.

For oral administration, the compounds can be readily formulated by combining the active peptides or peptide analogues with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. For oral solid formulations such as, for example, powders, capsules and tablets, suitable excipients include fillers such as sugars, such as lactose, sucrose, mannitol and sorbitol; cellulose preparations such as maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP); granulating agents; and binding agents. If desired, disintegrating agents may be added, such as the cross-linked polyvinylpyrrolidone, agar, or alginic acid or a salt thereof such as sodium alginate.

If desired, solid dosage forms may be sugar-coated or enteric-coated using standard techniques.

For oral liquid preparations such as, for example, suspensions, elixirs and solutions, suitable carriers, excipients or diluents include water, glycols, oils, alcohols, etc. Additionally, flavoring agents, preservatives, coloring agents and the like may be added.

For buccal administration, the compounds may take the form of tablets, lozenges, etc. formulated in conventional manner.

For administration by inhalation, the compounds for use according to the present invention are conveniently delivered in the form of an aerosol spray from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds may also be formulated in rectal or vaginal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Alternatively, other pharmaceutical delivery systems may be employed. Liposomes and emulsions are well known examples of delivery vehicles that may be used to deliver peptides and peptide analogues of the invention. Certain organic solvents such as dimethylsulfoxide also may be employed, although usually at the cost of greater toxicity. Additionally, the compounds may be delivered using a sustained-release system, such as semipermeable matrices of solid polymers containing the therapeutic agent. Various of sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

As the compounds of the invention may contain charged side chains or termini, they may be included in any of the above-described formulations as the free acids or bases or as pharmaceutically acceptable salts. Pharmaceutically acceptable salts are those salts which substantially retain the biologic activity of the free bases and which are prepared by reaction with inorganic acids. Pharmaceutical salts tend to be more soluble in aqueous and other protic solvents than are the corresponding free base forms.

6.10. Effective Dosages

The compounds of the invention will generally be used in an amount effective to achieve the intended purpose. For use to inhibit leukocyte activation-associated disorders, the compounds of the invention or pharmaceutical compositions thereof, are administered or applied in a therapeutically effective amount. By therapeutically effective amount is meant an amount effective ameliorate or prevent the symptoms, or prolong the survival of, the patient being treated. Determination of a therapeutically effective amount is well within the capabilities of those skilled in the art, especially in light of the detailed disclosure provided herein. An "inhibitory amount" or "inhibitory concentration" of a PL-PDZ binding inhibitor is an amount that reduces binding by at least about 40%, preferably at least about 50%, often at least about 70%, and even as much as at least about 90%. Binding can as measured in vitro (e.g., in an A assay or G assay) or in situ.

For systemic administration, a therapeutically effective dose can be estimated initially from in vitro assays. For example, a dose can be formulated in animal models to achieve a circulating concentration range that includes the $IC_{50}$ as determined in cell culture (i.e., the concentration of test compound that inhibits 50% of leukocyte surface receptor-PDZ domain-containing protein interactions). Such information can be used to more accurately determine useful doses in humans.

Initial dosages can also be estimated from in vivo data, e.g., animal models, using techniques that are well known in the art. One having ordinary skill in the art could readily optimize administration to humans based on animal data.

Dosage amount and interval may be adjusted individually to provide plasma levels of the compounds that are sufficient to maintain therapeutic effect. Usual patient dosages for administration by injection range from about 0.1 to 5 mg/kg/day, preferably from about 0.5 to 1 mg/kg/day. Therapeutically effective serum levels may be achieved by administering multiple doses each day.

In cases of local administration or selective uptake, the effective local concentration of the compounds may not be related to plasma concentration. One having skill in the art will be able to optimize therapeutically effective local dosages without undue experimentation.

The amount of compound administered will, of course, be dependent on the subject being treated, on the subject's weight, the severity of the affliction, the manner of administration and the judgment of the prescribing physician.

The therapy may be repeated intermittently while symptoms detectable or even when they are not detectable. The therapy may be provided alone or in combination with other drugs. In the case of conditions associated with leukocyte activation such as transplantation rejection and autoimmunity, the drugs that may be used in combination with the compounds of the invention include, but are not limited to, steroid and non-steroid anti-inflammatory agents.

6.10.1 Toxicity

Preferably, a therapeutically effective dose of the compounds described herein will provide therapeutic benefit without causing substantial toxicity.

Toxicity of the compounds described herein can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. Compounds which exhibit high therapeutic indices are preferred. The data obtained from these cell culture assays and animal studies can be used in formulating a dosage range that is not toxic for use in human. The dosage of the compounds described herein lies preferably within a range of circulating concentrations that include the effective dose with little or no toxicity. The dosage may vary within this range depending upon the dosage form employed and the route of administration utilized. The exact formulation, route of administration and dosage can be chosen by the individual physician in view of the patient's condition. (See, e.g., Fingi et al., 1975, In: The Pharmacological Basis of Therapeutics, Ch.1, p. 1).

6.11. EXAMPLE 1

TAT-T Cell Surface Receptor Carboxyl Terminus Fusion Peptides Inhibited T Cell Activation

6.11.1. Materials and Methods

6.11.1.1. Peptide Synthesis

All peptides were chemically synthesized by standard procedures. The Tat-CD3 carboxyl terminus fusion peptide, (GYGRKKRRQRRRGPPSSSSGL, SEQ ID NO:174); Tat-CLASP1 carboxyl terminus fusion peptide, (GYGRKKRRQRRRGSISSSAEV, SEQ ID NO:175); Tat-CLASP2 carboxyl terminus fusion peptide, (GYGRKKRRQRRRGMTSSSSVV, SEQ ID NO:176); and Tat peptide, (GYGRKKRRQRRRG, SEQ ID NO:289); were dissolved at 1 mM in PBS, pH 7, or dH2O. Stock MBPAc1-16 peptide, (AcASQKRPSQRHGSKYLA; SEQ ID NO:290), was dissolved at 5 mM. All peptides were aliquoted and stored at −80° C. until tested.

6.11.1.2 Cell Cultures

Cells were maintained and tested in RPMI 1640 media supplemented with 10% fetal calf serum (HyClone), 2 mM glutamine, 10 mM Hepes, 100 U/ml penicillin, 100 μg/ml streptomycin, 0.1 mM non-essential amino acids, 1 mM sodium pyruvate, and 50 μM beta mercaptoethanol.

6.11.1.3 T Cell Stimulation Assay

Supernatants were assayed for cytokine production following activation of T cell lines. Mouse T cell lines were stimulated using two different methods, either with antigen and antigen presenting cells or anti-mouse CD3.

Antigen-specific mouse T cells, BR4.2, were activated with the N-terminal 16 amino acid sequences of myelin basic protein (MBPAc1-16) and syngenic mouse splenocytes in 96-well plates. Mitomycin C-treated antigen presenting cells, $2 \times 10^5$ B10.BR, were added to each row of serially diluted MBPAc1-16 ranging from 0 to 200 μM. Next, 10 μM Tat-peptides or media alone was added to each row. Finally, $2 \times 10^4$ MBPAc1-16-specific T cell, pre-loaded with 10 μM Tat-peptides (see above), were added to all wells (Rabinowitz et al., 1997. Proc. Natl. Acad. Sci. U.S.A., 94:8702–8707). Cells were activated during an overnight incubation at 5% CO2, 37° C. Cell supernatant was collected and stored at −80° C. until assayed for cytokine production. The final volume was 200 μl/well.

Antibody against mouse CD3 (Pharmigen #145-2C11) was coated overnight at 4° C. using 96-well flat bottom Elisa plates at a final concentration of 0.5 μg/ml, diluted in PBS. Just prior to use, plates were washed three times with 200 μl/well PBS to remove excess anti-CD3. To ensure that cells were given sufficient time to transduce Tat-peptides before activation, T cells ($5 \times 10^5$ cells/ml) were pre-treated with or without 10 μM Tat-peptides for two hours at 5% CO2, 37° C. and then diluted in media with or without 10 μM Tat-peptides to a final concentration of $2 \times 10^4$ cells per well in a final volume of 200 μl. Cells were then treated as described above.

6.11.1.4 Cytokine ELISA

IFNγ was measured from cell supernatants, described above, at ambient temperature using the Endogen, Inc. ELISA protocol 3. Briefly, 96-well, flat bottom, high binding ELISA plates were preincubated overnight with coating antibody (MM700). Plates were washed with 50 mM TRIS, 0.2% tween-20, pH 8 and they blocked for one hour with PBS plus 2% BSA. Washed plates were then incubated one hour with 25 μl of cell supernatant and 25 μl blocking buffer, or with 50 μl IFNγ standard. The presence of IFNγ was detected with a biotin-labeled anti-mouse IFNγ monoclonal antibody (MM700B, Endogen, Inc.). Quantitative amounts of detection antibody are revealed with horseradishperoxidase-conjugated streptavidin. The enzymatic, color, substrate for HRP, tetramethylbenzidine (TMB), was developed for up to 30 minutes and stopped with 1.0 M $H_2SO_4$. The absorbance at 450 nm was measured using a microtiter plate reader (Thermo Max, Molecular Devices) and the concentration of unknown IFNγ from cell supernatants was calculated from a standard curve generated by Softmax Pro. software (Molecular Devices).

6.11.2 Results

Peptides containing Tat transporter sequences linked to C-terminal sequences of various PLs were testing for their ability to inhibit T cell activation. FIG. 4A shows that the Tat-CD3 fusion peptide inhibits T cell activation mediated by peptide:MHC as compared to controls of Tat-peptide alone or no peptide. FIG. 4B shows that Tat-CLASP2 carboxyl terminus fusion peptide inhibited T cell activation mediated by monoclonal anti-CD3 as compared to Tat-peptide alone. Tat-CLASP1 fusion peptide did not inhibit T cell activation in this experiment. These results indicate that peptides containing potential inhibitory sequences can be transported into T cells through transporter peptide such as Tat to disrupt surface receptor organization mediated by PDZ proteins. Disruption of PDZ-mediated surface receptor organization leads to blockage of T cell activation in response to antigen.

6.12. EXAMPLE 2

Design of an Inhibitor of DLG 1-Ligand Binding with Greater than 100 uM Potency A GST/DLG1 fusion protein (See TABLE 3) and a biotin-labeled peptide corresponding to the C-terminal 20 amino acids of the CLASP-2 protein, peptide AA2L (See TABLE 4), were synthesized and purified by standard techniques well known in the art as described supra. This PDZ-ligand combination was then shown to bind specifically using both the "A" assay and the "G" assay (See TABLE 2). Once specific binding was demonstrated, the apparent affinity of the binding interaction was determined using Approach 1 of the section entitled "Measurement of PDZ-ligand binding affinity" (see FIG. 2A). The measured apparent affinity was 21 uM. This implies that 21 uM labeled CLASP-2 peptide AA2L filled 50% of the binding sites for CLASP-2 on DLG1. Thus, 21 uM unlabeled CLASP-2 peptide should be able to block the binding of a given ligand to DLG1 by approximately 50%, assuming that the given ligand (1) binds to the same site(s) on DLG1 as Qasp~2 and (2) is not added at sufficient concentration to reduce significantly the binding of the CLASP-2 peptide (i.e. cannot out-compete the CLASP-2 peptide).

To detect such inhibition, it was necessary to synthesize an analogue of the CLASP2peptide AA2L that (1) retained similar DLG1 binding properties and (2) would not itself generate a signal in the assay selected to measure inhibition. Because most molecular interactions between PDZ proteins and their ligands involve only the C-terminal 6 amino acids of the ligand, an eight amino acid variant of the CLASP-2 peptide, MTSSSSVV (SEQ ID NO:227), was anticipated to retain similar DLG1 binding properties as the 20 amino acid AA2L CLASP-2 peptide. This eight amino acid CLASP-2 peptide (lacking a functional label) was therefore synthesized and purified by standard techniques as described supra. When 100 uM of the (functionally unlabeled) eight amino acid CLASP-2 peptide and 20 uM of the biotin-labeled AA2L CLASP-2 peptide were added simultaneously to DLG1 in a variant of the "G" assay (described supra), the binding of the labeled AA2L CLASP-2 peptide was, as predicted, inhibited by greater than 50% (FIG. 3A). An analogous experiment in which the labeled AA2L CLASP-2 peptide was replaced with another labeled DLG1 ligand, labeled AAI3L Fas peptide demonstrated similar inhibition by the eight amino acid CLASP-2 peptide (FIG. 3A). Thus, an effective inhibitor of DLG1-ligand binding (i.e. the eight amino acid CLASP-2 peptide MTSSSSVV; SEQ ID NO:227) with a known potency range (order of magnitude 21 uM) was designed based on knowledge of the affinity, 21 uM, with which a particular labeled ligand, the CLASP-2 peptide AA2L, bound to DLG1.

The present invention is not to be limited in scope by the exemplified embodiments which are intended as illustrations of single aspects of the invention and any sequences which are functionally equivalent are within the scope of the invention. Indeed, various modifications of the invention in addition to those shown and described herein will become apparent to those skilled in the art from the foregoing description and accompanying drawings. Such modifications are intended to fall within the scope of the appended claims.

All publications cited herein are incorporated by reference in their entirety and for all purposes.

What is claimed is:

1. A method for determining an interaction profile for a PDZ Ligand protein (PL protein) comprising:
    (a) contacting the PL protein to an array of at least 5 PDZ domain polypeptides of different amino acid sequence, each located at a different predetermined site on the array; and
    (b) detecting whether the PL protein interacts with the PDZ-domain polypeptide at each site of the array to determine which of the PDZ-domain polypeptides the PL protein interacts with, thereby obtaining the interaction profile for the PL protein.

2. The method of claim 1, wherein the array comprises at least 25 different PDZ-domain polypeptides of different sequence, whereby an interaction profile between the PL protein and at least 25 different PDZ-domain polypeptides is determined.

3. The method of claim 1, wherein
    the method is repeated with one or more additional PL proteins, whereby an interaction profile for each of the additional PL proteins is determined.

4. The method of claim 1, wherein the array comprises at least 40 PDZ-domain polypeptides of different amino acid sequence, whereby an interaction profile between the PL protein and at least 40 different PDZ-domain polypeptides is determined.

5. The method of claim 1, wherein interactions between the PL protein and the PDZ-domain polypeptides is detected by an enzyme-linked immunoabsorbent assay (ELISA).

6. The method of claim 1, further comprising determining for each interaction between the PL protein and one of the PDZ-domain polypeptides whether there is a statistical difference between a signal representative of the interaction and a signal for a control, wherein only those interactions in which there is a statistical difference are identified as involving an PDZ domain/PL interaction.

7. The method of claim 1, wherein each of the PDZ-domain polypeptides are immobilized in a well of a microtiter plate.

8. The method of claim 1, wherein at least some of the PDZ-domain polypeptides are from different families.

* * * * *

SEQUENCE LISTING

```
<160> NUMBER OF SEQ ID NOS: 383

<210> SEQ ID NO 1
<211> LENGTH: 5
<212> TYPE: PRT
<213> ORGANISM: Artificial Sequence
<220> FEATURE:
<223> OTHER INFORMATION: flexible polylinker

<400> SEQUENCE: 1

Gly Gly Gly Gly Ser
1               5

<210> SEQ ID NO 2
<211> LENGTH: 14
<212> TYPE: PRT
<213> ORGANISM: Artificial Sequence
<220> FEATURE:
<223> OTHER INFORMATION: linker

<400> SEQUENCE: 2

Glu Gly Lys Ser Ser Gly Ser Gly Ser Glu Ser Lys Val Asp
1               5                   10

<210> SEQ ID NO 3
<211> LENGTH: 18
<212> TYPE: PRT
<213> ORGANISM: Artificial Sequence
<220> FEATURE:
<223> OTHER INFORMATION: linker

<400> SEQUENCE: 3

Lys Glu Ser Gly Ser Val Ser Ser Glu Gln Leu Ala Gln Phe Arg Ser
1               5                   10                  15
```

-continued

Leu Asp

```
<210> SEQ ID NO 4
<211> LENGTH: 4
<212> TYPE: PRT
<213> ORGANISM: Artificial Sequence
<220> FEATURE:
<223> OTHER INFORMATION: PL motif, PDZ domain binding motif, C-terminal
      core sequence of CD3

<400> SEQUENCE: 4

Ser Ser Gln Leu
 1

<210> SEQ ID NO 5
<211> LENGTH: 5
<212> TYPE: PRT
<213> ORGANISM: Artificial Sequence
<220> FEATURE:
<223> OTHER INFORMATION: PL motif, PDZ domain binding motif, C-terminal
      sequence of CD3

<400> SEQUENCE: 5

Ser Ser Ser Gln Leu
 1               5

<210> SEQ ID NO 6
<211> LENGTH: 6
<212> TYPE: PRT
<213> ORGANISM: Artificial Sequence
<220> FEATURE:
<223> OTHER INFORMATION: PL motif, PDZ domain binding motif, C-terminal
      sequence of CD3

<400> SEQUENCE: 6

Ser Ser Ser Ser Gln Leu
 1               5

<210> SEQ ID NO 7
<211> LENGTH: 7
<212> TYPE: PRT
<213> ORGANISM: Artificial Sequence
<220> FEATURE:
<223> OTHER INFORMATION: PL motif, PDZ domain binding motif, C-terminal
      sequence of CD3

<400> SEQUENCE: 7

Pro Ser Ser Ser Ser Gln Leu
 1               5

<210> SEQ ID NO 8
<211> LENGTH: 8
<212> TYPE: PRT
<213> ORGANISM: Artificial Sequence
<220> FEATURE:
<223> OTHER INFORMATION: PL motif, PDZ domain binding motif, C-terminal
      sequence of CD3

<400> SEQUENCE: 8

Pro Pro Ser Ser Ser Ser Gln Leu
 1               5

<210> SEQ ID NO 9
<211> LENGTH: 4
<212> TYPE: PRT
<213> ORGANISM: Artificial Sequence
<220> FEATURE:
<223> OTHER INFORMATION: PL motif, PDZ domain binding motif, C-terminal
```

-continued core sequence of CD4

<400> SEQUENCE: 9

Cys Ser Pro Ile
1

<210> SEQ ID NO 10
<211> LENGTH: 5
<212> TYPE: PRT
<213> ORGANISM: Artificial Sequence
<220> FEATURE:
<223> OTHER INFORMATION: PL motif, PDZ domain binding motif, C-terminal
      sequence of CD4

<400> SEQUENCE: 10

Thr Cys Ser Pro Ile
1              5

<210> SEQ ID NO 11
<211> LENGTH: 6
<212> TYPE: PRT
<213> ORGANISM: Artificial Sequence
<220> FEATURE:
<223> OTHER INFORMATION: PL motif, PDZ domain binding motif, C-terminal
      sequence of CD4

<400> SEQUENCE: 11

Lys Thr Cys Ser Pro Ile
1              5

<210> SEQ ID NO 12
<211> LENGTH: 7
<212> TYPE: PRT
<213> ORGANISM: Artificial Sequence
<220> FEATURE:
<223> OTHER INFORMATION: PL motif, PDZ domain binding motif, C-terminal
      sequence of CD4

<400> SEQUENCE: 12

Gln Lys Thr Cys Ser Pro Ile
1              5

<210> SEQ ID NO 13
<211> LENGTH: 8
<212> TYPE: PRT
<213> ORGANISM: Artificial Sequence
<220> FEATURE:
<223> OTHER INFORMATION: PL motif, PDZ domain binding motif, C-terminal
      sequence of CD4

<400> SEQUENCE: 13

Phe Gln Lys Thr Cys Ser Pro Ile
1              5

<210> SEQ ID NO 14
<211> LENGTH: 4
<212> TYPE: PRT
<213> ORGANISM: Artificial Sequence
<220> FEATURE:
<223> OTHER INFORMATION: PL motif, PDZ domain binding motif, C-terminal
      core sequence of CD6

<400> SEQUENCE: 14

Ile Ser Ala Ala
1

```
<210> SEQ ID NO 15
<211> LENGTH: 5
<212> TYPE: PRT
<213> ORGANISM: Artificial Sequence
<220> FEATURE:
<223> OTHER INFORMATION: PL motif, PDZ domain binding motif, C-terminal
      sequence of CD6

<400> SEQUENCE: 15

Asp Ile Ser Ala Ala
 1               5

<210> SEQ ID NO 16
<211> LENGTH: 6
<212> TYPE: PRT
<213> ORGANISM: Artificial Sequence
<220> FEATURE:
<223> OTHER INFORMATION: PL motif, PDZ domain binding motif, C-terminal
      sequence of CD6

<400> SEQUENCE: 16

Asp Asp Ile Ser Ala Ala
 1               5

<210> SEQ ID NO 17
<211> LENGTH: 7
<212> TYPE: PRT
<213> ORGANISM: Artificial Sequence
<220> FEATURE:
<223> OTHER INFORMATION: PL motif, PDZ domain binding motif, C-terminal
      sequence of CD6

<400> SEQUENCE: 17

Tyr Asp Asp Ile Ser Ala Ala
 1               5

<210> SEQ ID NO 18
<211> LENGTH: 8
<212> TYPE: PRT
<213> ORGANISM: Artificial Sequence
<220> FEATURE:
<223> OTHER INFORMATION: PL motif, PDZ domain binding motif, C-terminal
      sequence of CD6

<400> SEQUENCE: 18

Asp Tyr Asp Asp Ile Ser Ala Ala
 1               5

<210> SEQ ID NO 19
<211> LENGTH: 4
<212> TYPE: PRT
<213> ORGANISM: Artificial Sequence
<220> FEATURE:
<223> OTHER INFORMATION: PL motif, PDZ domain binding motif, C-terminal
      core sequence of CD38

<400> SEQUENCE: 19

Thr Ser Glu Ile
 1

<210> SEQ ID NO 20
<211> LENGTH: 5
<212> TYPE: PRT
<213> ORGANISM: Artificial Sequence
<220> FEATURE:
<223> OTHER INFORMATION: PL motif, PDZ domain binding motif, C-terminal
      sequence of CD38
```

-continued

```
<400> SEQUENCE: 20

Cys Thr Ser Glu Ile
1               5

<210> SEQ ID NO 21
<211> LENGTH: 6
<212> TYPE: PRT
<213> ORGANISM: Artificial Sequence
<220> FEATURE:
<223> OTHER INFORMATION: PL motif, PDZ domain binding motif, C-terminal
      sequence of CD38

<400> SEQUENCE: 21

Ser Cys Thr Ser Glu Ile
1               5

<210> SEQ ID NO 22
<211> LENGTH: 7
<212> TYPE: PRT
<213> ORGANISM: Artificial Sequence
<220> FEATURE:
<223> OTHER INFORMATION: PL motif, PDZ domain binding motif, C-terminal
      sequence of CD38

<400> SEQUENCE: 22

Ser Ser Cys Thr Ser Glu Ile
1               5

<210> SEQ ID NO 23
<211> LENGTH: 8
<212> TYPE: PRT
<213> ORGANISM: Artificial Sequence
<220> FEATURE:
<223> OTHER INFORMATION: PL motif, PDZ domain binding motif, C-terminal
      sequence of CD38

<400> SEQUENCE: 23

Asp Ser Ser Cys Thr Ser Glu Ile
1               5

<210> SEQ ID NO 24
<211> LENGTH: 4
<212> TYPE: PRT
<213> ORGANISM: Artificial Sequence
<220> FEATURE:
<223> OTHER INFORMATION: PL motif, PDZ domain binding motif, C-terminal
      core sequence of CD49e and CD49f

<400> SEQUENCE: 24

Thr Ser Asp Ala
1

<210> SEQ ID NO 25
<211> LENGTH: 5
<212> TYPE: PRT
<213> ORGANISM: Artificial Sequence
<220> FEATURE:
<223> OTHER INFORMATION: PL motif, PDZ domain binding motif, C-terminal
      sequence of CD49e

<400> SEQUENCE: 25

Ala Thr Ser Asp Ala
1               5

<210> SEQ ID NO 26
<211> LENGTH: 6
<212> TYPE: PRT
```

```
<213> ORGANISM: Artificial Sequence
<220> FEATURE:
<223> OTHER INFORMATION: PL motif, PDZ domain binding motif, C-terminal
      sequence of CD49e

<400> SEQUENCE: 26

Pro Ala Thr Ser Asp Ala
1               5

<210> SEQ ID NO 27
<211> LENGTH: 7
<212> TYPE: PRT
<213> ORGANISM: Artificial Sequence
<220> FEATURE:
<223> OTHER INFORMATION: PL motif, PDZ domain binding motif, C-terminal
      sequence of CD49e

<400> SEQUENCE: 27

Pro Pro Ala Thr Ser Asp Ala
1               5

<210> SEQ ID NO 28
<211> LENGTH: 8
<212> TYPE: PRT
<213> ORGANISM: Artificial Sequence
<220> FEATURE:
<223> OTHER INFORMATION: PL motif, PDZ domain binding motif, C-terminal
      sequence of CD49e

<400> SEQUENCE: 28

Lys Pro Pro Ala Thr Ser Asp Ala
1               5

<210> SEQ ID NO 29
<211> LENGTH: 4
<212> TYPE: PRT
<213> ORGANISM: Artificial Sequence
<220> FEATURE:
<223> OTHER INFORMATION: PDZ domain signature sequence repeat

<400> SEQUENCE: 29

Gly Leu Gly Phe
1

<210> SEQ ID NO 30
<211> LENGTH: 5
<212> TYPE: PRT
<213> ORGANISM: Artificial Sequence
<220> FEATURE:
<223> OTHER INFORMATION: PL motif, PDZ domain binding motif, C-terminal
      sequence of CD49f

<400> SEQUENCE: 30

Leu Thr Ser Asp Ala
1               5

<210> SEQ ID NO 31
<211> LENGTH: 6
<212> TYPE: PRT
<213> ORGANISM: Artificial Sequence
<220> FEATURE:
<223> OTHER INFORMATION: PL motif, PDZ domain binding motif, C-terminal
      sequence of CD49f

<400> SEQUENCE: 31

Arg Leu Thr Ser Asp Ala
1               5
```

```
<210> SEQ ID NO 32
<211> LENGTH: 7
<212> TYPE: PRT
<213> ORGANISM: Artificial Sequence
<220> FEATURE:
<223> OTHER INFORMATION: PL motif, PDZ domain binding motif, C-terminal
      sequence of CD49f

<400> SEQUENCE: 32

Glu Arg Leu Thr Ser Asp Ala
 1               5

<210> SEQ ID NO 33
<211> LENGTH: 8
<212> TYPE: PRT
<213> ORGANISM: Artificial Sequence
<220> FEATURE:
<223> OTHER INFORMATION: PL motif, PDZ domain binding motif, C-terminal
      sequence of CD49f

<400> SEQUENCE: 33

Lys Glu Arg Leu Thr Ser Asp Ala
 1               5

<210> SEQ ID NO 34
<211> LENGTH: 4
<212> TYPE: PRT
<213> ORGANISM: Artificial Sequence
<220> FEATURE:
<223> OTHER INFORMATION: PL motif, PDZ domain binding motif, C-terminal
      core sequence of CD53

<400> SEQUENCE: 34

Thr Ile Gly Leu
 1

<210> SEQ ID NO 35
<211> LENGTH: 5
<212> TYPE: PRT
<213> ORGANISM: Artificial Sequence
<220> FEATURE:
<223> OTHER INFORMATION: PL motif, PDZ domain binding motif, C-terminal
      sequence of CD53

<400> SEQUENCE: 35

Gln Thr Ile Gly Leu
 1               5

<210> SEQ ID NO 36
<211> LENGTH: 6
<212> TYPE: PRT
<213> ORGANISM: Artificial Sequence
<220> FEATURE:
<223> OTHER INFORMATION: PL motif, PDZ domain binding motif, C-terminal
      sequence of CD53

<400> SEQUENCE: 36

Ser Gln Thr Ile Gly Leu
 1               5

<210> SEQ ID NO 37
<211> LENGTH: 7
<212> TYPE: PRT
<213> ORGANISM: Artificial Sequence
<220> FEATURE:
<223> OTHER INFORMATION: PL motif, PDZ domain binding motif, C-terminal
      sequence of CD53
```

```
<400> SEQUENCE: 37

Thr Ser Gln Thr Ile Gly Leu
 1               5

<210> SEQ ID NO 38
<211> LENGTH: 8
<212> TYPE: PRT
<213> ORGANISM: Artificial Sequence
<220> FEATURE:
<223> OTHER INFORMATION: PL motif, PDZ domain binding motif, C-terminal
      sequence of CD53

<400> SEQUENCE: 38

Lys Thr Ser Gln Thr Ile Gly Leu
 1               5

<210> SEQ ID NO 39
<211> LENGTH: 4
<212> TYPE: PRT
<213> ORGANISM: Artificial Sequence
<220> FEATURE:
<223> OTHER INFORMATION: PL motif, PDZ domain binding motif, C-terminal
      core sequence of CD90

<400> SEQUENCE: 39

Phe Met Ser Leu
 1

<210> SEQ ID NO 40
<211> LENGTH: 5
<212> TYPE: PRT
<213> ORGANISM: Artificial Sequence
<220> FEATURE:
<223> OTHER INFORMATION: PL motif, PDZ domain binding motif, C-terminal
      sequence of CD90

<400> SEQUENCE: 40

Asp Phe Met Ser Leu
 1               5

<210> SEQ ID NO 41
<211> LENGTH: 6
<212> TYPE: PRT
<213> ORGANISM: Artificial Sequence
<220> FEATURE:
<223> OTHER INFORMATION: PL motif, PDZ domain binding motif, C-terminal
      sequence of CD90

<400> SEQUENCE: 41

Thr Asp Phe Met Ser Leu
 1               5

<210> SEQ ID NO 42
<211> LENGTH: 7
<212> TYPE: PRT
<213> ORGANISM: Artificial Sequence
<220> FEATURE:
<223> OTHER INFORMATION: PL motif, PDZ domain binding motif, C-terminal
      sequence of CD90

<400> SEQUENCE: 42

Ala Thr Asp Phe Met Ser Leu
 1               5

<210> SEQ ID NO 43
<211> LENGTH: 8
<212> TYPE: PRT
```

```
<213> ORGANISM: Artificial Sequence
<220> FEATURE:
<223> OTHER INFORMATION: PL motif, PDZ domain binding motif, C-terminal
      sequence of CD90

<400> SEQUENCE: 43

Gln Ala Thr Asp Phe Met Ser Leu
1               5

<210> SEQ ID NO 44
<211> LENGTH: 4
<212> TYPE: PRT
<213> ORGANISM: Artificial Sequence
<220> FEATURE:
<223> OTHER INFORMATION: PL motif, PDZ domain binding motif, C-terminal
      core sequence of CD95

<400> SEQUENCE: 44

Gln Ser Leu Val
1

<210> SEQ ID NO 45
<211> LENGTH: 5
<212> TYPE: PRT
<213> ORGANISM: Artificial Sequence
<220> FEATURE:
<223> OTHER INFORMATION: PL motif, PDZ domain binding motif, C-terminal
      sequence of CD95

<400> SEQUENCE: 45

Ile Gln Ser Leu Val
1               5

<210> SEQ ID NO 46
<211> LENGTH: 6
<212> TYPE: PRT
<213> ORGANISM: Artificial Sequence
<220> FEATURE:
<223> OTHER INFORMATION: PL motif, PDZ domain binding motif, C-terminal
      sequence of CD95

<400> SEQUENCE: 46

Glu Ile Gln Ser Leu Val
1               5

<210> SEQ ID NO 47
<211> LENGTH: 7
<212> TYPE: PRT
<213> ORGANISM: Artificial Sequence
<220> FEATURE:
<223> OTHER INFORMATION: PL motif, PDZ domain binding motif, C-terminal
      sequence of CD95

<400> SEQUENCE: 47

Asn Glu Ile Gln Ser Leu Val
1               5

<210> SEQ ID NO 48
<211> LENGTH: 8
<212> TYPE: PRT
<213> ORGANISM: Artificial Sequence
<220> FEATURE:
<223> OTHER INFORMATION: PL motif, PDZ domain binding motif, C-terminal
      sequence of CD95

<400> SEQUENCE: 48

Arg Asn Glu Ile Gln Ser Leu Val
1               5
```

<210> SEQ ID NO 49
<211> LENGTH: 4
<212> TYPE: PRT
<213> ORGANISM: Artificial Sequence
<220> FEATURE:
<223> OTHER INFORMATION: PL motif, PDZ domain binding motif, C-terminal
      core sequence of CD97

<400> SEQUENCE: 49

Glu Ser Gly Ile
 1

<210> SEQ ID NO 50
<211> LENGTH: 5
<212> TYPE: PRT
<213> ORGANISM: Artificial Sequence
<220> FEATURE:
<223> OTHER INFORMATION: PL motif, PDZ domain binding motif, C-terminal
      sequence of CD97

<400> SEQUENCE: 50

Ser Glu Ser Gly Ile
 1               5

<210> SEQ ID NO 51
<211> LENGTH: 6
<212> TYPE: PRT
<213> ORGANISM: Artificial Sequence
<220> FEATURE:
<223> OTHER INFORMATION: PL motif, PDZ domain binding motif, C-terminal
      sequence of CD97

<400> SEQUENCE: 51

Ala Ser Glu Ser Gly Ile
 1               5

<210> SEQ ID NO 52
<211> LENGTH: 7
<212> TYPE: PRT
<213> ORGANISM: Artificial Sequence
<220> FEATURE:
<223> OTHER INFORMATION: PL motif, PDZ domain binding motif, C-terminal
      sequence of CD97

<400> SEQUENCE: 52

Arg Ala Ser Glu Ser Gly Ile
 1               5

<210> SEQ ID NO 53
<211> LENGTH: 8
<212> TYPE: PRT
<213> ORGANISM: Artificial Sequence
<220> FEATURE:
<223> OTHER INFORMATION: PL motif, PDZ domain binding motif, C-terminal
      sequence of CD97

<400> SEQUENCE: 53

Leu Arg Ala Ser Glu Ser Gly Ile
 1               5

<210> SEQ ID NO 54
<211> LENGTH: 4
<212> TYPE: PRT
<213> ORGANISM: Artificial Sequence
<220> FEATURE:
<223> OTHER INFORMATION: PL motif, PDZ domain binding motif, C-terminal
      core sequence of CD98

```
<400> SEQUENCE: 54

Pro Tyr Ala Ala
 1

<210> SEQ ID NO 55
<211> LENGTH: 5
<212> TYPE: PRT
<213> ORGANISM: Artificial Sequence
<220> FEATURE:
<223> OTHER INFORMATION: PL motif, PDZ domain binding motif, C-terminal
      sequence of CD98

<400> SEQUENCE: 55

Phe Pro Tyr Ala Ala
 1               5

<210> SEQ ID NO 56
<211> LENGTH: 6
<212> TYPE: PRT
<213> ORGANISM: Artificial Sequence
<220> FEATURE:
<223> OTHER INFORMATION: PL motif, PDZ domain binding motif, C-terminal
      sequence of CD98

<400> SEQUENCE: 56

Arg Phe Pro Tyr Ala Ala
 1               5

<210> SEQ ID NO 57
<211> LENGTH: 7
<212> TYPE: PRT
<213> ORGANISM: Artificial Sequence
<220> FEATURE:
<223> OTHER INFORMATION: PL motif, PDZ domain binding motif, C-terminal
      sequence of CD98

<400> SEQUENCE: 57

Leu Arg Phe Pro Tyr Ala Ala
 1               5

<210> SEQ ID NO 58
<211> LENGTH: 8
<212> TYPE: PRT
<213> ORGANISM: Artificial Sequence
<220> FEATURE:
<223> OTHER INFORMATION: PL motif, PDZ domain binding motif, C-terminal
      sequence of CD98

<400> SEQUENCE: 58

Leu Leu Arg Phe Pro Tyr Ala Ala
 1               5

<210> SEQ ID NO 59
<211> LENGTH: 4
<212> TYPE: PRT
<213> ORGANISM: Artificial Sequence
<220> FEATURE:
<223> OTHER INFORMATION: PL motif, PDZ domain binding motif, C-terminal
      core sequence of CDw137

<400> SEQUENCE: 59

Gly Cys Glu Leu
 1

<210> SEQ ID NO 60
<211> LENGTH: 5
```

-continued

```
<212> TYPE: PRT
<213> ORGANISM: Artificial Sequence
<220> FEATURE:
<223> OTHER INFORMATION: PL motif, PDZ domain binding motif, C-terminal
      sequence of CDw137

<400> SEQUENCE: 60

Gly Gly Cys Glu Leu
 1               5

<210> SEQ ID NO 61
<211> LENGTH: 6
<212> TYPE: PRT
<213> ORGANISM: Artificial Sequence
<220> FEATURE:
<223> OTHER INFORMATION: PL motif, PDZ domain binding motif, C-terminal
      sequence of CDw137

<400> SEQUENCE: 61

Glu Gly Gly Cys Glu Leu
 1               5

<210> SEQ ID NO 62
<211> LENGTH: 7
<212> TYPE: PRT
<213> ORGANISM: Artificial Sequence
<220> FEATURE:
<223> OTHER INFORMATION: PL motif, PDZ domain binding motif, C-terminal
      sequence of CDw137

<400> SEQUENCE: 62

Glu Glu Gly Gly Cys Glu Leu
 1               5

<210> SEQ ID NO 63
<211> LENGTH: 8
<212> TYPE: PRT
<213> ORGANISM: Artificial Sequence
<220> FEATURE:
<223> OTHER INFORMATION: PL motif, PDZ domain binding motif, C-terminal
      sequence of CDw137

<400> SEQUENCE: 63

Glu Glu Glu Gly Gly Cys Glu Leu
 1               5

<210> SEQ ID NO 64
<211> LENGTH: 4
<212> TYPE: PRT
<213> ORGANISM: Artificial Sequence
<220> FEATURE:
<223> OTHER INFORMATION: PL motif, PDZ domain binding motif, C-terminal
      core sequence of CD166

<400> SEQUENCE: 64

Lys Thr Glu Ala
 1

<210> SEQ ID NO 65
<211> LENGTH: 5
<212> TYPE: PRT
<213> ORGANISM: Artificial Sequence
<220> FEATURE:
<223> OTHER INFORMATION: PL motif, PDZ domain binding motif, C-terminal
      sequence of CD166
```

```
<400> SEQUENCE: 65

His Lys Thr Glu Ala
 1               5

<210> SEQ ID NO 66
<211> LENGTH: 6
<212> TYPE: PRT
<213> ORGANISM: Artificial Sequence
<220> FEATURE:
<223> OTHER INFORMATION: PL motif, PDZ domain binding motif, C-terminal
      sequence of CD166

<400> SEQUENCE: 66

Asn His Lys Thr Glu Ala
 1               5

<210> SEQ ID NO 67
<211> LENGTH: 7
<212> TYPE: PRT
<213> ORGANISM: Artificial Sequence
<220> FEATURE:
<223> OTHER INFORMATION: PL motif, PDZ domain binding motif, C-terminal
      sequence of CD166

<400> SEQUENCE: 67

Asn Asn His Lys Thr Glu Ala
 1               5

<210> SEQ ID NO 68
<211> LENGTH: 8
<212> TYPE: PRT
<213> ORGANISM: Artificial Sequence
<220> FEATURE:
<223> OTHER INFORMATION: PL motif, PDZ domain binding motif, C-terminal
      sequence of CD166

<400> SEQUENCE: 68

Glu Asn Asn His Lys Thr Glu Ala
 1               5

<210> SEQ ID NO 69
<211> LENGTH: 4
<212> TYPE: PRT
<213> ORGANISM: Artificial Sequence
<220> FEATURE:
<223> OTHER INFORMATION: PL motif, PDZ domain binding motif, C-terminal
      core sequence of CDw128

<400> SEQUENCE: 69

Ser Ser Asn Leu
 1

<210> SEQ ID NO 70
<211> LENGTH: 5
<212> TYPE: PRT
<213> ORGANISM: Artificial Sequence
<220> FEATURE:
<223> OTHER INFORMATION: PL motif, PDZ domain binding motif, C-terminal
      sequence of CDw128

<400> SEQUENCE: 70

Val Ser Ser Asn Leu
 1               5

<210> SEQ ID NO 71
<211> LENGTH: 6
<212> TYPE: PRT
```

```
<213> ORGANISM: Artificial Sequence
<220> FEATURE:
<223> OTHER INFORMATION: PL motif, PDZ domain binding motif, C-terminal
      sequence of CDw128

<400> SEQUENCE: 71

Asn Val Ser Ser Asn Leu
 1               5

<210> SEQ ID NO 72
<211> LENGTH: 7
<212> TYPE: PRT
<213> ORGANISM: Artificial Sequence
<220> FEATURE:
<223> OTHER INFORMATION: PL motif, PDZ domain binding motif, C-terminal
      sequence of CDw128

<400> SEQUENCE: 72

Val Asn Val Ser Ser Asn Leu
 1               5

<210> SEQ ID NO 73
<211> LENGTH: 8
<212> TYPE: PRT
<213> ORGANISM: Artificial Sequence
<220> FEATURE:
<223> OTHER INFORMATION: PL motif, PDZ domain binding motif, C-terminal
      sequence of CDw128

<400> SEQUENCE: 73

Ser Val Asn Val Ser Ser Asn Leu
 1               5

<210> SEQ ID NO 74
<211> LENGTH: 4
<212> TYPE: PRT
<213> ORGANISM: Artificial Sequence
<220> FEATURE:
<223> OTHER INFORMATION: PL motif, PDZ domain binding motif, C-terminal
      core sequence of DNAM-1

<400> SEQUENCE: 74

Lys Thr Arg Val
 1

<210> SEQ ID NO 75
<211> LENGTH: 5
<212> TYPE: PRT
<213> ORGANISM: Artificial Sequence
<220> FEATURE:
<223> OTHER INFORMATION: PL motif, PDZ domain binding motif, C-terminal
      sequence of DNAM-1

<400> SEQUENCE: 75

Pro Lys Thr Arg Val
 1               5

<210> SEQ ID NO 76
<211> LENGTH: 6
<212> TYPE: PRT
<213> ORGANISM: Artificial Sequence
<220> FEATURE:
<223> OTHER INFORMATION: PL motif, PDZ domain binding motif, C-terminal
      sequence of DNAM-1

<400> SEQUENCE: 76

Arg Pro Lys Thr Arg Val
 1               5
```

<210> SEQ ID NO 77
<211> LENGTH: 7
<212> TYPE: PRT
<213> ORGANISM: Artificial Sequence
<220> FEATURE:
<223> OTHER INFORMATION: PL motif, PDZ domain binding motif, C-terminal
      sequence of DNAM-1

<400> SEQUENCE: 77

Arg Arg Pro Lys Thr Arg Val
 1               5

<210> SEQ ID NO 78
<211> LENGTH: 8
<212> TYPE: PRT
<213> ORGANISM: Artificial Sequence
<220> FEATURE:
<223> OTHER INFORMATION: PL motif, PDZ domain binding motif, C-terminal
      sequence of DNAM-1

<400> SEQUENCE: 78

Ser Arg Arg Pro Lys Thr Arg Val
 1               5

<210> SEQ ID NO 79
<211> LENGTH: 4
<212> TYPE: PRT
<213> ORGANISM: Artificial Sequence
<220> FEATURE:
<223> OTHER INFORMATION: PL motif, PDZ domain binding motif, C-terminal
      core sequence of FasL

<400> SEQUENCE: 79

Leu Tyr Lys Leu
 1

<210> SEQ ID NO 80
<211> LENGTH: 5
<212> TYPE: PRT
<213> ORGANISM: Artificial Sequence
<220> FEATURE:
<223> OTHER INFORMATION: PL motif, PDZ domain binding motif, C-terminal
      sequence of FasL

<400> SEQUENCE: 80

Gly Leu Tyr Lys Leu
 1               5

<210> SEQ ID NO 81
<211> LENGTH: 6
<212> TYPE: PRT
<213> ORGANISM: Artificial Sequence
<220> FEATURE:
<223> OTHER INFORMATION: PL motif, PDZ domain binding motif, C-terminal
      sequence of FasL

<400> SEQUENCE: 81

Phe Gly Leu Tyr Lys Leu
 1               5

<210> SEQ ID NO 82
<211> LENGTH: 7
<212> TYPE: PRT
<213> ORGANISM: Artificial Sequence
<220> FEATURE:
<223> OTHER INFORMATION: PL motif, PDZ domain binding motif, C-terminal
      sequence of FasL

```
<400> SEQUENCE: 82

Phe Phe Gly Leu Tyr Lys Leu
1               5

<210> SEQ ID NO 83
<211> LENGTH: 8
<212> TYPE: PRT
<213> ORGANISM: Artificial Sequence
<220> FEATURE:
<223> OTHER INFORMATION: PL motif, PDZ domain binding motif, C-terminal
      sequence of FasL, competitor peptide

<400> SEQUENCE: 83

Thr Phe Phe Gly Leu Tyr Lys Leu
1               5

<210> SEQ ID NO 84
<211> LENGTH: 4
<212> TYPE: PRT
<213> ORGANISM: Artificial Sequence
<220> FEATURE:
<223> OTHER INFORMATION: PL motif, PDZ domain binding motif, C-terminal
      core sequence of LPAP

<400> SEQUENCE: 84

Val Thr Ala Leu
1

<210> SEQ ID NO 85
<211> LENGTH: 5
<212> TYPE: PRT
<213> ORGANISM: Artificial Sequence
<220> FEATURE:
<223> OTHER INFORMATION: PL motif, PDZ domain binding motif, C-terminal
      sequence of LPAP

<400> SEQUENCE: 85

His Val Thr Ala Leu
1               5

<210> SEQ ID NO 86
<211> LENGTH: 6
<212> TYPE: PRT
<213> ORGANISM: Artificial Sequence
<220> FEATURE:
<223> OTHER INFORMATION: PL motif, PDZ domain binding motif, C-terminal
      sequence of LPAP

<400> SEQUENCE: 86

Leu His Val Thr Ala Leu
1               5

<210> SEQ ID NO 87
<211> LENGTH: 7
<212> TYPE: PRT
<213> ORGANISM: Artificial Sequence
<220> FEATURE:
<223> OTHER INFORMATION: PL motif, PDZ domain binding motif, C-terminal
      sequence of LPAP

<400> SEQUENCE: 87

Gly Leu His Val Thr Ala Leu
1               5

<210> SEQ ID NO 88
<211> LENGTH: 8
```

```
<212> TYPE: PRT
<213> ORGANISM: Artificial Sequence
<220> FEATURE:
<223> OTHER INFORMATION: PL motif, PDZ domain binding motif, C-terminal
      sequence of LPAP

<400> SEQUENCE: 88

Gln Gly Leu His Val Thr Ala Leu
1               5

<210> SEQ ID NO 89
<211> LENGTH: 4
<212> TYPE: PRT
<213> ORGANISM: Artificial Sequence
<220> FEATURE:
<223> OTHER INFORMATION: PL motif, PDZ domain binding motif, C-terminal
      core sequence of CD138 and syndecan-2

<400> SEQUENCE: 89

Glu Phe Tyr Ala
1

<210> SEQ ID NO 90
<211> LENGTH: 5
<212> TYPE: PRT
<213> ORGANISM: Artificial Sequence
<220> FEATURE:
<223> OTHER INFORMATION: PL motif, PDZ domain binding motif, C-terminal
      sequence of CD138

<400> SEQUENCE: 90

Glu Glu Phe Tyr Ala
1               5

<210> SEQ ID NO 91
<211> LENGTH: 6
<212> TYPE: PRT
<213> ORGANISM: Artificial Sequence
<220> FEATURE:
<223> OTHER INFORMATION: PL motif, PDZ domain binding motif, C-terminal
      sequence of CD138

<400> SEQUENCE: 91

Gln Glu Glu Phe Tyr Ala
1               5

<210> SEQ ID NO 92
<211> LENGTH: 7
<212> TYPE: PRT
<213> ORGANISM: Artificial Sequence
<220> FEATURE:
<223> OTHER INFORMATION: PL motif, PDZ domain binding motif, C-terminal
      sequence of CD138

<400> SEQUENCE: 92

Lys Gln Glu Glu Phe Tyr Ala
1               5

<210> SEQ ID NO 93
<211> LENGTH: 8
<212> TYPE: PRT
<213> ORGANISM: Artificial Sequence
<220> FEATURE:
<223> OTHER INFORMATION: PL motif, PDZ domain binding motif, C-terminal
      sequence of CD138
```

```
<400> SEQUENCE: 93

Thr Lys Gln Glu Glu Phe Tyr Ala
 1               5

<210> SEQ ID NO 94
<211> LENGTH: 4
<212> TYPE: PRT
<213> ORGANISM: Artificial Sequence
<220> FEATURE:
<223> OTHER INFORMATION: PL motif, PDZ domain binding motif, C-terminal
      core sequence of CDw125

<400> SEQUENCE: 94

Asp Ser Val Phe
 1

<210> SEQ ID NO 95
<211> LENGTH: 5
<212> TYPE: PRT
<213> ORGANISM: Artificial Sequence
<220> FEATURE:
<223> OTHER INFORMATION: PL motif, PDZ domain binding motif, C-terminal
      sequence of CDw125

<400> SEQUENCE: 95

Glu Asp Ser Val Phe
 1               5

<210> SEQ ID NO 96
<211> LENGTH: 6
<212> TYPE: PRT
<213> ORGANISM: Artificial Sequence
<220> FEATURE:
<223> OTHER INFORMATION: PL motif, PDZ domain binding motif, C-terminal
      sequence of CDw125

<400> SEQUENCE: 96

Leu Glu Asp Ser Val Phe
 1               5

<210> SEQ ID NO 97
<211> LENGTH: 7
<212> TYPE: PRT
<213> ORGANISM: Artificial Sequence
<220> FEATURE:
<223> OTHER INFORMATION: PL motif, PDZ domain binding motif, C-terminal
      sequence of CDw125

<400> SEQUENCE: 97

Thr Leu Glu Asp Ser Val Phe
 1               5

<210> SEQ ID NO 98
<211> LENGTH: 8
<212> TYPE: PRT
<213> ORGANISM: Artificial Sequence
<220> FEATURE:
<223> OTHER INFORMATION: PL motif, PDZ domain binding motif, C-terminal
      sequence of CDw125

<400> SEQUENCE: 98

Glu Thr Leu Glu Asp Ser Val Phe
 1               5

<210> SEQ ID NO 99
<211> LENGTH: 4
<212> TYPE: PRT
```

```
<213> ORGANISM: Artificial Sequence
<220> FEATURE:
<223> OTHER INFORMATION: PL motif, PDZ domain binding motif, C-terminal
      core sequence of CD56

<400> SEQUENCE: 99

Glu Ser Lys Ala
1

<210> SEQ ID NO 100
<211> LENGTH: 5
<212> TYPE: PRT
<213> ORGANISM: Artificial Sequence
<220> FEATURE:
<223> OTHER INFORMATION: PL motif, PDZ domain binding motif, C-terminal
      sequence of CD56

<400> SEQUENCE: 100

Asn Glu Ser Lys Ala
1               5

<210> SEQ ID NO 101
<211> LENGTH: 6
<212> TYPE: PRT
<213> ORGANISM: Artificial Sequence
<220> FEATURE:
<223> OTHER INFORMATION: PL motif, PDZ domain binding motif, C-terminal
      sequence of CD56

<400> SEQUENCE: 101

Glu Asn Glu Ser Lys Ala
1               5

<210> SEQ ID NO 102
<211> LENGTH: 7
<212> TYPE: PRT
<213> ORGANISM: Artificial Sequence
<220> FEATURE:
<223> OTHER INFORMATION: PL motif, PDZ domain binding motif, C-terminal
      sequence of CD56

<400> SEQUENCE: 102

Lys Glu Asn Glu Ser Lys Ala
1               5

<210> SEQ ID NO 103
<211> LENGTH: 8
<212> TYPE: PRT
<213> ORGANISM: Artificial Sequence
<220> FEATURE:
<223> OTHER INFORMATION: PL motif, PDZ domain binding motif, C-terminal
      sequence of CD56

<400> SEQUENCE: 103

Thr Lys Glu Asn Glu Ser Lys Ala
1               5

<210> SEQ ID NO 104
<211> LENGTH: 4
<212> TYPE: PRT
<213> ORGANISM: Artificial Sequence
<220> FEATURE:
<223> OTHER INFORMATION: PL motif, PDZ domain binding motif, C-terminal
      core sequence of CD44

<400> SEQUENCE: 104

Lys Ile Gly Val
1
```

<210> SEQ ID NO 105
<211> LENGTH: 5
<212> TYPE: PRT
<213> ORGANISM: Artificial Sequence
<220> FEATURE:
<223> OTHER INFORMATION: PL motif, PDZ domain binding motif, C-terminal
      sequence of CD44

<400> SEQUENCE: 105

Met Lys Ile Gly Val
 1               5

<210> SEQ ID NO 106
<211> LENGTH: 6
<212> TYPE: PRT
<213> ORGANISM: Artificial Sequence
<220> FEATURE:
<223> OTHER INFORMATION: PL motif, PDZ domain binding motif, C-terminal
      sequence of CD44

<400> SEQUENCE: 106

Asp Met Lys Ile Gly Val
 1               5

<210> SEQ ID NO 107
<211> LENGTH: 7
<212> TYPE: PRT
<213> ORGANISM: Artificial Sequence
<220> FEATURE:
<223> OTHER INFORMATION: PL motif, PDZ domain binding motif, C-terminal
      sequence of CD44

<400> SEQUENCE: 107

Val Asp Met Lys Ile Gly Val
 1               5

<210> SEQ ID NO 108
<211> LENGTH: 8
<212> TYPE: PRT
<213> ORGANISM: Artificial Sequence
<220> FEATURE:
<223> OTHER INFORMATION: PL motif, PDZ domain binding motif, C-terminal
      sequence of CD44

<400> SEQUENCE: 108

Asn Val Asp Met Lys Ile Gly Val
 1               5

<210> SEQ ID NO 109
<211> LENGTH: 4
<212> TYPE: PRT
<213> ORGANISM: Artificial Sequence
<220> FEATURE:
<223> OTHER INFORMATION: PL motif, PDZ domain binding motif, C-terminal
      core sequence of CD46

<400> SEQUENCE: 109

Phe Thr Ser Leu
 1

<210> SEQ ID NO 110
<211> LENGTH: 5
<212> TYPE: PRT
<213> ORGANISM: Artificial Sequence
<220> FEATURE:
<223> OTHER INFORMATION: PL motif, PDZ domain binding motif, C-terminal
      sequence of CD46

```
<400> SEQUENCE: 110

Lys Phe Thr Ser Leu
1               5

<210> SEQ ID NO 111
<211> LENGTH: 6
<212> TYPE: PRT
<213> ORGANISM: Artificial Sequence
<220> FEATURE:
<223> OTHER INFORMATION: PL motif, PDZ domain binding motif, C-terminal
      sequence of CD46

<400> SEQUENCE: 111

Val Lys Phe Thr Ser Leu
1               5

<210> SEQ ID NO 112
<211> LENGTH: 7
<212> TYPE: PRT
<213> ORGANISM: Artificial Sequence
<220> FEATURE:
<223> OTHER INFORMATION: PL motif, PDZ domain binding motif, C-terminal
      sequence of CD46

<400> SEQUENCE: 112

Glu Val Lys Phe Thr Ser Leu
1               5

<210> SEQ ID NO 113
<211> LENGTH: 8
<212> TYPE: PRT
<213> ORGANISM: Artificial Sequence
<220> FEATURE:
<223> OTHER INFORMATION: PL motif, PDZ domain binding motif, C-terminal
      sequence of CD46, competitor peptide

<400> SEQUENCE: 113

Arg Glu Val Lys Phe Thr Ser Leu
1               5

<210> SEQ ID NO 114
<211> LENGTH: 4
<212> TYPE: PRT
<213> ORGANISM: Artificial Sequence
<220> FEATURE:
<223> OTHER INFORMATION: PL motif, PDZ domain binding motif, C-terminal
      core sequence of CD61

<400> SEQUENCE: 114

Lys Ser Leu Val
1

<210> SEQ ID NO 115
<211> LENGTH: 5
<212> TYPE: PRT
<213> ORGANISM: Artificial Sequence
<220> FEATURE:
<223> OTHER INFORMATION: PL motif, PDZ domain binding motif, C-terminal
      sequence of CD61

<400> SEQUENCE: 115

Leu Lys Ser Leu Val
1               5

<210> SEQ ID NO 116
<211> LENGTH: 6
```

```
<212> TYPE: PRT
<213> ORGANISM: Artificial Sequence
<220> FEATURE:
<223> OTHER INFORMATION: PL motif, PDZ domain binding motif, C-terminal
      sequence of CD61

<400> SEQUENCE: 116

Phe Leu Lys Ser Leu Val
 1               5

<210> SEQ ID NO 117
<211> LENGTH: 7
<212> TYPE: PRT
<213> ORGANISM: Artificial Sequence
<220> FEATURE:
<223> OTHER INFORMATION: PL motif, PDZ domain binding motif, C-terminal
      sequence of CD61

<400> SEQUENCE: 117

Arg Phe Leu Lys Ser Leu Val
 1               5

<210> SEQ ID NO 118
<211> LENGTH: 8
<212> TYPE: PRT
<213> ORGANISM: Artificial Sequence
<220> FEATURE:
<223> OTHER INFORMATION: PL motif, PDZ domain binding motif, C-terminal
      sequence of CD61

<400> SEQUENCE: 118

Gly Arg Phe Leu Lys Ser Leu Val
 1               5

<210> SEQ ID NO 119
<211> LENGTH: 4
<212> TYPE: PRT
<213> ORGANISM: Artificial Sequence
<220> FEATURE:
<223> OTHER INFORMATION: PL motif, PDZ domain binding motif, C-terminal
      core sequence of CD148

<400> SEQUENCE: 119

Gly Tyr Ile Ala
 1

<210> SEQ ID NO 120
<211> LENGTH: 5
<212> TYPE: PRT
<213> ORGANISM: Artificial Sequence
<220> FEATURE:
<223> OTHER INFORMATION: PL motif, PDZ domain binding motif, C-terminal
      sequence of CD148

<400> SEQUENCE: 120

Asn Gly Tyr Ile Ala
 1               5

<210> SEQ ID NO 121
<211> LENGTH: 6
<212> TYPE: PRT
<213> ORGANISM: Artificial Sequence
<220> FEATURE:
<223> OTHER INFORMATION: PL motif, PDZ domain binding motif, C-terminal
      sequence of CD148

<400> SEQUENCE: 121

Thr Asn Gly Tyr Ile Ala
```

```
1               5
```

<210> SEQ ID NO 122
<211> LENGTH: 7
<212> TYPE: PRT
<213> ORGANISM: Artificial Sequence
<220> FEATURE:
<223> OTHER INFORMATION: PL motif, PDZ domain binding motif, C-terminal
      sequence of CD148

<400> SEQUENCE: 122

```
Lys Thr Asn Gly Tyr Ile Ala
 1               5
```

<210> SEQ ID NO 123
<211> LENGTH: 8
<212> TYPE: PRT
<213> ORGANISM: Artificial Sequence
<220> FEATURE:
<223> OTHER INFORMATION: PL motif, PDZ domain binding motif, C-terminal
      sequence of CD148

<400> SEQUENCE: 123

```
Gly Lys Thr Asn Gly Tyr Ile Ala
 1               5
```

<210> SEQ ID NO 124
<211> LENGTH: 4
<212> TYPE: PRT
<213> ORGANISM: Artificial Sequence
<220> FEATURE:
<223> OTHER INFORMATION: PL motif, PDZ domain binding motif, C-terminal
      core sequence of Ly-6

<400> SEQUENCE: 124

```
Gln Thr Leu Leu
 1
```

<210> SEQ ID NO 125
<211> LENGTH: 5
<212> TYPE: PRT
<213> ORGANISM: Artificial Sequence
<220> FEATURE:
<223> OTHER INFORMATION: PL motif, PDZ domain binding motif, C-terminal
      sequence of Ly-6

<400> SEQUENCE: 125

```
Leu Gln Thr Leu Leu
 1               5
```

<210> SEQ ID NO 126
<211> LENGTH: 6
<212> TYPE: PRT
<213> ORGANISM: Artificial Sequence
<220> FEATURE:
<223> OTHER INFORMATION: PL motif, PDZ domain binding motif, C-terminal
      sequence of Ly-6

<400> SEQUENCE: 126

```
Leu Leu Gln Thr Leu Leu
 1               5
```

<210> SEQ ID NO 127
<211> LENGTH: 7
<212> TYPE: PRT
<213> ORGANISM: Artificial Sequence
<220> FEATURE:
<223> OTHER INFORMATION: PL motif, PDZ domain binding motif, C-terminal -continued sequence of Ly-6

<400> SEQUENCE: 127

Val Leu Leu Gln Thr Leu Leu
 1               5

<210> SEQ ID NO 128
<211> LENGTH: 8
<212> TYPE: PRT
<213> ORGANISM: Artificial Sequence
<220> FEATURE:
<223> OTHER INFORMATION: PL motif, PDZ domain binding motif, C-terminal
      sequence of Ly-6

<400> SEQUENCE: 128

Ser Val Leu Leu Gln Thr Leu Leu
 1               5

<210> SEQ ID NO 129
<211> LENGTH: 4
<212> TYPE: PRT
<213> ORGANISM: Artificial Sequence
<220> FEATURE:
<223> OTHER INFORMATION: PL motif, PDZ domain binding motif, C-terminal
      core sequence of FcepsilonRIbeta

<400> SEQUENCE: 129

Pro Ile Asp Leu
 1

<210> SEQ ID NO 130
<211> LENGTH: 5
<212> TYPE: PRT
<213> ORGANISM: Artificial Sequence
<220> FEATURE:
<223> OTHER INFORMATION: PL motif, PDZ domain binding motif, C-terminal
      sequence of FcepsilonRIbeta

<400> SEQUENCE: 130

Pro Pro Ile Asp Leu
 1               5

<210> SEQ ID NO 131
<211> LENGTH: 6
<212> TYPE: PRT
<213> ORGANISM: Artificial Sequence
<220> FEATURE:
<223> OTHER INFORMATION: PL motif, PDZ domain binding motif, C-terminal
      sequence of FcepsilonRIbeta

<400> SEQUENCE: 131

Ser Pro Pro Ile Asp Leu
 1               5

<210> SEQ ID NO 132
<211> LENGTH: 7
<212> TYPE: PRT
<213> ORGANISM: Artificial Sequence
<220> FEATURE:
<223> OTHER INFORMATION: PL motif, PDZ domain binding motif, C-terminal
      sequence of FcepsilonRIbeta

<400> SEQUENCE: 132

Met Ser Pro Pro Ile Asp Leu
 1               5

<210> SEQ ID NO 133

-continued

```
<211> LENGTH: 8
<212> TYPE: PRT
<213> ORGANISM: Artificial Sequence
<220> FEATURE:
<223> OTHER INFORMATION: PL motif, PDZ domain binding motif, C-terminal
      sequence of FcepsilonRIbeta

<400> SEQUENCE: 133

Glu Met Ser Pro Pro Ile Asp Leu
1               5

<210> SEQ ID NO 134
<211> LENGTH: 4
<212> TYPE: PRT
<213> ORGANISM: Artificial Sequence
<220> FEATURE:
<223> OTHER INFORMATION: PL motif, PDZ domain binding motif, C-terminal
      core sequence of galectin 3

<400> SEQUENCE: 134

Tyr Thr Met Ile
1

<210> SEQ ID NO 135
<211> LENGTH: 5
<212> TYPE: PRT
<213> ORGANISM: Artificial Sequence
<220> FEATURE:
<223> OTHER INFORMATION: PL motif, PDZ domain binding motif, C-terminal
      sequence of galectin 3

<400> SEQUENCE: 135

Ser Tyr Thr Met Ile
1               5

<210> SEQ ID NO 136
<211> LENGTH: 6
<212> TYPE: PRT
<213> ORGANISM: Artificial Sequence
<220> FEATURE:
<223> OTHER INFORMATION: PL motif, PDZ domain binding motif, C-terminal
      sequence of galection 3

<400> SEQUENCE: 136

Ala Ser Tyr Thr Met Ile
1               5

<210> SEQ ID NO 137
<211> LENGTH: 7
<212> TYPE: PRT
<213> ORGANISM: Artificial Sequence
<220> FEATURE:
<223> OTHER INFORMATION: PL motif, PDZ domain binding motif, C-terminal
      sequence of galectin 3

<400> SEQUENCE: 137

Ser Ala Ser Tyr Thr Met Ile
1               5

<210> SEQ ID NO 138
<211> LENGTH: 8
<212> TYPE: PRT
<213> ORGANISM: Artificial Sequence
<220> FEATURE:
<223> OTHER INFORMATION: PL motif, PDZ domain binding motif, C-terminal
      sequence of galectin 3

<400> SEQUENCE: 138
```

```
Thr Ser Ala Ser Tyr Thr Met Ile
 1               5
```

<210> SEQ ID NO 139
<211> LENGTH: 4
<212> TYPE: PRT
<213> ORGANISM: Artificial Sequence
<220> FEATURE:
<223> OTHER INFORMATION: PL motif, PDZ domain binding motif, C-terminal
      core sequence of mannose receptor

<400> SEQUENCE: 139

```
His Ser Val Ile
 1
```

<210> SEQ ID NO 140
<211> LENGTH: 5
<212> TYPE: PRT
<213> ORGANISM: Artificial Sequence
<220> FEATURE:
<223> OTHER INFORMATION: PL motif, PDZ domain binding motif, C-terminal
      sequence of mannose receptor

<400> SEQUENCE: 140

```
Glu His Ser Val Ile
 1               5
```

<210> SEQ ID NO 141
<211> LENGTH: 6
<212> TYPE: PRT
<213> ORGANISM: Artificial Sequence
<220> FEATURE:
<223> OTHER INFORMATION: PL motif, PDZ domain binding motif, C-terminal
      sequence of mannose receptor

<400> SEQUENCE: 141

```
Asn Glu His Ser Val Ile
 1               5
```

<210> SEQ ID NO 142
<211> LENGTH: 7
<212> TYPE: PRT
<213> ORGANISM: Artificial Sequence
<220> FEATURE:
<223> OTHER INFORMATION: PL motif, PDZ domain binding motif, C-terminal
      sequence of mannose receptor

<400> SEQUENCE: 142

```
Gln Asn Glu His Ser Val Ile
 1               5
```

<210> SEQ ID NO 143
<211> LENGTH: 8
<212> TYPE: PRT
<213> ORGANISM: Artificial Sequence
<220> FEATURE:
<223> OTHER INFORMATION: PL motif, PDZ domain binding motif, C-terminal
      sequence of mannose receptor

<400> SEQUENCE: 143

```
Glu Gln Asn Glu His Ser Val Ile
 1               5
```

<210> SEQ ID NO 144
<211> LENGTH: 4
<212> TYPE: PRT
<213> ORGANISM: Artificial Sequence
<220> FEATURE:

```
<223> OTHER INFORMATION: PL motif, PDZ domain binding motif, C-terminal
      core sequence of G-CSFR

<400> SEQUENCE: 144

Thr Ser Val Leu
 1

<210> SEQ ID NO 145
<211> LENGTH: 5
<212> TYPE: PRT
<213> ORGANISM: Artificial Sequence
<220> FEATURE:
<223> OTHER INFORMATION: PL motif, PDZ domain binding motif, C-terminal
      sequence of G-CSFR

<400> SEQUENCE: 145

Ile Thr Ser Val Leu
 1               5

<210> SEQ ID NO 146
<211> LENGTH: 6
<212> TYPE: PRT
<213> ORGANISM: Artificial Sequence
<220> FEATURE:
<223> OTHER INFORMATION: PL motif, PDZ domain binding motif, C-terminal
      sequence of G-CSFR

<400> SEQUENCE: 146

Pro Ile Thr Ser Val Leu
 1               5

<210> SEQ ID NO 147
<211> LENGTH: 7
<212> TYPE: PRT
<213> ORGANISM: Artificial Sequence
<220> FEATURE:
<223> OTHER INFORMATION: PL motif, PDZ domain binding motif, C-terminal
      sequence of G-CSFR

<400> SEQUENCE: 147

Phe Pro Ile Thr Ser Val Leu
 1               5

<210> SEQ ID NO 148
<211> LENGTH: 8
<212> TYPE: PRT
<213> ORGANISM: Artificial Sequence
<220> FEATURE:
<223> OTHER INFORMATION: PL motif, PDZ domain binding motif, C-terminal
      sequence of G-CSFR

<400> SEQUENCE: 148

Leu Phe Pro Ile Thr Ser Val Leu
 1               5

<210> SEQ ID NO 149
<211> LENGTH: 4
<212> TYPE: PRT
<213> ORGANISM: Artificial Sequence
<220> FEATURE:
<223> OTHER INFORMATION: PL motif, PDZ domain binding motif, C-terminal
      core sequence of CD34

<400> SEQUENCE: 149

Asp Thr Glu Leu
 1
```

```
<210> SEQ ID NO 150
<211> LENGTH: 5
<212> TYPE: PRT
<213> ORGANISM: Artificial Sequence
<220> FEATURE:
<223> OTHER INFORMATION: PL motif, PDZ domain binding motif, C-terminal
      sequence of CD34

<400> SEQUENCE: 150

Ala Asp Thr Glu Leu
 1               5

<210> SEQ ID NO 151
<211> LENGTH: 6
<212> TYPE: PRT
<213> ORGANISM: Artificial Sequence
<220> FEATURE:
<223> OTHER INFORMATION: PL motif, PDZ domain binding motif, C-terminal
      sequence of CD34

<400> SEQUENCE: 151

Val Ala Asp Thr Glu Leu
 1               5

<210> SEQ ID NO 152
<211> LENGTH: 7
<212> TYPE: PRT
<213> ORGANISM: Artificial Sequence
<220> FEATURE:
<223> OTHER INFORMATION: PL motif, PDZ domain binding motif, C-terminal
      sequence of CD34

<400> SEQUENCE: 152

Val Val Ala Asp Thr Glu Leu
 1               5

<210> SEQ ID NO 153
<211> LENGTH: 8
<212> TYPE: PRT
<213> ORGANISM: Artificial Sequence
<220> FEATURE:
<223> OTHER INFORMATION: PL motif, PDZ domain binding motif, C-terminal
      sequence of CD34

<400> SEQUENCE: 153

His Val Val Ala Asp Thr Glu Leu
 1               5

<210> SEQ ID NO 154
<211> LENGTH: 4
<212> TYPE: PRT
<213> ORGANISM: Artificial Sequence
<220> FEATURE:
<223> OTHER INFORMATION: PL motif, PDZ domain binding motif, C-terminal
      core sequence of CD66b and CD66c

<400> SEQUENCE: 154

Val Ala Leu Ile
 1

<210> SEQ ID NO 155
<211> LENGTH: 5
<212> TYPE: PRT
<213> ORGANISM: Artificial Sequence
<220> FEATURE:
<223> OTHER INFORMATION: PL motif, PDZ domain binding motif, C-terminal
      sequence of CD66b and CD66c

<400> SEQUENCE: 155
```

Arg Val Ala Leu Ile
1               5

<210> SEQ ID NO 156
<211> LENGTH: 6
<212> TYPE: PRT
<213> ORGANISM: Artificial Sequence
<220> FEATURE:
<223> OTHER INFORMATION: PL motif, PDZ domain binding motif, C-terminal
      sequence of CD66b and CD66c

<400> SEQUENCE: 156

Ala Arg Val Ala Leu Ile
1               5

<210> SEQ ID NO 157
<211> LENGTH: 7
<212> TYPE: PRT
<213> ORGANISM: Artificial Sequence
<220> FEATURE:
<223> OTHER INFORMATION: PL motif, PDZ domain binding motif, C-terminal
      sequence of CD66b and CD66c

<400> SEQUENCE: 157

Leu Ala Arg Val Ala Leu Ile
1               5

<210> SEQ ID NO 158
<211> LENGTH: 8
<212> TYPE: PRT
<213> ORGANISM: Artificial Sequence
<220> FEATURE:
<223> OTHER INFORMATION: PL motif, PDZ domain binding motif, C-terminal
      sequence of CD66b and CD66c

<400> SEQUENCE: 158

Val Leu Ala Arg Val Ala Leu Ile
1               5

<210> SEQ ID NO 159
<211> LENGTH: 4
<212> TYPE: PRT
<213> ORGANISM: Artificial Sequence
<220> FEATURE:
<223> OTHER INFORMATION: PL motif, PDZ domain binding motif, C-terminal
      core sequence of CD105

<400> SEQUENCE: 159

Ser Ser Met Ala
1

<210> SEQ ID NO 160
<211> LENGTH: 5
<212> TYPE: PRT
<213> ORGANISM: Artificial Sequence
<220> FEATURE:
<223> OTHER INFORMATION: PL motif, PDZ domain binding motif, C-terminal
      sequence of CD105

<400> SEQUENCE: 160

Thr Ser Ser Met Ala
1               5

<210> SEQ ID NO 161
<211> LENGTH: 6
<212> TYPE: PRT
<213> ORGANISM: Artificial Sequence -continued

```
<220> FEATURE:
<223> OTHER INFORMATION: PL motif, PDZ domain binding motif, C-terminal
      sequence of CD105

<400> SEQUENCE: 161

Ser Thr Ser Ser Met Ala
1               5

<210> SEQ ID NO 162
<211> LENGTH: 8
<212> TYPE: PRT
<213> ORGANISM: Artificial Sequence
<220> FEATURE:
<223> OTHER INFORMATION: PL motif, PDZ domain binding motif, C-terminal
      sequence of CD105

<400> SEQUENCE: 162

Pro Cys Ser Thr Ser Ser Met Ala
1               5

<210> SEQ ID NO 163
<211> LENGTH: 4
<212> TYPE: PRT
<213> ORGANISM: Artificial Sequence
<220> FEATURE:
<223> OTHER INFORMATION: PL motif, PDZ domain binding motif, C-terminal
      core sequence of CD106

<400> SEQUENCE: 163

Lys Ser Lys Val
1

<210> SEQ ID NO 164
<211> LENGTH: 5
<212> TYPE: PRT
<213> ORGANISM: Artificial Sequence
<220> FEATURE:
<223> OTHER INFORMATION: PL motif, PDZ domain binding motif, C-terminal
      sequence of CD106

<400> SEQUENCE: 164

Gln Lys Ser Lys Val
1               5

<210> SEQ ID NO 165
<211> LENGTH: 6
<212> TYPE: PRT
<213> ORGANISM: Artificial Sequence
<220> FEATURE:
<223> OTHER INFORMATION: PL motif, PDZ domain binding motif, C-terminal
      sequence of CD106

<400> SEQUENCE: 165

Ala Gln Lys Ser Lys Val
1               5

<210> SEQ ID NO 166
<211> LENGTH: 7
<212> TYPE: PRT
<213> ORGANISM: Artificial Sequence
<220> FEATURE:
<223> OTHER INFORMATION: PL motif, PDZ domain binding motif, C-terminal
      sequence of CD106

<400> SEQUENCE: 166

Glu Ala Gln Lys Ser Lys Val
1               5
```

```
<210> SEQ ID NO 167
<211> LENGTH: 8
<212> TYPE: PRT
<213> ORGANISM: Artificial Sequence
<220> FEATURE:
<223> OTHER INFORMATION: PL motif, PDZ domain binding motif, C-terminal
      sequence of CD106

<400> SEQUENCE: 167

Val Glu Ala Gln Lys Ser Lys Val
1               5

<210> SEQ ID NO 168
<211> LENGTH: 4
<212> TYPE: PRT
<213> ORGANISM: Artificial Sequence
<220> FEATURE:
<223> OTHER INFORMATION: PL motif, PDZ domain binding motif, C-terminal
      core sequence of CD62e

<400> SEQUENCE: 168

Ser Tyr Ile Leu
1

<210> SEQ ID NO 169
<211> LENGTH: 5
<212> TYPE: PRT
<213> ORGANISM: Artificial Sequence
<220> FEATURE:
<223> OTHER INFORMATION: PL motif, PDZ domain binding motif, C-terminal
      sequence of CD62e

<400> SEQUENCE: 169

Pro Ser Tyr Ile Leu
1               5

<210> SEQ ID NO 170
<211> LENGTH: 6
<212> TYPE: PRT
<213> ORGANISM: Artificial Sequence
<220> FEATURE:
<223> OTHER INFORMATION: PL motif, PDZ domain binding motif, C-terminal
      sequence of CD62e

<400> SEQUENCE: 170

Lys Pro Ser Tyr Ile Leu
1               5

<210> SEQ ID NO 171
<211> LENGTH: 7
<212> TYPE: PRT
<213> ORGANISM: Artificial Sequence
<220> FEATURE:
<223> OTHER INFORMATION: PL motif, PDZ domain binding motif, C-terminal
      sequence of CD62e

<400> SEQUENCE: 171

Gln Lys Pro Ser Tyr Ile Leu
1               5

<210> SEQ ID NO 172
<211> LENGTH: 8
<212> TYPE: PRT
<213> ORGANISM: Artificial Sequence
<220> FEATURE:
<223> OTHER INFORMATION: PL motif, PDZ domain binding motif, C-terminal
      sequence of CD62e
```

-continued

<400> SEQUENCE: 172

Tyr Gln Lys Pro Ser Tyr Ile Leu
1               5

<210> SEQ ID NO 173
<211> LENGTH: 13
<212> TYPE: PRT
<213> ORGANISM: Artificial Sequence
<220> FEATURE:
<223> OTHER INFORMATION: truncated HIV tat peptide

<400> SEQUENCE: 173

Gly Tyr Gly Arg Lys Lys Arg Arg Gln Arg Arg Arg Gly
1               5                   10

<210> SEQ ID NO 174
<211> LENGTH: 21
<212> TYPE: PRT
<213> ORGANISM: Artificial Sequence
<220> FEATURE:
<223> OTHER INFORMATION: Tat-CD3 carboxyl terminus fusion peptide

<400> SEQUENCE: 174

Gly Tyr Gly Arg Lys Lys Arg Arg Gln Arg Arg Arg Gly Pro Pro Ser
1               5                   10                  15

Ser Ser Ser Gly Leu
            20

<210> SEQ ID NO 175
<211> LENGTH: 21
<212> TYPE: PRT
<213> ORGANISM: Artificial Sequence
<220> FEATURE:
<223> OTHER INFORMATION: Tat-CLASP1 carboxyl terminus fusion peptide

<400> SEQUENCE: 175

Gly Tyr Gly Arg Lys Lys Arg Arg Gln Arg Arg Arg Gly Ser Ile Ser
1               5                   10                  15

Ser Ser Ala Glu Val
            20

<210> SEQ ID NO 176
<211> LENGTH: 21
<212> TYPE: PRT
<213> ORGANISM: Artificial Sequence
<220> FEATURE:
<223> OTHER INFORMATION: Tat-CLASP2 carboxyl terminus fusion peptide

<400> SEQUENCE: 176

Gly Tyr Gly Arg Lys Lys Arg Arg Gln Arg Arg Arg Gly Met Thr Ser
1               5                   10                  15

Ser Ser Ser Val Val
            20

<210> SEQ ID NO 177
<211> LENGTH: 19
<212> TYPE: PRT
<213> ORGANISM: Artificial Sequence
<220> FEATURE:
<223> OTHER INFORMATION: AA1L Clasp-1 PL peptide

<400> SEQUENCE: 177

Ile Ser Lys Ala Thr Pro Ala Leu Pro Thr Val Ser Ile Ser Ser Ser
1               5                   10                  15

-continued

Ala Glu Val

<210> SEQ ID NO 178
<211> LENGTH: 20
<212> TYPE: PRT
<213> ORGANISM: Artificial Sequence
<220> FEATURE:
<223> OTHER INFORMATION: AA2L Clasp-2 PL peptide

<400> SEQUENCE: 178

Ile Ser Gly Thr Pro Thr Ser Thr Met Val His Gly Met Thr Ser Ser
 1               5                  10                  15

Ser Ser Val Val
         20

<210> SEQ ID NO 179
<211> LENGTH: 20
<212> TYPE: PRT
<213> ORGANISM: Artificial Sequence
<220> FEATURE:
<223> OTHER INFORMATION: AA3L Clasp-4 PL peptide

<400> SEQUENCE: 179

Cys Ala Ile Ser Gly Thr Ser Ser Asp Arg Gly Tyr Gly Ser Pro Arg
 1               5                  10                  15

Tyr Ala Glu Val
         20

<210> SEQ ID NO 180
<211> LENGTH: 20
<212> TYPE: PRT
<213> ORGANISM: Artificial Sequence
<220> FEATURE:
<223> OTHER INFORMATION: AA4L CD3eta PL peptide

<400> SEQUENCE: 180

Ser Val Phe Ser Ile Pro Thr Leu Trp Ser Pro Trp Pro Pro Ser Ser
 1               5                  10                  15

Ser Ser Gln Leu
         20

<210> SEQ ID NO 181
<211> LENGTH: 19
<212> TYPE: PRT
<213> ORGANISM: Artificial Sequence
<220> FEATURE:
<223> OTHER INFORMATION: AA5L-M CD4 PL peptide

<400> SEQUENCE: 181

Ser Glu Lys Lys Thr Ser Gln Ser Pro His Arg Phe Gln Lys Thr Cys
 1               5                  10                  15

Ser Pro Ile

<210> SEQ ID NO 182
<211> LENGTH: 18
<212> TYPE: PRT
<213> ORGANISM: Artificial Sequence
<220> FEATURE:
<223> OTHER INFORMATION: AA6L CD6 PL peptide

<400> SEQUENCE: 182

Ser Pro Gln Pro Asp Ser Thr Asp Asn Asp Asp Tyr Asp Asp Ile Ser
 1               5                  10                  15

Ala Ala

```
<210> SEQ ID NO 183
<211> LENGTH: 20
<212> TYPE: PRT
<213> ORGANISM: Artificial Sequence
<220> FEATURE:
<223> OTHER INFORMATION: AA7L CD34 PL peptide

<400> SEQUENCE: 183

Gln Ala Thr Ser Arg Asn Gly His Ser Ala Arg Gln His Val Val Ala
 1               5                  10                  15

Asp Thr Glu Leu
            20

<210> SEQ ID NO 184
<211> LENGTH: 20
<212> TYPE: PRT
<213> ORGANISM: Artificial Sequence
<220> FEATURE:
<223> OTHER INFORMATION: AA9L CD44 PL peptide

<400> SEQUENCE: 184

Gln Phe Met Thr Ala Asp Glu Thr Arg Asn Leu Gln Asn Val Asp Met
 1               5                  10                  15

Lys Ile Gly Val
            20

<210> SEQ ID NO 185
<211> LENGTH: 19
<212> TYPE: PRT
<213> ORGANISM: Artificial Sequence
<220> FEATURE:
<223> OTHER INFORMATION: AA10L CD46 (form 1) PL peptide

<400> SEQUENCE: 185

Lys Lys Gly Thr Tyr Leu Thr Asp Glu Thr His Arg Glu Val Lys Phe
 1               5                  10                  15

Thr Ser Leu

<210> SEQ ID NO 186
<211> LENGTH: 19
<212> TYPE: PRT
<213> ORGANISM: Artificial Sequence
<220> FEATURE:
<223> OTHER INFORMATION: AA11L CD49e PL peptide

<400> SEQUENCE: 186

Pro Tyr Gly Thr Ala Met Glu Lys Ala Gln Leu Lys Pro Pro Ala Thr
 1               5                  10                  15

Ser Asp Ala

<210> SEQ ID NO 187
<211> LENGTH: 19
<212> TYPE: PRT
<213> ORGANISM: Artificial Sequence
<220> FEATURE:
<223> OTHER INFORMATION: AA12L CD49f PL peptide

<400> SEQUENCE: 187

His Lys Ala Glu Ile His Ala Gln Pro Ser Asp Lys Glu Arg Leu Thr
 1               5                  10                  15

Ser Asp Ala
```

```
<210> SEQ ID NO 188
<211> LENGTH: 20
<212> TYPE: PRT
<213> ORGANISM: Artificial Sequence
<220> FEATURE:
<223> OTHER INFORMATION: AA13L CD95 PL peptide

<400> SEQUENCE: 188

Lys Asp Ile Thr Ser Asp Ser Glu Asn Ser Asn Phe Arg Asn Glu Ile
 1               5                  10                  15

Gln Ser Leu Val
            20

<210> SEQ ID NO 189
<211> LENGTH: 19
<212> TYPE: PRT
<213> ORGANISM: Artificial Sequence
<220> FEATURE:
<223> OTHER INFORMATION: AA14L CD97 PL peptide

<400> SEQUENCE: 189

Thr Ser Gly Thr Gly His Asn Gln Thr Arg Ala Leu Arg Ala Ser Glu
 1               5                  10                  15

Ser Gly Ile

<210> SEQ ID NO 190
<211> LENGTH: 19
<212> TYPE: PRT
<213> ORGANISM: Artificial Sequence
<220> FEATURE:
<223> OTHER INFORMATION: AA15L CD98 PL peptide

<400> SEQUENCE: 190

Glu Arg Leu Lys Leu Glu Pro His Glu Gly Leu Leu Leu Arg Phe Pro
 1               5                  10                  15

Tyr Ala Ala

<210> SEQ ID NO 191
<211> LENGTH: 20
<212> TYPE: PRT
<213> ORGANISM: Artificial Sequence
<220> FEATURE:
<223> OTHER INFORMATION: AA16L CD105 PL peptide

<400> SEQUENCE: 191

Ser Thr Asn His Ser Ile Gly Ser Thr Gln Ser Thr Pro Cys Ser Thr
 1               5                  10                  15

Ser Ser Met Ala
            20

<210> SEQ ID NO 192
<211> LENGTH: 20
<212> TYPE: PRT
<213> ORGANISM: Artificial Sequence
<220> FEATURE:
<223> OTHER INFORMATION: AA17L VCAM1 PL peptide

<400> SEQUENCE: 192

Ala Arg Lys Ala Asn Met Lys Gly Ser Tyr Ser Leu Val Glu Ala Gln
 1               5                  10                  15

Lys Ser Lys Val
            20

<210> SEQ ID NO 193
```

```
<211> LENGTH: 20
<212> TYPE: PRT
<213> ORGANISM: Artificial Sequence
<220> FEATURE:
<223> OTHER INFORMATION: AA18L CD138 PL peptide

<400> SEQUENCE: 193

Pro Lys Gln Ala Asn Gly Gly Ala Tyr Gln Lys Pro Thr Lys Gln Glu
 1               5                  10                  15

Glu Phe Tyr Ala
            20

<210> SEQ ID NO 194
<211> LENGTH: 17
<212> TYPE: PRT
<213> ORGANISM: Artificial Sequence
<220> FEATURE:
<223> OTHER INFORMATION: AA19L CD148 PL peptide

<400> SEQUENCE: 194

Glu Asn Leu Ala Pro Val Thr Thr Phe Gly Lys Thr Asn Gly Tyr Ile
 1               5                  10                  15

Ala

<210> SEQ ID NO 195
<211> LENGTH: 20
<212> TYPE: PRT
<213> ORGANISM: Artificial Sequence
<220> FEATURE:
<223> OTHER INFORMATION: AA20L CD166 PL peptide

<400> SEQUENCE: 195

Asp Leu Gly Asn Met Glu Glu Asn Lys Lys Leu Glu Glu Asn Asn His
 1               5                  10                  15

Lys Thr Glu Ala
            20

<210> SEQ ID NO 196
<211> LENGTH: 20
<212> TYPE: PRT
<213> ORGANISM: Artificial Sequence
<220> FEATURE:
<223> OTHER INFORMATION: AA22L DNAM-1 PL peptide

<400> SEQUENCE: 196

Thr Arg Glu Asp Ile Tyr Val Asn Tyr Pro Thr Phe Ser Arg Arg Pro
 1               5                  10                  15

Lys Thr Arg Val
            20

<210> SEQ ID NO 197
<211> LENGTH: 19
<212> TYPE: PRT
<213> ORGANISM: Artificial Sequence
<220> FEATURE:
<223> OTHER INFORMATION: AA23L-M FasL PL peptide

<400> SEQUENCE: 197

Ser Ser Lys Ser Lys Ser Ser Glu Glu Ser Gln Thr Phe Phe Gly Leu
 1               5                  10                  15

Tyr Lys Leu

<210> SEQ ID NO 198
<211> LENGTH: 20
```

```
<212> TYPE: PRT
<213> ORGANISM: Artificial Sequence
<220> FEATURE:
<223> OTHER INFORMATION: AA25L FcepsilonRIbeta PL peptide

<400> SEQUENCE: 198

Tyr Ser Ala Thr Tyr Ser Glu Leu Glu Asp Pro Gly Glu Met Ser Pro
 1               5                  10                  15

Pro Ile Asp Leu
            20

<210> SEQ ID NO 199
<211> LENGTH: 19
<212> TYPE: PRT
<213> ORGANISM: Artificial Sequence
<220> FEATURE:
<223> OTHER INFORMATION: AA28L CDw125 (IL5R) PL peptide

<400> SEQUENCE: 199

Glu Val Ile Cys Tyr Ile Glu Lys Pro Gly Val Glu Thr Leu Glu Asp
 1               5                  10                  15

Ser Val Phe

<210> SEQ ID NO 200
<211> LENGTH: 19
<212> TYPE: PRT
<213> ORGANISM: Artificial Sequence
<220> FEATURE:
<223> OTHER INFORMATION: AA29.1L CDw128A (IL8RA) PL peptide

<400> SEQUENCE: 200

Ala Arg His Arg Val Thr Ser Tyr Thr Ser Ser Ser Val Asn Val Ser
 1               5                  10                  15

Ser Asn Leu

<210> SEQ ID NO 201
<211> LENGTH: 19
<212> TYPE: PRT
<213> ORGANISM: Artificial Sequence
<220> FEATURE:
<223> OTHER INFORMATION: AA29.2L CD128B (IL8RB) PL peptide

<400> SEQUENCE: 201

Lys Asp Ser Arg Pro Ser Phe Val Gly Ser Ser Ser Gly His Thr Ser
 1               5                  10                  15

Thr Thr Leu

<210> SEQ ID NO 202
<211> LENGTH: 19
<212> TYPE: PRT
<213> ORGANISM: Artificial Sequence
<220> FEATURE:
<223> OTHER INFORMATION: AA30L LPAP PL peptide

<400> SEQUENCE: 202

Ala Trp Asp Asp Ser Ala Arg Ala Ala Gly Gly Gln Gly Leu His Val
 1               5                  10                  15

Thr Ala Leu

<210> SEQ ID NO 203
<211> LENGTH: 19
<212> TYPE: PRT
<213> ORGANISM: Artificial Sequence
<220> FEATURE:
```

-continued

<223> OTHER INFORMATION: AA33L KV1.3 PL peptide

<400> SEQUENCE: 203

Thr Thr Asn Asn Asn Pro Asn Ser Ala Val Asn Ile Lys Lys Ile Phe
1               5                   10                  15

Thr Asp Val

<210> SEQ ID NO 204
<211> LENGTH: 20
<212> TYPE: PRT
<213> ORGANISM: Artificial Sequence
<220> FEATURE:
<223> OTHER INFORMATION: AA34.2L NMDA PL peptide

<400> SEQUENCE: 204

Leu Asn Ser Cys Ser Asn Arg Arg Val Tyr Lys Lys Met Pro Ser Ile
1               5                   10                  15

Glu Ser Asp Val
            20

<210> SEQ ID NO 205
<211> LENGTH: 19
<212> TYPE: PRT
<213> ORGANISM: Artificial Sequence
<220> FEATURE:
<223> OTHER INFORMATION: AA37L Glycophorin C PL peptide

<400> SEQUENCE: 205

Gln Gly Asp Pro Ala Leu Gln Asp Ala Gly Asp Ser Ser Arg Lys Glu
1               5                   10                  15

Tyr Phe Ile

<210> SEQ ID NO 206
<211> LENGTH: 19
<212> TYPE: PRT
<213> ORGANISM: Artificial Sequence
<220> FEATURE:
<223> OTHER INFORMATION: AA38L Neurexin PL peptide

<400> SEQUENCE: 206

Ser Ser Ala Lys Ser Ser Asn Lys Asn Lys Lys Asn Lys Asp Lys Glu
1               5                   10                  15

Tyr Tyr Val

<210> SEQ ID NO 207
<211> LENGTH: 20
<212> TYPE: PRT
<213> ORGANISM: Artificial Sequence
<220> FEATURE:
<223> OTHER INFORMATION: AA39L Syndecan-2 PL peptide

<400> SEQUENCE: 207

Gly Glu Arg Lys Pro Ser Ser Ala Ala Tyr Gln Lys Ala Pro Thr Lys
1               5                   10                  15

Glu Phe Tyr Ala
            20

<210> SEQ ID NO 208
<211> LENGTH: 20
<212> TYPE: PRT
<213> ORGANISM: Artificial Sequence
<220> FEATURE:
<223> OTHER INFORMATION: AA40L DOCK2 PL peptide -continued

```
<400> SEQUENCE: 208

Leu Ala Ser Lys Ser Ala Glu Glu Gly Lys Gln Ile Pro Asp Ser Leu
 1               5                  10                  15

Ser Thr Asp Leu
            20

<210> SEQ ID NO 209
<211> LENGTH: 20
<212> TYPE: PRT
<213> ORGANISM: Artificial Sequence
<220> FEATURE:
<223> OTHER INFORMATION: AA41L CC CKR-1R PL peptide

<400> SEQUENCE: 209

Leu Glu Arg Val Ser Ser Thr Ser Pro Ser Thr Gly Glu His Glu Leu
 1               5                  10                  15

Ser Ala Gly Phe
            20

<210> SEQ ID NO 210
<211> LENGTH: 20
<212> TYPE: PRT
<213> ORGANISM: Artificial Sequence
<220> FEATURE:
<223> OTHER INFORMATION: AA42L CC CKR-2 PL peptide

<400> SEQUENCE: 210

Gly Lys Gly Lys Ser Ile Gly Arg Ala Pro Glu Ala Ser Leu Gln Asp
 1               5                  10                  15

Lys Glu Gly Ala
            20

<210> SEQ ID NO 211
<211> LENGTH: 20
<212> TYPE: PRT
<213> ORGANISM: Artificial Sequence
<220> FEATURE:
<223> OTHER INFORMATION: AA43L CC CKR-3 PL peptide

<400> SEQUENCE: 211

Leu Glu Arg Thr Ser Ser Val Ser Pro Ser Thr Ala Glu Pro Glu Leu
 1               5                  10                  15

Ser Ile Val Phe
            20

<210> SEQ ID NO 212
<211> LENGTH: 20
<212> TYPE: PRT
<213> ORGANISM: Artificial Sequence
<220> FEATURE:
<223> OTHER INFORMATION: AA44L CC CKR-4 PL peptide

<400> SEQUENCE: 212

Asp Thr Pro Ser Ser Ser Tyr Thr Gln Ser Thr Met Asp His Asp Leu
 1               5                  10                  15

His Asp Ala Leu
            20

<210> SEQ ID NO 213
<211> LENGTH: 20
<212> TYPE: PRT
<213> ORGANISM: Artificial Sequence
<220> FEATURE:
<223> OTHER INFORMATION: AA45L BLR-1 PL peptide
```

-continued

```
<400> SEQUENCE: 213

Pro Ser Trp Arg Arg Ser Ser Leu Ser Glu Ser Glu Asn Ala Thr Ser
1               5                   10                  15

Leu Thr Thr Phe
            20

<210> SEQ ID NO 214
<211> LENGTH: 19
<212> TYPE: PRT
<213> ORGANISM: Artificial Sequence
<220> FEATURE:
<223> OTHER INFORMATION: AA47L CD83 PL peptide

<400> SEQUENCE: 214

Val Thr Ser Pro Asn Lys His Leu Gly Leu Val Thr Pro His Lys Thr
1               5                   10                  15

Glu Leu Val

<210> SEQ ID NO 215
<211> LENGTH: 19
<212> TYPE: PRT
<213> ORGANISM: Artificial Sequence
<220> FEATURE:
<223> OTHER INFORMATION: AA48L CD62e PL peptide

<400> SEQUENCE: 215

Ser Ser Ser Gln Ser Leu Glu Ser Asp Gly Ser Tyr Gln Lys Pro Ser
1               5                   10                  15

Tyr Ile Leu

<210> SEQ ID NO 216
<211> LENGTH: 20
<212> TYPE: PRT
<213> ORGANISM: Artificial Sequence
<220> FEATURE:
<223> OTHER INFORMATION: AA49L CD5 PL peptide

<400> SEQUENCE: 216

Ser Met Gln Pro Asp Asn Ser Ser Asp Ser Asp Tyr Asp Leu His Gly
1               5                   10                  15

Ala Gln Arg Leu
            20

<210> SEQ ID NO 217
<211> LENGTH: 17
<212> TYPE: PRT
<213> ORGANISM: Artificial Sequence
<220> FEATURE:
<223> OTHER INFORMATION: AA55L CD148 PL peptide

<400> SEQUENCE: 217

Thr Ile Tyr Glu Asn Leu Ala Pro Val Thr Thr Phe Gly Lys Thr Ile
1               5                   10                  15

Ala

<210> SEQ ID NO 218
<211> LENGTH: 4
<212> TYPE: PRT
<213> ORGANISM: Artificial Sequence
<220> FEATURE:
<223> OTHER INFORMATION: PL motif, PDZ domain binding motif, C-terminal
      core sequence of CLASP-1
```

```
<400> SEQUENCE: 218

Ser Ala Gln Val
1

<210> SEQ ID NO 219
<211> LENGTH: 5
<212> TYPE: PRT
<213> ORGANISM: Artificial Sequence
<220> FEATURE:
<223> OTHER INFORMATION: PL motif, PDZ domain binding motif, C-terminal
      sequence of CLASP-1

<400> SEQUENCE: 219

Ser Ser Ala Gln Val
1               5

<210> SEQ ID NO 220
<211> LENGTH: 6
<212> TYPE: PRT
<213> ORGANISM: Artificial Sequence
<220> FEATURE:
<223> OTHER INFORMATION: PL motif, PDZ domain binding motif, C-terminal
      sequence of CLASP-1

<400> SEQUENCE: 220

Ser Ser Ser Ala Gln Val
1               5

<210> SEQ ID NO 221
<211> LENGTH: 7
<212> TYPE: PRT
<213> ORGANISM: Artificial Sequence
<220> FEATURE:
<223> OTHER INFORMATION: PL motif, PDZ domain binding motif, C-terminal
      sequence of CLASP-1

<400> SEQUENCE: 221

Ile Ser Ser Ser Ala Gln Val
1               5

<210> SEQ ID NO 222
<211> LENGTH: 8
<212> TYPE: PRT
<213> ORGANISM: Artificial Sequence
<220> FEATURE:
<223> OTHER INFORMATION: PL motif, PDZ domain binding motif, C-terminal
      sequence of CLASP-1

<400> SEQUENCE: 222

Ser Ile Ser Ser Ser Ala Gln Val
1               5

<210> SEQ ID NO 223
<211> LENGTH: 4
<212> TYPE: PRT
<213> ORGANISM: Artificial Sequence
<220> FEATURE:
<223> OTHER INFORMATION: PL motif, PDZ domain binding motif, C-terminal
      core sequence of CLASP-2

<400> SEQUENCE: 223

Ser Ser Val Val
1

<210> SEQ ID NO 224
<211> LENGTH: 5
<212> TYPE: PRT
```

```
<213> ORGANISM: Artificial Sequence
<220> FEATURE:
<223> OTHER INFORMATION: PL motif, PDZ domain binding motif, C-terminal
      sequence of CLASP-2

<400> SEQUENCE: 224

Ser Ser Ser Val Val
1               5

<210> SEQ ID NO 225
<211> LENGTH: 6
<212> TYPE: PRT
<213> ORGANISM: Artificial Sequence
<220> FEATURE:
<223> OTHER INFORMATION: PL motif, PDZ domain binding motif, C-terminal
      sequence of CLASP-2

<400> SEQUENCE: 225

Ser Ser Ser Ser Val Val
1               5

<210> SEQ ID NO 226
<211> LENGTH: 7
<212> TYPE: PRT
<213> ORGANISM: Artificial Sequence
<220> FEATURE:
<223> OTHER INFORMATION: PL motif, PDZ domain binding motif, C-terminal
      sequence of CLASP-2

<400> SEQUENCE: 226

Thr Ser Ser Ser Ser Val Val
1               5

<210> SEQ ID NO 227
<211> LENGTH: 8
<212> TYPE: PRT
<213> ORGANISM: Artificial Sequence
<220> FEATURE:
<223> OTHER INFORMATION: PL motif, PDZ domain binding motif, C-terminal
      sequence of CLASP-2, competitor peptide

<400> SEQUENCE: 227

Met Thr Ser Ser Ser Ser Val Val
1               5

<210> SEQ ID NO 228
<211> LENGTH: 4
<212> TYPE: PRT
<213> ORGANISM: Artificial Sequence
<220> FEATURE:
<223> OTHER INFORMATION: PL motif, PDZ domain binding motif, C-terminal
      core sequence of CLASP-4

<400> SEQUENCE: 228

Tyr Ala Glu Val
1

<210> SEQ ID NO 229
<211> LENGTH: 5
<212> TYPE: PRT
<213> ORGANISM: Artificial Sequence
<220> FEATURE:
<223> OTHER INFORMATION: PL motif, PDZ domain binding motif, C-terminal
      sequence of CLASP-4

<400> SEQUENCE: 229

Arg Tyr Ala Glu Val
1               5
```

<210> SEQ ID NO 230
<211> LENGTH: 6
<212> TYPE: PRT
<213> ORGANISM: Artificial Sequence
<220> FEATURE:
<223> OTHER INFORMATION: PL motif, PDZ domain binding motif, C-terminal
      sequence of CLASP-4

<400> SEQUENCE: 230

Pro Arg Tyr Ala Glu Val
 1               5

<210> SEQ ID NO 231
<211> LENGTH: 7
<212> TYPE: PRT
<213> ORGANISM: Artificial Sequence
<220> FEATURE:
<223> OTHER INFORMATION: PL motif, PDZ domain binding motif, C-terminal
      sequence of CLASP-4

<400> SEQUENCE: 231

Ser Pro Arg Tyr Ala Glu Val
 1               5

<210> SEQ ID NO 232
<211> LENGTH: 8
<212> TYPE: PRT
<213> ORGANISM: Artificial Sequence
<220> FEATURE:
<223> OTHER INFORMATION: PL motif, PDZ domain binding motif, C-terminal
      sequence of CLASP-4

<400> SEQUENCE: 232

Gly Ser Pro Arg Tyr Ala Glu Val
 1               5

<210> SEQ ID NO 233
<211> LENGTH: 4
<212> TYPE: PRT
<213> ORGANISM: Artificial Sequence
<220> FEATURE:
<223> OTHER INFORMATION: PL motif, PDZ domain binding motif, C-terminal
      core sequence of IL-8RB

<400> SEQUENCE: 233

Ser Thr Thr Leu
 1

<210> SEQ ID NO 234
<211> LENGTH: 5
<212> TYPE: PRT
<213> ORGANISM: Artificial Sequence
<220> FEATURE:
<223> OTHER INFORMATION: PL motif, PDZ domain binding motif, C-terminal
      sequence of IL-8RB

<400> SEQUENCE: 234

Thr Ser Thr Thr Leu
 1               5

<210> SEQ ID NO 235
<211> LENGTH: 6
<212> TYPE: PRT
<213> ORGANISM: Artificial Sequence
<220> FEATURE:
<223> OTHER INFORMATION: PL motif, PDZ domain binding motif, C-terminal
      sequence of IL-8RB

```
<400> SEQUENCE: 235

His Thr Ser Thr Thr Leu
 1               5

<210> SEQ ID NO 236
<211> LENGTH: 7
<212> TYPE: PRT
<213> ORGANISM: Artificial Sequence
<220> FEATURE:
<223> OTHER INFORMATION: PL motif, PDZ domain binding motif, C-terminal
      sequence of IL-8RB

<400> SEQUENCE: 236

Gly His Thr Ser Thr Thr Leu
 1               5

<210> SEQ ID NO 237
<211> LENGTH: 8
<212> TYPE: PRT
<213> ORGANISM: Artificial Sequence
<220> FEATURE:
<223> OTHER INFORMATION: PL motif, PDZ domain binding motif, C-terminal
      sequence of IL-8RB

<400> SEQUENCE: 237

Ser Gly His Thr Ser Thr Thr Leu
 1               5

<210> SEQ ID NO 238
<211> LENGTH: 4
<212> TYPE: PRT
<213> ORGANISM: Artificial Sequence
<220> FEATURE:
<223> OTHER INFORMATION: PL motif, PDZ domain binding motif, C-terminal
      core sequence of KV1.3

<400> SEQUENCE: 238

Phe Thr Asp Val
 1

<210> SEQ ID NO 239
<211> LENGTH: 5
<212> TYPE: PRT
<213> ORGANISM: Artificial Sequence
<220> FEATURE:
<223> OTHER INFORMATION: PL motif, PDZ domain binding motif, C-terminal
      sequence of KV1.3

<400> SEQUENCE: 239

Ile Phe Thr Asp Val
 1               5

<210> SEQ ID NO 240
<211> LENGTH: 6
<212> TYPE: PRT
<213> ORGANISM: Artificial Sequence
<220> FEATURE:
<223> OTHER INFORMATION: PL motif, PDZ domain binding motif, C-terminal
      sequence of KV1.3

<400> SEQUENCE: 240

Lys Ile Phe Thr Asp Val
 1               5

<210> SEQ ID NO 241
<211> LENGTH: 7
```

```
<212> TYPE: PRT
<213> ORGANISM: Artificial Sequence
<220> FEATURE:
<223> OTHER INFORMATION: PL motif, PDZ domain binding motif, C-terminal
      sequence of KV1.3

<400> SEQUENCE: 241

Lys Lys Ile Phe Thr Asp Val
1               5

<210> SEQ ID NO 242
<211> LENGTH: 8
<212> TYPE: PRT
<213> ORGANISM: Artificial Sequence
<220> FEATURE:
<223> OTHER INFORMATION: PL motif, PDZ domain binding motif, C-terminal
      sequence of KV1.3

<400> SEQUENCE: 242

Ile Lys Lys Ile Phe Thr Asp Val
1               5

<210> SEQ ID NO 243
<211> LENGTH: 4
<212> TYPE: PRT
<213> ORGANISM: Artificial Sequence
<220> FEATURE:
<223> OTHER INFORMATION: PL motif, PDZ domain binding motif, C-terminal
      core sequence of DOCK2

<400> SEQUENCE: 243

Ser Thr Asp Leu
1

<210> SEQ ID NO 244
<211> LENGTH: 5
<212> TYPE: PRT
<213> ORGANISM: Artificial Sequence
<220> FEATURE:
<223> OTHER INFORMATION: PL motif, PDZ domain binding motif, C-terminal
      sequence of DOCK2

<400> SEQUENCE: 244

Leu Ser Thr Asp Leu
1               5

<210> SEQ ID NO 245
<211> LENGTH: 6
<212> TYPE: PRT
<213> ORGANISM: Artificial Sequence
<220> FEATURE:
<223> OTHER INFORMATION: PL motif, PDZ domain binding motif, C-terminal
      sequence of DOCK2

<400> SEQUENCE: 245

Ser Leu Ser Thr Asp Leu
1               5

<210> SEQ ID NO 246
<211> LENGTH: 7
<212> TYPE: PRT
<213> ORGANISM: Artificial Sequence
<220> FEATURE:
<223> OTHER INFORMATION: PL motif, PDZ domain binding motif, C-terminal
      sequence of DOCK2

<400> SEQUENCE: 246

Asp Ser Leu Ser Thr Asp Leu
```

```
<210> SEQ ID NO 247
<211> LENGTH: 8
<212> TYPE: PRT
<213> ORGANISM: Artificial Sequence
<220> FEATURE:
<223> OTHER INFORMATION: PL motif, PDZ domain binding motif, C-terminal
      sequence of DOCK2

<400> SEQUENCE: 247

Pro Asp Ser Leu Ser Thr Asp Leu
  1               5

<210> SEQ ID NO 248
<211> LENGTH: 4
<212> TYPE: PRT
<213> ORGANISM: Artificial Sequence
<220> FEATURE:
<223> OTHER INFORMATION: PL motif, PDZ domain binding motif, C-terminal
      core sequence of CD83

<400> SEQUENCE: 248

Thr Glu Leu Val
  1

<210> SEQ ID NO 249
<211> LENGTH: 5
<212> TYPE: PRT
<213> ORGANISM: Artificial Sequence
<220> FEATURE:
<223> OTHER INFORMATION: PL motif, PDZ domain binding motif, C-terminal
      sequence of CD83

<400> SEQUENCE: 249

Lys Thr Glu Leu Val
  1               5

<210> SEQ ID NO 250
<211> LENGTH: 6
<212> TYPE: PRT
<213> ORGANISM: Artificial Sequence
<220> FEATURE:
<223> OTHER INFORMATION: PL motif, PDZ domain binding motif, C-terminal
      sequence of CD83

<400> SEQUENCE: 250

His Lys Thr Glu Leu Val
  1               5

<210> SEQ ID NO 251
<211> LENGTH: 7
<212> TYPE: PRT
<213> ORGANISM: Artificial Sequence
<220> FEATURE:
<223> OTHER INFORMATION: PL motif, PDZ domain binding motif, C-terminal
      sequence of CD83

<400> SEQUENCE: 251

Pro His Lys Thr Glu Leu Val
  1               5

<210> SEQ ID NO 252
<211> LENGTH: 8
<212> TYPE: PRT
<213> ORGANISM: Artificial Sequence
<220> FEATURE:
<223> OTHER INFORMATION: PL motif, PDZ domain binding motif, C-terminal
``` sequence of CD83

<400> SEQUENCE: 252

Thr Pro His Lys Thr Glu Leu Val
1               5

<210> SEQ ID NO 253
<211> LENGTH: 4
<212> TYPE: PRT
<213> ORGANISM: Artificial Sequence
<220> FEATURE:
<223> OTHER INFORMATION: PL motif, PDZ domain binding motif, C-terminal
      core sequence of BLR-1

<400> SEQUENCE: 253

Leu Thr Thr Phe
1

<210> SEQ ID NO 254
<211> LENGTH: 5
<212> TYPE: PRT
<213> ORGANISM: Artificial Sequence
<220> FEATURE:
<223> OTHER INFORMATION: PL motif, PDZ domain binding motif, C-terminal
      sequence of BLR-1

<400> SEQUENCE: 254

Ser Leu Thr Thr Phe
1               5

<210> SEQ ID NO 255
<211> LENGTH: 6
<212> TYPE: PRT
<213> ORGANISM: Artificial Sequence
<220> FEATURE:
<223> OTHER INFORMATION: PL motif, PDZ domain binding motif, C-terminal
      sequence of BLR-1

<400> SEQUENCE: 255

Thr Ser Leu Thr Thr Phe
1               5

<210> SEQ ID NO 256
<211> LENGTH: 7
<212> TYPE: PRT
<213> ORGANISM: Artificial Sequence
<220> FEATURE:
<223> OTHER INFORMATION: PL motif, PDZ domain binding motif, C-terminal
      sequence of BLR-1

<400> SEQUENCE: 256

Ala Thr Ser Leu Thr Thr Phe
1               5

<210> SEQ ID NO 257
<211> LENGTH: 8
<212> TYPE: PRT
<213> ORGANISM: Artificial Sequence
<220> FEATURE:
<223> OTHER INFORMATION: PL motif, PDZ domain binding motif, C-terminal
      sequence of BLR-1

<400> SEQUENCE: 257

Asn Ala Thr Ser Leu Thr Thr Phe
1               5

<210> SEQ ID NO 258

```
<211> LENGTH: 5
<212> TYPE: PRT
<213> ORGANISM: Artificial Sequence
<220> FEATURE:
<223> OTHER INFORMATION: linker region between glutathione-S transferase
      (GST) and PDZ domain in GST-PDZ fusion protein

<400> SEQUENCE: 258

Gly Ile Pro Gly Asn
 1               5

<210> SEQ ID NO 259
<211> LENGTH: 5
<212> TYPE: PRT
<213> ORGANISM: Artificial Sequence
<220> FEATURE:
<223> OTHER INFORMATION: PL motif, PDZ domain binding motif, C-terminal
      sequence of syndecan-2

<400> SEQUENCE: 259

Lys Glu Phe Tyr Ala
 1               5

<210> SEQ ID NO 260
<211> LENGTH: 6
<212> TYPE: PRT
<213> ORGANISM: Artificial Sequence
<220> FEATURE:
<223> OTHER INFORMATION: PL motif, PDZ domain binding motif, C-terminal
      sequence of syndecan-2

<400> SEQUENCE: 260

Thr Lys Glu Phe Tyr Ala
 1               5

<210> SEQ ID NO 261
<211> LENGTH: 7
<212> TYPE: PRT
<213> ORGANISM: Artificial Sequence
<220> FEATURE:
<223> OTHER INFORMATION: PL motif, PDZ domain binding motif, C-terminal
      sequence of syndecan-2

<400> SEQUENCE: 261

Pro Thr Lys Glu Phe Tyr Ala
 1               5

<210> SEQ ID NO 262
<211> LENGTH: 8
<212> TYPE: PRT
<213> ORGANISM: Artificial Sequence
<220> FEATURE:
<223> OTHER INFORMATION: PL motif, PDZ domain binding motif, C-terminal
      sequence of syndecan-2

<400> SEQUENCE: 262

Ala Pro Thr Lys Glu Phe Tyr Ala
 1               5

<210> SEQ ID NO 263
<211> LENGTH: 4
<212> TYPE: PRT
<213> ORGANISM: Artificial Sequence
<220> FEATURE:
<223> OTHER INFORMATION: PL motif, PDZ domain binding motif, C-terminal
      core sequence of NMDA

<400> SEQUENCE: 263
```

-continued

```
Glu Ser Asp Val
1

<210> SEQ ID NO 264
<211> LENGTH: 5
<212> TYPE: PRT
<213> ORGANISM: Artificial Sequence
<220> FEATURE:
<223> OTHER INFORMATION: PL motif, PDZ domain binding motif, C-terminal
      sequence of NMDA

<400> SEQUENCE: 264

Ile Glu Ser Asp Val
1               5

<210> SEQ ID NO 265
<211> LENGTH: 6
<212> TYPE: PRT
<213> ORGANISM: Artificial Sequence
<220> FEATURE:
<223> OTHER INFORMATION: PL motif, PDZ domain binding motif, C-terminal
      sequence of NMDA

<400> SEQUENCE: 265

Ser Ile Glu Ser Asp Val
1               5

<210> SEQ ID NO 266
<211> LENGTH: 7
<212> TYPE: PRT
<213> ORGANISM: Artificial Sequence
<220> FEATURE:
<223> OTHER INFORMATION: PL motif, PDZ domain binding motif, C-terminal
      sequence of NMDA

<400> SEQUENCE: 266

Pro Ser Ile Glu Ser Asp Val
1               5

<210> SEQ ID NO 267
<211> LENGTH: 8
<212> TYPE: PRT
<213> ORGANISM: Artificial Sequence
<220> FEATURE:
<223> OTHER INFORMATION: PL motif, PDZ domain binding motif, C-terminal
      sequence of NMDA

<400> SEQUENCE: 267

Met Pro Ser Ile Glu Ser Asp Val
1               5

<210> SEQ ID NO 268
<211> LENGTH: 4
<212> TYPE: PRT
<213> ORGANISM: Artificial Sequence
<220> FEATURE:
<223> OTHER INFORMATION: PL motif, PDZ domain binding motif, C-terminal
      core sequence of neurexin

<400> SEQUENCE: 268

Glu Tyr Tyr Val
1

<210> SEQ ID NO 269
<211> LENGTH: 5
<212> TYPE: PRT
<213> ORGANISM: Artificial Sequence
<220> FEATURE:
```

```
<223> OTHER INFORMATION: PL motif, PDZ domain binding motif, C-terminal
      sequence of neurexin

<400> SEQUENCE: 269

Lys Glu Tyr Tyr Val
 1               5

<210> SEQ ID NO 270
<211> LENGTH: 6
<212> TYPE: PRT
<213> ORGANISM: Artificial Sequence
<220> FEATURE:
<223> OTHER INFORMATION: PL motif, PDZ domain binding motif, C-terminal
      sequence of neurexin

<400> SEQUENCE: 270

Asp Lys Glu Tyr Tyr Val
 1               5

<210> SEQ ID NO 271
<211> LENGTH: 7
<212> TYPE: PRT
<213> ORGANISM: Artificial Sequence
<220> FEATURE:
<223> OTHER INFORMATION: PL motif, PDZ domain binding motif, C-terminal
      sequence of neurexin

<400> SEQUENCE: 271

Lys Asp Lys Glu Tyr Tyr Val
 1               5

<210> SEQ ID NO 272
<211> LENGTH: 8
<212> TYPE: PRT
<213> ORGANISM: Artificial Sequence
<220> FEATURE:
<223> OTHER INFORMATION: PL motif, PDZ domain binding motif, C-terminal
      sequence of neurexin

<400> SEQUENCE: 272

Asn Lys Asp Lys Glu Tyr Tyr Val
 1               5

<210> SEQ ID NO 273
<211> LENGTH: 4
<212> TYPE: PRT
<213> ORGANISM: Artificial Sequence
<220> FEATURE:
<223> OTHER INFORMATION: PL motif, PDZ domain binding motif, C-terminal
      core sequence of glycophorin C

<400> SEQUENCE: 273

Glu Tyr Phe Ile
 1

<210> SEQ ID NO 274
<211> LENGTH: 5
<212> TYPE: PRT
<213> ORGANISM: Artificial Sequence
<220> FEATURE:
<223> OTHER INFORMATION: PL motif, PDZ domain binding motif, C-terminal
      sequence of glycophorin C

<400> SEQUENCE: 274

Lys Glu Tyr Phe Ile
 1               5
```

<210> SEQ ID NO 275
<211> LENGTH: 6
<212> TYPE: PRT
<213> ORGANISM: Artificial Sequence
<220> FEATURE:
<223> OTHER INFORMATION: PL motif, PDZ domain binding motif, C-terminal
      sequence of glycophorin C

<400> SEQUENCE: 275

Arg Lys Glu Tyr Phe Ile
 1               5

<210> SEQ ID NO 276
<211> LENGTH: 7
<212> TYPE: PRT
<213> ORGANISM: Artificial Sequence
<220> FEATURE:
<223> OTHER INFORMATION: PL motif, PDZ domain binding motif, C-terminal
      sequence of glycophorin C

<400> SEQUENCE: 276

Ser Arg Lys Glu Tyr Phe Ile
 1               5

<210> SEQ ID NO 277
<211> LENGTH: 8
<212> TYPE: PRT
<213> ORGANISM: Artificial Sequence
<220> FEATURE:
<223> OTHER INFORMATION: PL motif, PDZ domain binding motif, C-terminal
      sequence of glycophorin C

<400> SEQUENCE: 277

Ser Ser Arg Lys Glu Tyr Phe Ile
 1               5

<210> SEQ ID NO 278
<211> LENGTH: 4
<212> TYPE: PRT
<213> ORGANISM: Artificial Sequence
<220> FEATURE:
<223> OTHER INFORMATION: PL motif, PDZ domain binding motif, C-terminal
      core sequence of CD148

<400> SEQUENCE: 278

Lys Thr Ile Ala
 1

<210> SEQ ID NO 279
<211> LENGTH: 5
<212> TYPE: PRT
<213> ORGANISM: Artificial Sequence
<220> FEATURE:
<223> OTHER INFORMATION: PL motif, PDZ domain binding motif, C-terminal
      sequence of CD148

<400> SEQUENCE: 279

Gly Lys Thr Ile Ala
 1               5

<210> SEQ ID NO 280
<211> LENGTH: 6
<212> TYPE: PRT
<213> ORGANISM: Artificial Sequence
<220> FEATURE:
<223> OTHER INFORMATION: PL motif, PDZ domain binding motif, C-terminal
      sequence of CD148

<400> SEQUENCE: 280

```
Phe Gly Lys Thr Ile Ala
  1               5

<210> SEQ ID NO 281
<211> LENGTH: 7
<212> TYPE: PRT
<213> ORGANISM: Artificial Sequence
<220> FEATURE:
<223> OTHER INFORMATION: PL motif, PDZ domain binding motif, C-terminal
      sequence of CD148

<400> SEQUENCE: 281

Thr Phe Gly Lys Thr Ile Ala
  1               5

<210> SEQ ID NO 282
<211> LENGTH: 8
<212> TYPE: PRT
<213> ORGANISM: Artificial Sequence
<220> FEATURE:
<223> OTHER INFORMATION: PL motif, PDZ domain binding motif, C-terminal
      sequence of CD148

<400> SEQUENCE: 282

Thr Thr Phe Gly Lys Thr Ile Ala
  1               5

<210> SEQ ID NO 283
<211> LENGTH: 4
<212> TYPE: PRT
<213> ORGANISM: Artificial Sequence
<220> FEATURE:
<223> OTHER INFORMATION: CC CKR-2 PDZ ligand

<400> SEQUENCE: 283

Lys Glu Gly Ala
  1

<210> SEQ ID NO 284
<211> LENGTH: 4
<212> TYPE: PRT
<213> ORGANISM: Artificial Sequence
<220> FEATURE:
<223> OTHER INFORMATION: CLASP-1 PDZ ligand

<400> SEQUENCE: 284

Ser Ala Glu Val
  1

<210> SEQ ID NO 285
<211> LENGTH: 4
<212> TYPE: PRT
<213> ORGANISM: Artificial Sequence
<220> FEATURE:
<223> OTHER INFORMATION: CD5 PDZ ligand

<400> SEQUENCE: 285

Ala Gln Arg Leu
  1

<210> SEQ ID NO 286
<211> LENGTH: 4
<212> TYPE: PRT
<213> ORGANISM: Artificial Sequence
<220> FEATURE:
<223> OTHER INFORMATION: CC CKR-4 PDZ ligand

<400> SEQUENCE: 286
```

```
His Asp Ala Leu
  1

<210> SEQ ID NO 287
<211> LENGTH: 4
<212> TYPE: PRT
<213> ORGANISM: Artificial Sequence
<220> FEATURE:
<223> OTHER INFORMATION: CC CKR-1R PDZ ligand

<400> SEQUENCE: 287

Ser Ala Gly Phe
  1

<210> SEQ ID NO 288
<211> LENGTH: 4
<212> TYPE: PRT
<213> ORGANISM: Artificial Sequence
<220> FEATURE:
<223> OTHER INFORMATION: CC CKR-3 PDZ ligand

<400> SEQUENCE: 288

Ser Ile Val Phe
  1

<210> SEQ ID NO 289
<211> LENGTH: 13
<212> TYPE: PRT
<213> ORGANISM: Artificial Sequence
<220> FEATURE:
<223> OTHER INFORMATION: Tat peptide

<400> SEQUENCE: 289

Gly Tyr Gly Arg Lys Lys Arg Arg Gln Arg Arg Arg Gly
  1               5                  10

<210> SEQ ID NO 290
<211> LENGTH: 16
<212> TYPE: PRT
<213> ORGANISM: Artificial Sequence
<220> FEATURE:
<223> OTHER INFORMATION: MBPAc1-16 peptide
<220> FEATURE:
<221> NAME/KEY: MOD_RES
<222> LOCATION: (1)...(1)
<223> OTHER INFORMATION: Xaa = N-acetyl alanine

<400> SEQUENCE: 290

Xaa Ser Gln Lys Arg Pro Ser Gln Arg His Gly Ser Lys Tyr Leu Ala
  1               5                  10                  15

<210> SEQ ID NO 291
<211> LENGTH: 7
<212> TYPE: PRT
<213> ORGANISM: Artificial Sequence
<220> FEATURE:
<223> OTHER INFORMATION: PL motif, PDZ domain binding motif, C-terminal
      sequence of CD105

<400> SEQUENCE: 291

Cys Ser Thr Ser Ser Met Ala
  1               5

<210> SEQ ID NO 292
<211> LENGTH: 96
<212> TYPE: PRT
<213> ORGANISM: Artificial Sequence
```

```
<220> FEATURE:
<223> OTHER INFORMATION: CASK PDZ domain 1

<400> SEQUENCE: 292

His Val Thr Arg Val Arg Leu Val Gln Phe Gln Lys Asn Thr Asp Glu
 1               5                  10                  15

Pro Met Gly Ile Thr Leu Lys Met Asn Glu Leu Asn His Cys Ile Val
            20                  25                  30

Ala Arg Ile Met His Gly Gly Met Ile His Arg Gln Gly Thr Leu His
        35                  40                  45

Val Gly Asp Glu Ile Arg Glu Ile Asn Gly Ile Ser Val Ala Asn Gln
 50                  55                  60

Thr Val Glu Gln Leu Gln Lys Met Leu Arg Glu Met Arg Gly Ser Ile
 65                  70                  75                  80

Thr Phe Lys Ile Val Pro Ser Tyr Arg Thr Gln Ser Leu Asn Ser Ser
                85                  90                  95

<210> SEQ ID NO 293
<211> LENGTH: 93
<212> TYPE: PRT
<213> ORGANISM: Artificial Sequence
<220> FEATURE:
<223> OTHER INFORMATION: MPP1 55 Kd erythrocyte membrane protein PDZ
      domain 1

<400> SEQUENCE: 293

Arg Lys Val Arg Leu Ile Gln Phe Glu Lys Val Thr Glu Glu Pro Met
 1               5                  10                  15

Gly Ile Thr Leu Lys Leu Asn Glu Lys Gln Ser Cys Thr Val Ala Arg
            20                  25                  30

Ile Leu His Gly Gly Met Ile His Arg Gln Gly Ser Leu His Val Gly
        35                  40                  45

Asp Glu Ile Leu Glu Ile Asn Gly Thr Asn Val Thr Asn His Ser Val
 50                  55                  60

Asp Gln Leu Gln Lys Ala Met Lys Glu Thr Lys Gly Met Ile Ser Leu
 65                  70                  75                  80

Lys Val Ile Pro Asn Gln Arg Glu Phe Ile Val Thr Asp
                85                  90

<210> SEQ ID NO 294
<211> LENGTH: 208
<212> TYPE: PRT
<213> ORGANISM: Artificial Sequence
<220> FEATURE:
<223> OTHER INFORMATION: DLG1 human homolog of Drosophila discs large
      protein PDZ domains 1 and 2

<400> SEQUENCE: 294

Gln Val Asn Gly Thr Asp Ala Asp Tyr Glu Tyr Glu Glu Ile Thr Leu
 1               5                  10                  15

Glu Arg Gly Asn Ser Gly Leu Gly Phe Ser Ile Ala Gly Gly Thr Asp
            20                  25                  30

Asn Pro His Ile Gly Asp Asp Ser Ser Ile Phe Ile Thr Lys Ile Ile
        35                  40                  45

Thr Gly Gly Ala Ala Gln Asp Gly Arg Leu Arg Val Asn Asp Cys
 50                  55                  60

Ile Leu Gln Val Asn Glu Val Asp Val Arg Asp Val Thr His Ser Lys
 65                  70                  75                  80

Ala Val Glu Ala Leu Lys Glu Ala Gly Ser Ile Val Arg Leu Tyr Val
```

-continued

```
                    85                  90                  95
Lys Arg Arg Lys Pro Val Ser Glu Lys Ile Met Glu Ile Lys Leu Ile
                100                 105                 110
Lys Gly Pro Lys Gly Leu Gly Phe Ser Ile Ala Gly Gly Val Gly Asn
            115                 120                 125
Gln His Ile Pro Gly Asp Asn Ser Ile Tyr Val Thr Lys Ile Ile Glu
    130                 135                 140
Gly Gly Ala Ala His Lys Asp Gly Lys Leu Gln Ile Gly Asp Lys Leu
145                 150                 155                 160
Leu Ala Val Asn Val Cys Leu Glu Glu Val Thr His Glu Glu Ala
                165                 170                 175
Val Thr Ala Leu Lys Asn Thr Ser Asp Phe Val Tyr Leu Lys Val Ala
                180                 185                 190
Lys Pro Thr Ser Met Tyr Met Asn Asp Gly Tyr Ala Pro Asn Ser Ser
            195                 200                 205

<210> SEQ ID NO 295
<211> LENGTH: 344
<212> TYPE: PRT
<213> ORGANISM: Artificial Sequence
<220> FEATURE:
<223> OTHER INFORMATION: PSD95 human post-synaptic density protein PDZ
      domains 1-3

<400> SEQUENCE: 295

Leu Glu Gly Glu Gly Met Glu Tyr Glu Glu Ile Thr Leu Glu Arg
1               5                   10                  15
Gly Asn Ser Gly Leu Gly Phe Ser Ile Ala Gly Gly Thr Asp Asn Pro
                20                  25                  30
His Ile Gly Asp Asp Pro Ser Ile Phe Ile Thr Lys Ile Ile Pro Gly
            35                  40                  45
Gly Ala Ala Ala Gln Asp Gly Arg Leu Arg Val Asn Asp Ser Ile Leu
        50                  55                  60
Phe Val Asn Glu Val Asp Val Arg Glu Val Thr His Ser Ala Ala Val
65                  70                  75                  80
Glu Ala Leu Lys Glu Ala Gly Ser Ile Val Arg Leu Tyr Val Met Arg
                85                  90                  95
Arg Lys Pro Pro Ala Glu Lys Val Met Glu Ile Lys Leu Ile Lys Gly
                100                 105                 110
Pro Lys Gly Leu Gly Phe Ser Ile Ala Gly Gly Val Gly Asn Gln His
            115                 120                 125
Ile Pro Gly Asp Asn Ser Ile Tyr Val Thr Lys Ile Ile Glu Gly Gly
    130                 135                 140
Ala Ala His Lys Asp Gly Arg Leu Gln Ile Gly Asp Lys Ile Leu Ala
145                 150                 155                 160
Val Asn Ser Val Gly Leu Glu Asp Val Met His Glu Asp Ala Val Ala
                165                 170                 175
Ala Leu Lys Asn Thr Tyr Asp Val Val Tyr Leu Lys Val Ala Lys Pro
                180                 185                 190
Ser Asn Ala Tyr Leu Ser Asp Ser Tyr Ala Pro Pro Asp Ile Thr Thr
            195                 200                 205
Ser Tyr Ser Gln His Leu Asp Asn Glu Ile Ser His Ser Ser Tyr Leu
    210                 215                 220
Gly Thr Asp Tyr Pro Thr Ala Met Thr Pro Thr Ser Pro Arg Arg Tyr
225                 230                 235                 240
```

-continued

```
Ser Pro Val Ala Lys Asp Leu Leu Gly Glu Glu Asp Ile Pro Arg Glu
            245                 250                 255

Pro Arg Arg Ile Val Ile His Arg Gly Ser Thr Gly Leu Gly Phe Asn
            260                 265                 270

Ile Val Gly Gly Glu Asp Gly Glu Gly Ile Phe Ile Ser Phe Ile Leu
            275                 280                 285

Ala Gly Gly Pro Ala Asp Leu Ser Gly Glu Leu Arg Lys Gly Asp Gln
            290                 295                 300

Ile Leu Ser Val Asn Gly Val Asp Leu Arg Asn Ala Ser His Glu Gln
305                 310                 315                 320

Ala Ala Ile Ala Leu Lys Asn Ala Gly Gln Thr Val Thr Ile Ile Ala
            325                 330                 335

Gln Tyr Lys Pro Glu Phe Ile Val
            340
```

<210> SEQ ID NO 296
<211> LENGTH: 189
<212> TYPE: PRT
<213> ORGANISM: Artificial Sequence
<220> FEATURE:
<223> OTHER INFORMATION: NeDLG presynaptic protein sao102
      (neuroendocrine dlg) PDZ domains 1-2

<400> SEQUENCE: 296

```
Gln Tyr Glu Glu Ile Val Leu Glu Arg Gly Asn Ser Gly Leu Gly Phe
1               5                   10                  15

Ser Ile Ala Gly Gly Ile Asp Asn Pro His Val Pro Asp Asp Pro Gly
            20                  25                  30

Ile Phe Ile Thr Lys Ile Ile Pro Gly Gly Ala Ala Ala Met Asp Gly
            35                  40                  45

Arg Leu Gly Val Asn Asp Cys Val Leu Arg Val Asn Glu Val Glu Val
        50                  55                  60

Ser Glu Val Val His Ser Arg Ala Val Glu Ala Leu Lys Glu Ala Gly
65                  70                  75                  80

Pro Val Val Arg Leu Val Arg Arg Arg Gln Pro Pro Glu Thr
            85                  90                  95

Ile Met Glu Val Asn Leu Leu Lys Gly Pro Lys Gly Leu Gly Phe Ser
            100                 105                 110

Ile Ala Gly Gly Ile Gly Asn Gln His Ile Pro Gly Asp Asn Ser Ile
            115                 120                 125

Tyr Ile Thr Lys Ile Ile Glu Gly Gly Ala Ala Gln Lys Asp Gly Arg
            130                 135                 140

Leu Gln Ile Gly Asp Arg Leu Leu Ala Val Asn Asn Thr Asn Leu Gln
145                 150                 155                 160

Asp Val Arg His Glu Glu Ala Val Ala Ser Leu Lys Asn Thr Ser Asp
            165                 170                 175

Met Val Tyr Leu Lys Val Ala Lys Pro Gly Ser Pro Arg
            180                 185
```

<210> SEQ ID NO 297
<211> LENGTH: 97
<212> TYPE: PRT
<213> ORGANISM: Artificial Sequence
<220> FEATURE:
<223> OTHER INFORMATION: TAX33 tax interaction protein 33 PDZ domain 1

<400> SEQUENCE: 297

His Ser His Pro Arg Val Val Glu Leu Pro Lys Thr Asp Glu Gly Leu

-continued

```
                1               5                  10                 15
Gly Phe Asn Val Met Gly Gly Lys Glu Gln Asn Ser Pro Ile Tyr Ile
                      20                 25                 30

Ser Arg Ile Ile Pro Gly Gly Val Ala Glu Arg His Gly Gly Leu Lys
                      35                 40                 45

Arg Gly Asp Gln Leu Leu Ser Val Asn Gly Val Ser Val Glu Gly Glu
                      50                 55                 60

His His Glu Lys Ala Val Glu Leu Leu Lys Ala Ala Lys Asp Ser Val
 65                   70                 75                 80

Lys Leu Val Val Arg Tyr Thr Pro Lys Val Leu Glu Phe Ile Val Thr
                      85                 90                 95
Asn

<210> SEQ ID NO 298
<211> LENGTH: 97
<212> TYPE: PRT
<213> ORGANISM: Artificial Sequence
<220> FEATURE:
<223> OTHER INFORMATION: SYN 1 alpha alpha1-syntrophin PDZ domain 1

<400> SEQUENCE: 298

Gln Arg Arg Arg Val Thr Val Arg Lys Ala Asp Ala Gly Gly Leu Gly
 1               5                  10                 15

Ile Ser Ile Lys Gly Gly Arg Glu Asn Lys Met Pro Ile Leu Ile Ser
                      20                 25                 30

Lys Ile Phe Lys Gly Leu Ala Ala Asp Gln Thr Glu Ala Leu Phe Val
                      35                 40                 45

Gly Asp Ala Ile Leu Ser Val Asn Gly Glu Asp Leu Ser Ser Ala Thr
                      50                 55                 60

His Asp Glu Ala Val Gln Val Leu Lys Lys Thr Gly Lys Glu Val Val
 65                   70                 75                 80

Leu Glu Val Lys Tyr Met Lys Asp Val Ser Pro Tyr Phe Lys Asn Ser
                      85                 90                 95
Ser

<210> SEQ ID NO 299
<211> LENGTH: 78
<212> TYPE: PRT
<213> ORGANISM: Artificial Sequence
<220> FEATURE:
<223> OTHER INFORMATION: TAX43 human tax interaction protein 43 PDZ
      domain 1

<400> SEQUENCE: 299

Gln Lys Arg Gly Val Lys Val Leu Lys Gln Glu Leu Gly Gly Leu Gly
 1               5                  10                 15

Ile Ser Ile Lys Gly Gly Lys Glu Asn Lys Met Pro Ile Leu Ile Ser
                      20                 25                 30

Lys Ile Phe Lys Gly Leu Ala Ala Asp Gln Thr Gln Ala Leu Tyr Val
                      35                 40                 45

Gly Asp Ala Ile Leu Ser Val Asn Gly Ala Asp Leu Arg Asp Ala Thr
                      50                 55                 60

His Asp Glu Ala Val Gln Ala Leu Gln Phe Ile Val Thr Asn
 65                   70                 75

<210> SEQ ID NO 300
<211> LENGTH: 46
<212> TYPE: PRT
<213> ORGANISM: Artificial Sequence
```

```
<220> FEATURE:
<223> OTHER INFORMATION: LDP lim domain protein clp-36 PDZ domain 1

<400> SEQUENCE: 300

Arg Gly Met Thr Thr Gln Gln Ile Asp Leu Gln Gly Pro Gly Pro Trp
 1               5                  10                  15

Gly Phe Arg Leu Val Gly Arg Lys Asp Phe Glu Gln Pro Leu Ala Ile
                20                  25                  30

Ser Arg Val Thr Pro Gly Ser Lys Ala Ala Leu Ala Ser Ser
            35                  40                  45

<210> SEQ ID NO 301
<211> LENGTH: 86
<212> TYPE: PRT
<213> ORGANISM: Artificial Sequence
<220> FEATURE:
<223> OTHER INFORMATION: LIM human LIM protein PDZ domain 1

<400> SEQUENCE: 301

Leu Ser Asn Tyr Ser Val Ser Leu Val Gly Pro Ala Pro Trp Gly Phe
 1               5                  10                  15

Arg Leu Gln Gly Gly Lys Asp Phe Asn Met Pro Leu Thr Ile Ser Ser
                20                  25                  30

Leu Lys Asp Gly Gly Lys Ala Ala Gln Ala Asn Val Arg Ile Gly Asp
            35                  40                  45

Val Val Leu Ser Ile Asp Gly Ile Asn Ala Gln Gly Met Thr His Leu
        50                  55                  60

Glu Ala Gln Asn Lys Ile Lys Gly Cys Thr Gly Ser Leu Asn Met Thr
65                  70                  75                  80

Leu Gln Arg Ala Ser Cys
                85

<210> SEQ ID NO 302
<211> LENGTH: 102
<212> TYPE: PRT
<213> ORGANISM: Artificial Sequence
<220> FEATURE:
<223> OTHER INFORMATION: LIMK1 human LIM domain kinase 1 PDZ domain 1

<400> SEQUENCE: 302

Thr Val Thr Leu Val Ser Ile Pro Ala Ser Ser His Gly Lys Arg Gly
 1               5                  10                  15

Leu Ser Val Ser Ile Asp Pro Pro His Gly Pro Pro Gly Cys Gly Thr
                20                  25                  30

Glu His Ser His Thr Val Arg Val Gln Gly Val Asp Pro Gly Cys Met
            35                  40                  45

Ser Pro Asp Val Lys Asn Ser Ile His Val Gly Asp Arg Ile Leu Glu
        50                  55                  60

Ile Asn Gly Thr Pro Ile Arg Asn Val Pro Leu Asp Glu Ile Asp Leu
65                  70                  75                  80

Leu Ile Gln Glu Thr Ser Arg Leu Leu Gln Leu Thr Leu Glu His Asp
                85                  90                  95

Pro Gly Ile His Arg Asp
                100

<210> SEQ ID NO 303
<211> LENGTH: 97
<212> TYPE: PRT
<213> ORGANISM: Artificial Sequence
<220> FEATURE:
```

-continued

<223> OTHER INFORMATION: LIMK2 human LIM domain kinase 2 PDZ domain 1

<400> SEQUENCE: 303

Pro Tyr Ser Val Thr Leu Ile Ser Met Pro Ala Thr Thr Glu Gly Arg
1               5                   10                  15

Arg Gly Phe Ser Val Ser Val Glu Ser Ala Cys Ser Asn Tyr Ala Thr
            20                  25                  30

Thr Val Gln Val Lys Glu Val Asn Arg Met His Ile Ser Pro Asn Asn
        35                  40                  45

Arg Asn Ala Ile His Pro Gly Asp Arg Ile Leu Glu Ile Asn Gly Thr
    50                  55                  60

Pro Val Arg Thr Leu Arg Val Glu Glu Val Glu Asp Ala Ile Ser Gln
65                  70                  75                  80

Thr Ser Gln Thr Leu Gln Leu Leu Ile Glu His Glu Phe Ile Val Thr
                85                  90                  95

Asn

<210> SEQ ID NO 304
<211> LENGTH: 96
<212> TYPE: PRT
<213> ORGANISM: Artificial Sequence
<220> FEATURE:
<223> OTHER INFORMATION: MPP2 maguk p55 subfamily member 2 (DLG2) PDZ
      domain 1

<400> SEQUENCE: 304

Gln Pro Val Pro Pro Asp Ala Val Arg Met Val Gly Ile Arg Lys Thr
1               5                   10                  15

Ala Gly Glu His Leu Gly Val Thr Phe Arg Val Glu Gly Gly Glu Leu
            20                  25                  30

Val Ile Ala Arg Ile Leu His Gly Gly Met Val Ala Gln Gln Gly Leu
        35                  40                  45

Leu His Val Gly Asp Ile Ile Lys Glu Val Asn Gly Gln Pro Val Gly
    50                  55                  60

Ser Asp Pro Arg Ala Leu Gln Glu Leu Leu Arg Asn Ala Ser Gly Ser
65                  70                  75                  80

Val Ile Leu Lys Ile Leu Pro Asn Tyr Gln Val Phe Ile Val Thr Asp
                85                  90                  95

<210> SEQ ID NO 305
<211> LENGTH: 96
<212> TYPE: PRT
<213> ORGANISM: Artificial Sequence
<220> FEATURE:
<223> OTHER INFORMATION: NOS1 human neuronal nitric oxide synthase PDZ
      domain 1

<400> SEQUENCE: 305

Ile Gln Pro Asn Val Ile Ser Val Arg Leu Phe Lys Arg Lys Val Gly
1               5                   10                  15

Gly Leu Gly Phe Leu Val Lys Glu Arg Val Ser Lys Pro Pro Val Ile
            20                  25                  30

Ile Ser Asp Leu Ile Arg Gly Gly Ala Ala Glu Gln Ser Gly Leu Ile
        35                  40                  45

Gln Ala Gly Asp Ile Ile Leu Ala Val Asn Gly Arg Pro Leu Val Asp
    50                  55                  60

Leu Ser Tyr Asp Ser Ala Leu Glu Val Leu Arg Gly Ile Ala Ser Glu
65                  70                  75                  80

```
Thr His Val Val Leu Ile Leu Arg Gly Pro Glu Phe Ile Val Thr Asp
                85                  90                  95

<210> SEQ ID NO 306
<211> LENGTH: 99
<212> TYPE: PRT
<213> ORGANISM: Artificial Sequence
<220> FEATURE:
<223> OTHER INFORMATION: AF6 af-6 protein PDZ domain 1

<400> SEQUENCE: 306

Leu Arg Lys Glu Pro Glu Ile Ile Thr Val Thr Leu Lys Lys Gln Asn
 1               5                  10                  15

Gly Met Gly Leu Ser Ile Val Ala Ala Lys Gly Ala Gly Gln Asp Lys
                20                  25                  30

Leu Gly Ile Tyr Val Lys Ser Val Lys Gly Gly Ala Ala Asp Val
                35                  40                  45

Asp Gly Arg Leu Ala Ala Gly Asp Gln Leu Leu Ser Val Asp Gly Arg
 50                  55                  60

Ser Leu Val Gly Leu Ser Gln Glu Arg Ala Ala Glu Leu Met Thr Arg
65                  70                  75                  80

Thr Ser Ser Val Val Thr Leu Glu Val Ala Lys Gln Gly Glu Phe Ile
                85                  90                  95

Val Thr Asp

<210> SEQ ID NO 307
<211> LENGTH: 95
<212> TYPE: PRT
<213> ORGANISM: Artificial Sequence
<220> FEATURE:
<223> OTHER INFORMATION: PTN-4 protein-tyrosine phosphatase meg1 PDZ
      domain 1

<400> SEQUENCE: 307

Leu Ile Arg Met Lys Pro Asp Glu Asn Gly Arg Phe Gly Phe Asn Val
 1               5                  10                  15

Lys Gly Gly Tyr Asp Gln Lys Met Pro Val Ile Val Ser Arg Val Ala
                20                  25                  30

Pro Gly Thr Pro Ala Asp Leu Cys Val Pro Arg Leu Asn Glu Gly Asp
                35                  40                  45

Gln Val Val Leu Ile Asn Gly Arg Asp Ile Ala Glu His Thr His Asp
     50                  55                  60

Gln Val Val Leu Phe Ile Lys Ala Ser Cys Glu Arg His Ser Gly Glu
65                  70                  75                  80

Leu Met Leu Leu Val Arg Pro Asn Ala Glu Phe Ile Val Thr Asp
                85                  90                  95

<210> SEQ ID NO 308
<211> LENGTH: 219
<212> TYPE: PRT
<213> ORGANISM: Artificial Sequence
<220> FEATURE:
<223> OTHER INFORMATION: prIL16 putative interleukin 16 precursor PDZ
      domain 1-2

<400> SEQUENCE: 308

His Val Thr Ile Leu His Lys Glu Glu Gly Ala Gly Leu Gly Phe Ser
 1               5                  10                  15

Leu Ala Gly Gly Ala Asp Leu Glu Asn Lys Val Ile Thr Val His Arg
                20                  25                  30
```

```
Val Phe Pro Asn Gly Leu Ala Ser Gln Glu Gly Thr Ile Gln Lys Gly
        35                  40                  45

Asn Glu Val Leu Ser Ile Asn Gly Lys Ser Leu Lys Gly Thr Thr His
 50                  55                  60

His Asp Ala Leu Ala Ile Leu Arg Gln Ala Arg Glu Pro Arg Gln Ala
 65                  70                  75                  80

Val Ile Val Thr Arg Lys Leu Thr Pro Glu Ala Met Pro Asp Leu Asn
                 85                  90                  95

Ser Ser Thr Asp Ser Ala Ala Ser Ala Ser Ala Ser Asp Val Ser
                100                 105                 110

Val Glu Ser Thr Ala Glu Ala Thr Val Cys Thr Val Thr Leu Glu Lys
            115                 120                 125

Met Ser Ala Gly Leu Gly Phe Ser Leu Glu Gly Gly Lys Gly Ser Leu
130                 135                 140

His Gly Asp Lys Pro Leu Thr Ile Asn Arg Ile Phe Lys Gly Ala Ala
145                 150                 155                 160

Ser Glu Gln Ser Glu Thr Val Gln Pro Gly Asp Glu Ile Leu Gln Leu
                165                 170                 175

Gly Gly Thr Ala Met Gln Gly Leu Thr Arg Phe Glu Ala Trp Asn Ile
            180                 185                 190

Ile Lys Ala Leu Pro Asp Gly Pro Val Thr Ile Val Ile Arg Arg Lys
        195                 200                 205

Ser Leu Gln Ser Lys Glu Phe Ile Val Thr Asp
    210                 215

<210> SEQ ID NO 309
<211> LENGTH: 86
<212> TYPE: PRT
<213> ORGANISM: Artificial Sequence
<220> FEATURE:
<223> OTHER INFORMATION: 41.8 kD hypothetical 41.8 kD protein PDZ
      domain 1

<400> SEQUENCE: 309

Arg Asp Ser Gly Ala Met Leu Gly Leu Lys Val Val Gly Gly Lys Met
 1               5                  10                  15

Thr Glu Ser Gly Arg Leu Cys Ala Phe Ile Thr Lys Val Lys Lys Gly
            20                  25                  30

Ser Leu Ala Asp Thr Val Gly His Leu Arg Pro Gly Asp Glu Val Leu
        35                  40                  45

Glu Trp Asn Gly Arg Leu Leu Gln Gly Ala Thr Phe Glu Glu Val Tyr
 50                  55                  60

Asn Ile Ile Leu Glu Ser Lys Pro Glu Pro Gln Val Glu Leu Val Val
 65                  70                  75                  80

Ser Arg Ala Asn Ser Ser
                85

<210> SEQ ID NO 310
<211> LENGTH: 109
<212> TYPE: PRT
<213> ORGANISM: Artificial Sequence
<220> FEATURE:
<223> OTHER INFORMATION: K559 KIAA0559 PDZ domain 1

<400> SEQUENCE: 310

His Tyr Ile Phe Pro His Ala Arg Ile Lys Ile Thr Arg Asp Ser Lys
 1               5                  10                  15

Asp His Thr Val Ser Gly Asn Gly Leu Gly Ile Arg Ile Val Gly Gly
```

```
                20              25              30
Lys Glu Ile Pro Gly His Ser Gly Glu Ile Gly Ala Tyr Ile Ala Lys
            35                  40                  45

Ile Leu Pro Gly Gly Ser Ala Glu Gln Thr Gly Lys Leu Met Glu Gly
 50                      55                  60

Met Gln Val Leu Glu Trp Asn Gly Ile Pro Leu Thr Ser Lys Thr Tyr
 65                  70                  75                  80

Glu Glu Val Gln Ser Ile Ile Ser Gln Gln Ser Gly Glu Ala Glu Ile
                    85                  90                  95

Cys Val Arg Leu Asp Leu Asn Met Leu Ser Asn Ser Ser
                100                 105

<210> SEQ ID NO 311
<211> LENGTH: 73
<212> TYPE: PRT
<213> ORGANISM: Artificial Sequence
<220> FEATURE:
<223> OTHER INFORMATION: RGS12 human regulator of G-protein signalling
      12 PDZ domain 1

<400> SEQUENCE: 311

Pro Pro Pro Arg Val Arg Ser Val Glu Val Ala Arg Gly Arg Ala Gly
 1               5                  10                  15

Tyr Gly Phe Thr Leu Ser Gly Gln Ala Pro Cys Val Leu Ser Cys Val
                20                  25                  30

Met Arg Gly Ser Pro Ala Asp Phe Val Gly Leu Arg Ala Gly Asp Gln
            35                  40                  45

Ile Leu Ala Val Asn Glu Ile Asn Val Lys Lys Ala Ser His Glu Asp
 50                      55                  60

Val Val Lys Leu Ile Gly Asn Ser Ser
 65                      70

<210> SEQ ID NO 312
<211> LENGTH: 92
<212> TYPE: PRT
<213> ORGANISM: Artificial Sequence
<220> FEATURE:
<223> OTHER INFORMATION: K316 KIAA0316 PDZ domain 1

<400> SEQUENCE: 312

Pro Pro Ala Pro Arg Lys Val Glu Met Arg Arg Asp Pro Val Leu Gly
 1               5                  10                  15

Phe Gly Phe Val Ala Gly Ser Glu Lys Pro Val Val Arg Ser Val
                20                  25                  30

Thr Pro Gly Gly Pro Ser Glu Gly Lys Leu Ile Pro Gly Asp Gln Ile
            35                  40                  45

Val Met Ile Asn Asp Glu Pro Val Ser Ala Ala Pro Arg Glu Arg Val
 50                      55                  60

Ile Asp Leu Val Arg Ser Cys Lys Glu Ser Ile Leu Leu Thr Val Ile
 65                      70                  75                  80

Gln Pro Tyr Pro Ser Pro Lys Ile Arg Asn Ser Ser
                85                  90

<210> SEQ ID NO 313
<211> LENGTH: 103
<212> TYPE: PRT
<213> ORGANISM: Artificial Sequence
<220> FEATURE:
<223> OTHER INFORMATION: DVL1 human dishevelled segment polarity protein
      homolog PDZ domain 1
```

-continued

```
<400> SEQUENCE: 313

Gln Ser Thr Val Leu Asn Ile Val Thr Val Thr Leu Asn Met Glu Arg
1               5                   10                  15

His His Phe Leu Gly Ile Ser Ile Val Gly Gln Ser Asn Asp Arg Gly
            20                  25                  30

Asp Gly Gly Ile Tyr Ile Gly Ser Ile Met Lys Gly Gly Ala Val Ala
        35                  40                  45

Ala Asp Gly Arg Ile Glu Pro Gly Asp Met Leu Leu Gln Val Asn Asp
    50                  55                  60

Val Asn Phe Glu Asn Met Ser Asn Asp Asp Ala Val Arg Val Leu Arg
65                  70                  75                  80

Glu Ile Val Ser Gln Thr Gly Pro Ile Ser Leu Thr Val Ala Lys Cys
                85                  90                  95

Trp Glu Phe Ile Val Thr Asp
            100

<210> SEQ ID NO 314
<211> LENGTH: 106
<212> TYPE: PRT
<213> ORGANISM: Artificial Sequence
<220> FEATURE:
<223> OTHER INFORMATION: TAX40 human tax interaction protein 40 PDZ
      domain 1

<400> SEQUENCE: 314

Leu Leu Pro Glu Thr His Arg Arg Val Arg Leu His Lys His Gly Ser
1               5                   10                  15

Asp Arg Pro Leu Gly Phe Tyr Ile Arg Asp Gly Met Ser Val Arg Val
            20                  25                  30

Ala Pro Gln Gly Leu Glu Arg Val Pro Gly Ile Phe Ile Ser Arg Leu
        35                  40                  45

Val Arg Gly Gly Leu Ala Glu Ser Thr Gly Leu Leu Ala Val Ser Asp
    50                  55                  60

Glu Ile Leu Glu Val Asn Gly Ile Glu Val Ala Gly Lys Thr Leu Asp
65                  70                  75                  80

Gln Val Thr Asp Met Met Val Ala Asn Ser His Asn Leu Ile Val Thr
                85                  90                  95

Val Lys Pro Ala Asn Gln Ala Asn Ser Ser
            100                 105

<210> SEQ ID NO 315
<211> LENGTH: 94
<212> TYPE: PRT
<213> ORGANISM: Artificial Sequence
<220> FEATURE:
<223> OTHER INFORMATION: TIAM1 T-lymphoma invasion and metastasis
      inducing protein 1 PDZ domain 1

<400> SEQUENCE: 315

His Ser Ile His Ile Glu Lys Ser Asp Thr Ala Ala Asp Thr Tyr Gly
1               5                   10                  15

Phe Ser Leu Ser Ser Val Glu Glu Asp Gly Ile Arg Arg Leu Tyr Val
            20                  25                  30

Asn Ser Val Lys Glu Thr Gly Leu Ala Ser Lys Lys Gly Leu Lys Ala
        35                  40                  45

Gly Asp Glu Ile Leu Glu Ile Asn Asn Arg Ala Ala Asp Ala Leu Asn
    50                  55                  60
```

```
Ser Ser Met Leu Lys Asp Phe Leu Ser Gln Pro Ser Leu Gly Leu Leu
 65                  70                  75                  80

Val Arg Thr Tyr Pro Glu Leu Glu Glu Phe Ile Val Thr Asp
                 85                  90

<210> SEQ ID NO 316
<211> LENGTH: 181
<212> TYPE: PRT
<213> ORGANISM: Artificial Sequence
<220> FEATURE:
<223> OTHER INFORMATION: MINT1 human X11 protein PDZ domains 1-2

<400> SEQUENCE: 316

Ser Glu Asn Cys Lys Asp Val Phe Ile Glu Lys Gln Lys Gly Glu Ile
  1               5                  10                  15

Leu Gly Val Val Ile Val Glu Ser Gly Trp Gly Ser Ile Leu Pro Thr
                 20                  25                  30

Val Ile Ile Ala Asn Met Met His Gly Gly Pro Ala Glu Lys Ser Gly
             35                  40                  45

Lys Leu Asn Ile Gly Asp Gln Ile Met Ser Ile Asn Gly Thr Ser Leu
 50                  55                  60

Val Gly Leu Pro Leu Ser Thr Cys Gln Ser Ile Ile Lys Gly Leu Glu
 65                  70                  75                  80

Asn Gln Ser Arg Val Lys Leu Asn Ile Val Arg Cys Pro Pro Val Thr
                 85                  90                  95

Thr Val Leu Ile Arg Arg Pro Asp Leu Arg Tyr Gln Leu Gly Phe Ser
            100                 105                 110

Val Gln Asn Gly Ile Ile Cys Ser Leu Met Arg Gly Gly Ile Ala Glu
            115                 120                 125

Arg Gly Gly Val Arg Val Gly His Arg Ile Ile Glu Ile Asn Gly Gln
        130                 135                 140

Ser Val Val Ala Thr Pro His Glu Lys Ile Val His Ile Leu Ser Asn
145                 150                 155                 160

Ala Val Gly Glu Ile His Met Lys Thr Met Pro Ala Ala Met Tyr Arg
                165                 170                 175

Leu Leu Asn Ser Ser
            180

<210> SEQ ID NO 317
<211> LENGTH: 97
<212> TYPE: PRT
<213> ORGANISM: Artificial Sequence
<220> FEATURE:
<223> OTHER INFORMATION: K303 KIAA0303 PDZ domain 1

<400> SEQUENCE: 317

Pro His Gln Pro Ile Val Ile His Ser Ser Gly Lys Asn Tyr Gly Phe
  1               5                  10                  15

Thr Ile Arg Ala Ile Arg Val Tyr Val Gly Asp Ser Asp Ile Tyr Thr
                 20                  25                  30

Val His His Ile Val Trp Asn Val Glu Glu Gly Ser Pro Ala Cys Gln
             35                  40                  45

Ala Gly Leu Lys Ala Gly Asp Leu Ile Thr His Ile Asn Gly Glu Pro
 50                  55                  60

Val His Gly Leu Val His Thr Glu Val Ile Glu Leu Leu Leu Lys Ser
 65                  70                  75                  80

Gly Asn Lys Val Ser Ile Thr Thr Thr Pro Phe Glu Phe Ile Val Thr
                 85                  90                  95
```

Asp

<210> SEQ ID NO 318
<211> LENGTH: 95
<212> TYPE: PRT
<213> ORGANISM: Artificial Sequence
<220> FEATURE:
<223> OTHER INFORMATION: CBP cytohesin binding protein HE PDZ domain 1

<400> SEQUENCE: 318

Gln Arg Lys Leu Val Thr Val Glu Lys Gln Asp Asn Glu Thr Phe Gly
 1               5                  10                  15

Phe Glu Ile Gln Ser Tyr Arg Pro Gln Asn Gln Asn Ala Cys Ser Ser
            20                  25                  30

Glu Met Phe Thr Leu Ile Cys Lys Ile Gln Glu Asp Ser Pro Ala His
        35                  40                  45

Cys Ala Gly Leu Gln Ala Gly Asp Val Leu Ala Asn Ile Asn Gly Val
    50                  55                  60

Ser Thr Glu Gly Phe Thr Tyr Lys Gln Val Val Asp Leu Ile Arg Ser
65                  70                  75                  80

Ser Gly Asn Leu Leu Thr Ile Glu Thr Leu Asn Gly Asn Ser Ser
                85                  90                  95

<210> SEQ ID NO 319
<211> LENGTH: 48
<212> TYPE: PRT
<213> ORGANISM: Artificial Sequence
<220> FEATURE:
<223> OTHER INFORMATION: human MINT3 PDZ domain 1

<400> SEQUENCE: 319

Pro Val Thr Thr Ala Ile Ile His Arg Pro His Ala Arg Glu Gln Leu
 1               5                  10                  15

Gly Phe Cys Val Glu Asp Gly Ile Val Arg Pro Arg Pro Leu Ala Pro
            20                  25                  30

Gly Trp Gly Gly Arg Ala Ala Leu Ser Thr Glu Phe Ile Val Thr Asp
        35                  40                  45

<210> SEQ ID NO 320
<211> LENGTH: 92
<212> TYPE: PRT
<213> ORGANISM: Artificial Sequence
<220> FEATURE:
<223> OTHER INFORMATION: TAX2 human tax interaction protein 2 PDZ
      domain 1

<400> SEQUENCE: 320

Arg Lys Glu Val Glu Val Phe Lys Ser Glu Asp Ala Leu Gly Leu Thr
 1               5                  10                  15

Ile Thr Asp Asn Gly Ala Gly Tyr Ala Phe Ile Lys Arg Ile Lys Glu
            20                  25                  30

Gly Ser Val Ile Asp His Ile His Leu Ile Ser Val Gly Asp Met Ile
        35                  40                  45

Glu Ala Ile Asn Gly Gln Ser Leu Leu Gly Cys Arg His Tyr Glu Val
    50                  55                  60

Ala Arg Leu Leu Lys Glu Leu Pro Arg Gly Arg Thr Phe Thr Leu Lys
65                  70                  75                  80

Leu Thr Glu Pro Arg Lys Glu Phe Ile Val Thr Asp
                85                  90

<210> SEQ ID NO 321
<211> LENGTH: 94
<212> TYPE: PRT
<213> ORGANISM: Artificial Sequence
<220> FEATURE:
<223> OTHER INFORMATION: K561 KIAA0561 PDZ domain 1

<400> SEQUENCE: 321

```
Pro Pro Ser Leu Ser Thr Ala Leu Ala Arg Ser Thr Ala Ser Ala Cys
 1               5                  10                  15
Gly Arg Ser Ala Ser Thr Trp Val Ile Ala Thr Ser Thr Leu Cys Thr
            20                  25                  30
Thr Ser Ser Gly Val Trp Arg Thr Glu Ala Pro Pro Arg Arg Arg Ala
        35                  40                  45
Cys Gly Leu Gly Thr Ser Pro Thr Ser Thr Gly Ser Gln Cys Trp
 50                  55                  60
Gly Trp Cys Thr Trp Thr Ser Trp Ser Cys Cys Glx Arg Ala Ala Thr
 65                  70                  75                  80
Arg Tyr Pro Cys Gly Pro Gln Pro Trp Arg Ile His Arg Asp
                85                  90
```

<210> SEQ ID NO 322
<211> LENGTH: 25
<212> TYPE: DNA
<213> ORGANISM: Artificial Sequence
<220> FEATURE:
<223> OTHER INFORMATION: 6CAF forward primer

<400> SEQUENCE: 322
tcggatccat gtgaccagag ttcgg                                    25

<210> SEQ ID NO 323
<211> LENGTH: 24
<212> TYPE: DNA
<213> ORGANISM: Artificial Sequence
<220> FEATURE:
<223> OTHER INFORMATION: 7CAR reverse primer

<400> SEQUENCE: 323
tcggaattca gactgagtgc ggta                                     24

<210> SEQ ID NO 324
<211> LENGTH: 25
<212> TYPE: DNA
<213> ORGANISM: Artificial Sequence
<220> FEATURE:
<223> OTHER INFORMATION: 62MPF forward primer

<400> SEQUENCE: 324
gggatccgga aagtgcgact catac                                    25

<210> SEQ ID NO 325
<211> LENGTH: 26
<212> TYPE: DNA
<213> ORGANISM: Artificial Sequence
<220> FEATURE:
<223> OTHER INFORMATION: 63MPR reverse primer

<400> SEQUENCE: 325
acggatccgc tggttgggaa ttactt                                   26

<210> SEQ ID NO 326
<211> LENGTH: 26

```
<212> TYPE: DNA
<213> ORGANISM: Artificial Sequence
<220> FEATURE:
<223> OTHER INFORMATION: 1DF forward primer

<400> SEQUENCE: 326
tcggatccag gttaatggct cagatg                                          26

<210> SEQ ID NO 327
<211> LENGTH: 22
<212> TYPE: DNA
<213> ORGANISM: Artificial Sequence
<220> FEATURE:
<223> OTHER INFORMATION: 2DR reverse primer

<400> SEQUENCE: 327
cggaattcgg tgcatagcca tc                                              22

<210> SEQ ID NO 328
<211> LENGTH: 24
<212> TYPE: DNA
<213> ORGANISM: Artificial Sequence
<220> FEATURE:
<223> OTHER INFORMATION: 8PSF forward primer

<400> SEQUENCE: 328
tcggatcctt gaggggggaga tgga                                           24

<210> SEQ ID NO 329
<211> LENGTH: 24
<212> TYPE: DNA
<213> ORGANISM: Artificial Sequence
<220> FEATURE:
<223> OTHER INFORMATION: 11PSR reverse primer

<400> SEQUENCE: 329
tcggaattcg ctatactctt ctgg                                            24

<210> SEQ ID NO 330
<211> LENGTH: 29
<212> TYPE: DNA
<213> ORGANISM: Artificial Sequence
<220> FEATURE:
<223> OTHER INFORMATION: 71NEDF forward primer

<400> SEQUENCE: 330
caggatccaa tatgaggaaa tcgtacttg                                       29

<210> SEQ ID NO 331
<211> LENGTH: 26
<212> TYPE: DNA
<213> ORGANISM: Artificial Sequence
<220> FEATURE:
<223> OTHER INFORMATION: 72NEDR reverse primer

<400> SEQUENCE: 331
ttgaattcga ggctgcctgg cttggc                                          26

<210> SEQ ID NO 332
<211> LENGTH: 27
<212> TYPE: DNA
<213> ORGANISM: Artificial Sequence
<220> FEATURE:
<223> OTHER INFORMATION: 92TAF forward primer

<400> SEQUENCE: 332
```

```
gtgggatcca ctcccaccct cgagtag                                               27

<210> SEQ ID NO 333
<211> LENGTH: 30
<212> TYPE: DNA
<213> ORGANISM: Artificial Sequence
<220> FEATURE:
<223> OTHER INFORMATION: 93TAR reverse primer

<400> SEQUENCE: 333
catgaattcc agaactttg ggtgtatcgc                                              30

<210> SEQ ID NO 334
<211> LENGTH: 26
<212> TYPE: DNA
<213> ORGANISM: Artificial Sequence
<220> FEATURE:
<223> OTHER INFORMATION: 124SYF forward primer

<400> SEQUENCE: 334
tacggatcca gcggccgccg cgtgac                                                 26

<210> SEQ ID NO 335
<211> LENGTH: 26
<212> TYPE: DNA
<213> ORGANISM: Artificial Sequence
<220> FEATURE:
<223> OTHER INFORMATION: 125SYR reverse primer

<400> SEQUENCE: 335
gtagaattct tgaaatacgg tgagac                                                 26

<210> SEQ ID NO 336
<211> LENGTH: 27
<212> TYPE: DNA
<213> ORGANISM: Artificial Sequence
<220> FEATURE:
<223> OTHER INFORMATION: 97TAF forward primer

<400> SEQUENCE: 336
tctggatcca gaagcgtggc gtgaagg                                                27

<210> SEQ ID NO 337
<211> LENGTH: 25
<212> TYPE: DNA
<213> ORGANISM: Artificial Sequence
<220> FEATURE:
<223> OTHER INFORMATION: 98TAR reverse primer

<400> SEQUENCE: 337
cggaattcaa cgcctgcacc gcctc                                                  25

<210> SEQ ID NO 338
<211> LENGTH: 27
<212> TYPE: DNA
<213> ORGANISM: Artificial Sequence
<220> FEATURE:
<223> OTHER INFORMATION: 146LIF forward primer

<400> SEQUENCE: 338
ccaggatccg cggaatgacc acccagc                                                27

<210> SEQ ID NO 339
<211> LENGTH: 27
<212> TYPE: DNA
<213> ORGANISM: Artificial Sequence
```

```
<220> FEATURE:
<223> OTHER INFORMATION: 147LIR reverse primer

<400> SEQUENCE: 339
catgaattcg ctagagccgc cttgctt                                    27

<210> SEQ ID NO 340
<211> LENGTH: 30
<212> TYPE: DNA
<213> ORGANISM: Artificial Sequence
<220> FEATURE:
<223> OTHER INFORMATION: 182LF forward primer

<400> SEQUENCE: 340
ttaggatcct gagcaagtac agtgtgtcac                                 30

<210> SEQ ID NO 341
<211> LENGTH: 31
<212> TYPE: DNA
<213> ORGANISM: Artificial Sequence
<220> FEATURE:
<223> OTHER INFORMATION: 183LR reverse primer

<400> SEQUENCE: 341
cttgaattca gcagatgctc tttgcagagt c                               31

<210> SEQ ID NO 342
<211> LENGTH: 27
<212> TYPE: DNA
<213> ORGANISM: Artificial Sequence
<220> FEATURE:
<223> OTHER INFORMATION: 52LIFP forward primer

<400> SEQUENCE: 342
ctgcccggga ccgtcaccct ggtgtcc                                    27

<210> SEQ ID NO 343
<211> LENGTH: 24
<212> TYPE: DNA
<213> ORGANISM: Artificial Sequence
<220> FEATURE:
<223> OTHER INFORMATION: 53LIRP reverse primer

<400> SEQUENCE: 343
tcgcccgggt catgctcgag ggtc                                       24

<210> SEQ ID NO 344
<211> LENGTH: 29
<212> TYPE: DNA
<213> ORGANISM: Artificial Sequence
<220> FEATURE:
<223> OTHER INFORMATION: 185LF forward primer

<400> SEQUENCE: 344
agcggatccc ctactctgtc acgctcatc                                  29

<210> SEQ ID NO 345
<211> LENGTH: 30
<212> TYPE: DNA
<213> ORGANISM: Artificial Sequence
<220> FEATURE:
<223> OTHER INFORMATION: 186LR reverse primer

<400> SEQUENCE: 345
gacgaattca tgttcaatca acagctgaag                                 30
```

-continued

```
<210> SEQ ID NO 346
<211> LENGTH: 28
<212> TYPE: DNA
<213> ORGANISM: Artificial Sequence
<220> FEATURE:
<223> OTHER INFORMATION: 142MF forward primer

<400> SEQUENCE: 346
tcaggatcca gcctgtacct cccgatgc                                    28

<210> SEQ ID NO 347
<211> LENGTH: 28
<212> TYPE: DNA
<213> ORGANISM: Artificial Sequence
<220> FEATURE:
<223> OTHER INFORMATION: 143MR reverse primer

<400> SEQUENCE: 347
atggaattcc tggtagttgg gcaggatc                                    28

<210> SEQ ID NO 348
<211> LENGTH: 25
<212> TYPE: DNA
<213> ORGANISM: Artificial Sequence
<220> FEATURE:
<223> OTHER INFORMATION: 155NOF forward primer

<400> SEQUENCE: 348
agcggatcca gcccaatgtc atttc                                       25

<210> SEQ ID NO 349
<211> LENGTH: 25
<212> TYPE: DNA
<213> ORGANISM: Artificial Sequence
<220> FEATURE:
<223> OTHER INFORMATION: 156NOR reverse primer

<400> SEQUENCE: 349
gaagaattca gggcccctca gaatg                                       25

<210> SEQ ID NO 350
<211> LENGTH: 25
<212> TYPE: DNA
<213> ORGANISM: Artificial Sequence
<220> FEATURE:
<223> OTHER INFORMATION: 66AFF forward primer

<400> SEQUENCE: 350
tcggatcctg aggaaagaac ctgaa                                       25

<210> SEQ ID NO 351
<211> LENGTH: 26
<212> TYPE: DNA
<213> ORGANISM: Artificial Sequence
<220> FEATURE:
<223> OTHER INFORMATION: 67AFR reverse primer

<400> SEQUENCE: 351
tagaattcac cctgctttgc tacttc                                      26

<210> SEQ ID NO 352
<211> LENGTH: 27
<212> TYPE: DNA
<213> ORGANISM: Artificial Sequence
<220> FEATURE:
<223> OTHER INFORMATION: 247PTF forward primer
```

<400> SEQUENCE: 352
atcggatcct aatcagaatg aaacctg                                27

<210> SEQ ID NO 353
<211> LENGTH: 27
<212> TYPE: DNA
<213> ORGANISM: Artificial Sequence
<220> FEATURE:
<223> OTHER INFORMATION: 248PTR reverse primer

<400> SEQUENCE: 353
atcgaattca gcattaggtc gaactag                                27

<210> SEQ ID NO 354
<211> LENGTH: 26
<212> TYPE: DNA
<213> ORGANISM: Artificial Sequence
<220> FEATURE:
<223> OTHER INFORMATION: 75PRF forward primer

<400> SEQUENCE: 354
acgggatcca tgtcaccatc ttacac                                 26

<210> SEQ ID NO 355
<211> LENGTH: 28
<212> TYPE: DNA
<213> ORGANISM: Artificial Sequence
<220> FEATURE:
<223> OTHER INFORMATION: 76PRR reverse primer

<400> SEQUENCE: 355
gtgaattcct tggactggag gcttttc                                28

<210> SEQ ID NO 356
<211> LENGTH: 27
<212> TYPE: DNA
<213> ORGANISM: Artificial Sequence
<220> FEATURE:
<223> OTHER INFORMATION: 145HF forward primer

<400> SEQUENCE: 356
gtgggatccg agattcagga gcaatgc                                27

<210> SEQ ID NO 357
<211> LENGTH: 28
<212> TYPE: DNA
<213> ORGANISM: Artificial Sequence
<220> FEATURE:
<223> OTHER INFORMATION: 146HR reverse primer

<400> SEQUENCE: 357
ctggaattcg ccttgaaact acaagttc                               28

<210> SEQ ID NO 358
<211> LENGTH: 27
<212> TYPE: DNA
<213> ORGANISM: Artificial Sequence
<220> FEATURE:
<223> OTHER INFORMATION: 130KIF forward primer

<400> SEQUENCE: 358
aaaggatcca ctacatcttt cctcacg                                27

<210> SEQ ID NO 359

```
<211> LENGTH: 29
<212> TYPE: DNA
<213> ORGANISM: Artificial Sequence
<220> FEATURE:
<223> OTHER INFORMATION: 131KIR reverse primer

<400> SEQUENCE: 359
tcacaattgg atagcatatt gaggtccag                                  29

<210> SEQ ID NO 360
<211> LENGTH: 27
<212> TYPE: DNA
<213> ORGANISM: Artificial Sequence
<220> FEATURE:
<223> OTHER INFORMATION: 64RGF forward primer

<400> SEQUENCE: 360
tgggatcccg cccccaaggg tgcggag                                    27

<210> SEQ ID NO 361
<211> LENGTH: 25
<212> TYPE: DNA
<213> ORGANISM: Artificial Sequence
<220> FEATURE:
<223> OTHER INFORMATION: 65RGR reverse primer

<400> SEQUENCE: 361
aggaattccc aattaatttc actac                                      25

<210> SEQ ID NO 362
<211> LENGTH: 26
<212> TYPE: DNA
<213> ORGANISM: Artificial Sequence
<220> FEATURE:
<223> OTHER INFORMATION: 158KIF forward primer

<400> SEQUENCE: 362
aaaggatccc tccggctcct cggaag                                     26

<210> SEQ ID NO 363
<211> LENGTH: 29
<212> TYPE: DNA
<213> ORGANISM: Artificial Sequence
<220> FEATURE:
<223> OTHER INFORMATION: 159KIR reverse primer

<400> SEQUENCE: 363
ttagaattct gatttgggag aagggtaag                                  29

<210> SEQ ID NO 364
<211> LENGTH: 21
<212> TYPE: DNA
<213> ORGANISM: Artificial Sequence
<220> FEATURE:
<223> OTHER INFORMATION: 55DVISF 1st PCR forward primer

<400> SEQUENCE: 364
tcatccagac tcatccggaa g                                          21

<210> SEQ ID NO 365
<211> LENGTH: 20
<212> TYPE: DNA
<213> ORGANISM: Artificial Sequence
<220> FEATURE:
<223> OTHER INFORMATION: 56DVISR 1st PCR reverse primer

<400> SEQUENCE: 365
```

```
gctcatgtca ctcttcaccg                                                    20

<210> SEQ ID NO 366
<211> LENGTH: 25
<212> TYPE: DNA
<213> ORGANISM: Artificial Sequence
<220> FEATURE:
<223> OTHER INFORMATION: 37DVF 2nd PCR nested forward primer

<400> SEQUENCE: 366
tcggatccaa acggtcactc tcaac                                              25

<210> SEQ ID NO 367
<211> LENGTH: 26
<212> TYPE: DNA
<213> ORGANISM: Artificial Sequence
<220> FEATURE:
<223> OTHER INFORMATION: 38DVR 2nd PCR nested reverse primer

<400> SEQUENCE: 367
tcggaattcc cagcacttgg ctacag                                             26

<210> SEQ ID NO 368
<211> LENGTH: 27
<212> TYPE: DNA
<213> ORGANISM: Artificial Sequence
<220> FEATURE:
<223> OTHER INFORMATION: 136TF forward primer

<400> SEQUENCE: 368
acgggatcct actgcctgag acccacc                                            27

<210> SEQ ID NO 369
<211> LENGTH: 29
<212> TYPE: DNA
<213> ORGANISM: Artificial Sequence
<220> FEATURE:
<223> OTHER INFORMATION: 137TR reverse primer

<400> SEQUENCE: 369
acggaattcc gctggttggc gggcttgac                                          29

<210> SEQ ID NO 370
<211> LENGTH: 25
<212> TYPE: DNA
<213> ORGANISM: Artificial Sequence
<220> FEATURE:
<223> OTHER INFORMATION: 39TF forward primer

<400> SEQUENCE: 370
tcggatccac agcatccaca ttgag                                              25

<210> SEQ ID NO 371
<211> LENGTH: 23
<212> TYPE: DNA
<213> ORGANISM: Artificial Sequence
<220> FEATURE:
<223> OTHER INFORMATION: 40TR reverse primer

<400> SEQUENCE: 371
tcggaattcc tccagctcgg ggt                                                23

<210> SEQ ID NO 372
<211> LENGTH: 25
<212> TYPE: DNA
```

```
<213> ORGANISM: Artificial Sequence
<220> FEATURE:
<223> OTHER INFORMATION: 34MIF forward primer

<400> SEQUENCE: 372
cggaattcgg aaaactgtaa agatg                                    25

<210> SEQ ID NO 373
<211> LENGTH: 25
<212> TYPE: DNA
<213> ORGANISM: Artificial Sequence
<220> FEATURE:
<223> OTHER INFORMATION: 20MR reverse primer

<400> SEQUENCE: 373
tcggaattca gcagcctgta catcg                                    25

<210> SEQ ID NO 374
<211> LENGTH: 27
<212> TYPE: DNA
<213> ORGANISM: Artificial Sequence
<220> FEATURE:
<223> OTHER INFORMATION: 152KIF forward primer

<400> SEQUENCE: 374
ctgggatccc acatcagccg attgtga                                  27

<210> SEQ ID NO 375
<211> LENGTH: 29
<212> TYPE: DNA
<213> ORGANISM: Artificial Sequence
<220> FEATURE:
<223> OTHER INFORMATION: 153KIR reverse primer

<400> SEQUENCE: 375
tgtgaattca aatggggtag tagtgattg                                29

<210> SEQ ID NO 376
<211> LENGTH: 29
<212> TYPE: DNA
<213> ORGANISM: Artificial Sequence
<220> FEATURE:
<223> OTHER INFORMATION: 235CYF forward primer

<400> SEQUENCE: 376
cctggatcca agaaaagctt gttactgtg                                29

<210> SEQ ID NO 377
<211> LENGTH: 26
<212> TYPE: DNA
<213> ORGANISM: Artificial Sequence
<220> FEATURE:
<223> OTHER INFORMATION: 236CYR reverse primer

<400> SEQUENCE: 377
tcagaattcc attaagagtc tctatc                                   26

<210> SEQ ID NO 378
<211> LENGTH: 29
<212> TYPE: DNA
<213> ORGANISM: Artificial Sequence
<220> FEATURE:
<223> OTHER INFORMATION: 188MF forward primer

<400> SEQUENCE: 378
actggatccc cgtcaccacc gccatcatc                                29
```

```
<210> SEQ ID NO 379
<211> LENGTH: 28
<212> TYPE: DNA
<213> ORGANISM: Artificial Sequence
<220> FEATURE:
<223> OTHER INFORMATION: 189MR reverse primer

<400> SEQUENCE: 379
ctcgaattcc gtgctcaggg ccgcccta                                     28

<210> SEQ ID NO 380
<211> LENGTH: 29
<212> TYPE: DNA
<213> ORGANISM: Artificial Sequence
<220> FEATURE:
<223> OTHER INFORMATION: 197 TF forward primer

<400> SEQUENCE: 380
aggggatccg caaggaggtg gaggtgttc                                    29

<210> SEQ ID NO 381
<211> LENGTH: 29
<212> TYPE: DNA
<213> ORGANISM: Artificial Sequence
<220> FEATURE:
<223> OTHER INFORMATION: 198 TR reverse primer

<400> SEQUENCE: 381
tgtggaattc cttgcgaggc tccgtgagc                                    29

<210> SEQ ID NO 382
<211> LENGTH: 28
<212> TYPE: DNA
<213> ORGANISM: Artificial Sequence
<220> FEATURE:
<223> OTHER INFORMATION: 161KIF forward primer

<400> SEQUENCE: 382
cctggatccc cccatcgtta tccacagc                                     28

<210> SEQ ID NO 383
<211> LENGTH: 26
<212> TYPE: DNA
<213> ORGANISM: Artificial Sequence
<220> FEATURE:
<223> OTHER INFORMATION: 162KIR reverse primer

<400> SEQUENCE: 383
gaggaattct ccagggctgt ggtccg                                       26
```